United States Patent
Becker et al.

(10) Patent No.: US 8,354,093 B2
(45) Date of Patent: Jan. 15, 2013

(54) CELL PERMEABLE NANOCONJUGATES OF SHELL-CROSSLINKED KNEDEL (SCK) AND PEPTIDE NUCLEIC ACIDS ("PNAS") WITH UNIQUELY EXPRESSED OR OVER-EXPRESSED MRNA TARGETING SEQUENCES FOR EARLY DIAGNOSIS AND THERAPY OF CANCER

(75) Inventors: Matthew L. Becker, Frederick, MD (US); Huafeng Fang, St. Louis, MO (US); Xiaoxu Li, New York, NY (US); Dipanjan Pan, West Bengal (IN); Raffaella Rossin, St. Louis, MO (US); Xiankai Sun, Coppell, TX (US); John-Stephen Taylor, St. Louis, MO (US); Jeffrey L. Turner, St. Louis, MO (US); Michael John Welch, Clayton, MO (US); Karen L. Wooley, St. Louis, MO (US)

(73) Assignee: Washington University, St. Louis, MO (US)

( * ) Notice: Subject to any disclaimer, the term of this patent is extended or adjusted under 35 U.S.C. 154(b) by 1642 days.

(21) Appl. No.: 11/250,830

(22) Filed: Oct. 14, 2005

(65) Prior Publication Data

US 2006/0159619 A1 Jul. 20, 2006

Related U.S. Application Data

(60) Provisional application No. 60/619,242, filed on Oct. 15, 2004.

(51) Int. Cl.
*A61K 51/00* (2006.01)
*A61M 36/14* (2006.01)

(52) U.S. Cl. ............. 424/1.69; 424/1.11; 424/1.65; 424/1.73; 514/1; 514/1.1

(58) Field of Classification Search .......... 424/1.11, 424/1.29, 1.33, 1.37, 1.53, 1.65, 1.69, 1.73, 424/1.81, 9.1, 9.3, 9.4, 9.5, 9.6, 9.7, 9.8; 206/223, 569, 570; 514/1, 1.1
See application file for complete search history.

(56) References Cited

U.S. PATENT DOCUMENTS 6,165,720 A * 12/2000 Felgner et al. ............... 435/6
2005/0038239 A1 * 2/2005 Catchpole ................. 536/24.3

OTHER PUBLICATIONS

Lewis et al (2002), Bioconjugate Chemistry, vol. 13, No. 6, pp. 1176-1180.*
Golub et al., Science, Oct. 15, 1999, pp. 531-537.*

\* cited by examiner

*Primary Examiner* — D L Jones
(74) *Attorney, Agent, or Firm* — Armstrong Teasdale LLP

(57) ABSTRACT

A functional biologically active particle conjugate useful for diagnosis and treating cancer as a bioportal comprises a nanoscale particle having associated therewith an intracellular targeting ligand comprising a PNA, or another nuclease resistant oligonucleotide analog such as MOE-mRNA (2'-methoxyethyl mRNA) or LNA (locked nucleic acid), having a sequence that binds selectively to an uniquely expressed or overexpressed mRNA specific to the cancer or disease state in a living mammal. In one aspect the uniquely overexpressed target specific to the cancer or disease state is the unr mRNA which can be targeted by the antisense sequence PNA50.

8 Claims, 41 Drawing Sheets

XN9-tag (X = A, C, G or T):
5'-GGATTTGCTGGTGCAGTACANNNNNNNNNX-3'

A.

B.

71-77 x: no RNA, y: no ³²P-labeled ODN

A.

B.

SEQUENCE LISTING

<160> NUMBER OF SEQ ID NOS: 50

<210> SEQ ID NO 1
<211> LENGTH: 11
<212> TYPE: PRT
<213> ORGANISM: Human immunodeficiency virus type 1

<400> SEQUENCE: 1

Tyr Gly Arg Lys Lys Arg Arg Gln Arg Arg Arg
 1               5                  10

<210> SEQ ID NO 2
<211> LENGTH: 4076
<212> TYPE: DNA
<213> ORGANISM: Homo sapiens

<400> SEQUENCE: 2

| | | | | | | |
|---|---|---|---|---|---|---|
| gcttatggcg | gcgctggaga | gggggcgctg | agctgttggg | tatgaagtgt | aacagaacag | 60 |
| actttaccac | ctgaaactgc | tgcttcaagt | tcagatcagg | caaggaacaa | acctcgtaac | 120 |
| aactaacaag | accaaagaag | agtacactta | agttgaagac | acaacacttg | atctgaaaca | 180 |
| agaagtttgt | gcctactcaa | cagctttgaa | agagcacttc | ccaacgctgc | tagtagtctt | 240 |
| tgttttcttc | agtgctgtac | tgtgagattg | cccggtacag | cagcagttgt | attctttatt | 300 |
| agcttggtag | atcattttct | ctcgctcttt | tttttaatac | tagcaacttt | catcctttga | 360 |
| aacgtgtgct | gaaaagaag | aatcagcaaa | tactactgaa | agtgcaatat | ttgagtatca | 420 |
| ctgcgagatg | agctttgatc | caaaccttct | ccacaacaat | ggacataatg | ggtaccctaa | 480 |
| tggtacttca | gcagcactgc | gtgaaactgg | ggttattgaa | aaactgttaa | cctcttacgg | 540 |
| atttattcag | tgttcagaac | gtcaagctag | acttttcttc | cactgttcac | agtataatgg | 600 |
| caacctgcaa | gacttaaaag | taggagatga | tgttgaattt | gaagtatcat | cggaccgacg | 660 |
| gactgggaaa | cccattgctg | ttaaactggt | gaagataaaa | caagaaatcc | tccctgaaga | 720 |
| acgaatgaat | ggacaagttg | tgtgcgctgt | tcctcacaac | ttagagagta | aatctccagc | 780 |
| tgccccgggt | cagagtccaa | cagggagtgt | atgctacgaa | cgtaatgggg | aagtgtttta | 840 |
| tctgacttac | accctgaag | atgtcgaagg | gaacgttcag | ctggaaactg | agataaaat | 900 |
| aaactttgta | attgataaca | ataaacatac | tggtgctgta | agtgctcgca | acattatgct | 960 |
| gttgaaaaag | aaacaagccc | gctgtcaggg | agtagtttgt | gccatgaagg | aggcatttgg | 1020 |
| ctttattgaa | agaggtgatg | ttgtaaaaga | gatattcttt | cactatagtg | aatttaaggg | 1080 |
| tgacttagaa | accttacagc | ctggcgatga | tgtggaattc | acaatcaagg | acagaaatgg | 1140 |
| taaagaagtt | gcaacagatg | tcagactatt | gcctcaagga | acagtcattt | ttgaagatat | 1200 |
| cagcattgaa | cattttgaag | gaactgtaac | caaagttatc | ccaaaagtac | ccagtaaaaa | 1260 |
| ccagaatgac | ccattgccag | gacgcatcaa | agttgacttt | gtgatcccta | agaacttcc | 1320 |
| ctttggagac | aaagatacga | aatccaaggt | gaccctgctg | gaaggtgacc | atgttaggtt | 1380 |
| taatatttca | acagaccgac | gtgacaaatt | agagcgagca | accaatatag | aagttctgtc | 1440 |
| aaatacattt | cagttcacta | atgaagcccg | agaaatgggt | gtgattgctg | ccatgagaga | 1500 |
| tggttttggt | ttcatcaagt | gtgtggatcg | tgatgttcgt | atgttcttcc | acttcagtga | 1560 |
| aattctggat | gggaaccagc | tccatattgc | agatgaagta | gagtttactg | tggttcctga | 1620 |
| tatgctctct | gctcaaagaa | atcatgctat | taggattaaa | aaacttccca | agggcacggt | 1680 |
| ttcatttcat | tcccattcag | atcaccgttt | tctgggcacg | gtagaaaaag | aagccacttt | 1740 |

```
ttccaatcct aaaaccacta gcccaaataa aggcaaagag aaggaggctg aggatggcat   1800
tattgcttat gatgactgtg gggtgaaact gactattgct tttcaagcca aggatgtgga   1860
aggatctact tctcctcaaa taggagataa ggttgaattt agtattagtg acaaacagag   1920
gcctggacag caggttgcaa cttgtgtgcg acttttaggt cgtaattcta actccaagag   1980
gctcttgggt tatgtggcaa ctctgaagga taattttgga tttattgaaa cagccaatca   2040
tgataaggaa atcttttttcc attacagtga gttctctggt gatgttgata gcctggaact   2100
gggggacatg gtcgagtata gcttgtccaa aggcaaaggc aacaaagtca gtgcagaaaa   2160
agtgaacaaa acacactcag tgaatggcat tactgaggaa gctgatccca ccatttactc   2220
tggcaaagta attcgccccc tgaggagtgt tgatccaaca cagactgagt accaaggaat   2280
gattgagatt gtggaggagg gcgatatgaa aggtgaggtc tatccatttg gcatcgttgg   2340
gatggccaac aaaggggatt gcctgcagaa aggggagagc gtcaagttcc aattgtgtgt   2400
cctgggccaa aatgcacaaa ctatggctta caacatcaca ccccctgcgca gggccacagt   2460
ggaatgtgtg aaagatcagt ttggcttcat taactatgaa gtaggagata gcaagaagct   2520
cttttttccat gtgaaagaag ttcaggatgg cattgagcta caggcaggag atgaggtgga   2580
gttctcagtg attcttaatc agcgcactgg caagtgcagc gcctgtaatg tttggcgagt   2640
ctgtgagggc cccaaggctg ttgcagctcc tcgacctgat cggttggtca atcgcttgaa   2700
gaatatcact ctggatgatg ccagtgctcc tcgcctaatg gttcttcgtc agccaagggg   2760
accagataac tcaatggggt ttggtgcaga aagaaagatc cgtcaagctg gtgtcattga   2820
ctaaccacat ccacaaagca caccattaat ccactatgat caagttgggg ggaatctggt   2880
gaagggttct gaatatctcc ctcttcatcc ctcccgaaat ctggaatact tattctattg   2940
agctattaca ccagttttaa caccttcctc gtgttatgtt taaaaaaata aataaattta   3000
agaaaaccat tttaaataat gcacagttgc agcctggaaa aacttaaggt ggcgccttat   3060
agtatcaatt ttaggagctt tatttggtgc atttaacgca actggtaatt gcagaatcca   3120
cttttgcctgt gtaagtgaaa aatatagact gttatcttgt tggccctatg aaattctgca   3180
cttttcatta tatactctac cttcattaat tacttctggc aagatgttct gccttagcac   3240
tcagttgcat tcttttcctt tttcttcctg ttcattatgc tttaattctg aggaccatat   3300
gagggtagaa tatattatct tttaaaaatt acaaaaattt gtataggcaa accatttctt   3360
aaagttgatg gccaaatttt aaaatgttat ttttcatatc atttataatc ttgtcacaat   3420
ccacttaaag aagtttggtt atatttcagt gaaaattttc ttccagagta ggttttttttt   3480
cgtgggttgg ggggtaactt tactacaatt agtaagtatg gtgcagaatt tcatgcaaat   3540
gaggagtgcc agcagtgtga taatttaaac atatttaaac aaaaacaaaa aaaatgaatg   3600
cacaaacttg ctgctgctta gatcactgca gcttctagga cccggtttct tttactgatt   3660
taaaaacaaa acaaaaaaaa ataaaaaagt tgtgcctgaa atgaatcttg ttttttttta   3720
taagtagccg cctggttact gtgtcctgta aaatacagac acttgaccct tggtgtagct   3780
tctgttcaac tttatatcac gggaatggat gggtctgatt tcttgccct cttcttgaat   3840
tggccatata caggtccct ggccagtgga ctgaaggctt tgtctaagat gacaagggtc   3900
agctcagggg atgtggggga gggcggtttt atcttccccc ttgtcgtttg aggttttgat   3960
ctctgggtaa agaggccgtt tatctttgta aacacgaaac attttgtgctt tctccagttt   4020
tctgttaatg gcgaaagaat ggaagcgaat aaagttttac tgattttga gacact        4076
```

-continued

<210> SEQ ID NO 3
<211> LENGTH: 18
<212> TYPE: DNA
<213> ORGANISM: Homo sapiens

<400> SEQUENCE: 3
tggtgtgctt tgtggatg                                                 18

<210> SEQ ID NO 4
<211> LENGTH: 18
<212> TYPE: DNA
<213> ORGANISM: Homo sapiens

<400> SEQUENCE: 4
catccacaaa gcacacca                                                 18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgagctgt tgggtatgaa g                                             21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcatcctttg aaacgtgtgc                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgaacgtaa tggggaagtg                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaatccaagg tgaccctgct                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
tgactgtggg gtgaaactga                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagggcgata tgaaaggtga                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaccacatcc acaaagcaca                                               20

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(28)
<223> OTHER INFORMATION: a, c, g, t, unknown, or other

<400> SEQUENCE: 12
ggatttgctg gtgcaacatg nnnnnnnnca tgaagcttga aattcgagg               49

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggatttgctg gtgcaacatg                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
catgttgcac cagcaaatcc                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                                oligonucleotide

<400> SEQUENCE: 15
cctcgaattc aagcttcatg                                                    20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tggtcctcag aattaaagca taatg                                              25

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Pro Lys Lys Lys Arg Lys Val
 1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Lys Lys
 1

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Tyr Gly Arg Lys Lys Arg Arg Gln Arg Arg Arg
 1               5                  10                  15

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agcgaccaaa ggaaccataa                                                    20

<210> SEQ ID NO 21
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 21
gctctctcct cctcctcctc                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tttcctccca ataccccttc                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagaaacctc ggaaacgtga                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgtgaaatgc caccttttga                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctcttcgac accgtcgatg                                               20

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Arg Arg Arg Arg Arg Arg Arg Arg Arg
 1               5                  10

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
tggtgtgctt tgtgg                                                    15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tttcccagtc cgtcg                                                    15

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atctccagtt tccag                                                    15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tttgtcacgt cggtc                                                    15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
catttctgtc cttga                                                    15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
catcctcagc ctcct                                                    15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 33
cacttcccca ttacg                                                       15

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
attcgttctt cagggaggat                                                  20

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tatgtccatt gttgt                                                       15

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccaaaattat ccttcagagt                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tctgttgaaa tattaaacct                                                  20

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cctctgtttg tcact                                                       15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
```

-continued tgtcccccag ttcca                                                     15

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aatattaaac ctaacatggt                                                20

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
atgtccccca gttcc                                                     15

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgattggagc gc                                                        12

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agatcgcaac tcata                                                     15

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cattatgtcc attgttgt                                                  18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttcccagtc cgtcggtc                                                  18

```
<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
taatttgtca cgtcggtc                                                   18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tatctccagt ttccagct                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttcccagtc cgtgggtc                                                   18

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Tyr Arg Lys Lys Arg Arg Gln Arg Arg Arg
 1               5                  10

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(30)
<223> OTHER INFORMATION: a, c, g, or t

<400> SEQUENCE: 50
ggatttgctg gtgcagtaca nnnnnnnnnn                                      30
```

CELL PERMEABLE NANOCONJUGATES OF SHELL-CROSSLINKED KNEDEL (SCK) AND PEPTIDE NUCLEIC ACIDS ("PNAS") WITH UNIQUELY EXPRESSED OR OVER-EXPRESSED MRNA TARGETING SEQUENCES FOR EARLY DIAGNOSIS AND THERAPY OF CANCER

This application claims the benefit of U.S. provisional patent application 60/619,242 filed Oct. 15, 2004 which is incorporated herein by reference in its entirety.

STATEMENT REGARDING FEDERALLY SPONSORED RESEARCH AND DEVELOPMENT

This discovery was made with Government support under Grant 0210247 awarded by the National Science Foundation and Contract N01-CO-27103 from the National Cancer Institute and NIH-NRSA(5-T32-GM08785-02). The Government has certain rights in this discovery.

FIELD OF THE DISCOVERY

This discovery relates to diagnostic and therapeutic conjugates and use of such conjugates to diagnose and treat cancer. More in particular this discovery relates to biomedical polymer nanoconjugates and their use to diagnose and treat cancer.

BACKGROUND OF THE DISCOVERY

Cancer (malignant neoplasm) is the number two killer of people in the U.S. Each year in the U.S. more than a million people are diagnosed with cancer and half of those will ultimately die from the disease. Cancer occurs when normal living mammalian cells undergo neoplastic (malignant) transformation. Cancer is tenacious in its ability to uncontrollably and rapidly metastasize throughout the mammalian body, thus giving rise to a high mortality rate.

Cancer cure rates have increased dramatically over the years. This positive trend is a result of the widespread use of improved screening procedures that often lead to the early diagnosis/detection of cancer. However, as more selective treatment strategies have been developed, it is necessary to develop new and improved early stage clinical diagnostic procedures that can be used far earlier to determine a potential treatment strategy based on the biological properties and proliferation of the cancer. In addition, it is desired to develop non-invasive procedures that can provide the means for determining either a positive or negative response to a treatment strategy as early as possible thus extending the mammalian host's viability.

The first step in clinically treating cancer is to accurately diagnose the location and presence of the disease. This means determine the location of the cancer and confirm that the suspected cancer is cancer. The area of the body where the tumor or cancer is identified using symptomatology reports from a patient and then x-rays or other diagnostic tools are utilized to verify the initial symptoms and to identify the specific location of the cancer. That the location is cancerous is ultimately determined from a biopsy. Examination of a sample of suspected cancerous growth by a cancer specialist examining the biopsy confirms that the tissue is either benign or it is malignant cancer and if it is cancer, then what type of cancer and what the stage of development of the cancer is determined. Non-invasive imaging techniques are revolutionizing understanding diseases at the cellular and molecular levels. However, more is needed.

Among the current available non-invasive imaging modalities, positron emission tomography (PET) has demonstrated its great potential in the field of molecular imaging due to its superior sensitivity and specificity in diverse applications, the very small amount of agent required and the ability to quantitatively analyze the regions of interest. Since the completion of human genome sequence, there have been considerable research interests in the assessment of gene functions and protein-protein interactions non-invasively using molecular imaging approaches. Of the various PET probes that have been developed to image gene expression in small animal models, oligonucleotides appear to be an inexhaustible gold mine for the development of new tracers with high specificity considering that an oligonucleotide with more than 12 nucleobases could represent a unique sequence in the whole human genome with a gene number estimated between 24,000 and 30,000, and alternative polyadenylation and splicing could result in a number of messenger ribonucleic acid (mRNA) between 46,000 and 85,000.

The techniques of antisense mRNA originated from the natural modulation of gene replication and expression in bacteria via small complementary RNA molecules in an opposite direction (antisense). However, the naturally occurring oligonucleotides with 2'-deoxyphosphodiester cannot be directly applied to nuclear imaging because they are rapidly degraded in vivo by endo- and exo-nucleases. To increase the in vivo stability of oligonucleotides without significant alteration of their pharmacokinetics and targeting properties, many chemical modifications have been made to the sugar-phosphate backbone, including morpholino, phosphorothioate, phosphoroamidate, methylphosphonate, 2'- or 3'-modified derivatives, peptide nucleic acids (PNAs), and locked nucleic acids. Peptide nucleic acids (PNAs) are a unique type of oligonucleotides, which was initially introduced by Nielsen et al. in 1991 as ligands for the double stranded DNA recognition. They are synthetic DNA mimics featuring a chain with repeating N-(2-aminoethyl) glycine units instead of the sugar-phosphate backbone.

Due to the structural characteristics (e.g., neutrality and flexibility), PNAs are resistant to the in vivo enzymatic degradation. PNAs bind complementary DNAs or RNAs with high affinity and specificity even under low ionic strength conditions. Recent work has shown that PNAs can be used as molecular hybridization probes, and nuclear imaging tracers.

Using antisense PNAs as molecular imaging probes has a major obstacle in that they have very poor permeability across biologic membranes, which is inherent from their structural feature. Therefore for the hybridization of an unmodified PNA with its target mRNA molecule in vitro, it often requires that the PNA be physically injected into the intracellular plasma. Attempts to overcome this obstacle have been resorted to the drug-delivery techniques, which include using cationic lipids (or polyamines) and liposomes, nanoparticles, and direct conjugation with monoclonal antibody or peptides, etc. Recently it was reported that PNAs with four lysines at the C terminus (PNA-K4 oligomers) demonstrated sequence-specific antisense activity in most tissues that expressed a specific gene.

Radionuclides such as $^{60}$Cu, $^{61}$Cu and $^{64}$Cu among other radionuclides respectively are utilized extensively in the diagnosis and treatment of cancer in living mammals. These radionuclides are useful for diagnosis ($^{60}$Cu, $^{61}$Cu and $^{64}$Cu); internal radiation therapy ($^{61}$Cu and $^{64}$Cu) because of their positron-emission and/or toxicity to cancer and their characteristic intermediate half-life and multiple decay mode. Such diagnostic and therapeutic efforts against cancer include the effective administration of radiolabeled chemicals using highly purified $^{60}$Cu, $^{61}$Cu and $^{64}$Cu. $^{64}$Cu is especially useful. The principal advantage to such use is that the radionuclide identifies a location for the cancer as well as provides a cytotoxic effect against the cancer.

Synthetic methodologies are enabling advances in the design of polymeric materials that actively control cellular and physiologic responses. These methods produce materials that are incorporated into scaffolds adaptive to body blood lumens and capable of performing specific functions while being minimally detrimental to normal cellular processes and surrounding tissues for use in therapeutic, drug delivery, and tissue engineering applications.

However, a need continues to exist for enhanced methods that can more accurately diagnose cancer and more particularly assess the response to anticancer therapy, as such methods would have a significant positive impact on determining optimal therapy for treating cancer patients. Also new methods are needed to treat cancer.

So despite the aforegoing remarkable advances and other advances in cancer diagnostics and cancer detection technology, it remains highly desirable to have an enhanced cancer detection and treatment system for use in a living mammal such as in a living human.

BRIEF DESCRIPTION OF THE DISCOVERY

This discovery provides a functional biologically active functional water dispersible synthetic conjugate useful for early stage diagnosing and treating cancer in a living mammal, comprising a nanoscale particle having associated therewith an intracellular targeting ligand comprising a PNA, or another nuclease resistant oligonucleotide analog such as MOE-mRNA (2'-methoxyethyl mRNA) or LNA (locked nucleic acid), having a sequence that binds selectively to an uniquely expressed or overexpressed mRNA specific to the cancer or disease state in a living mammal. In one aspect the uniquely overexpressed target specific to the cancer or disease state is the unr mRNA (see SEQ ID 2) which can be targeted by the antisense sequence PNA50 (see SEQ ID 3).

In a further aspect, a permeation peptide is additionally associated with a biologically active particle conjugate and PNA. In a further aspect the permeation peptide is an effective permeation peptide which comprises the HIV-1 TAT protein transduction domain further comprising a polypeptide having a sequence such as the sequence shown in SEQ ID 1.

In a further aspect, a functional biologically active particle conjugate comprises water dispersible biomedically and pharmacologically acceptable polydispersity globular macromolecules, particles, or nanoparticles. Useful particles include those particles disclosed in the U.S. Pat. No. 6,383,500 which issued to Karen Wooley et al. on May 7, 2002 (hereafter referred to as the '500 patent) which is incorporated herein in its entirety by reference. Further useful particles include dendrimers, micelles, liposomes, etc. as disclosed in Pharmacol. Rev. 2001, 53, 283-318; Nature Rev. Drug Disc. 2003, 2, 347-360.

In an aspect a method of identifying uniquely expressed or overexpressed mRNA comprises using SAGE or DNA chip to quantify gene expression in a target cell, comparing the gene expression profile to expression databases, and identifying a sequence that is most differentially expressed and is in the highest amount or is uniquely expressed to identify an mRNA of interest, obtaining a clone containing the cDNA for the mRNA of interest and producing the mRNA in vitro by RNA polymerase, mapping accessible sites by either the modified RT-ROL assay and/or SAABS assay, screening potential ODNs by the Dynabead dot blot assay and quantifying the binding of ODNs by the Dynabead direct binding assay with $^{32}$P-labeled ODN.

In a further aspect, the identified sequence is modified to obtain a useful targeting ligand by synthesizing and recovering Cys-Tyr-PNA-Lys4 corresponding to the tightest binding ODNs (or with another permeation peptide in place of Lys4), quantifying binding of the hybrid PNAs by the Dynabead direct binding assay with radioiodinated PNA, conjoining the highest affinity PNAs to fluorescein and DOTA for fluorescence assays of cell binding in vitro or in vivo (mouse xenograft) and conjoining PNAs with the highest affinity to SCK nanoparticles through an appended lysine or other suitable accommodating site-specific coupling moiety.

In an aspect, an isolated, purified and characterized PNA having a unr mRNA binding antisense sequence PNA50 (see SEQ ID 3).

In an aspect, an intracellular targeting ligand comprises a PNA, or another nuclease resistant oligonucleotide analog such as MOE-mRNA or LNA, having a sequence that binds selectively to an uniquely expressed or overexpressed mRNA specific to the cancer or disease state and a permeation peptide (e.g., HIV-1 TAT protein transduction domain, See SEQ ID. 1). In one aspect the uniquely overexpressed target specific to the cancer or disease state is the unr mRNA (see SEQ ID 2) which can be targeted by the antisense sequence PNA50 (See SEQ ID 3).

In an aspect, an intra intracellular targeting ligand useful for detection of cancer in a living mammal comprises a PNA, or another nuclease resistant oligonucleotide analog such as MOE-mRNA or LNA, having a sequence that binds selectively to an uniquely expressed or overexpressed mRNA specific to the cancer or a nuclease resistant oligonucleotide analog MOE-mRNA or LNA, a permeation peptide and a reporter capable of detecting cancer, such as an emission capable fluorophore or a radionuclide or both a fluorophore and a radionuclide. In an aspect the living mammal is a living human.

In an aspect, an active targeting cancer detection system comprises a particle based moiety having associated therewith a PNA or another nuclease resistant oligonucleotide analog that does not activate the degradation of the mRNA by RNase H, such as MOE-mRNA or LNA, having a unr mRNA binding sequence such as PNA50 (See SEQ ID 3) or any sequence that binds selectively to an unique or overexpressed mRNA specific to the cancer or disease state, a permeation peptide (e.g., HIV-1 TAT protein transduction domain See SEQ ID 1), and a reporter capable of detecting cancer, such as an emission capable fluorophore or a radionuclide or both a fluorophore and a radionuclide.

In an aspect, a diagnostic target-specific imaging probe comprises a particle-based moiety having associated therewith a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to an uniquely expressed or overexpressed mRNA specific to the cancer or disease state, a permeation peptide (e.g., HIV-1 TAT protein transduction domain, see SEQ ID 1), and a diagnostic imaging detectable amount of at least one detectably labeled compound.

In an aspect, a method of detecting cancer comprises administering an effective amount of a particle-based moiety having associated therewith a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that reactively and selectively binds to an uniquely expressed or overexpressed mRNA specific to the cancer, and a permeation peptide and a reporter capable of detecting the cancer, such as an emission-capable fluorophore, or a radionuclide, or both a fluorophore and a radionuclide. In an aspect the detected reporter identifies the locus of the cancer in the living mammal.

In an aspect, an anticancer composition effective for treating human or non-human neoplastic disorders comprises a particle-based moiety having associated therewith at least a PNA or another nuclease resistant oligonucleotide analog that does not activate the degradation of the mRNA by RNAseH, such as MOE-mRNA or LNA, having a unr mRNA binding sequence such as PNA50 (see SEQ ID 3) or any sequence that binds selectively to an uniquely expressed or overexpressed mRNA specific to the cancer or disease state, a permeation peptide, and an effective amount of at least one chemotherapeutic compound, cytotoxic compound, radionuclide or prodrug in the composition, and optionally further comprising a pharmaceutically acceptable carrier such as saline solution.

In an aspect, a radiotherapeutic composition effective for treating human or non-human neoplastic disorders comprises a particle conjugate comprising a particle-based moiety having associated therewith at least a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to an uniquely expressed or overexpressed mRNA specific to the cancer or disease state, a permeation peptide, and an effective amount of at least one radionuclide with cytotoxic properties, and optionally further comprising a pharmaceutically acceptable carrier such as saline solution.

In an aspect, a method for determining response to anticancer therapy in a living mammal comprises administering to a living mammal an imaging probe comprising a particle-based moiety having associated therewith a PNA or another nuclease resistant oligonucleotide analog that does not activate the degradation of the target mRNA by RNase H, such as MOE-mRNA or LNA, having a unr mRNA binding sequence such as PNA50 (see SEQ ID 3) or any sequence that binds selectively to a unique or overexpressed mRNA specific to the cancer or disease state, a permeation peptide, and a diagnostic imaging detectable amount of at least one detectably labeled compound at a first selected time, detecting an image of a tissue, administering the imaging probe a second time after the anticancer therapy, detecting an image of the same tissue, comparing the two images and determining a response based on that comparison.

In an aspect, a method of screening candidate chemicals for toxicity/lethality to cancer comprises administering, to a mammal, a particle conjugate comprising a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to a uniquely or overexpressed mRNA specific to the cancer or disease state, a permeation peptide, and diagnostic imaging detectable amount of at least one detectably labeled compound at a first time, detecting and acquiring an image of a tissue, administering to the mammal a candidate chemical, detecting and acquiring an image of tissue, comparing the detected images and making a determination as to whether there has been a prophylactic effect on the progression of the cancer. In an aspect the PNA is conjugated to a biologically active water dispersible nanoparticle.

In as aspect, a pharmaceutical kit comprises a container. In an aspect the container houses a PNA or another nuclease resistant oligonucleotide analog that does not activate the degradation of the target mRNA by RNase H, such as MOE-mRNA or LNA, having a unr mRNA binding sequence such as PNA50 (see SEQ ID 3) or any sequence that binds selectively to an unique or overexpressed mRNA specific to a cancer or disease state, a permeation peptide, a pharmaceutical agent selected from the group consisting of chemotherapeutic drugs, cytotoxic drugs, prodrugs, and a radiopharmaceutical, and optionally a suitable pharmaceutically acceptable carrier. In an aspect the PNA is conjugated to a biologically active nanoparticle.

In an aspect, a PNA-guided tumor therapy comprises administering to a mammalian patient a therapeutically effective amount of a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to a unique or overexpressed mRNA specific to the cancer or disease state and a permeation peptide, whereby the particle conjugate is self guided to the tumor by the PNA and a pharmaceutical agent selected from at least one chemotherapeutic drug, cytotoxic drug, prodrug and a radiopharmaceutical. In an aspect the PNA is conjugated to a biologically active nanoparticle.

In an aspect, a medical apparatus useful for treating and detecting cancer, comprises a particle based moiety functioning as a scaffold and having associated therewith a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to a unique or overexpressed mRNA specific to cancer or disease state, and a permeation peptide. In an aspect the unique or overexpressed mRNA is a signature of cancer or a disease state in a living mammal and the methods, compositions, apparatus and scaffolding described herein provide a method of uniquely diagnosing and targeting that signature.

In an aspect, a bioactive pharmaceutical composition useful for treating cancer comprises a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to a uniquely expressed or overexpressed mRNA specific to the cancer or disease state, and a permeation peptide. If desired, the pharmaceutical composition comprises a pharmaceutical, or a pharmaceutically acceptable water soluble salt thereof, and a pharmaceutically acceptable carrier, excipient, or diluent or saline composition. The pharmaceutically active agent can be present within the particles. In an aspect a nano-scale particle-based moiety is conjugated to the PNA or analog.

In a further aspect, a method of effectively delivering a bioactive pharmaceutically active agent to a cell, tissue, organ, or animal, comprises contacting the cell, tissue, organ, or animal in vivo or in vitro, with a PNA or another nuclease resistant oligonucleotide analog that does not activate the degradation of the mRNA by RNase H, such as MOE-mRNA or LNA, having a unr mRNA binding sequence such as PNA50 (see SEQ ID 3) or any sequence that binds selectively to a unique or overexpressed mRNA specific to the cancer or disease state, a permeation peptide and further comprising a pharmaceutically active agent. In aspect the permeation peptide comprises HIV-1 TAT protein transduction domain having SEQ ID. 1). In an aspect a biologically active particle is associated with the PNA or analog.

BRIEF DESCRIPTION OF THE DRAWINGS

FIG. 5 (left side) shows data from the result of a sedimentation velocity analysis of SCK-PNA50 conjugate. The loss of absorbance at 260 nm at the top of the cell (near the meniscus) demonstrated the desired absence of free PNA within the reaction solution. The data is data of intensity as a function of radius. FIG. 5 (right side) shows a detail of UV spectrum recorded near the meniscus.

In FIG. 13(A) the dramatic increase in weight average molecular weight (Mw) was due to a small percentage of interparticle cross-linking (covalent or electostatic), which contributed significantly to the molecular weight calculations. In FIG. 13(B), UV spectra recorded near the meniscus of solutions at sedimentation equilibrium showed negligible absorbance due to free tyrosine residues within the PTD relative to controls. In FIG. 13(C) data show the repeating of the sedimentation test at 8000 rpm and indicated that the meniscus was fully depleted of SCK at 8000 rpm, but not at 5000 rpm, and also confirmed that all the PTD was desirably attached to the SCK.

FIG. 16(A) and FIG. 16(B) show confocal reconstructions of the respective SCK samples at 37° C. and 4° C. respectively, following 1 hour incubations and cell fixation. FIG. 16(C) shows CHO cells that were incubated for 1 hour in 0.1% sodium azide with the SCK samples.

FIG. 17 depicts an antisense agent synthesized against an abundant unique or overexpressed mRNA and conjoined to a probe (or prodrug) and permeation peptide, directly or via an attached nanoparticle. The permeation peptide allows the hybrid PNA to equilibrate with other cells and ultimately concentrate in the cell containing the more abundant mRNA.

FIG. 19 shows the location of unrX (X=1-7) priming sites. FIG. 19(B) shows phosphorimages of acrylamide gels of PCR products for each section (X=1-7) of the unr transcript. The boxed site of FIG. 19 is analyzed in FIG. 20. Primer sequences: unr1: GCTGAGCT-GTTGGGTATGAAG, unr2: TCATCCTTTGAAACGT-GTGC, unr3: ACGAACGTAATGGGGAAGTG; unr4: AAATCCAAGGTGACCCTGCT; unr5: TGACT-GTGGGGTGAAACTGA; unr6: GAGGGCGATAT-GAAAGGTGA unr7: AACCACATCCACAAAGCACA.

FIG. 20(A) is an enlargement of boxed section of gel in FIG. 19 showing approximate size of bands. FIG. 20(B) shows alignment of the observed bands with the mRNA sequence, taking into account that the PCR tag adds an additional 20 nucleotides to the extra 9 random nucleotides in the PCR amplified product band.

FIG. 23(A) Determining the loading capacity of the streptavidin coated dynabead by titrating 20 µL of bead solution in 40 µL total volume of 0.5 M NaCl with biotinylated radiolabeled unr mRNA. FIG. 23(B) shows a determination of the µL of Dynabead bound RNA needed to completely bind 1 pmol of ODN5 in a total volume of 40 µL. FIG. 23(C-D) Solutions of RNA were incubated with 1 pmol of ODN (1-54 from RT-ROL assay, and 57-68 (S1-S12) from the SAABS assay) and then incubated with 10 µL of Dynabeads and spotted on a Nylon membrane. FIG. 23(C) is a photograph of blot showing equal loading of beads. Panel D is a radiograph showing relative amounts of retained ODN.

FIG. 32(A) (top): $^{64}$Cu-DOTA-PNA50-K4; FIG. 32(B) (bottom): $^{64}$Cu-DOTA-PNA50S-K4. Data are presented as percent injected dose per organ (% ID/organ). Error bars are representative of one standard deviation from the mean of three living animals.

FIG. 33(A) (top): $^{64}$Cu-DOTA-PNA50-K4; FIG. 33(B) (bottom): $^{64}$Cu-DOTA-PNA50S-K4. Data are presented as percent injected dose per organ (% ID/organ). Error bars are representative of one standard deviation from the mean of three living animals.

FIG. 34(a) $^{64}$Cu-DOTA-PNA50-K4 (injection dose:

210 μCi); FIG. 34(b) $^{64}$Cu-DOTA-PNA50S-K4 (injection dose: 347 μCi); FIG. 34(c) $^{64}$Cu-DOTA-PNA5-K4 (injection dose: 253 μCi); and FIG. 34(d) $^{64}$Cu-DOTA-PNA7-K4 (injection dose: 361 μCi). The intensity of the images was decay-corrected and normalized to the injection dose.

DETAILED DESCRIPTION OF THE DISCOVERY

Figure 1:
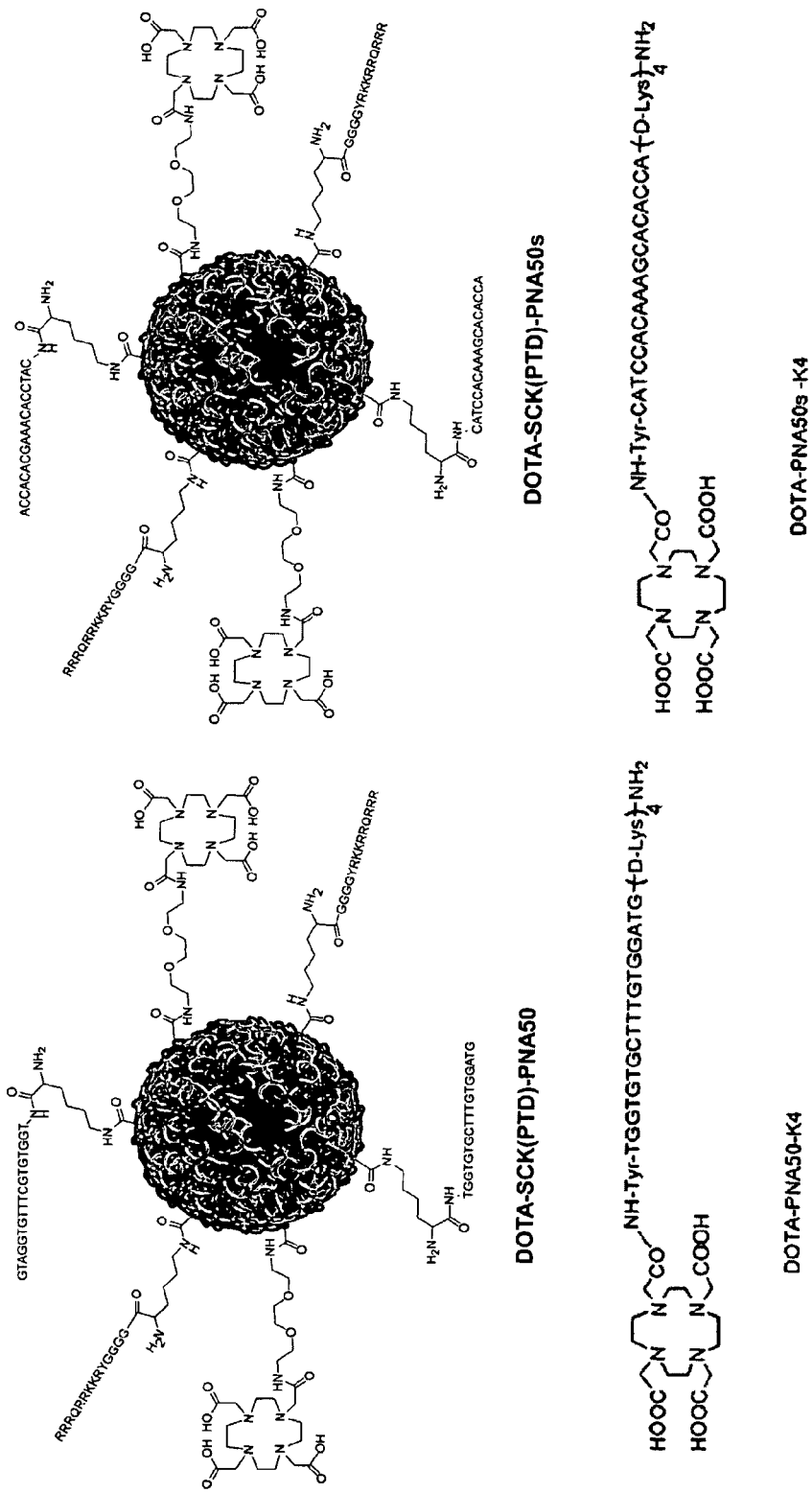
FIG. 1 is a schematic depicting some aspects of the invention: the particle-based unr mRNA targeting moiety DOTA-SCK(PTD)-PNA50 and non-targeting control DOTA-SCK (PTD)-PNA50S, and the unr mRNA targeting moiety DOTA-PNA50-K4 and non-targeting control DOTA-PNA50S-K4

This discovery provides new beneficial therapeutic nanoparticle conjugates and their use as molecular probes for the early stage detection of cancer and/or as therapeutic agents for the treatment of cancer. More in particular this discovery provides a unique targeting ligand optionally associated with biomedical nanoparticles which is useful in a medical diagnostic method to diagnose cancer or in a therapeutic method to treat cancer in a living mammal such as cancer in a living human.

This discovery provides an enhanced functional delivery system and process for effectively delivering particle conjugates into cells as effective cell, gene therapy, drug therapy and radiotherapy to living mammals such as to living humans.

The inventors discovered cell permeable SCK-PNA nanoconjugates having as an intracellular targeting ligand a PNA or another nuclease resistant oligonucleotide analog that does not activate the degradation of the mRNA by RNase H, such as MOE-mRNA or LNA, having a functional unr mRNA binding sequence such as PNA50 (see SEQ ID 3) or a sequence that binds selectively to a unique or overexpressed marker mRNA specific to the cancer or disease state. The inventors have shown utility here in that their nanoconjugates with PNA50 concentrate in MCF-7 cells in vitro and in a mouse xenograft. The uniquely or overexpressed mRNA is referred to herein as a recognition element.

SCK nanoparticles are especially useful in this discovery in that SCK nanoparticles provide high valency and functionality for highly functionally capable association with chelators and chemotherapeutic drugs, cytotoxic drugs and prodrugs. The increased valency is highly desired in that an increased number of functionalities can be advantageously capably attached to or associated with the nanoparticles thereby providing increased efficacy to the conjugated nanoparticles.

SCK nanoparticles useful herein include, but are not limited to, self-assemblying micellar assemblies of amphiphilic copolymers that have been stabilized through the incorporation of covalent cross-links in the shell layer. More particularly the particles comprise amphiphilic copolymers, having a cross linked shell domain and an interior core domain. Also provided are compositions comprising such particles including pharmaceutical compositions, methods of making the present particles and methods of using such particles for example for effective delivery of pharmaceutically active agents. In an aspect a useful particle includes a particle comprising an amphiphilic copolymer and having a core and a crosslinked shell which differs from the core in hydrophilicity and hydrophobicity, the shell comprising a region of the copolymer which differs in hydrophilicity and hydrophobicity from another region of the copolymer in the core, the copolymer being cross linked in the region within the shell, the copolymer region in the shell having a degree of crosslinking ranging from about 1% to about 80%, the copolymer being selected from among amphiphilic copolymers physically conducive to forming micelles prior to crosslinking. In an aspect an illustrative useful multifunctional nanodevice platform comprises the platforms disclosed in U.S. Pat. No. 6,471,968 which issued to Baker, Jr., et al on Oct. 29, 2002 and particles disclosed in U.S. Pat. No. 6,383,500 which issued to Karen L. Wooley et al On May 7, 2002. U.S. Pat. No. 6,471,968 and U.S. Pat. No. 6,383,500 are incorporated herein in their entirety by reference.

As used herein the term "SCK" means shell crosslinked knedel shell crosslinked nanoparticle.

As used herein, the term "nanodevice" refers to and includes, but is not limited to, small (e.g., invisible to the unaided human eye) compositions containing or associated with one or more useful "agents." In its simplest form, the nanodevice comprises a physical composition such as a nanoparticle or a dendrimer associated with at least one agent that provides biological functionality (e.g., a radionuclide or a therapeutic agent).

In an aspect, a useful permeation peptide is the transduction domain of the HIV-1 TAT protein which is used to capably enable cell membrane transduction. (Seq. Id. 1)

As used herein the term "PTD" means Protein Transduction Domain and indicates the HIV-1 TAT protein transduction domain (Seq. Id. No. 1)

In another aspect, a useful permeation peptide is the nuclear localizing sequence, herein referred to as "NLS" (Seq. KPKKKRKV), or the Lys4 tetrapeptide, which are used to capably enable cell membrane transduction of attached molecules or nanodevices.

Without being bound by theory these permeation peptide(s) are believed to capably and effectively enable reversible intracellular mobility/translocation of attached molecules and naodevices and advantageously thereby allow useful cell targeting of molecules or nanodevices through binding to intracellular targets such as mRNA or other cell receptors, such as intracellular cytostolic proteins or membrane receptors, thereby increasing the numbers of cancer or disease-specific receptors.

In an aspect, the nanodevice is targeted to that target mRNA which is uniquely expressed or is significantly overexpressed in a living mammal afflicted with a disease such that the unique expression or significantly overexpression is significantly indicative of the presence of a disease or disease state in that living mammal having that unique or over expression of mRNA. Without being bound by theory, this enhanced targeting availability is believed to provide an enhanced method and system for the diagnosis and detection of cancer. Such targeting of a diseased cell is effected by an antisense PNA or other nucleic acid analog on the nanoconjugate that is complementary to a unique or overexpressed mRNA sequence that is unique to the diseased cancer cell in the living mammal. By complementary it is meant that the PNA or analog has a sequence that can recognize and bind to the mRNA which is associated with a disease by Watson Crick base pairing. Alternatively the targeting is effected by the PNA or other nucleic acid analog acting in a stand alone capacity. In an aspect the living mammal is a living human.

As used herein, the phrase " . . . does not activate the degradation of the mRNA by RNase H . . . " is meant that the moiety "avoids mRNA degradation by RNase H" and the mRNA remains significantly viable and functional.

In some aspects of the present discovery, the living human is suspected of having cancer and a diagnosis is desired to confirm that, or in some aspects the presence of cancer is confirmed and a therapeutic treatment is desired.

In some aspects the cancer includes, but is not limited to, lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningioma, liver, spleen, lymph node, small intestine, colon, stomach, thyroid, endometrium, prostate, skin, esophagus, and bone marrow cancer. In some embodiments, compositions comprising nanodevices, and any other desired components (e.g., pharmaceutically acceptable carriers, adjuvants and excipients) are administered to the subject. The present discovery is not limited by the route of administration. Such efficacious administration routes include, but are not limited to, endoscopic, intratracheal, intralesion, percutaneous, intravenous, subcutaneous, and intratumoral administration.

Briefly, as is described herein, the inventors synthesized PNAs by using automated Fmoc solid phase synthesis on an ABI 8909 synthesizer using commercially available PNA and amino acid monomers and tri-tert-butyl-DOTA. PNA50 (see SEQ ID 3) is a sequence that is complementary to (i.e., antisense), and shows high affinity ($K_D$ 20 pM) for site 2828-2845 of the unr mRNA (GI: 20070240) that is overexpressed in MCF-7 breast cancer cell line, as discovered by the inventors by a reverse transcriptase random oligodeoxynucleotide library assay (RT-ROL).

PNA50S (see SEQ ID 4) is the sense sequence (has the same sequence as site 2828-2845) and is not complementary and shows little affinity ($K_D$>10,000 pM) for the unr mRNA. The mRNA-recognition element is not limited to PNA, but in an aspect is a nuclease resistant oligonucleotide analog such as MOE-mRNA or LNA. In an aspect the mRNA-recognition element is MOE-mRNA. In an aspect the mRNA recognition element is LNA.

Bifunctional chelators ("BFC") used to prepare new bioconjugates labeled with radionuclides of 2+ and 3+metals include functional derivatives of 1,4,7,10-tetraazacyclododecane-1,4,7,10-tetraacetic acid (DOTA, CAS Reg # 60239-18-1), 1,4,8,11-tetraazacyclotetradecane-1,4,8,11-tetraacetic acid (TETA, CAS Reg # 339091-75-7), diethylenetriaminepentaacetic acid (DTPA, CAS Reg # 67-43-6), wherein CAS means Chemical Abstracts Service.

The aforementioned three BFCs (herein after respectively DOTA, TETA, and DTPA) are commercially available from Macrocyclics Inc. (2110 Research Row, Suite 425, Dallas Tex. U.S.A.), Sigma-Aldrich Chemical Co. (3050 Spruce St., St. Louis Mo. U.S.A.), and/or Strem Chemicals, Inc. (7 Mulliken Way Newburyport Mass. U.S.A.). If desired, one of skill in the art can synthesize BFCs useful herein after reading this application.

In an aspect functional group(s) are effectively used for conjugation of radionuclides to SCK nanoparticles, including but not limited to carboxylic acid or amino groups. They are conjugated through multi-atom spacers (for example —$(CH_2)_n$—) to the nitrogen or carbon atoms of BFCs wherein n is an integer independently varying from 2 to about 10. In a further aspect, functional groups are useful for effective conjugation of a pharmaceutical agent such as a cytotoxic prodrug and radiopharmaceutical to the particle conjugate.

As to radionuclides, useful but not limiting radionuclides include 2+ and 3+ metal radioisotopes of biomedical interests (transition metals, lanthanides and actinides). The radionuclides may further extend to using radioiodine upon successful introduction of tyrosine or p-hydroxystyrene into the SCK.

The inventors provide data demonstrating the tumor-targeting (diagnostic) capability of a $^{64}$Cu-labeled SCK(PTD)-PNA nanoconjugate in MCF-7 tumor-bearing laboratory living mice as evidence of the credible, specific and general utility of this discovery.

The inventors synthesized and recovered (DOTA-SCK (PTD)-PNA50) and (DOTA-SCK(PTD)-PNA50S) as shown hereinafter. These nanoconjugates were each respectively recovered and purified as the titled respective material.

Nanoconjugate (DOTA-SCK(PTD)-PNA50) has a targeting sequence (PNA50) that is complementary (antisense) to the unr mRNA, which the inventors discovered is overexpressed in living MCF-7 breast cancer cells.

Nanoconjugate (DOTA-SCK(PTD)-PNA50S) has a control sequence (PNA50S) that is not complementary (sense). Both these nanoconjugates were respectively radiolabeled by the inventors with $^{64}$Cu, and were evaluated in a breast cancer mouse model (MCF-7 xenograft).

The inventors' data from that evaluation (of the aforementioned nanoconjugates) show that the MCF-7 tumor specificity of both nanoconjugates is about the same as the specificity of free respective DOTA-PNA50-K4 and DOTA-PNA50S-K4. Furthermore, compared to free PNAs and free SCKs, the SCK nanoconjugates surprisingly showed more optimal features (e.g., lower accumulation in the mice liver and kidneys) for either imaging by PET or therapy.

Advantageously the transduceable medical system of this discovery is capable of reversibly transducing peptides, proteins and synthetic constructs, which are not normally able to access intracellular components, across the cellular plasma membrane of living cells. This utility provides an enhanced technique available as a research tool.

As an aspect of the present discovery the inventors identified and selected the MCF-7 breast cancer cell line as a target cell line because the inventors discovered by analysis of SAGE libraries that that this breast cancer cell line possesses an overexpressed (10-fold) mRNA (unr) that is also very abundant (about 5,000 copies per cell). This invention is not limited to MCF-7 cells and unr mRNA as over-expressed or uniquely expressed mRNAs can be found in other cancer cells by analysis of SAGE libraries or by DNA chip analysis.

The inventors identified sequences in the folded unr mRNA that are tightly bound by a complementary PNA (in this instance PNA50) by a RT-ROL assay. These are targeted sequences.

The inventors confirmed tight binding of PNA50 (approx. 10 pM $K_D$) by a newly developed binding assay (Dynabead assay). The inventors confirmed that the sense sequence that is complementary to PNA50 (PNA50S) does not bind significantly.

The inventors confirmed binding to MCF-7 cells in cell culture by preparing and using fluorescently tagged PNA50 and PNA50S with attached NLS peptide sequence (F-PNA50x-NLS). X is either 50 or 50S.

The inventors confirmed selective targeting of MCF-7 tumor cells in mice by a $^{64}$Cu-tagged DOTA-PNA50x-K4, where DOTA binds the $^{64}$Cu, and K4 is four lysines for cell permeation. A selectivity of about 3:1 was observed for PNA50 as compared to PNA50S.

The inventors synthesized PNA50x-Lys for attachment to $^{64}$Cu-SCK-PTD and generated MCF-7 tumor detection device, which showed a selectivity level similar to that of free PNA. X is either 50 or 50S.

As used herein the singular forms "a", "an" and "the" include plural referents unless the context clearly dictates otherwise. As used herein, the term "unr mRNA" means mRNA deriving from the transcription of the unr gene, the transcription unit located immediately upstream of the N-ras gene in the genome of several mammalian species.

As used herein the therm "MOE-mRNA" means 2'-methoxyethyl mRNA which is a class of nucleic acid analogs complementary to the RNA template region and substituted in 2' position with a 2-methoxyethyl group.

As used herein the term "ODN" means oligodeoxynucleotide.

As used herein the term "cDNA" means complementary DNA which is DNA that is synthesized, by reverse transcriptase, from a mRNA template.

As used herein, the term "PNA" means Peptide Nucleic Acid which is a synthetic DNA mimic featuring a chain with repeating N-(2-aminoethyl) glycine units instead of the sugar-phosphate backbone. Commercial monomers used to synthesize PNAs are N-aminoethyl-N-(adenin-9-ylacetyl) glycine, herein referred to as "A" in PNA sequences, N-aminoethyl-N-(cytosin-1-ylacetyl)glycine, herein referred to as "C" in PNA sequences, N-aminoethyl-N-(guanin-9-ylacetyl) glycine, herein referred to as "G" in PNA sequences, and N-aminoethyl-N-(thymin-1-ylacetyl)glycine, herein referred to as "T" in PNA sequences.

Without being bound by theory, it is believed that PNA mimics the behavior of DNA and binds complementary nucleic acid strands and because of the neutral backbone of PNA results in stronger binding and greater specificity than normally achieved.

As used herein the term "PNA-K4" means a PNA-conjugate with four lysines at the C terminus.

As used herein the term "LNA" means Locked Nucleic Acid which is an RNA derivative in which the ribose ring is constrained by a methylene linkage between the 2'-oxygen and the 4'-carbon. LNA monomers are bicyclic compounds structurally similar to RNA nucleosides. In LNA the furanose ring conformation is restricted by a methylene linker that connects the 2'-O position to the 4'-C position. Thus nucleic acids containing one or more LNA modifications are referred to herein as LNA.

As used therein the term "RT-ROL assay" means Reverse Transcriptase Random Oligodeoxynucleotide Library assay. In this assay antisense binding sites are identified by the ability of a random 9-mer oligonucleotide library terminating a specific base and a PCR tag to prime complementary DNA synthesis by reverse transcriptase. The cDNA is then amplified by PCR with a radiolabeled primer having the same sense as the RNA, and an unlabelled primer having the same sequence as the PCR tag.

As used herein the term "PCR" means Polymerase Chain Reaction which is a technique to amplify a specific region of single or double-stranded DNA.

As used herein the term "RT-PCR" means Reverse Transcriptase Polymerase Chain Reaction (aka RNA phenotyping, RNA-PCR or message amplification phenotyping) which is a method for amplification of a specific mRNA by prior use of reverse transcriptase to form a cDNA, then use of PCR to amplify the cDNA.

As used herein the term "SAABS" means Serial Analysis of Antisense Binding Sites.

As used herein the terms "PET" and "SPECT" mean Positron Emission Tomography and Single Photon Emission Computed Tomography, respectively.

As used herein, microPET (microPET®, Concorde Microsystems Inc., Knoxville, Tenn. USA) is a non limiting example of small animal imaging devices with high resolution useful in detecting the invention in vivo. Other manufacturer also offers other small animal scanner, for example Mosaic® from Phillips.

The term "biologically active," as used herein, refers to a protein or other biologically active molecules (e.g., catalytic RNA) having structural, regulatory, or biochemical functions of a naturally occurring molecule.

The term "shell domain" means the outermost domain or peripheral layer of a particle of the present discovery. When produced in a hydrophilic continuous medium, the peripheral layer of the micelles giving rise to such particles (and the peripheral layer of the particles themselves) is substantially hydrophilic; when produced in a hydrophobic continuous medium, the peripheral layer of the micelles giving rise to such particles (and the peripheral layer of the particles themselves) is substantially hydrophobic.

The term "interior core domain" means the domain of a micelle or particle interior to the shell domain.

The term "amphiphilic copolymer" means a copolymer which contains at least one hydrophilic domain and at least one hydrophobic domain.

The term "block copolymer" means a linear polymer having regions or blocks along its backbone chain which are characterized by similar hydrophilicity, hydrophobicity, or chemistry. The term "diblock copolymer" means a block copolymer comprising two blocks. The term "triblock copolymer" means a block copolymer comprising three blocks. The term "multiblock copolymer" means a block copolymer comprising a plurality of blocks.

The term "aggregation number" means the average number of amphiphilic copolymer molecules per micelle or particle.

The term "glass transition temperature", herein referred to also with the symbol "$T_g$", means the temperature at which a polymer changes from a glassy, hard state to a flexible state.

The term "micelle" includes without limitation micelles having shapes of spheres, cylinders, discs, needles, cones, vesicles, globules, rods, elipsoids, and any other shape that a micelle can assume under the conditions described herein, or any other shape that can be adopted through aggregation of the amphiphilic copolymers.

The term "particle" means a particle and the largest domain of which is less than one micron includes, but is not limited to, nanoparticles. Dendrimer may be employed as particles herein. Their branching shape provides them with large surface area to which to attach therapeutic agents or other biologically active molecules. In an aspect one dendrimer is associated or carries a molecule that recognizes cancer cells, a therapeutic agent to kill those cells, and a molecule that recognizes the signals of cell death. The shape of the particles includes spheres, cylinders, discs, needles, cones, vesicles, globules, rods, elipsoids, and any other shape that a micelle can assume under the conditions described herein, or any other shape that can be adopted through aggregation of the amphiphilic copolymers.

The term "monomer" means a molecule which is capable of combining with a number of like or unlike molecules to form a polymer.

The term "isolated" with respect to a composition such as a protein that the material has been prepared and recovered in a state substantially free of any and all components which might be normally present with it in nature.

The term "pharmaceutically active agent" means any physiologically or pharmacologically active substance that produces a local or systemic effect in animals, including warm-blooded mammals, humans, and primates; avians; household, sport, and farm animals; laboratory animals; fishes; reptiles; and zoo animals. As used herein, the term "test compound" or "candidate" refers to any chemical entity, pharmaceutical, drug and the like that can possibly be used to treat or prevent a disease, illness, sickness or disorder of bodily function. Test compounds include both known and potential therapeutic compounds. A test compound can be determined to be therapeutic by screening using the screening methods and screening compositions of this discovery. A known therapeutic compound refers to a therapeutic compound that has been shown to be effective in such treatment or prevention.

The term "sample" as used herein is used in its broadest sense and includes environmental and biological samples. Biological samples include viable and representative samples including animal, including human, fluid (e.g., blood, plasma and serum), solid (e.g., stool), tissue, liquid foods (e.g., milk) and solid foods (e.g., vegetables).

The term "permeable" pertains to the property of a domain whereby selected atoms or molecules can pass through the domain.

As used herein, the term "peptide" is any of a group of compounds comprising two or more amino acids linked by chemical bonding between their respective carboxyl and amino groups. The term "peptide" includes peptides and proteins that are of sufficient length and composition to affect a biological response, e.g. antibody production or cytokine activity whether or not the peptide is a hapten. The term "peptide" includes modified amino acids, such modifications including, but not limited to, phosphorylation, glycosylation, pegylation, lipidization and methylation.

As used herein, the term "polypeptide" is any of a group of natural or synthetic polymers made up of amino acids chemically linked together such as peptides linked together. The term "polypeptide" includes peptides, proteins, translated nucleic acid and fragments thereof.

As used herein, the term "polynucleotide" includes nucleotide sequences and partial sequences, DNA, cDNA, RNA variant isoforms, splice variants, allelic variants and fragments thereof.

The terms "protein", "polypeptide" and "peptide" are used interchangeably herein when referring to a translated nucleic acid (e.g. a gene product).

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analogs any of which are in single or double stranded form. As used herein the phrase "The Expedite 8909 Nucleic Acid Synthesis System" includes the 8909 synthesis system as well as synthesis systems which effectively synthesize DNA and RNA oligonucleotides as well as peptide nucleic acids (PNA) The 8909 system synthesizes short primers and probes as well as sequences exceeding 100-mer in scales ranging from 50 nmol to 15 µmol. This is available from SCIENTIFIC INC., Suite 111, 2131 Pleasant, Hill Rd Duluth Ga. 30096.

As used herein the term "nuclease resistant oligonucleotides" includes oligonucleotides usefully modified to exhibit resistance to nucleases and to hybridize with appropriate strength and fidelity to its targeted mRNA. Useful nuclease resistant oligonucleotides include those having various 2'-substitutions have been introduced in the oligonucleotides. The nuclease resistance of these compounds has been increased by the introduction of 2'-substituents such as halo, alkoxy and allyloxy groups.

As used herein the term "oligonucleotide" refers to a plurality of nucleotides joined together in a specific sequence from naturally and non-naturally occurring nucleobases. Useful nucleobases inside these joined through a sugar moiety via phosphorus linkages, and include adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. Useful oligonucleotides comprise modified nucleobases or nucleobases having other modifications, and in particular modifications that increase their nuclease resistance.

As used herein, the terms "bifunctional chelator" or "BFC" refer to organic compounds containing two or more donor atoms spatially situated so as to form coordinate bonds with the same metal atom (first function) and a chemical group suitable for conjugation to a biologically active moiety (second function). Useful chelators include those which are "multidentate", which means they have multiple donor atoms available for simultaneous complexing with a suitable metal atom.

As used herein, the term "patient" and "subject" are synonymous and are used interchangeably herein and refer to living organisms.

As used herein, the term "expression" includes the biosynthesis of a product as an expression product from a gene such as the transcription of a structural gene into mRNA and the translation of mRNA into at least one peptide or at least one polypeptide.

As used here, the terms "isoforms" and "splice variant" includes alternative occurring forms of RNA transcribed from a genome as well as polypeptides encoded by a splice variant of mRNA transcribed from a gene.

As used herein, the term "therapeutic agent" is any molecule or atom which is conjugated, fused or otherwise affixed to a tumor targeting moiety to produce a conjugate which is useful for cancer therapy.

As used herein, the term "label" includes a detectable label which includes any radiolabeled species including $^{64}$Cu, fluorescent agents such as fluorescent proteins, and paramagnetic ions.

As used herein, the term "mammal" includes living mammals including living humans and living non-human animals such as murine, porcine, canine, rodentia and feline.

As used herein, the term "antisense" means a polynucleotide or analog whose sequence of bases is complementary to messenger RNA.

As used herein, the term "sense" means a polynucleotide or analog whose sequence of bases is identical to messenger RNA.

As used herein a "therapeutic amount" is an amount of drug or drug-conjugated moiety which produces a desired or detectable therapeutic effect on or in a mammal.

As used herein, the term "probe" includes DNA or RNA molecules of specific base sequence, labeled either radioactively or with a fluorophore, that are used to detect the complementary base sequence by hybridization.

As used herein pZero plasmid is used for a SAGE analysis from Invitrogen.

As used herein, the term "radiolabeled counterpart(s)" includes respective radiolabeled compounds.

As used herein, the term "detectably labeled" includes the respective radiolabeled compounds having an effective amount of an emitting radiolabel therewith and suitably accepting an emitting radiolabel for use in effective administration to living mammals.

As used herein, the symbol "Cu" means copper, "C" means carbon, "H" means hydrogen, "O" means oxygen, "N" means nitrogen, "Br" means bromine, "D" means deuterium, "Cl" means chlorine, "P" means phosphorous, "I" means iodine, "Na" means sodium, "Ar" means argon, "Kr" means krypton, "He" means helium, "Ne" means neon, "Ni" means nickel, "Li" means lithium.

As used herein in peptide sequences the codes "K" and "Lys" mean Lysine, "C" and "Cys" mean Cysteine, "Y" and "Tyr" mean Tyrosine, "P" and "Pro" mean Proline, "R" and "Arg" mean Arginine, "V" and "Val" mean Valine, "Q" and "Gln" mean Glutamine, "G" and "Gly" mean Glycine.

As used herein, the term "administration" includes the effective giving of a compound or moiety by any useful means to a living mammal and its successful introduction into the mammal such as in its gastrointestinal tract or in a blood lumen of the mammal in an effective method which results in that compound, its salt, its ions, metabolites or derivatives thereof being made biologically available to that mammal receiving administration of compound for medicinal use. In an aspect the mammal is a human. In an aspect the mammal is a nonhuman such as a rodent, a canine, or a feline. In an aspect the compound is made biologically available to the gastrointestinal tract of a living mammal patient.

As used herein, the expression "pharmaceutically acceptable" applies to a composition or its radiolabeled counterpart which contains composition ingredients that are compatible with other ingredients of the composition as well as physiologically acceptable to the recipient, e.g. a mammal such as a human, without the resulting production of excessive undesirable and unacceptable physiological effects or a deleterious impact on the mammal being administered the pharmaceutical composition. In an aspect, a composition for use comprises one or more carriers, useful excipients and/or diluents.

As used herein, the term "dosage" includes that amount of compound which, when effectively administered to a living mammal, provides an effective amount of biologically available compound to the living mammal.

As used herein the term "patient" includes a living human subject and a human individual. In an aspect the patient includes a human, and a living non-human such as feline, canine, horse and murine.

Particle based moieties useful in the polymer conjugates herein include those particles disclosed in U.S. Pat. No. 6,383,500 which issued to Karen L. Wooley et al. on May 7, 2002 (hereinafter the '500 patent) which is incorporated herein in its entirety by references. The particles of the '500 patent comprise amphiphilic copolymers and have a crosslinked shell domain, which can be permeable, and an interior core domain. Such particles can comprise a hydrophilic, crosslinked, permeable shell domain and a hydrophobic interior core domain. The amphiphilic copolymers of the particles can be crosslinked via functional groups within the hydrophilic shell domain, for example by condensation reactions, addition reactions, or chain polymerization reactions.

In an aspect of the present discovery, the hydrophobic interior core domain of the particles disclosed in the '500 patent can also be crosslinked via functional groups in their hydrophobic domains.

In an aspect of the present discovery, the particles disclosed in the '500 patent comprising amphiphilic copolymers having a crosslinked shell domain and an interior core domain comprise a hydrophobic, crosslinked shell domain, which is permeable, and a hydrophilic interior core domain. The amphiphilic copolymers of such particles can be crosslinked via functional groups within the hydrophobic shell domain, for example by condensation reactions, addition reactions, or chain polymerization reactions. In another embodiment of the present discovery, the hydrophilic interior core domain of such particles can also be crosslinked. In this case, the amphiphilic copolymers can be crosslinked via functional groups in their hydrophilic domains.

In an aspect, useful nanoparticles comprise an inner core and an outer coating. The particles are attached to a cancer targeting moiety that interact preferably with cancer calls. The particles are also affixed with a substance akin to a dye that makes them visible on magnetic resonance imagining or are labeled with an appropriate emitting ligand such as radioactive copper-64.

In yet another aspect, the particles of the present discovery comprise aliphatic copolymers, comprising an outermost crosslinked domain, which can be permeable, a series of additional crosslinked (permeable) domains, and a domain interior to each of the crosslinked (permeable) domains, producing an "onion-like" structure.

The inventors have discovered a method for identifying a mRNA for selective targeting and then identifying the PNAs that will bind to it.

In practicing this method, one first identifies the mRNA for targeting.

Basically one uses a SAGE or DNA chip to quantify gene expression in the target cell, compares the gene expression profile to all expression databases and identifies a sequence that is most differentially expressed and is in the highest amount or is uniquely expressed to identify an mRNA of interest, obtains a clone containing the cDNA for the mRNA of interest and produces the mRNA in vitro by RNA polymerase, maps accessible sites by either the modified RT-ROL assay and/or SAABS assay, screens potential ODNs by the Dynabead dot blot assay, quantifies the binding of ODNs by the Dynabead direct binding assay with $^{32}$P-labeled ODN, synthesizes and recovers Cys-Tyr-PNA-Lys4 corresponding to the tightest binding ODNs (or with another permeation peptide in place of Lys4)

quantifies binding of the hybrid PNAs by the Dynabead direct binding assay with radioiodinated PNA, conjoins the highest affinity PNAs to fluorescein and DOTA for fluorescence assays of cell binding in vitro or in vivo (mouse xenograft) and conjoins PNAs with the highest affinity to SCK nanoparticles through an appended lysine or other suitable accommodating site-specific coupling moiety.

As used herein the term "SAGE" means Serial Analysis of Gene Expression which is a method to efficiently count large numbers of mRNA transcripts by sequencing short tags.

Radionuclides:

In an aspect, a diagnostic imaging composition is provided comprising a polymer conjugate, a chelator and a radionuclide. Typically a chelator is employed to functionally and capably associate a radionuclide with the polymer conjugate. The radionuclide may be conjugated with the polymer or with the PNA alone.

For example, a radioisotope can be appended to the polymer conjugate using techniques known in the art, for example, techniques analogous to those described in Lewis et al. (Bioconjug Chem 2001, 12:320-324) and in Liu et al. (Bioconjug Chem 1997, 8:621-636).

The polymer conjugate can be conjugated with a chelating group which is then labeled with a radionuclide, such as a metallic radioisotope. Such chelating groups are well known in the art and include polycarboxylic acids such as for example ethylenediaminetetraacetic acid (EDTA, CAS Reg # 60-00-4), derivatives of 1,4,7,10-tetraazacyclododecane-1,4,7,10-tetraacetic acid (DOTA, CAS Reg # 60239-18-1), 1,4,8,11-Tetraazacyclotetradecane-1,4,8,11-tetraacetic acid (TETA, CAS Reg # 339091-75-7), diethylenetriaminepentaacetic acid (DTPA, CAS Reg # 67-43-6) and the cross-bridged CB-TE2A. and the like, or analogs or homologs thereof, as well as the chelating groups disclosed in Anderson and Welch (Chem Rev. 99: 2219-2234, 1999) and Jurisson and Lydon (Chem. Rev. 99: 2205-2218, 1999).

A chelating group for the radionuclide therein may be attached directly to the polymer conjugate by means of a divalent or bifunctional organic linker group. Such bifunctional linker groups are well known in the art and are preferably less than about 50 angstroms in length. Illustrative, non-limiting examples of useful suitable linker groups include 2-carboxymethyl, 3-carboxypropyl, 4-carboxybutyl, and the like.

A bifunctional chelator is of value in this discovery in this aspect. As used herein, the term "bifunctional chelator" refers to any organic compound containing two or more donor atoms spatially situated so as to form coordinate bonds with the same metal atom (first functionality) and a functional group suitable for the conjugation to the targeting moiety (second functionality). Useful chelators are those which are "multidentate", which means they have multiple donor atoms available for simultaneous complexing with a metal atom. If desired, one or more bifunctional chelators may be employed.

For diagnostic applications herein, acyclic bifunctional chelators may be satisfactory. For therapy type applications herein macrocyclic bifunctionals are better suited.

In an aspect, a radioactive metal ion, such as $^{64}Cu^{2+}$, is attached to a polymer conjugate via a bifunctional chelator, the latter functioning as a metal coordinating bifunctional chelator. In an aspect the radioactive metal ion is said to be associated with the polymer conjugate and the metal coordinating bifunctional chelator produces that association.

Without being bound by theory, the purpose of the bifunctional chelator, is to maintain a stable complex with the radioactive metal ion to produce a high-contrast image and, for radiotherapy, to prevent leakage spread of radioactivity into healthy (non-target) organs and tissues throughout the living mammalian body.

The emissions from the radioactive metal allow both 3-D visualization of tumors through PET, SPECT, and microPET, and therapy of tumors due to specific delivery of a cytotoxic radiation dose to tumor cells.

The reactions between the chelator, the polymer conjugate, and the detectable radionuclide are carried out using known methods, and preferably are performed at a pH at which the polymer conjugate is stable and under condition effective to enable the efficient carrying out of the reactions. Illustratively in a method, a complex is formed between the chelator and a detectable radionuclide prior to coupling with the polymer conjugate. In another method, a chelator is complexed first with a non-detectable metal ion and then with the polymer conjugate. The non-detectable metal ion may subsequently be replaced by the desired detectable element via a transmetallation process. It is understood that all reactions and synthesis conditions employed herein are those which suitably accommodate the desired reaction and synthesis and allow it to satisfactorily progress to its desired completion.

With respect to radionuclides, PET (including microPET) and SPECT are useful non-invasive molecular diagnostic imaging (standard) procedures that produce (i.e., capture and optionally record) multiple acquisitions i.e. images of the body's biological functions and in an aspect are used to determine the extent of malignant disease. In an aspect, these imaging procedures show the presence and distribution of a radiolabeled detectable functionally emitting chemical associated with the polymer conjugate acquired at various selected times. Advantageously these imaging procedures depict metabolic characteristics of tissues and changes therein.

A "detectable element" as used herein is defined as any element, preferably a metal ion, which exhibits a property detectable in therapeutic or in vivo diagnostic techniques. For example, a nonlimiting example of a detectable element is a metal ion that emits detectable radiation or a metal ion that is capable of influencing NMR relaxation properties and that is capable of forming a conjugate or complex with the described nanoparticle moiety. Suitable detectable metal ions as used herein include, for example, heavy elements or rare earth ions such as the paramagnetic ions, $Gd^{3+}$, $Fe^{3+}$, $Mn^{2+}$ and $Cr^{2+}$. By way of example, a nonlimiting example of detectable element is a fluorescent metal ions, such as $Eu^{3+}$, and radionuclides, such as gamma-emitting radionuclides, beta-emitting radionuclides, and positron-emitting radionuclides.

Any radionuclide suitable for imaging or therapy can be employed to prepare a functional polymer conjugate. For example, suitable nonlimiting examples of useful radionuclides include: Actinium-$_{225}$, Astatine-$_{225}$, Bismuth-$_{212}$, Bismuth-$_{213}$, Bromine-$_{75}$, Bromine-$_{76}$, Carbon-$_{11}$, Cerium-$_{141}$, Chromium-$_{51}$, Copper-$_{60}$, Copper-$_{61}$, Copper-$_{62}$, Copper-64, Copper-$_{67}$, Dysprosium-$_{166}$, Fluorine-$_{18}$, Gadolinium-$_{152}$, Gadolinium-$153$, Gold-$195m$, Holmium-$166$, Indium-$111$, Indium-$110m$, Iodine-$123$, Iodine-$124$, Iodine-$131$, Iron-$55$, Iron-$59$, Lutetium-$177$, Nitrogen-$13$, Oxygen-$15$, Palladium-$103$, Radium-$224$, Rhenium-$186$, Rhenium-$188$, Rubidium-$81$, Rubidium-$82$, Rubidium-$86$, Ruthenium-$103$, Ruthenium-$106$, Samarium-$153$, Scandium-$46$, Tantalum-$178$, Technetium-$94m$, Technetium-$99m$, Thallium-$201$, Titanium-$45$, Ytterbium-$169$, Yttrium-$86$, Yttrium-$90$, and Zirconium-$89$.

In an aspect, positron emission tomography (PET) comprises detection of two gamma-rays deriving from annihilation of positrons emitted from radionuclides that decay by positron emission and are located within a mammalian patient's body.

A large number of scintillation detectors detect these photon pairs and measure the sum of radioactivity along many different paths through the patient undergoing measurement. Appropriate software associated with the instrument reconstructs a three-dimensional image of the patient and the concentrations of radionuclides can be expressed in quantitative units of radiotracer concentration per ml of tissue.

In an aspect, single photon emission computed tomography (SPECT) comprises detection of single gamma-rays emitted from radionuclides that decay by gamma emission and are located within a mammalian patient's body.

SPECT imaging comprises external measurement of the single photon emitted anisotropically by a radioactive compound labeled with gamma-emitting radionuclides. Photons are selected by a collimator. Generally collimators for SPECT imaging are lead and comprise thousands of various shaped parallel channels through which—and only through which—gamma rays are allowed to pass. Generally such collimators are positioned over a single crystal of NaI contained in the Gamma camera in an arrangement referred to as an Anger camera. The image or acquisition from the camera is the captured image which is presented to a human operator as part of the image. In an aspect multi-acquisition is used. In an aspect a multi-acquisition is carried out over an elapsed time interval.

In an aspect a PET and/or a SPECT and/or microPET image is taken of a mammal after the satisfactory administration of a radionuclide of to the mammal.

In an aspect, images are taken over elapsed time in dynamic fashion to assemble a developing or developed scenario of situations in the mammalian patient.

Once a radiolabeled compound(s) is adequately administered to a patient, the emitting radioactivity travels through gastro-intestinal tract or through the vascular system of the body and localizes in the appropriate areas of the body (based on targeting) and is detected by PET or SPECT scanners.

Typically an adequate amount of time is allowed to pass for the treated living mammal to come to an equilibrium state following satisfactory administration of the radioligand to the mammal. Typically the mammal is placed in a position near the PET or SPECT or microPET instrument allowing satisfactory operation of the instrument. The PET, microPET, and SPECT instruments are equipped with all necessary operable software and operation requirements. They are turned on i.e. energized and made operable by supplying 100/220 volts electric power to the respective instruments.

Generally after a living mammal has received its administration of the radiolabeled moiety, the mammal is taken to an examination room that houses the scanner, which has an opening in the middle. In an aspect the mammal is moved into the hole of the machine. The images are displayed on the monitor of a computer, suitably equipped and operably coupled to the scanner instrument for acquiring.

In an aspect a copper radiolabeled material (compound(s)) is administered to a living mammal patient. In an aspect the radiolabeled emits a functional externally detectable amount of desired radioactivity in the mammal. In a medical aspect the amount of emitted radioactivity is an amount which imparts a diagnostic or therapeutic benefit to the mammalian patient having cancer. In an aspect a therapeutic benefit is that benefit which is medicinally and therapeutically beneficial to the living mammalian afflicted with cancer. In an aspect a cytotoxic amount is an effective lethal amount of a therapeutic compound which beneficially kills or retards cancer cells.

Useful radiochemical methods are found in the textbook Welch M J, Redvanly C S, Handbook of Radiopharmaceuticals: Radiochemistry and Applications, Chichester: Wiley, 2003.

In an aspect a copper radiolabeled material is effectively administered to a mammal or to a biological sample thereof or there from and the sample is analyzed and a diagnosis is made or obtained. In an aspect, a biological sample of the mammal comprises a representative sample taken of at least one of blood, vessels, atheroma, liver, and other body tissues a well as biopsies of body organs such as a liver biopsy or a muscle biopsy of a living mammal. In an aspect, the amount of biological sample is that amount or volume which is sufficient to provide for an effective and discerning analysis.

In an aspect a mammal host is selected from at least one of a living human and non human animal such as canine, feline, equestrian, murine including dogs, cats, rabbits, guinea pigs, hamsters, mice, rats, rodents, horses, goats, sheep, pigs and cows. In an aspect the mammal host is a living patient.

In an aspect, depending on its form, the administered formulation is suitably formulated for ease of facilitation of administration and use by the mammal patient and may contain a binder, disintegrating agent, lubricant, sweetener, a liquid carrier.

In an aspect, a copper radiolabeled compound is administered to a mammal as a pharmacologically acceptable composition. Pharmacologically acceptable compositions such as solutions of a labeled compound or its salts can be prepared in water, optionally mixed with a nontoxic surfactant.

In an aspect, the amount of time elapsing between imaging procedures is a sufficient time which provides for a useful and meaningful comparison of acquired images.

Accordingly, the discovery includes a pharmaceutical composition comprising a labeled compound as described hereinabove; or a pharmaceutically acceptable salt thereof; and a pharmaceutically acceptable diluent or carrier.

In an aspect a therapeutic rate titration is performed wherein the living mammalian afflicted with cancer is administered a series of dosages and respective effects therefrom or thereafter are determined at respective dosages and times by methods known to those in the pharmacology art. In this manner a therapeutic dosage curve or titration is obtained for determining dosage for that mammal patient.

Administration may be performed by any effective local or systemic application as appropriate. Administration of compositions may be done by inhalation, orally, rectally or parenterally, such as by intramuscular, subcutaneous, intraarticular, intracranial, intradermal, intraocular, intraperitoneal, intrathecal and intravenous injection.

In an aspect, an internal radiation cancer therapy useful on living mammals comprises administering anti-cancer compounds synthetically labeled with $^{64}$Cu to such living mammals. In an aspect, a treatment of malignant neoplasms in living mammals (human and nonhuman) comprises administering anti-cancer compounds labeled with $^{64}$Cu.

In an aspect, a method for pharmacologically treating a mammalian tumor in a mammal comprises administering to a mammal having a tumor a composition including a tumor-inhibiting amount of at least one $^{64}$Cu labeled compound. In an aspect the living mammal is nonhuman.

In an aspect, a method for in vivo detection of cancer cell(s) in living mammalian tissue samples comprises contacting a mammalian tissue sample with an in vivo effective diagnostic imaging amount of at least one $^{64}$Cu labeled compound for a time and under conditions sufficient and effective for binding of labeled compound to the cancer cell(s) and detecting such binding indicative of an association with the presence and location of cancer in the contacted cell(s). In an aspect the detecting is by image acquisition. In an aspect the $^{64}$Cu labeled compound is a tracer for cancer. In an aspect, the cell(s) is in a previously obtained biological sample from a mammal. In an aspect such binding is indicative of the presence of and location of a cancer cell. In an aspect, the mammal is a living human and the radionuclide is $^{60}$Cu, $^{61}$Cu or $^{64}$Cu. In an aspect the living mammal is a nonhuman mammal. In an aspect the extent of binding is determined by comparing the amount of radioactivity administered to the animal with the amount of radioactivity and location of radioactivity detected by image acquisition.

In an aspect, a method for determining progression or regression of a cancer in a living mammal comprises administering to a living mammal a diagnostic imaging detectable amount of at least one highly purified $^{64}$Cu labeled compound at a first selected time, detecting an image of a cancer tissue in the mammal being treated at a second selected (later) time respectively detecting an image of a cancer tissue at both times, comparing the images and determining if the detected cancer tissue in the image at the later time is bigger or smaller than the detected cancer tissue in the image at the first time. In an aspect the elapsed time between the first time and second time is selected to be a time duration significant amount. In an aspect the living mammal is nonhuman. In an aspect the comparison is used to determine progression or regression of a cancer in a mammal.

Pharmaceutical Compositions

In an aspect a pharmaceutical composition comprises a particle conjugate and a pharmaceutical agent or a PNA and a pharmaceutical agent. In an aspect the pharmaceutical agent comprises at least one of a cancer drug, a prodrug or a radionuclide.

The particle conjugate further comprises a nano-scale particle based moiety having associated therewith a permeation peptide (e.g., the HIV-1 TAT protein transduction domain) and a nucleic acid analog capable of binding to a complementary disease specific mRNA sequence, wherein use of the nucleic acid analog does not lead to the destruction of the disease specific mRNA sequence, wherein particles comprise amphiphilic copolymers having a crosslinked shell domain, which can be permeable, and an interior core domain, or a pharmaceutically acceptable salt thereof, and a pharmaceutically acceptable carrier, excipient, or diluent.

The pharmaceutically active agent can be contained within the particle or conjugated to it. The pharmaceutically active agent can be present in the particle dissolved in the crosslinked shell domain (which can be permeable), or covalently attached to a component of the crosslinked shell domain, or in the form of a fine dispersion within the crosslinked shell domain, or on the surface of the crosslinked shell domain.

Alternatively, the pharmaceutically active agent can be present in the particle dissolved in the interior core domain, or covalently attached to a component of the interior core domain, in the form of a fine dispersion within the interior core domain, or on the surface of the interior core domain, or at the interface between the crosslinked shell domain and the interior core domain.

The pharmaceutically active agent can also be present both in the crosslinked shell domain and in the interior core domain, or covalently attached to components of each domain, or in the form of a fine dispersion within each domain, or on the surface of each domain.

The pharmaceutically active agent can be introduced to the polymer conjugate in a variety of different ways. For example, in the process of forming particles of the present discovery, the pharmaceutically active agent can be present in the solvent system employed to form the micelles that are the precursors to the particles of the discovery. Upon formation of the particles, the pharmaceutically active agent is entrapped therein. Alternatively, pre-formed particles can be suspended in a solvent containing the active agent, and thus take up the pharmaceutically active agent from solution. In addition, the pharmaceutically active agent can be sprayed in the form of a solution or a melt onto the surface of the pre-formed particles. In another example, the pre-formed particles can be treated with a vapor containing the pharmaceutically active agent. The pharmaceutically active agent can also be vacuum infiltrated into the pre-formed particles.

The pharmaceutically active agent can be associated with or affixed to the amphiphilic copolymers which comprise the particles of this discovery either chemically or physically. The association or affixing can be performed either prior to the preparation of the particles or after the preparation of the particles.

When present in polymer conjugate of the present discovery as described above, the pharmaceutically active agent can be released there from. It is fully expected that such release can be sustained, i.e. not immediate, but rather over an extended period of time, thereby making particles of the present discovery containing pharmaceutically (or other active) agents useful as sustained release delivery vehicles.

Pharmaceutically Active Agents

Nonlimiting examples of useful pharmaceutically active agents that can be used with these polymer conjugates include inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, alimentary and excretory systems, inhibitory of autocoids and histamine systems. The active drugs that can be delivered for the purpose of acting on these recipients include anticonvulsants, analgesics, anti-inflammatories, calcium antagonists, anesthetics, antimicrobials, antimalarials, antiparasitics, antihypertensives, antihistamines, antipyretics, alpha-andrenergic agonist, alpha-blockers, anti-tumor compounds, biocides, bactericides, bronchial dilators, beta-andrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Nonlimiting examples of useful pharmaceutically active agents that are highly soluble in water and that can be used in conjunction with the particles of the present discovery include prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary pharmaceutically active agents that are poorly soluble in water and that can be used in conjunction with the particles of the present discovery include diphenidol, meclizine hydrochloride, prochlorperazine maleate, phenoxybenzamine, thiethylperazine maleate, anisindone, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, sterogenic, progestational, corticosteroids, hydrocortisone hydrocorticosterone acetate, cortisone acetate, triamcinolone, methyltestosterone, 17 beta-estradiol, ethinyl estradiol, ethinyl estradiol 3-methyl ether, prednisolone, 17 beta-hydroxyprogesterone acetate, 19-nor-progesterone, norgestrel, morethindrone, norethisterone, norethiederone, progesterone, norgesterone, norethynodrel, and the like.

Examples of other pharmaceutically active agents that can be used in conjunction with the particles of the present discovery include aspirin, boron-containing antitumor compounds, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chloropromazine, methyldopa, dihydroxyphenylalanine, pivaloyloxyethyl ester of alpha-methyl dopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, quanabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, famotidine, nizatidine, sucralfate, etinidine, tertatolol, minoxidil, chlordiazepoxide, chlordiazepoxide hydrochloride, diazepan, amitriptylin hydrochloride, imipramine hydrochloride, imipramine pamoate, enitabas, verapamil, losartan, and the like. Other beneficial pharmaceutically active agents known in the art that can be used in conjunction with the particles of the present discovery are disclosed in Pharmaceutical Sciences, 14th Ed., edited by Remington, (1979) published by Mack Publishing Co., Easton Pa.; The Drug, The Nurse, The Patient, Including Current Drug Handbook, by Falconer, et al., (1974-1976) published by Saunders Company, Philadelphia, Pa.; Medicinal Chemistry, 3rd Ed., Vol. 1 and 2, by Burger, published by Wiley-Interscience, New York; Goodman & Gilman's The Pharmacological Basis of Therapeutics, 9th Ed., edited by Hardman, et al., (1996) published by McGraw-Hill, New York, N.Y.; and in Physicians' Desk Reference, 51st Ed., (1997) published by Medical Economics Co., Montvale, N.J.

Prodrugs

Prodrugs are useful in pharmaceutical compositions of this discovery and in an aspect such drugs may be conjugated to the polymer conjugate. Prodrugs are pharmacologically inactive derivatives of active drugs. Prodrugs are designed to maximize the amount of active drug that reaches its respective effective site of action through manipulation of the physicochemical, biopharmaceutical or pharmacokinetic properties of the drug. Prodrugs are capably converted into the pharmaceutically active drug within the body through enzymatic or non-enzymatic reactions after the prodrugs are administered to the patient.

In an aspect, a useful drug has cytotoxicity greater than that of the prodrug. Typically, the prodrug has an enzyme cleavable covalent link between a drug and a chemical moiety associated therewith although some useful moieties of prodrug include the salt form (such as water soluble form) of an active drug molecule. Typically a partly or essentially water soluble salt form would be employed, including those moieties wherein there is a covalent link between a drug and chemical moiety and includes salts of the prodrug such as those which are moderately or highly water soluble such as alkali metals, ammonium and amine salts and alkaline earth metal salts.

Nonlimiting examples of useful prodrugs include 5-(aziridine-1-yl)-2,4-nitrobenzamide, peptidyl-p-phenylenediamine-mustard, benzoic acid mustard glutamates, 6-methoxypurine arabinonucleoside, 5-fluorocytosine, glucose, hypoxanithine, methotrexate-alane, N-(94-(-D-galactopyranosyl), benzyloxycarbonyl)-daunorubicine, amygdalin, azobenzene mustards, gamma-glutamyl-p-phenylenediamine mustard, phenolmustard-glucuronide, epirubicin-glucuronide, vinca-cephalosporin, nitrogen-mustard-cephalosporin, phenolmustard phosphate, doxorubicine phosphate, mitomycin phosphate, etoposide phosphate, palytoxin-4-hydroxyphenyl-acetamide, cyclophosphamide isofamide and 4-nitrobenzyloxycarbonyl derivatives.

Additional typical useful non-limiting drugs include 5-(aziridin-1-yl)-4-hydroxyl-amino-2-nitrobenzamide, phenylenediamine-mustard, ganciclovir triphosphate, adenine arabinonucleoside, triphosphate(araATP), 5-fluorouracid, hydrogen peroxide, superoxide, methotrexate, daunorubicin, cyanide, phenylendiamine mustards, phenyldiamine mustard, phenolmustard, epirubicin, 4-desacetylvinblastine-3-carboxyhydrazide, nitrogen mustards, doxorubicin, mitomycin alcohol, etoposide, palytoxin, melphalan, phosphoamide mustard (+acrolein), 5-(aziridin-1-yl)-4-hydroxylamino-2-nitrobenzamine, actinomycin D and mitomycin C.

Cancer Drugs (Cytotoxic)

Drugs cytotoxic to cancer are useful in pharmaceutical compositions of this discovery and in an aspect such drugs may be conjugated to the polymer conjugate or to the PNA.

Typical non-limiting examples of useful cytotoxic drugs include aldesleukin, alemtuzumab, alitretinoin, allopurinol, altretamine, amifostine, anastrozole, arsenic trioxide, BCG Live, bexarotene, bleomycin, calusterone, capecitabine, carboplatin, carmustine, celecoxib, chlorambucil, cisplatin, cladribine, cyclophosphamide, cytarabine, dacarbazine, dactinomycin, darbepoetin alfa, denileukin diftitox, dexrazoxane, docetaxel, doxorubicin, dromostanolone, Elliot's B solution, epirubicin, epoetin alfa, estramustine, etoposide phosphate, exemestane, filgrastim, floxuridine, fludarabine, fulvestrant, gemcitabine, gemtuzumab, goserelin acetate, hydroxyurea, ibritumomab tiuxetan, idarubicin, ifosfamide, imatinib mesylate, interferon alfa-2a, interferon alfa-2b, irinotecan, letrozole, leucovorin, levamisole, mechlorethamine, megestrol acetate, melphalan, L-PAM, mercaptopurine 6-MP, mesna, methotrexate, methoxsalen, mitomycin C, mitotane, mitoxantrone, androlone phenpropionate, nofetumomab, oprelvekin, oxaliplatin, paclitaxel, pamidronate, pegademase, pegaspargase, pegfilgrastim, entostatin, pipobroman, plicamycin, mithramycin, porfimer sodium, procarbazine, quinacrine, rasburicase, rituximab, sargramostim, streptozocin, talc, tamoxifen, trastuzumab, tretinoin, uracil mustard, valrubicin, vinblastine, tamoxifen, temozolomide, teniposide, testolactone, 6-thioguanine, thiotepa, topotecan, toremifene, tositumomab, vincristine, vinorelbine and zoledronate.

In another aspect, the present discovery provides a method for delivering a nucleic acid molecule to a cell, tissue, or organ, comprising contacting the cell, tissue, or organ, in vivo or in vitro, with a composition containing a polymer conjugate of the present discovery and a nucleic acid molecule for a period time sufficient to deliver the nucleic acid molecule to the cell, tissue, or organ. The nucleic acid molecule can, for example, be present on the surface of the particle, or within the particle. The nucleic acid molecule can be DNA or RNA for example, an antisense oligonucleotide, a vector, or any other type of nucleic acid molecule commonly employed in genetic engineering techniques Pharmaceutical Methods As noted above, polymer conjugates of the present discovery comprising a pharmaceutically active agent can be used for sustained release and delivery of such agents to treat a variety of conditions.

As used herein the term "pharmaceutically active agent" includes at least one of a prodrug, a cytotoxic drug or a radiopharmaceutical. Optionally if desired one may label prodrug, cytotoxic drug or both.

In one aspect, the present discovery provides a method of effectively delivering a pharmaceutical composition chemically or physically associated with the particles of the present discovery. The method comprises administering to the mammal a composition comprising the particles having associated therewith at least one of a permeation peptide (e.g., HIV-1 TAT protein transduction domain, see SEQ ID 1) and a PNA or another nuclease resistant oligonucleotide analog, such as MOE-mRNA or LNA, having a unr mRNA binding sequence such as PNA50 (see SEQ ID 3) or any sequence that binds selectively to an unique or overexpressed mRNA specific to the cancer or disease state.

In another aspect, the present discovery provides a method of delivering a pharmaceutically active agent to a cell, tissue, or organ, comprising contacting the cell, tissue, or organ with an effective amount of a polymer conjugate, the polymer conjugate comprising a particle based moiety having associated therewith at least one of a permeation peptide (e.g., the HIV-1 TAT protein transduction domain) and a PNA or another nuclease resistant oligonucleotide analog, such as MOE-mRNA or LNA, having unr mRNA binding sequence such as PNA50 (see SEQ ID 3) or any sequence that binds selectively to an unique or overexpressed mRNA specific to the cancer or disease state and a pharmaceutically active agent, the contact being for a period of time sufficient to introduce the pharmaceutically active agent to the locus of the cell, tissue, or organ. The method, for example, can comprise contacting the cell, tissue, or organ in vitro or in vivo with the effective amount of the particles.

As to dosages, formulations, and routes of administration for the prophylaxis or treatment of the conditions referred to above, the particles of the present discovery can be used as particles per se. Pharmaceutically acceptable salts are particularly suitable for medical applications because of their greater aqueous solubility and physiological compatibility relative to the parent particle. Such salts must clearly have pharmaceutically acceptable anions or cations. Suitable pharmaceutically acceptable acid addition salts of the particles of the present discovery when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, lactic, lactobionic, maleic, malic, methanesulfonic, succinic, toluenesulfonic, tartaric, and trifluoroacetic acids. The chloride salt is particularly preferred for medical purposes. Suitable pharmaceutically acceptable base salts include ammonium salts, alkaline metal salts such as sodium and potassium salts, and alkaline earth salts such as magnesium and calcium salts.

The polymer conjugates of the present discovery can be effectively and sufficiently administered to a living mammal with an acceptable carrier in the form of a pharmaceutical composition. The carrier must, of course, be acceptable in the sense of being compatible with the other ingredients of the composition and must not be deleterious to the recipient. The carrier can be a solid or a liquid or both, and is preferably formulated with the particle as a unit-dose composition, for example a powder or tablet, which can contain from 0.05% to 95% by weight of the active particles. Other pharmacologically active substances can also be present, including other particles of the present discovery. The pharmaceutical compositions of the discovery can be prepared by any of the well known techniques of pharmacy, consisting essentially of admixing the components together.

In an aspect, a living patient such as a living mammal such as a living human is treated for cancer according to this discovery. In that situation a pharmaceutically useful moiety is administered to the patient in a "therapeutically effective amount".

In an aspect pharmaceutical compositions for use herein include in addition to active ingredient, such as a prodrug, cytotoxic drug or radiopharmaceutical, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

These pharmaceutical compositions may be administered by any conventional means available for administering pharmaceutical compositions to living mammals.

The amount of pharmaceutical composition required to achieve the desired biological effect will, of course, depend on a number of factors such as the specific particle or agent chosen, the use for which it is intended, the mode of administration, and the clinical condition of the recipient.

In general, an effective daily pharmaceutical composition dose can be in the range of from about 5 to about 5,000 mg/kg of bodyweight/day, preferably from about 10 to about 2,000 mg/kg bodyweight/day, more preferably from about 20 to about 1,000 mg/kg bodyweight/day. This total daily dose can be administered to the patient in a single dose, or in proportionate multiple subdoses. Subdoses can be administered 2 to 6 times per day. If desired, doses can be in sustained release form effective to obtain the desired results.

Orally administrable unit dose formulations, such as liquids, tablets, or capsules, can contain, for example, from about 1 to about 5,000 mg of the particles, preferably about 2 to about 2,000 mg of the particles, more preferably from about 10 to about 1,000 mg of the particles. In the case of pharmaceutically acceptable salts, the weights indicated above refer to the weight of the particle ion derived from the salt.

Oral delivery of particles of the present discovery can include formulations, as are well known in the art, to provide prolonged or sustained delivery of the particles to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the particles from the dosage form. The intended effect is to extend the time period over which the active particles are delivered to the site of action (the gastrointestinal tract) by manipulation of the dosage form. Thus, enteric-coated and enteric-coated controlled release formulations are within the scope of the present discovery. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions according to the present discovery include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular particle which is being used. In most cases, the preferred route of administration is oral.

Pharmaceutical compositions suitable for oral administration can be presented in discrete units, such as liquids, capsules, cachets, lozenges, or tablets, each containing a predetermined amount of at least one type of particle of the present discovery; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active particle(s) and the carrier (which can constitute one or more accessory ingredients). In general, the compositions are prepared by uniformly and intimately admixing the active particles with a liquid or finely divided solid carrier, or both, and then, if necessary, shaping the product. For example, a tablet can be prepared by compressing or molding a powder or granules containing the particles, optionally with one or more assessory ingredients. Compressed tablets can be prepared by compressing, in a suitable machine, the particles in a free-flowing form, such as a powder or granules optionally mixed with a binder, lubricant, inert diluent and/or surface active/dispersing agent(s). Molded tablets can be made by molding, in a suitable machine, the powdered particles moistened with an inert liquid diluent.

Pharmaceutical compositions suitable for buccal (sub-lingual) administration include lozenges comprising particles of the present discovery in a flavored base, usually sucrose, and acacia or tragacanth, and pastilles comprising particles in an inert base such as gelatin and glycerin or sucrose and acacia.

Pharmaceutical compositions suitable for parenteral administration conveniently comprise sterile aqueous preparations of particles of the present discovery. These preparations are preferably administered intravenously, although administration can also be effected by means of subcutaneous, intramuscular, or intradermal injection. Such preparations can conveniently be prepared by admixing the particles with water and rendering the resulting solution sterile and isotonic with the blood. Injectable compositions according to the discovery will generally contain from 0.1 to 5% w/w of a particles disclosed herein.

Pharmaceutical compositions suitable for rectal administration are preferably presented as unit-dose suppositories. These can be prepared by admixing particles of the present discovery with one or more onventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active particle is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain particles of the present discovery in an optionally buffered, aqueous solution, dissolved and/or dispersed in an adhesive, or dispersed in a polymer. A suitable concentration of the active particle is about 1% to 35%, preferably about 3% to 15%. As one particular possibility, the particle can be delivered from the patch by electrotransport or iontophoresis, for example, as described in Pharmaceutical Research, 3(6), 318 (1986).

If desired, the amount of particles that can be combined with carrier materials to produce a single dosage form to be administered will vary depending upon the host treated and the particular mode of administration.

The solid dosage forms for oral administration including capsules, tablets, pills, powders, and granules noted above comprise one or more types of particle of the present discovery admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Injectable preparations, for example, sterile injectable aqueous or oleaginous suspensions can be formulated according to the known art using suitable dispersing or setting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Pharmaceutically acceptable carriers encompass all the foregoing and the like.

As those of ordinary skill in the art will recognize, after reading this specification the foregoing discussion is also applicable to the use of particles as described herein, wherein such particles comprise a pharmaceutically active agent intended to be self delivered to a site in the body.

Treatment Regimen

The dosage regimen to prevent, give relief from, or ameliorate a disease condition, is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular particle or particle/pharmaceutically active agent combination employed, whether a drug delivery system is utilized, and whether the particles are administered as part of a drug combination. Thus, the dosage regimen actually employed can vary widely and therefore deviate from the preferred dosage regimen illustratively set forth above.

Detectable Emitting Fluorescence Labeling

Various useful fluorescent compounds may be successfully employed to label the polymer nano-conjugate including using fluorescing moieties, such as green fluorescent proteins, organelle-specific dyes and ion indicators, or a combination of fluorescing markers (for example a fluorochrome with green emission light for one moiety and another fluorochrome with blue emission for a different moiety).

Fluorescent moieties such as proteins may be employed as a fluorescing marker if desired and would be visualized through a microscope with appropriate light source or quantified by exposing to a suitable light source and determining fluorescence by a spectrofluorometer.

In an aspect, the fluorescence signal from the probe is expressed directly as the emission of GFP or any other fluorescent protein attached to the probe when the fluorescent protein is excited at an appropriate wavelength of bombarded light. In an aspect, a functional immunoprobe produces a discernible, detectable and measurable fluorescence signal (or luminescence signal), an image (of captured fluorescence) which is competently reliably and accurately captured by visual inspection aided by a microscope or acquired by appropriate camera and computer software to be displayed visually on a computer monitor for a person for viewing. The intensity and duration of the fluorescence signal is detectable and is reproducible. The images of fluorescing cells may be projected on a monitor and compared to another image of a standard. A person can then visually compare such images and make a determination on whether there is a difference between the images compared.

As used herein the term "fluorescent protein" refers to any protein that is genetically encoded and expressed as a fusion with a wild type or mutant subunit type such that it emits a fluorescent signal that is detectable using appropriate methods when excited at the necessary wavelength of light.

As used herein, the term "GFP" refers to the Green Fluorescent Protein from *Aequorea victoria*.

In an aspect, useful nonlimiting illustrative fluorescent proteins include modified green fluorescent proteins including but not limited to those disclosed in U.S. Pat. No. 6,319,669 which issued to Roger Tsien on Nov. 20, 2001, Wavelength Engineering Fluorescent Proteins, Modified Green Fluorescent Proteins as disclosed in U.S. Pat. No. 5,625,048 which issued to Roger Tsien on Apr. 29, 1997 and Modified Green Fluorescent Proteins as disclosed in U.S. Pat. No. 5,777,079 which issued to Roger Tsien on Jul. 7, 1998. See http://www.uspto.gov/patft/index.html in this regard.

Advantageously because of the selective reactivity of the SCK shell or core and the hydrophobicity of the SCK core, many fluorophores (in number and type) may be are attached or sequestered if desired into the SCK nanostructure.

Sequence Listings

SEQ ID NO. 1

PTD Amino Acid Sequence—protein transduction domain of HIV-1 TAT (Yoon et al., J. Microbiol., 2004, 42(4), 328-335): Tyr-Gly-Arg-Lys-Lys-Arg-Arg-Gln-Arg-Arg-Arg[a]

Note: [a]Gly-Arg-Lys-Lys-Arg-Arg is a potential nuclear localization sequence. Abbreviation: PTD, protein-transduction domain.

SEQ ID NO. 2

Sequence of the unr mRNA (from the GenBank database: *Homo Sapiens* NRAS-related gene (UNR) mRNA) with the PNA50 binding site underlined.

```
  1 gcttatggcg gcgctggaga gggggcgctg agctgttggg tatgaagtgt aacagaacag
 61 actttaccac ctgaaactgc tgcttcaagt tcagatcagg caaggaacaa acctcgtaac
121 aactaacaag accaaagaag agtacactta agttgaagac acaacacttg atctgaaaca
181 agaagtttgt gcctactcaa cagctttgaa agagcacttc ccaacgctgc tagtagtctt
241 tgttttcttc agtgctgtac tgtgagattg cccggtacag cagcagttgt attctttatt
301 agcttggtag atcattttct ctcgctcttt tttttaatac tagcaacttt catcctttga
361 aacgtgtgct gaaaaagaag aatcagcaaa tactactgaa agtgcaatat ttgagtatca
421 ctgcgagatg agctttgatc caaaccttct ccacaacaat ggacataatg ggtaccctaa
481 tggtacttca gcagcactgc gtgaaactgg ggttattgaa aaactgttaa cctcttacgg
541 atttattcag tgttcagaac gtcaagctag acttttcttc cactgttcac agtataatgg
601 caacctgcaa gacttaaaag taggagatga tgttgaattt gaagtatcat cggaccgacg
661 gactgggaaa cccattgctg ttaaactggt gaagataaaa caagaaatcc tccctgaaga
721 acgaatgaat ggacaagttg tgtgcgctgt tcctcacaac ttagagagta aatctccagc
781 tgccccgggt cagagtccaa cagggagtgt atgctacgaa cgtaatgggg aagtgtttta
841 tctgacttac accoctgaag atgtcgaagg gaacgttcag ctggaaactg gagataaaat
901 aaactttgta attgataaca ataaacatac tggtgctgta agtgctcgca acattatgct
```

```
 961 gttgaaaaag aaacaagccc gctgtcaggg agtagtttgt gccatgaagg aggcatttgg
1021 ctttattgaa agaggtgatg ttgtaaaaga gatattcttt cactatagtg aatttaaggg
1081 tgacttagaa accttacagc ctggcgatga tgtggaattc acaatcaagg acagaaatgg
1141 taaagaagtt gcaacagatg tcagactatt gcctcaagga acagtcattt ttgaagatat
1201 cagcattgaa cattttgaag gaactgtaac caaagttatc ccaaaagtac ccagtaaaaa
1261 ccagaatgac ccattgccag gacgcatcaa agttgacttt gtgatcccta agaacttcc
1321 ctttggagac aaagatacga atccaaggt gaccctgctg gaaggtgacc atgttaggtt
1381 taatatttca acagaccgac gtgacaaatt agagcgagca accaatatag aagttctgtc
1441 aaatacatt cagttcacta atgaagcccg agaaatgggt gtgattgctg ccatgagaga
1501 tggttttggt ttcatcaagt gtgtggatcg tgatgttcgt atgttcttcc acttcagtga
1561 aattctggat gggaaccagc tccatattgc agatgaagta gagtttactg tggttcctga
1621 tatgctctct gctcaaagaa atcatgctat taggattaaa aaacttccca agggcacggt
1681 ttcatttcat tcccattcag atcaccgttt tctgggcacg gtagaaaaag aagccacttt
1741 ttccaatcct aaaaccacta gcccaaataa aggcaaagag aaggaggctg aggatggcat
1801 tattgcttat gatgactgtg gggtgaaact gactattgct tttcaagcca aggatgtgga
1861 aggatctact tctcctcaaa taggagataa ggttgaattt agtattagtg acaaacagag
1921 gcctggacag caggttgcaa cttgtgtgcg acttttaggt cgtaattcta actccaagag
1981 gctcttgggt tatgtggcaa ctctgaagga taattttgga tttattgaaa cagccaatca
2041 tgataaggaa atcttttttcc attacagtga gttctctggt gatgttgata gcctggaact
2101 gggggacatg gtcgagtata gcttgtccaa aggcaaaggc aacaaagtca gtgcagaaaa
2161 agtgaacaaa acacactcag tgaatggcat tactgaggaa gctgatccca ccatttactc
2221 tggcaaagta attcgccccc tgaggagtgt tgatccaaca cagactgagt accaaggaat
2281 gattgagatt gtggaggagg gcgatatgaa aggtgaggtc tatccatttg gcatcgttgg
2341 gatggccaac aaaggggatt gcctgcagaa aggggagagc gtcaagttcc aattgtgtgt
2401 cctgggccaa aatgcacaaa ctatggctta caacatcaca cccctgcgca gggccacagt
2461 ggaatgtgtg aaagatcagt ttggcttcat taactatgaa gtaggagata gcaagaagct
2521 cttttttccat gtgaaagaag ttcaggatgg cattgagcta caggcaggag atgaggtgga
2581 gttctcagtg attcttaatc agcgcactgg caagtgcagc gcctgtaatg tttggcgagt
2641 ctgtgagggc cccaaggctg ttgcagctcc tcgacctgat cggttggtca atcgcttgaa
2701 gaatatcact ctggatgatg ccagtgctcc tcgcctaatg gttcttcgtc agccaagggg
2761 accagataac tcaatggggt ttggtgcaga aagaaagatc cgtcaagctg gtgtcattga
2821 ctaaccacat ccacaaagca caccattaat ccactatgat caagttgggg ggaatctggt
2881 gaagggttct gaatatctcc ctcttcatcc ctcccgaaat ctggaatact tattctattg
2941 agctattaca ccagttttaa caccttcctc gtgttatgtt taaaaaaata aataaattta
3001 agaaaaccat tttaaataat gcacagttgc agcctggaaa aacttaaggt ggcgccttat
3061 agtatcaatt ttaggagctt tatttggtgc atttaacgca actggtaatt gcagaatcca
3121 ctttgcctgt gtaagtgaaa aatatagact gttatcttgt tggccctatg aaattctgca
3181 cttttcatta tatactctac cttcattaat tacttctggc aagatgttct gccttagcac
3241 tcagttgcat tcttttcctt tttcttcctg ttcattatgc tttaattctg aggaccatat
3301 gagggtagaa tatattatct tttaaaaatt acaaaaattt gtataggcaa accatttctt
3361 aaagttgatg gccaaatttt aaaatgttat ttttcatatc atttataatc ttgtcacaat
```

```
3421 ccacttaaag aagtttggtt atatttcagt gaaaattttc ttccagagta ggttttttt 3481 cgtgggttgg ggggtaactt tactacaatt agtaagtatg gtgcagaatt tcatgcaaat 3541 gaggagtgcc agcagtgtga taatttaaac atatttaaac aaaaacaaaa aaaatgaatg 3601 cacaaacttg ctgctgctta gatcactgca gcttctagga cccggtttct tttactgatt 3661 taaaaacaaa acaaaaaaaa ataaaaaagt tgtgcctgaa atgaatcttg tttttttta 3721 taagtagccg cctggttact gtgtcctgta aaatacagac acttgaccct tggtgtagct 3781 tctgttcaac tttatatcac gggaatggat gggtctgatt tcttggccct cttcttgaat 3841 tggccatata cagggtccct ggccagtgga ctgaaggctt tgtctaagat gacaagggtc 3901 agctcagggg atgtggggga gggcggtttt atcttccccc ttgtcgtttg aggttttgat 3961 ctctgggtaa agaggccgtt tatctttgta aacacgaaac atttttgctt tctccagttt 4021 tctgttaatg gcgaaagaat ggaagcgaat aaagttttac tgattttga gacact
```

SEQ ID NO. 3 PNA50: TGGTGTGCTTTGTGGATG

SEQ ID NO. 4 PNA50S: CATCCACAAAGCACACCA

The following non-limiting examples illustrate various aspects of the present discovery.

EXAMPLE Sets A-F hereinafter shows aspects of this discovery.

EXAMPLE Set A shows preparation of SCK nanoparticles

EXAMPLE Set B shows peptide-derivatized SCK-cross-linked nanoparticles along with synthesis and characterization illustrating preparing of peptide permeation associated with a biologically active particle as disclosed in Becker et al. (Bioconjug. Chem., 2004, 15, 699-709) which is incorporated herein in its entirety by reference.

EXAMPLE Set C shows peptide-derivatized shell-cross-linked nanoparticles and associated biocompatibility evaluation as disclosed in Becker et al. (Bioconjug. Chem., 2004, 15, 710-717) which is incorporated herein in its entirety by reference.

EXAMPLE Set D shows microPET imaging of MCF-7 tumor in mice via unr mRNA-targeted peptide nucleic acids as disclosed in Sun et al. (Bioconj. Chem., 2005, 16, 294-305) which is incorporated herein in its entirety by reference.

EXAMPLE Set E shows targeting MCF-7 cells with antisense PNAs to uniquely overexpressed unr mRNA.

EXAMPLE Set F shows microPET imaging of MCF-7 tumor in mice via shell-cross-linked nanoparticles conjugated to unr mRNA-targeted peptide nucleic acids and a permeation peptide.

Abbreviations used in the following examples: "ζ" means zeta potential, "5(6)-FAM SE" means 5(6)-carboxyfluorescein succinimidyl ester, "7-AAD" means 7-aminoactinomysin, "AFM" means atomic force microscopy, "ATCC" means American Type Culture Collection, "ATRP" means atom transfer radical polymerization, "Bio-dUTP" means biotinylated deoxyuridine triphosphate, "BSS" means Earle's balanced salt solution, "cDNA" means complementary DNA, "Chloramine-T" means N-chloro-p-toluensulfonamide sodium salt, "CHO cells" means chinese hamster ovary cells, "DCM" means dichloromethane, "DIEA" means diisopropylethylamine, "DLS" means dynamic light scattering, "DMF" means dimethylformamide, "$D_n$" means number-average hydrodynamic diameter, "dNTP" means deoxynucleotide triphosphate, "DOTA" means 1,4,7,10-tetraazacyclododecane-N,N',N'',N'''-tetraacetic acid, "DSC" means differential scanning calorimetry, "DTPA" means diethylenetriaminepentaacetic acid, "$D_v$" means volume-average diameter, "$D_z$" means intensity-average diameter, "EDTA" means ethylenediaminetetraacetic acid, "ELISA" means enzyme-linked immunosorbent assay, "EOB" means end of bombardment, "equiv." means equivalent(s), "FACS" means fluorescence activated cell sorting, "FBS" means fetal bovine serum, "FITC" means fluorescein isothiocyanate, "Fmoc" means 9-fluorenylmethoxycarbonyl, "FPLC" means fast protein liquid chromatography, "FTSC" means fluorescein-5-thiosemicarbazide, "HATU" means O-(7-Azabenzo-triazol-1-yl)-1,1,3,3-tetramethyluronium hexafluorophosphate, "HBSS" means Hank's balanced salt solution, "HEPES" means 4-(2-hydroxyethyl)piperazine-1-ethanesulfonic acid, "HPLC" means high performance liquid chromatography, "i.p." means intraperitoneal, "i.v." means intravenous, "ID" means injected dose, "IgG" means immunoglobulin G, "IL1-β" means interleukin-1 beta, "IR" means infra-red, "$K_d$" means dissociation constant, "MALDI-TOF" means matrix assisted laser desorption ionization—time of flight, "MALS" means multi angle light scattering, "MEM" means Eagle's minimum essential medium, "$M_n$" means number-average molecular weight, "$M_p$" means peak-average molecular weight, "MS" means mass spectrometry, "MTT" means 3-(4,5-dimethylthiazol-2-yl)-2,5-diphenyl-2H-tetrazolium bromide, "$M_w$" means weigh-average molecular weight, "MWCO" means molecula weight cut-off, "NLS" means nuclear localization sequence, "NMP" means N-methylpyrrolidone, "NMR" means nuclear magnetic resonance, "NTP" means nucleotide triphosphate, "ODN" means oligodeoxynucleotide, "p.i." means post injection, "PAA" means poly (acrylic acid), "PAGE" means polyacrylamide gel electrophoresis, "PALS" means phase analysis light scattering, "PBS" means phosphate buffered saline, "PCR" means polymerase chain reaction, "PET" means positron emission tomography, "PMA" means poly(methyl acrylate), "PMDETA" means N-[2-(Dimethylamino)ethyl]N,N',N'-trimethyl-1,2-ethanediamine, "PNA" means peptide nucleic acid, "PS" means phosphatidylserine, "PTA" phosphotungstinic acid, "PTD" means protein transduction domain (See Seq. 1), "r.t." means room temperature, "RES" means reticulo-endothelial system, "ROI" means region of interest, "RT-PCR" means real-time polymerase chain reaction, "RT-ROL" means reverse transcriptase random oligodeoxynucleotide library, "s.c." means subcutaneous, "SAABS" means serial analysis of antisense binding sites, "SAGE" means serial analysis of gene expression, "SCID" means severe combined immunodeficiency, "SCK" means shell crosslinked nanoparticles, "SDS" means sodium dodecyl sulfate, "SE" means sedimentation equilibrium, "SEC" means size exclusion chromatography, "SPECT" means single photon emission computed tomography, "SUV" means standard uptake value, "T/B" means tumor to blood ratio, "T/M" means tumor to muscle ratio, "TCPS" means tissue culture polystyrene, "TEM" means transmission electron microscopy, "TFA" means trifluoroacetic acid, "$T_g$" means glass transition temperature, "THF" means tetrahydrofuran, "TIS" means triisopropyl silane, "TNF-α" means tumor necrosis factor alpha, "unr" means upstream of N-ras or N-ras related gene, "UV" means ultra-violet, "v" means partial specific volume, "δ" means chemical shift.

EXAMPLE SET A

Preparation of SCK Nanoparticles

Poly(tert-butyl acrylate): A 100 mL Schlenk flask that had been oven dried overnight, flame dried under vacuum, and back filled with argon was charged with copper(I) bromide (891.6 mg, 6.21 mmol). Tert-butyl acrylate (38.00 mL, 259.4 mmol), N-[2-(Dimethylamino)ethyl]N,N',N'-trimethyl-1,2-ethanediamine) (PMDETA) (1.297 mL, 6.21 mmol), and ethyl-2-bromoproprionate (403 µL, 3.10 mmol), were added via argon washed syringes. The solution was degassed by three cycles of freeze-pump-thaw, and following the final thaw cycle the mixture was allowed to stir for 10 min before being immersed in an oil bath at 50° C. After 80 min, the oil bath was removed and the reaction vessel was immersed in liquid nitrogen to quench the polymerization reaction. The reaction mixture was dissolved in tetrahydrofuran (THF), and passed through an alumina plug to remove the metal/ligand catalyst system. The polymer solution was concentrated and then precipitated and recovered into cold methanol. The isolated yield was 28.83 g (85%).

Poly(tert-butyl acrylate-b-styrene-$d_8$): A 100 mL Schlenk flask that had been oven dried overnight, flame dried under vacuum, and back filled with argon was charged with copper (I) bromide (45.8 mg, 0.32 mmol) and poly(tert-butyl acrylate) 2 (0.7234 g, 9.77 $e^{-2}$ mmol). PMDETA (66.5 µL, 0.32 mmol), and styrene-$d_8$ (3.000 mL, 2.62 mmol), were added via argon washed syringes. The solution was degassed by three cycles of freeze-pump-thaw, and following the final thaw cycle the mixture was allowed to stir for 10 min before being immersed in an oil bath at 75° C. After 150 min, the oil bath was removed and the reaction vessel was immersed in liquid nitrogen to quench the polymerization reaction. The reaction mixture was dissolved in THF, and passed through an alumina plug to remove the metal/ligand catalyst system. The polymer solution was concentrated and then precipitated and recovered into a cold methanol/water solution. $M_n$=22,500 from SEC, based on MALS. $M_w/M_n$=1.06. The isolated yield was 2.0714 g (44%).

Poly(acrylic acid-b-styrene-$d_8$): The poly(tert-butyl acrylate) block of 3 was cleaved selectively by adding 50.00 mL of trifluoroacetic acid (TFA) to 1.0624 g (4.72 $e^{-2}$ mmol) of the diblock 2 in 150 mL of dichloromethane. After 36 hours, the solvent was evaporated in vacuo; the residue was dissolved in THF and purified by dialysis in presoaked cellulose dialysis tubing (12-14 kDa Molecular weight cut-off (MWCO)) against nanopure water for 3 days. Lyophilization yielded pure poly(acrylic acid-b-styrene-$d_8$) recovered as a white powder. Yield: 0.8956 g (98%)

Micelle Formation: Spherical micelles of narrow size distribution were obtained by dissolving the purified block copolymer 4 (0.5186 g, 2.30 $e^{-5}$ mol) in 250.00 mL of THF (2.07 mg/mL) followed by gradual addition (15.00 mL/h) of an equal volume 5 mM sodium phosphate, 5 mM sodium chloride, pH 7.4 buffer to induce micellization. The micelles were allowed to stir for 12 h before being transferred to a dialysis and concentration cell (10 kDa MWCO) and dialyzed with 3.0 L of buffer. The final volume was 650 mL of buffered micelle solution for a final concentration of 0.80 mg/mL.

Figure 2:
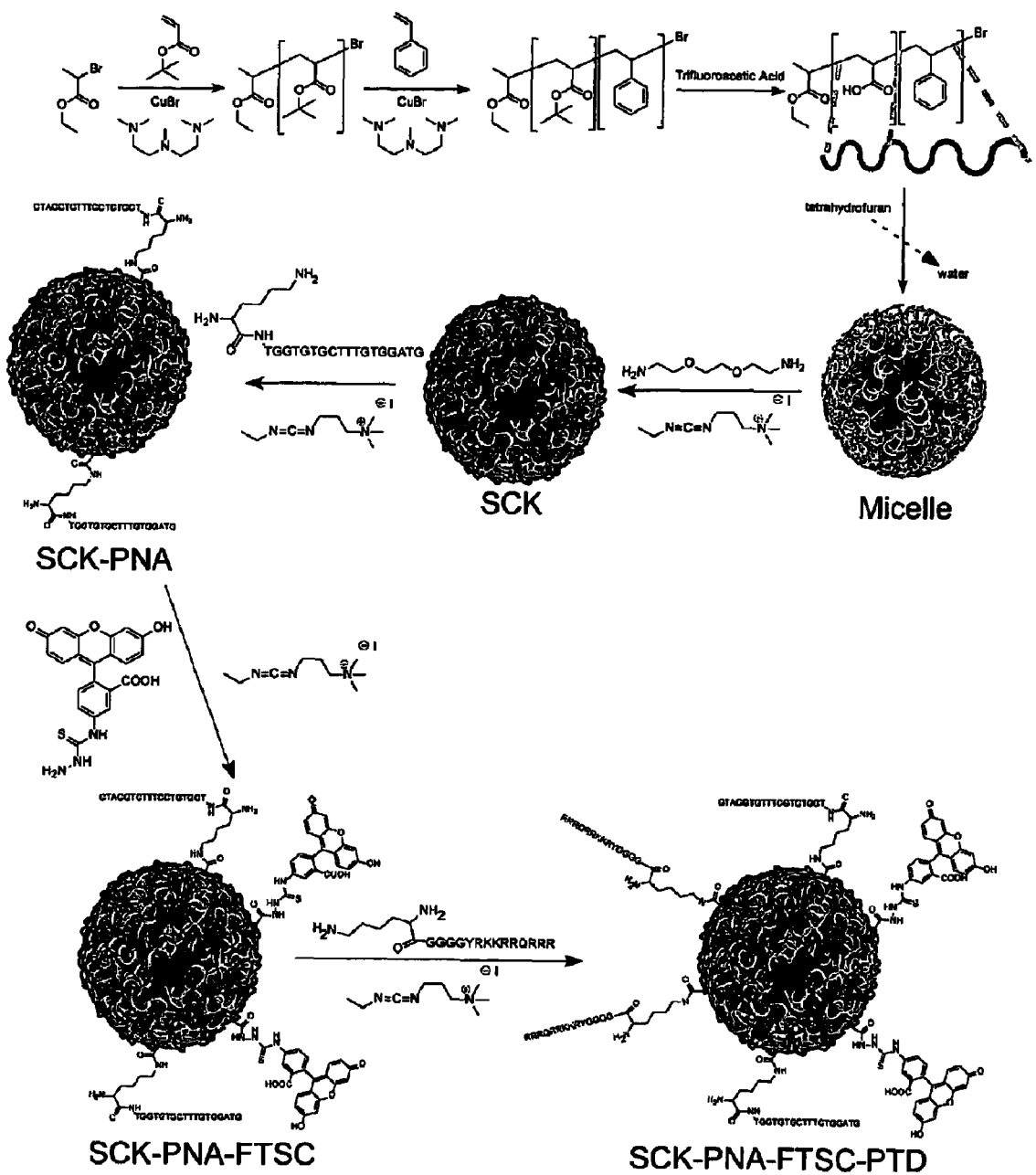
FIG. 2 depicts the synthesis of a SCK-PNA-FTSC-PTD construct.
Figure 3:
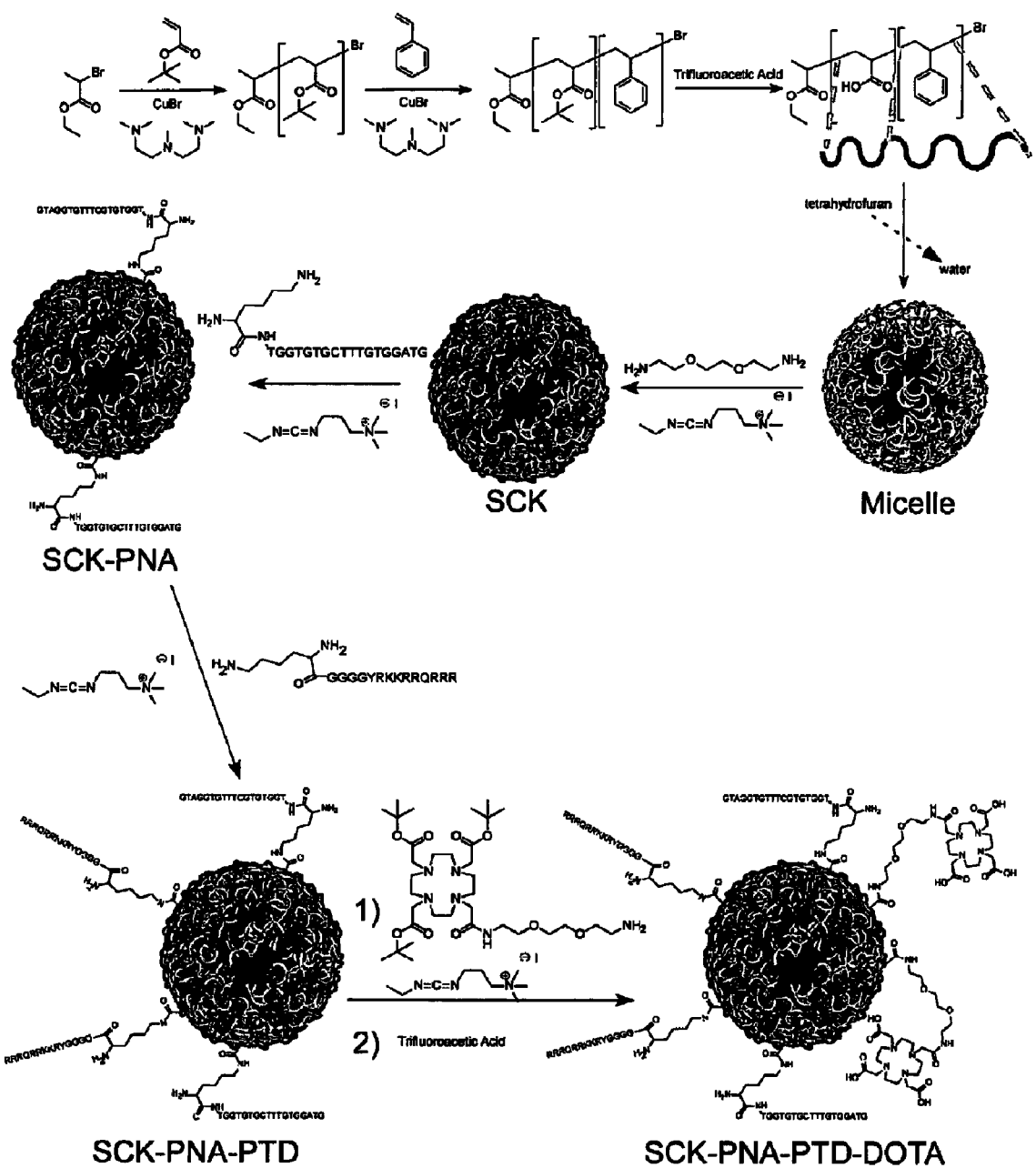
FIG. 3 depicts the synthesis of a SCK-PNA-PTD-DOTA construct.

Shell Crosslinked (SCK) Nanoparticle Formation. Vil21: 2,2'-(ethylenedioxy)-bis(ethylamine) (67 µL, 0.46 mmol) was added to 0.500 L of micelle solution (0.80 mg/mL) of poly(acrylic acid-b-styrene-$d_8$). After 30 minutes, an aqueous solution (100 mg/mL) of 1-(3-dimethylaminopropyl)-3-ethylcarbodiimide hydrochloride (1.040 g, 5.46 mmol) was added to the reaction vessel. The reaction mixture was allowed to stir for 24 h, and the SCK solution was concentrated to 200 mL in a concentration cell and washed with 3.0 L of nanopure water to remove the reaction byproducts. A small portion was removed for analysis and the remainder of the SCK solution was lyophilized. (FIG. 2)

Preparation of PNA-Functionalized SCK Nanoparticles

General Procedure for SCK-PNA conjugate formation: To a stirred solution of SCK (0.53 mg/mL, 2.4 nmoles (particle)) was added Lys-PNA (12 nmoles, 5 equiv.) in 0.5 mL water over a 3 minute period. The mixture was allowed to stir for 30 minutes prior to the addition of 50 equiv. of 1-(3-dimethylaminopropyl)-3-ethylcarbodiimide methiodide (120 nmoles) as a solution in 0.3 mL of water over a 2 minute period. The reaction was stirred for 16 hours at ambient temperature, and subsequently transferred to dialysis tubing (10 kDa MWCO) and allowed to dialyze for 4 days against nanopure water. UV-visible spectroscopy demonstrated an average of 4 PNAs per particle (80% coupling efficiency).

Characterization of the SCK-PNA Conjugate Prepared Above

Figure 4:
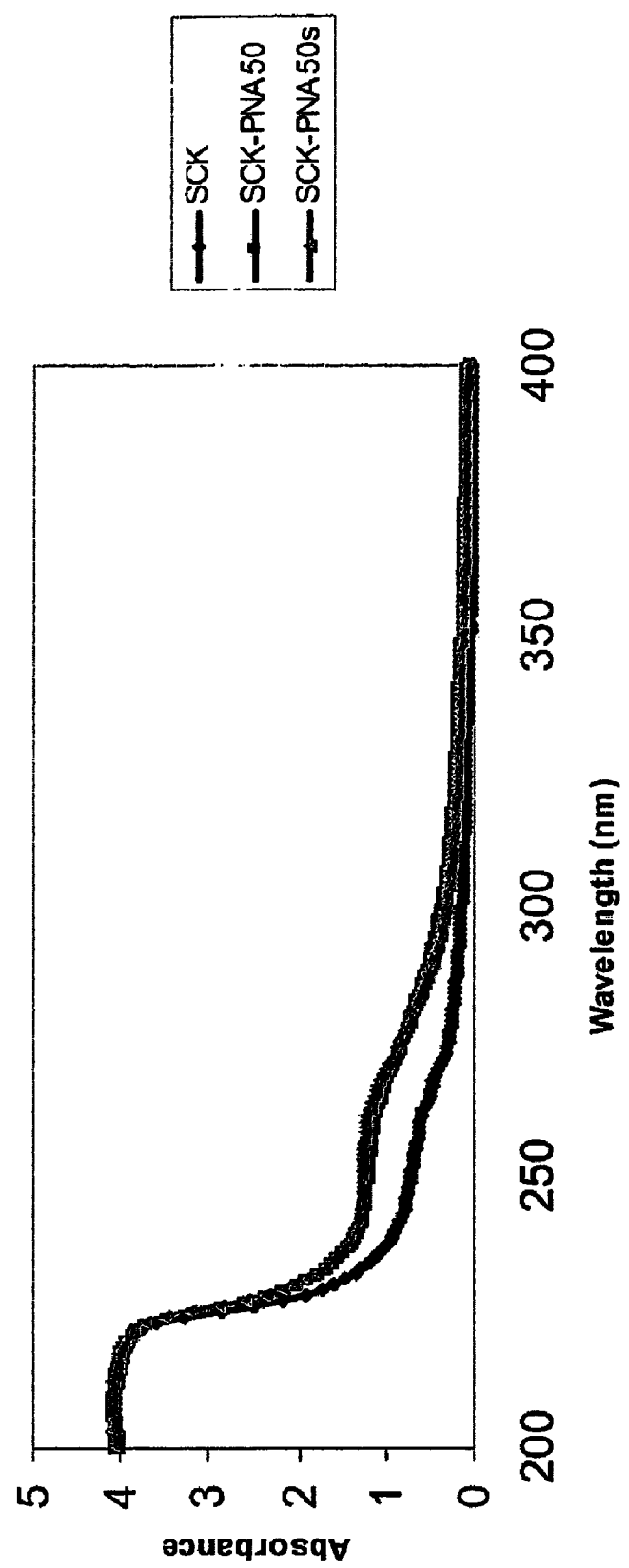
FIG. 4 shows UV visible spectra of SCK and recovered SCK-PNA conjugates showing a graph of absorbance data as a function of wavelength for SCK, SCK-PNA50 and SCK-PNA50S.

Equimolar amounts of SCK and SCK-PNA conjugate were analyzed by UV-visible spectroscopy to determine the concentrations of PNA within solution, by subtracting the measured absorbance of the SCK at 260 nm from the measured absorbance at 260 nm for the PNA-SCK conjugate, and the molarity of PNA within solution was determined using a molar extinction coefficient of 150,000 $M^{-1}$ $cm^{-1}$ (See FIG. 4). Successful conjugation of the PNA and loss of non-coupled PNA was determined by sedimentation velocity analysis. The PNA-SCK conjugate was centrifuged at 25,000 rpm and the meniscus demonstrated a loss of absorbance at 260 nm indicating a lack of free PNA within the solution (See FIG. 5).

Preparation of SCK-PNA-FTSC: (Fluorescent Labeling)

To a stirred solution of the aforementioned SCK-PNA (1.8 mL, 0.53 mg/mL, 1.7 nmoles (particle)) was added Fluorescein-5-thiosemicarbazide (FTSC) (8.5 nmoles, 7.4 µg, 5 equiv. per particle) in 0.2 mL water over a 5 minute period. The mixture was allowed to stir for 30 minutes prior to the addition of 7.5 equiv. of 1-(3-dimethylaminopropyl)-3-ethylcarbodiimide methiodide (13.6 nmoles, 3.9 µg) as a solution in 0.1 mL of water over a 2 minute period. The reaction was allowed to stir for 16 hours at ambient temperature, and subsequently transferred to dialysis tubing (10 kDa MWCO) and allowed to dialyze for 2 days against nanopure water. Final volume was 2.0 mL, which was subsequently concentrated again to its original volume (1.8 mL)

Preparation of PNA- and PTD-Functionalized SCK Nanoparticles and Fluorescent Labeling SCK-PNA-FTSC-PTD: To a stirred solution of SCK-PNA-PTD (1.8 mL, 0.53 mg/mL, 1.7 nmoles (particle)) was added PTD (17 nmoles, 0.030 mg, 10 equiv. per particle) in 0.3 mL water over a 5 minute period. The mixture was allowed to stir for 30 minutes prior to the addition of 7.5 equiv. of 1-(3-dimethylaminopropyl)-3-ethylcarbodiimide methiodide (26 nmoles, 7.7 µg) as a solution in 0.1 mL of water over a 2 minute period. The reaction was allowed to stir for 16 hours at ambient temperature, and subsequently transferred to dialysis tubing (10 kDa MWCO) and allowed to dialyze for 3 days against nanopure water.

SCK-PNA-PTD: To a stirred solution of SCK-PNA (9.0 mL, 0.53 mg/mL, 8.6 nmoles (particle)) was added PTD from an aqueous solution (190 nmoles, 0.35 mg, 22 equiv. per particle). The mixture was allowed to stir for 30 minutes prior to the addition of 22 equiv. of 1-(3-dimethylaminopropyl)-3-ethylcarbodiimide methiodide as a solution in 0.2 mL of water over a 5 minute period. The reaction was allowed to stir for 16 hours at ambient temperature, after which the reaction was transferred to dialysis bag (10 kDa MWCO) and dialyzed against water for 5 days. The final volume was returned to 8.0 mL via stirred cell ultrafiltration.

Preparation of PNA- and PTD-Functionalized SCK Nanoparticles and Conjugation with Chelator for Radiolabeling.

SCK-PNA-PTD-DOTA: To a stirred solution of SCK-PNA-PTD (8.0 mL, 0.53 mg/mL, 7.8 nmoles (particle)) was added DOTA-$NH_2$-tri-tert-butyl ester (structure shown in FIG. 6) from a THF solution (400 nmoles, 50 equiv. per particle). The mixture was allowed to stir for 30 minutes prior to the addition of 50 equiv. of 1-(3-dimethylaminopropyl)-3-ethylcarbodiimide methiodide (119 µg) as a solution in 0.1 mL of water over a 2 minute period. The reaction was stirred for 16 hours at ambient temperature, after which 1 mL of concentrated TFA was added to the solution. The deprotection reaction was monitored in a separate vial against the small molecule component in an aqueous 10% TFA solution, and was continued until no tert-butyl resonance was observed in the $^1$H NMR spectrum of the small molecule. After 17 hours, the reaction was subsequently transferred to dialysis bag (10 kDa MWCO) and dialyzed for 5 days against deionized water. The final volume was returned to 8.0 mL via stirred cell ultrafiltration.

FIG. 4 shows UV-visible spectra of SCK and SCK-PNA conjugates. Increase in absorbance at 260 nm demonstrated the concentration of PNAs within solution.

Figure 5:
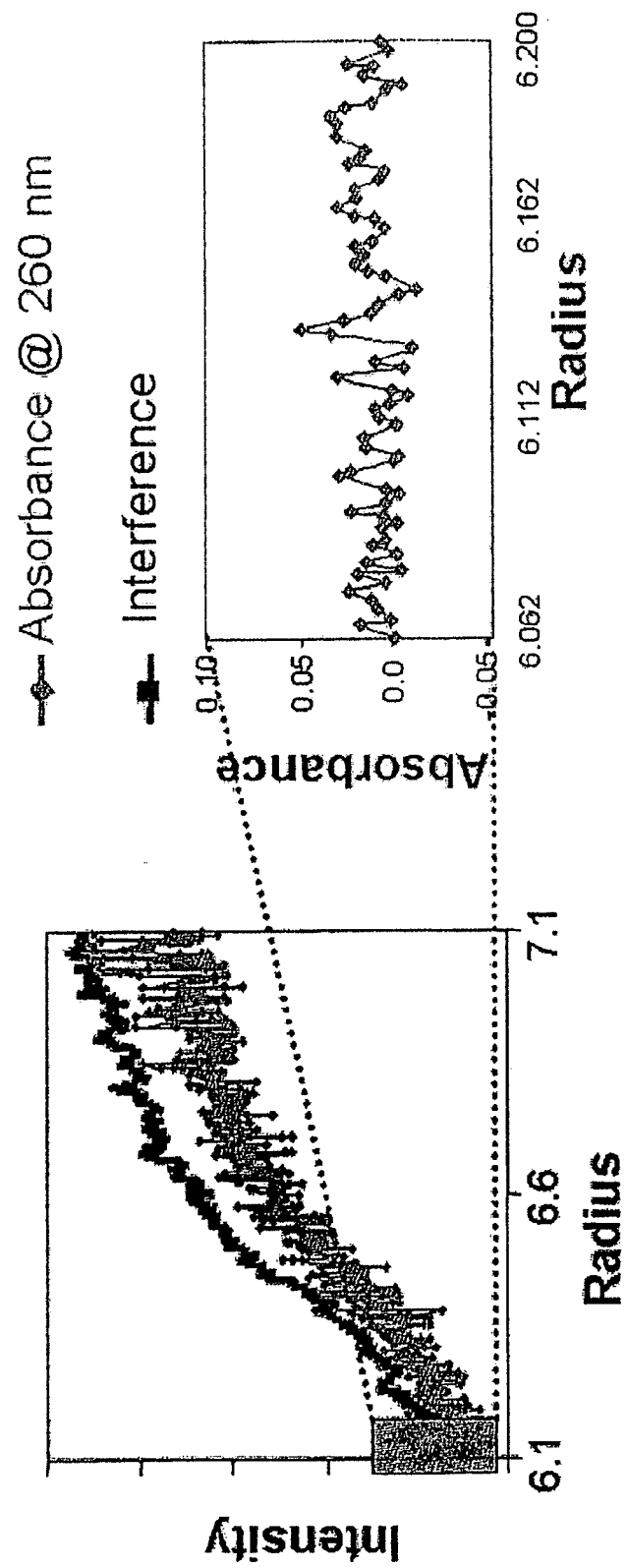
FIG. 5 shows inventor generated data of sedimentation velocity analysis.

FIG. 5 shows a structure for sedimentation velocity analysis of SCK-PNA50 conjugate. The loss of absorbance at 260 nm at the top of the cell, demonstrated the desired lack of free PNA within the solution.

Figure 6:
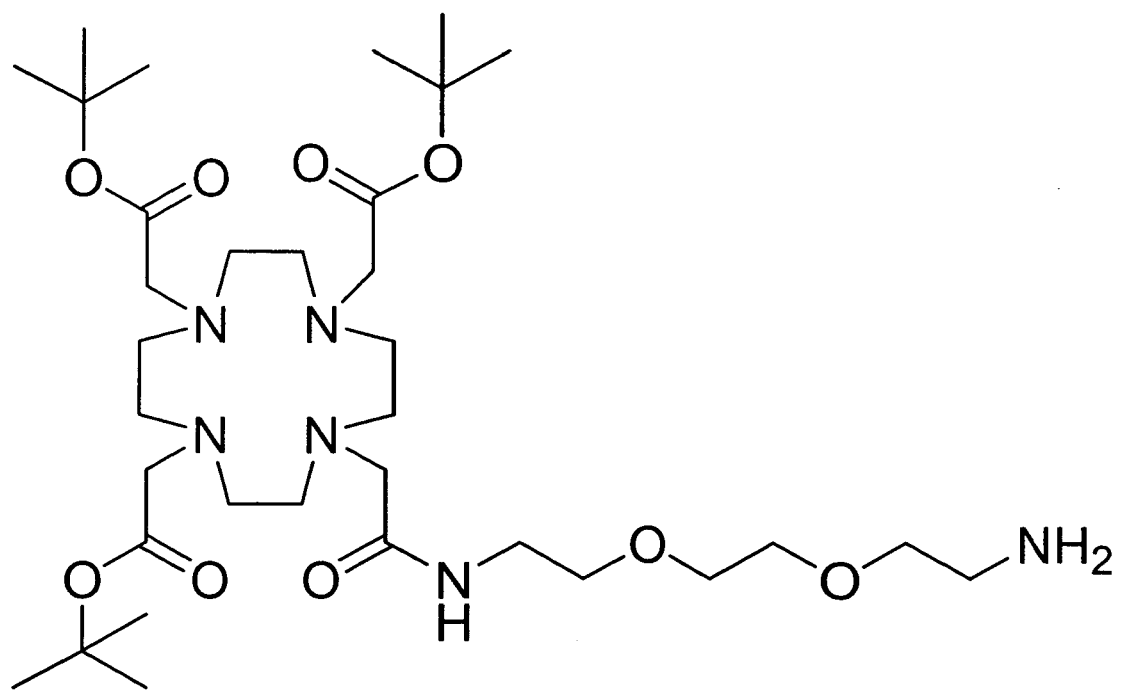
FIG. 6 depicts schematically the structure of DOTA-$NH_2$-tri-tert-butyl ester, the chelator used for effective conjugation to the SCK-PNA-PTD construct.

FIG. 6 shows the DOTA-$NH_2$-tri-tert-butyl ester chelator used for conjugation to the SCK-PNA-PTD construct.

EXAMPLE SET B

Preparation and Recovery of Peptide-Derivatized Shell-Cross-Linked Nanoparticles We have demonstrated that our conjugation of the protein transduction domain (PTD) from the HIV-1 Tat protein to shell-cross-linked (SCK) nanoparticles is an efficacious method to facilitate cell surface binding and transduction of SCK nanoparticles (Liu et al., Biomacromol., 2001, 2, 362-368). Attaching increasing numbers of peptide sequences to SCK nanoparticles in a global solution-state functionalization strategy has been devised as a method for increasing the efficiency of the cell-penetrating process.

In this example, the numbers of peptides per SCK were controlled through stoichiometric balance and measured by using two independent methods, UV-visible spectroscopy and phenylglyoxal analysis. PTD was conjugated in 0.005, 0.01, and 0.02 molar ratios, relative to the acrylic acid residues in the shell, to the SCK nanoparticles resulting in SCK populations possessing nominally 52, 104, and 210 (41, 83, and 202 as measured by phenylglyoxal analysis) PTD peptides per particle, respectively. The methodologies for the block copolymer and nanoparticle syntheses, peptide derivatization, and characterization of peptide-functionalized SCK nanoparticles are reported and the feasibility and efficiency of intracellular internalization of the respective SCKs were quantified.

Test Procedures

Materials. Unless otherwise listed, all solvents and reagents were purchased from Sigma Aldrich Chemical Co. (St. Louis, Mo.) and used as received. Monomers were purchased from Sigma Aldrich and distilled over calcium hydride. Fmoc-protected amino acids and preloaded solid-phase Wang resins were purchased from NovaBiochem-CalBiochem Corp (San Diego, Calif.). Spectra/Por dialysis membranes (Spectrum Laboratories, Inc., Rancho Dominguez, Calif.) were purchased from Fisher Scientific Company (Pittsburgh, Pa.). Prolong antifade mounting medium was purchased from Molecular Probes Inc. (Eugene, Oreg.).

Measurements. $^1$H NMR (300 MHz) and $^{13}$C NMR (75 MHz) spectra were recorded as solutions on a Varian Mercury 300 MHz spectrometer with the solvent signal as standard. IR spectra were obtained on a Perkin-Elmer Spectrum BX FT-IR system using diffuse reflectance sampling accessories. Mass spectra were obtained from a Voyager DE-RP MALDI-TOF mass spectrometer (PE Biosystem). HPLC was performed using a Hewlett-Packard Series 1100 with reversed phase C18 column (Dynamax, 300 Å, Rainin) equipped with quaternary pump, solvent degasser, and diode array detector.

Size Exclusion Chromatography (SEC). Size exclusion chromatography was conducted on a Model 150-CV (Waters Chromatography Inc., Medford, Mass.). The instrument was equipped with a Model 410 differential refractometer, a Model PD2040 dual-angle (15° and 90°) light scattering detector (Precision Detectors Inc., Bellingham, Mass.), and a three-column set of gel-mixed-bed styrene-divinylbenzene columns (Polymer Laboratories Inc., Amherst, Mass.). The SEC system was equilibrated at 35° C. in anhydrous THF, which served as the polymer solvent and eluent (flow rate set to 1.00 mL/min then determined gravimetrically). An injection volume of 400 µL was used, and the polymer concentrations ranged from 5 to 10 mg/mL. Data collection was performed with program Precision Acquire (Precision Detectors Inc., Bellingham, Mass.). Data analysis was performed with program Discovery32 (Precision Detectors Inc., Bellingham, Mass.). Interdetector delay volume and the light scattering detector calibration constant were determined from a nearly monodisperse polystyrene calibrant ($M_p$=90000 g/mol, $M_w/M_n$<1.04: Pressure Chemical Co., Pittsburgh, Pa.). The differential refractometer was calibrated with standard polystyrene reference material (SRM 706; NIST, Gaithersburg, Md.), of known specific refractive index increment, dn/dc (0.184 mL/g). The dn/dc of the analyzed polymers was then determined from the differential refractometer response.

Differential Scanning Calorimetry (DSC). The glass transition temperature ($T_g$) was measured by differential scanning calorimetry on a Perkin-Elmer DSC-4 differential scanning calorimeter. Heating rates were 10° C./min and reported values of $T_g$ were measured at the midpoint of the inflection tangent, upon the third heating scan.

Sedimentation Equilibrium (SE). A Beckman Instruments Co. Model Optima XL-I analytical ultracentrifuge operated with a Model An60-Ti, four-hole rotor was used to centrifuge 50 mM $NaH_2PO_4$, 50 mM NaCl, pH 7.1 solutions of the SCK to sedimentation equilibrium. All measurements were made at 20±0.1° C. Rotor speeds of 2000, 3000, 5000 and 8000 rpm were used. Sedimentation equilibrium data were obtained for three SCK solution concentrations. Resulting sedimentation equilibrium profiles were recorded with the instrument's Rayleigh interferometric (refractive index) detection optics. The ultracentrifuge sample cell was assembled from an Epon charcoal-filled, six-channel centerpiece and matched sapphire windows. The solution volume and the cell's optical path length were 110 µL and 12 mm, respectively. The solution volume and optical path length employed corresponded to a "short" column sedimenta-tion equilibrium test with a column height of approximately 2.5 mm. A centrifugation time of 3 to 5 days was used to reach sedimentation equilibrium. Partial specific volume (v) values for the SCKs were determined via sedimentation equilibrium analysis for protonated and deuterated buffer solutions of SCKs as described in Remsen et al. (Macromol., 1999, 32, 3685-3689). Solutions of the SCK in deuterated buffer were prepared by exhaustive dialysis of protonated buffer stock solutions of SCKs against 50 mM phosphate buffered saline (PBS), pD 7.1. In 99.9 atom % $D_2O$, Calculation of molecular weight employed a built-in data analysis program that employed standard multicomponent least-squares fitting routines. Density at 20.0±0.1° C. for protonated and deuterated buffers was determined with a Mettler-Parr digital density meter. Measurements of v were reproducible to within ±1% of the mean value given by three determinations. The values of v obtained by SE were also used for the determination of the weight concentrations of SCK nanoparticle solutions. The digital density meter was employed to measure the solution density at 20.0±0.1° C. for the SCK solutions and their corresponding PBS to an accuracy of ±0.0001 g/mL.

These values were used in conjunction with the SE-measured value of v to determine the weight concentration ($C_{SCK}$) of the SCK solution in PBS:

$C_{SCK}=(p_{SCK}-p_b)/(1-vp_b)$ where $p_b$ is the density of the buffer and $p_{SCK}$ is the density of the SCK solution.

UV-Visible Spectroscopy. Absorption measurements were made using a Molecular Devices Corp (Sunnyvale, Calif.) UV-visible spectrophotometer. A Thermomax multiplate reader using SOFTmax PRO software was employed. The concentrations of PTD and SCK in aqueous solutions of functionalized SCK nanoparticles were simultaneously determined using the UV absorbance measured at 230 and 276 nm. Measurements obtained at 230 and 276 nm corresponded to the turbidity of the SCK nanoparticle and the tyrosine (TYR) absorbance of the PTD at these wavelengths. The total absorbance for a functionalized SCK at a given wavelength, $A^\lambda$, was given by the sum of the absorbances of the nanoparticle's SCK component, $A_{SCK}^\lambda$, and its PTD component, $A_{TYR}^\lambda$:

$$A^{230}=A_{SCK}^{230}+A_{TYR}^{230} \quad \text{Equation (1)}$$

$$A^{276}=A_{SCK}^{276}+A_{TYR}^{276} \quad \text{Equation (2)}$$

The individual concentrations of the SCK and PTD ($C_{SCK}$ and $C_{TYR}$, respectively) components constituting a functionalized nanoparticle were obtained by simultaneously solving equations 1 and 2 after calibration of the UV spectrum at 230 and 276 nm with PTD and SCK standards of known concentration. The calibration yielded a set of calibration coefficients, K, for the components at 230 and 276 nm:

$$A^{230}=K_{SCK}^{230}+C_{SCK}+K_{TYR}^{230}C_{TYR} \quad \text{Equation (3)}$$

$$A^{276}=K_{SCK}^{276}+C_{SCK}+K_{TYR}^{276}C_{TYR} \quad \text{Equation (4)}$$

Measured values $A^{230}$ and $A^{276}$ were substituted into equations 3 and 4 which were expressed in matrix form (equation 5) and then solved by inversion of the matrix of calibration coefficients, K:

$$A=KC \quad \text{Equation (5)}$$

$$K^{-1}A=K^{-1}KC \quad \text{Equation (6)}$$

$$C=K^{-1}A \quad \text{Equation (7)}$$

Substitution of computed values of $K^{-1}$ in equation 7 above provided the expressions used to calculate the weight concentrations of SCK and PTD in solution:

$$C_{SCK}=8.6405A^{230}-41.5418A^{276} \quad \text{Equation (8)}$$

$$C_{TYR}=9.5652A^{230}-1.5869A^{276} \quad \text{Equation (9)}$$

Testally determined weight concentrations were converted to molar concentrations using the known molecular weight of the PTD and the measured molecular weight of the SCK. Molar concentrations of each component provided the requisite information to evaluate the number of peptides (PTD) per SCK nanoparticle (no. peptides per SCK=$C_{PTD}$ (M)/$C_{SCK}$ (M)).

Phenylglyoxal Analysis Measurements. The number of arginine residues (and PTD) was determined using phenylglyoxal analysis. The assay was calibrated by adding aliquots (100 µL) of a PTD solution (100 µL in PBS with 10% methanol, volume fraction) in row 1 of a quartz 96-well plate and diluting serially through column 11. SCK solutions (100 µL) (0.0, 0.5, 1.0, and 2.0%) of known concentrations (1.20, 2.00, 1.20, and 0.60 mg/mL. respectively) were added to each well in the first column and diluted serially as described above. An aliquot (100 µL) of a phenylglyoxal solution (600 µM), in identical buffer, was then added to each well of the plate, and the reaction was allowed to incubate at 4° C. overnight. The 96-well plate was read for absorbance at λ=310 nm in each well. The control phenylglyoxal absorbance spectrum was subtracted from the PTD absorbance spectra, and by plotting the residual absorbance numbers vs the known concentration of PTD in each well, a calibration curve was generated from which the amount of PTD in unknown solutions could be determined. Measurement of the SCK concentrations by other methods and converting molar ratios provided quantitative information on the number of peptides per particle in each of the four samples.

Dynamic Light Scattering (DLS). Hydrodynamic diameter distribution and distribution averages for the SCKs in PBS solution were determined by dynamic light scattering. A Brookhaven Instruments Co. (Holtsville, N.Y.) DLS system equipped with a Model BI-9000AT digital correlator, a Model EMI-9865 photomultiplier, and a Model 95-2 Ar ion laser (Lexel Corporation, Fremont, Calif.), operated at 514.5 nm, was used. Measurements were made at 20±0.1° C. Nanoparticles were dialyzed into 50 mM PBS, pH 7.1, prior to analysis. Buffered nanoparticle solutions were either centrifuged in a model 5414 microfuge (Brinkman Instrument Company, Westbury, N.Y.) for 4 min or filtered through 0.22 µm poly (vinylidene fluoride) and 0.1 µm ceramic filters (Whatman, Maidstone, UK) to remove dust particles. Scattered light was collected at a fixed angle of 90°. The digital correlator was operated with 522 ratio spaced channels, an initial delay of 1.6 µs, a final delay of 10 ms, and a duration time of 15 min. A photomultiplier aperture of 400 µm was used, and the incident laser power was adjusted to obtain a photon counting rate between 200 and 300 Kcps. Only measurements for which the measured and calculated baselines of the intensity autocorrelation function agreed to within ±0.1% were used to calculate nanoparticle hydrodynamic diameter values. All determinations were made in triplicate. The calculations of the nanoparticle diameter distributions and distribution averages were performed with the ISDA software package (Brookhaven Instruments Co, Brookhaven Instruments Limited, Chapel House, Stock Wood, Redditch, Worcestershire, B96 6ST, UK), which employed single-exponential fitting, cumulants analysis, and non-negatively constrained least-squares particle size distribution analysis routines.

Zeta Potential. Zeta potential ($\zeta$) values for the SCKs were determined with a Brookhaven Instrument Co. (Holtsville, N.Y., USA) Model ZetaPlus zeta potential analyzer. Measurements were made following dialysis (MWCO 12-14 kDa dialysis tubing, Spectrum Laboratories, Rancho Dominguez, Calif., USA) of SCK solutions into 1 mM $KH_2PO_4$, 1 mM KCl, pH 7.1 buffer. Data were acquired in the phase analysis light scattering (PALS) mode, following solution equilibration at 25° C. Calculation of $\zeta$ from the measured nanoparticle electrophoretic mobility ($\mu$) employed the Smoluchowski equation: $\mu = \in \zeta/\eta$ where $\in$ and $\eta$ are the dielectric constant and the absolute viscosity of the medium, respectively. Measurements of $\zeta$ were reproducible to within ±2 mV of the mean value given by 16 determinations of 10 data accumulations.

Transmission Electron Microscopy (TEM). Transmission electron microscopy carbon grids were prepared by oxygen plasma treatment to make the surface hydrophilic. Particle samples were diluted 9:1 in water and further diluted 1:1 with a 1% (mass fraction) phospho-tungstinic acid (PTA) stain. Micrographs were collected at 100000 magnifications and calibrated using a 41 nm polyacrylamide bead from NIST. Histograms of particle diameters were generated from the analyses of a minimum of 150 particles from at least three different micrographs.

Atomic Force Microscopy (AFM). Tapping-mode atomic force microscopy measurements were conducted in air with a Nanoscope III Bioscope system (Digital Instruments, Santa Barbara, Calif.) operated under ambient conditions with standard silicon tips (OTESPA-70; L, 160 µm; normal spring constant, 50 N/m; resonance frequency, 246-282 kHz). The samples were prepared for AFM analysis by depositing a 2-µL drop of the solution onto freshly cleaved mica and allowing it to dry freely in air. Histograms of particle heights were generated from the section analysis of a minimum of 150 particles from at least five different analyses regions. Cell Lines. Chinese hamster ovary (CHO) cells (ATCC, American Type Culture Collection, Manassas, Va.) were obtained from Washington University in St. Louis. CHO cells were maintained in RPMI 1640 (Life Technologies, Rockville, Md.) culture medium supplemented with 10% (volume fraction) heat-inactivated fetal bovine serum (FBS, Life Technologies, Rockville, Md.), in 5% $CO_2$:95% air (volume fractions) at 37° C.

Transduction Tests. CHO cells were cultured, counted, and resuspended to a final concentration of 100,000 cells/mL. An aliquot of the cell suspension (3.00 mL) was deposited into each well of a tissue culture treated six-well plate (Falcon, 3043), which contained a No. 1.5 glass cover slip (Corning). After 48 h, the cells (50-60% confluence) in each six-well plate were washed with PBS (2×5.00 mL). An aliquot of serum free RPMI 1640 medium (3.00 mL) was added to each well followed by the respective SCK solutions (1.00 mL each). The plates were then returned to the incubator to incubate at 37° C. After 1 h, the nanoparticles were removed, and each well was washed with PBS (3×5.00 mL). The cells were then fixed using a 4% (mass fraction) paraformaldehyde solution (2.00 mL) in each well and allowing ambient temperature incubation for 1 h. After fixation, the cells were mounted in Prolong antifade mounting medium (Molecular Probes, Eugene, Oreg.) and viewed under bright field and fluorescent conditions using an Olympus IX-70 inverted microscope. The transduction tests were repeated using RPMI 1640 medium supplemented with 0.1% (mass fraction) sodium azide, and at 4 and 37° C. For quantification by flow cytometry, the transduction tests were repeated except that the cells were grown directly on the tissue cultured plates instead of glass cover slips. The cells were trypsinized to remove most of the surface bound particles and release the cells from the plate, centrifuged at 4° C., and resuspended in PBS and stored on ice briefly. Less than 5 min prior to flow cytometry analysis, propidium iodide (5.0 µL) was added to each centrifuge tube. Analysis was done on a FACS Calibur (BD Biosciences, Franklin Lakes, N.J.) instrument using CellQuest software.

Fluorescence and Confocal Microscopy. Confocal microscopy was accomplished using a Leica TCS SP2 scanning confocal microscopy system equipped with $Ar^+$, $Kr^+$, and HeNe laser systems. The excitation wavelength was 488 nm, and the emission was collected over the range of 510-530 nm. Optical slices were taken on 0.5 µm centers with the Leica software, compiling the collections of images into the 3-D reconstructions. The incubation and fixation testal parameters outlined previously were strictly adhered to in the confocal microscopy tests with the following exceptions. The cover slips from the 37° C. tests were mounted on slides fitted with a small spacer and PBS was added as the medium. These tests were repeated with cells being incubated at 4° C. for 1 h and washed and mounted with cold buffer. The cells were viewed for a maximum of 20 min as live whole, unfixed specimens.

Fmoc-Solid-Phase Synthesis of PTD on Resin. The protein transduction domain sequence (GGGGYGRKKRRQRRR) was synthesized by standard solid-phase synthesis using 9-fluorenylmethoxycarbonyl (Fmoc) chemistry. A small amount of beads were removed and washed with N-methylpyrrolidone (NMP), dimethylformamide (DMF), $CH_2Cl_2$, and methanol three times each. Peptide cleavage was achieved through treatment of the resin with a 10 mL 95% TFA: 2.5% triisopropyl silane (TIS): 2.5% water solution (volume fractions) for a minimum of 4 h. The solution was filtered, and the beads were rinsed with TFA. The solution was concentrated in vacuo, and the concentrate was precipitated into cold ether. The precipitates were effectively centrifuged at 3500 rpm for 10 min. The supernatant was decanted, the pellet was resuspended in cold ether, and the centrifugation process was repeated. The pellet was purified and recovered by reversed phase HPLC. MS (MALDI): 1789.5022 $[M+H]^+$ (calcd: 1788.03 MW). TFA is $C_2HF_3O_2$, available from AppliChem GmbH, Ottoweg 4, D-64291 Darmstadt, Germany Poly(tert-butyl acrylate) (2). A 100 mL Schlenk flask that had been oven-dried overnight, flame-dried under vacuum, and back-filled with argon was charged with copper(I) bromide (891.6 mg, $6.2 \times 10^{-3}$ mol). tert-Butyl acrylate (38.00 mL, $2.6 \times 10^{-1}$ mol), PMDETA (1.30 mL, $6.2 \times 10^{-3}$ mol), and ethyl-2-bromopropionate (403 µL, $3.1 \times 10^{-3}$ mol) were added via argon-washed syringes. The solution was degassed by three cycles of freeze-pump-thaw, and following the final thaw cycle, the mixture was stirred for 10 min before being immersed in an oil bath at 50° C. After 80 min, the polymerization was quenched by immersion in liquid nitrogen. The reaction mixture was dissolved in THF and passed through an alumina plug to remove the metal/ligand catalyst system. The polymer solution was concentrated and the product recoved by being precipitated into cold methanol. $M_n$ 7400 from SEC. based on MALS. $M_w/M_n$=1.12. The recovery yield of the isolated product was 28.83 g (85%). $(T_g)_{tBA}$=33° C. IR: 3440, 2980. 1750, 1450. 1380, 1265, 1150, 850, 760, 625 cm$^{-1}$. $^1$H NMR (CDCl$_3$) δ 1.05 (d, CH$_3$CH end group), 1.22 (t, CH$_3$CH$_2$O end group), 1.20-1.50 (broad, (CH$_3$)$_3$C), 1.24-1.70 (broad, meso and racemo CH$_2$ of the polymer backbone), 1.74-1.94 (broad, meso CH$_2$ of the polymer backbone), 2.15-2.35 (broad, CH of the polymer backbone), 4.05 (br overlapping m, CH$_3$CH$_2$O and CHBr end groups) ppm. $^{13}$C NMR (CDCl$_3$,) δ 27.9-28, 35.5-37.4, 41.5-41.4, 80.3, 173.6, 173.9 ppm.

Poly(tert-butyl acrylate-b-methyl acrylate) (3). A Schlenk flask (100 mL) was oven-dried overnight, flame-dried under vacuum, back-filled with argon, and charged with copper I bromide (184.1 mg, 1.3×10$^{-3}$ mol) and poly(tert-butyl acrylate) 2 (4.7381 g, 6.4×10$^{-4}$ mol). PMDETA (268 μL, 1.3×10$^{-3}$ mol) and methyl acrylate (30.00 mL, 3.3×10$^{-1}$ mol) were added via argon-washed syringes. The solution was degassed by three cycles of freeze-pump-thaw, and following the final thaw cycle, the mixture was stirred for 10 min before being immersed in an oil bath at 68° C. After 70 min, the polymerization was quenched by immersion in liquid nitrogen. The reaction mixture was dissolved in THF and passed through an alumina plug to remove the metal/ligand catalyst system. The polymer solution was concentrated and then precipitated into a cold methanol/water solution. $M_n$=23400 from SEC, based on MALS. $M_w/M_n$=1.13. The yield was 9.18 g (16%). $(T_g)_{PtBA}$=32° C. $(T_g)_{PMA}$=14° C. IR: 3650. 3450, 2970, 1990, 1550, 1450, 1180, 1080, 850 750. 625 cm$^{-1}$. $^1$H NMR (CDCl$_3$) δ 1.20-1.50 (broad, (CH$_3$)$_3$C), 1.25-1.95 (broad, CH$_2$ of the polymer backbone), 1.74-1.94 (broad, CH$_2$ of the polymer backbone), 2.15-2.40 (broad, CH of the polymer back-bone), 3.55-3.65 (broad. OCH$_3$,) ppm. $^{13}$C NMR (CDCl$_3$) δ 27.9-28, 35.5-37.4, 41.5-41.4, 51.5, 80.3, 173.4, 173.6 ppm.

Poly(acrylic acid-b-methyl acrylate) (4). The tert-butyl esters along the poly(tert-butyl acrylate) block of 3 were cleaved selectively by adding TFA (30.00 mL) to the diblock, 3 (8.5600 g. 3.66×10$^{-4}$ mol), in dichloromethane (100 mL). After 36 h, the solvent was evaporated in vacuo, and the residue was dissolved in THF and purified by dialysis in presoaked dialysis tubing (MWCO 12-14 kDa) against Nanopure (18.0 mΩ cm$^{-1}$) water for 3 days. Lyophilization yielded poly(acrylic acid-b-methyl acrylate) as a white powder. Yield: 7.25 g (98%); $(T_g)_{PAA}$=145° C. $(T_g)_{PMA}$=14° C. IR: 3500-2500, 1760, 1660, 1445. 1280, 1180, 1050, 850, 725, 610 cm$^{-1}$. $^1$H NMR (CDCl$_3$) δ 1.25-2.0 (broad, CH$_2$ of the polymer backbone), 1.74-1.94 (broad, CH$_2$ of the polymer backbone), 2.20-2.45 (broad, CH of the polymer backbone), 3.55-3.65 (broad. OCH$_3$,) ppm. $^{13}$C NMR (CDCl$_3$,) δ 34-36.4, 40.5-42.4, 50.5, 173, 178 ppm.

Micelle Formation. Polymer micelles of narrow size distribution were obtained by dissolving the block copolymer 4 (1.9968 g, 8.53×10$^{-5}$ mol) in THF (1.000 L, 1.997 mg/mL) followed by gradual addition (20.00 mL/h) of an equal volume of nonsolvent (H$_2$O) for the hydrophobic poly(methyl acrylate) to induce micellization. The micelles were stirred for 12 h before being transferred to presoaked and rinsed dialysis bags (MWCO 12-14 kDa) and dialyzed against Nanopure (18.0 MΩ cm$^{-1}$) water for 3 days to remove the organic solvent. The final volume was 2.250 L of aqueous micelle solution for a final concentration of 0.89 mg/mL. DLS: $D_n$=38 nm, ZETA: ζ=−27±0.7 mV, TEM: 21.3±3.8 nm.

Shell-Crosslinked (SCK) Nanoparticle Formation. 2,2'-(Ethylenedioxy)-bis(ethylamine) (192 μL, 1.3×10$^{-3}$ mol) was added to 2.125 L of micelle solution (0.90 mg/mL) of poly(acrylic acid-b-methyl acrylate). After 30 mm, an aqueous solution of 1-(3'-dimethylaminopropyl)-3-ethylcarbodiimide hydrochloride (2.0201 g, 1.05×10$^{-2}$ mol) was added to the reaction vessel. The reaction mixture was stirred for 24 h, and it was then dialyzed.

Figure 11:
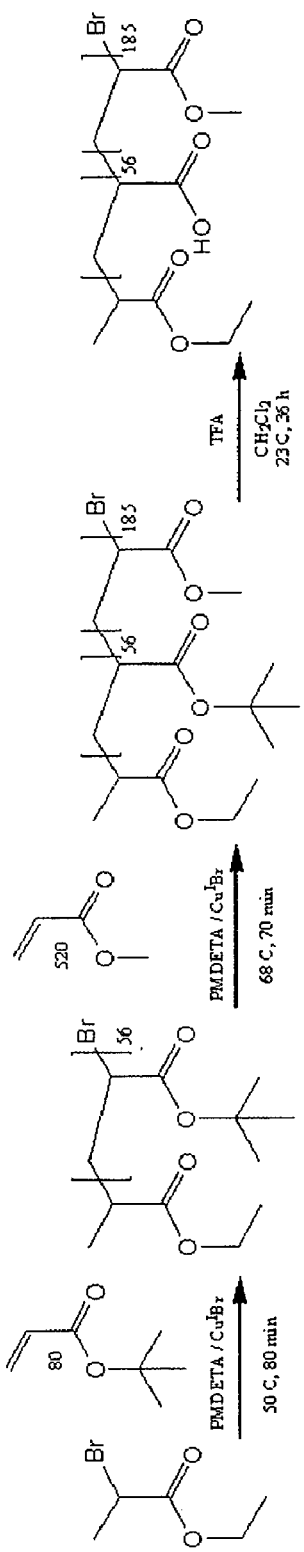
FIG. 11 shows that sequential ATRP of tert-butyl and methyl acrylate afforded well-defined poly (tert-butyl acrylate-b-methyl acrylate). The tert-butyl esters were successfully cleaved selectively through treatment of the diblock copolymer with TFA in $CH_2Cl_2$ for 36 hours.

FIG. 11 shows sequential atom transfer radical polimerization (ATRP) of tert-butyl acrylate and methyl acrylate afforded well-defined poly(tert-butyl acrylate-b-methyl acrylate)

The tert-butyl esters were cleaved selectively through treatment of the diblock copolymer with TFA in CH$_2$Cl$_2$ for 36 h, against Nanopure water for 3 days to remove residuals. The SCKs were dialyzed into 50 mM sodium phosphate. 50 mM sodium chloride, pH 7.4 buffer, and the number-average hydrodynamic diameter ($D_n$) of were determined by dynamic light scattering. DLS: $D_n$=37 nm. ZETA: ζ=−20±0.5 mV. TEM: 18.3±3.6 nm. AFM: 3.8±1.8 nm. IR: 3385, 2949, 1738, 1568, 1442, 1163, 829 cm$^{-1}$. DSC: $T_g$=15° C. $^1$H NMR (D$_2$O:THF-d$_8$, 1:2 (volume fraction)) δ 1-3.0 (aliphatic protons of polymer backbone), 3.50-3.70 (OCH$_3$) ppm.

General procedure for global solution state functionalization of (SCK) nanoparticles with various molar ratios of PTD. An SCK solution (50.00 mL, 0.895 mg/mL) was placed into a 100 mL round-bottom flask equipped with a stir bar. Sodium chloride (1.00 g) was placed into each of the flasks to minimize aggregation. A stock solution (50.00 mg/mL) of 1-(3'-dimethylaminopropyl)-3-ethylcarbodiimide hydrochloride in sodium phosphate buffer, pH 7.4 was prepared, and 1.00 mL aliquots (2.5×10$^{-4}$ mol) were added to each flask to activate the acrylic acid residues. A stock solution (18.21 mg/mL) of the PTD peptide was made in sodium phosphate buffer, pH 7.4, and aliquots of the solution were added to the respective flasks 20 min after the addition of the carbodiimide.

0.5% PTD Functionalized. A PTD stock solution (61 μL, 18.21 mg/mL, 6.25×10$^{-7}$ mol) was added to the activated SCK solution, and the mixture was allowed to react overnight. Following the allocated reaction time, the solution was transferred to presoaked dialysis tubing (MWCO 12-14 kDa) and allowed to dialyze for 3 days against 50 mM sodium phosphate, 50 mM sodium chloride, pH 7.4 buffer, prior to analysis. DLS: $D_n$=35±3 nm. ZETA: ζ=−28±0.9 mV. TEM: 20.2±3.7 nm.

1.0% PTD Functionalized. A PTD stock solution (123 μL, 18.21 mg/mL, 1.25×10$^{-6}$ mol) was added to the activated SCK solution, and the mixture was allowed to react overnight. Following the allocated reaction time, the solution was transferred to presoaked dialysis tubing (MWCO 12-14 kDa) and allowed to dialyze for 3 days against 50 mM sodium phosphate, 50 mM sodium chloride, pH 7.4 buffer, prior to analysis. DLS: $D_n$=36±3 nm. ZETA: ζ=−23±0.7 mV. TEM: 21.4±3.6 nm.

2.0% PTD Functionalized. A PTD stock solution (245 μL, 18.21 mg/mL, 2.50×10$^{-6}$ mol) was added to the activated SCK solution, and the mixture was allowed to react overnight. Following the allocated reaction time, the solution was transferred to presoaked dialysis tubing (MWCO 12-14 kDa) and allowed to dialyze for 3 days against 50 mM sodium phosphate, 50 mM sodium chloride, pH 7.4 buffer, prior to analysis. DLS: $D_n$=32±3 nm. ZETA: ζ=−22±0.5 mV. TEM: 21.6±3.3 nm.

General procedure for the conjugation of a fluorescent tag to the PTD-functionalized nanoparticles. The respective PTD-functionalized SCK solutions (10.00 mL, 0.895 mg/mL) ($2.24\times10^{-9}$ mol) were placed into 50 mL round-bottom flasks. A 4.0 M KCl solution (1.00 mL) was added to each flask. The vessels were allowed to equilibrate for 30 min before 0.500 mL of a 50 mg/mL carbodiimide stock solution ($1.25\times10^{-4}$ mol) was added to each vessel. After 15 min, 200 µL of a 0.400 mg/mL stock solution ($1.58\times10^{-7}$ mol) of the fluorescein derivative was added to each round-bottom flask, and the reactions were stirred overnight. The solutions were then transferred to successfully presoaked dialysis bags (MWCO 12-14 kDa) and allowed to dialyze for 3 days against 50 mM phosphate, 50 mM NaCl buffer at pH 7.4. The reaction resulted in approximately 70 fluorophores being coupled to each nanoparticle based on calculations assuming ideal reaction efficiency.

Results and Discussion

SCK Synthesis and Peptide Derivitization. The amphiphilic block copolymer precursor to the SCKs was prepared by sequential atom transfer radical polymerizations of tert-butyl acrylate and methyl acrylate followed by the selective acidolysis of the tert-butyl esters. The poly(tert-butyl acrylate) macroinitiator was afforded through the polymerization of tert-butyl acrylate at 50° C. for 80 min using ethyl 2-bromopropionate as the initiator and the Cu$^I$Br/PMDETA catalytic system. The chain was further extended through the addition polymerization of methyl acrylate in bulk in the presence of Cu$^I$Br/PMDETA at 68° C. for 70 min as shown in FIG. 11. By allowing the reaction to proceed under conditions of high dilution (in monomer), low conversion, and by using a liquid nitrogen quench, a narrow molecular weight distribution for the block copolymer was maintained. The tert-butyl esters were cleaved selectively upon reaction with TFA in $CH_2Cl_2$. The solvation of the purified poly(acrylic acid-b-methyl acrylate) block copolymer in tetrahydrofuran (1.99 mg/mL) followed by the controlled addition of Nanopure (18 MΩ cm) water (20.00 mL/h), and extensive dialysis against deionized water afforded micelles.

Figure 12:
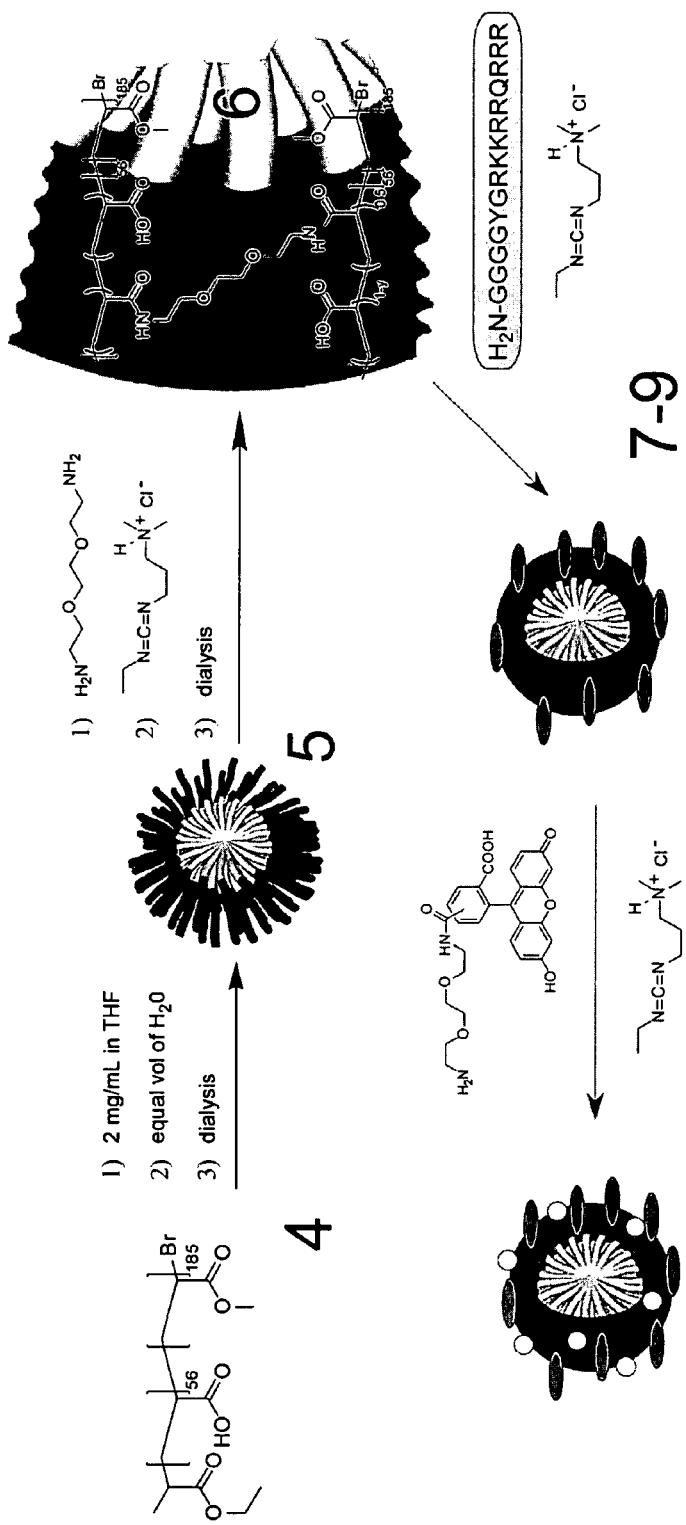
FIG. 12 shows that SCK (denoted as 6 in FIG. 12) was prepared through the micellization of the block copolymer 4, followed by the cross linking of approximately 50% acrylic acid residues in the shell layer with 2,2' (ethylenedioxy bis (ethylamine)) The SCKs (denoted as 7-9 in FIG. 12) were functionalized with various molar quantities of PTD under high ionic strength conditions to minimize aggregation and interparticle cross linking. A linker derivatized 5(6)-carboxyfluorescein dye (approximately 70 fluorophores per particle) was coupled to each of the SCK samples 6-9 to facilitate observation under fluorescence conditions.

SCKs were formed by intramicellar conversion of approximately 50% of the 1-[3'-(dimethylamino)propyl]-3-ethylcarbodiimide hydrochloride activated acrylic acid residues in the shell layer to amides using 2,2'-(ethyl-enedioxy)bis(ethylamine), as shown in process FIG. 12. The protein transduction domain sequence of HIV-1 Tat protein extended by four glycine residues (GGGGYGRKKRRQRRR) used in this study was chemically synthesized by Fmoc solid-phase peptide methodologies. The four additional glycine residues were placed at the N-terminus to function as a spacer between the active peptide sequence and the macromolecular assembly. The peptide was cleaved from the support, purified by reverse phase HPLC, and then coupled in 0.005, 0.01 and 0.02 molar ratios, relative to the acrylic acid residues within the SCK nanoparticles. The peptide coupling to the SCKs involved amidation of the N-terminus to the carboxylic acid residues within the SCK shell. The molar amounts correspond to approximately 52, 104 and 210 PTD sequences per particle, respectively, assuming complete conversion and using the aggregation number (185±7) of block copolymers within each particle. Following the conjugation, the respective solutions were then purified by dialysis against buffer for 5 days to remove the noncoupled peptide sequences. Non-coupled PTD was identified by UV measurements made at sedimentation equilibrium (SE), as described below.

The SCKs were effectively and successfully functionalized with various molar quantities of PTD under high ionic strength conditions to minimize aggregation and interparticle cross-linking in a global solution state functionalization process. A linker-derivatized 5(6)-carboxylfluorescein dye (approximately 70 fluorophores per particle) was coupled to each of the SCK samples 6-9 to facilitate observation under fluorescence conditions.

FIG. 12 shows the SCK (labelled "6" herein) was prepared through the micellization of the block copolymer labelled "4" therein, followed by the crosslinking of approximately 50% of the acrylic acid residues in the shell layer with 2,2'-(ethylenedioxy)-bis(ethylamine)$^a$ Molecular Weight and Aggregation Number. The absolute weight-average molecular weight, $M_w$, of PTD-functionalized SCK nanoparticles was evaluated by sedimentation equilibrium (SE) analysis. Representative SE data (fringe displacement versus radial position, r) are presented in FIG. 13(A). The partial specific volume, v, for the SCKs was also determined by SE using a methodology that employed sedimentation equilibrium profiles collected for the SCK dispersed in both protonated and deuterated buffer. Linear SE plots were obtained by plotting the log(fringe displacement) versus $r^2/2$ from which the slopes of the plots were determined and v was computed by use of $v=[k-(\sigma_D/\sigma_H)]/[(\rho_D-\rho_H(\sigma_D/\sigma_H)]$ where $\rho_D$ is the density of the deuterated buffer, $\rho_H$ is the density of the protonated buffer, and k is the ratio of the molar masses for the deuterated SCK to the protonated SCK.

Figure 13:
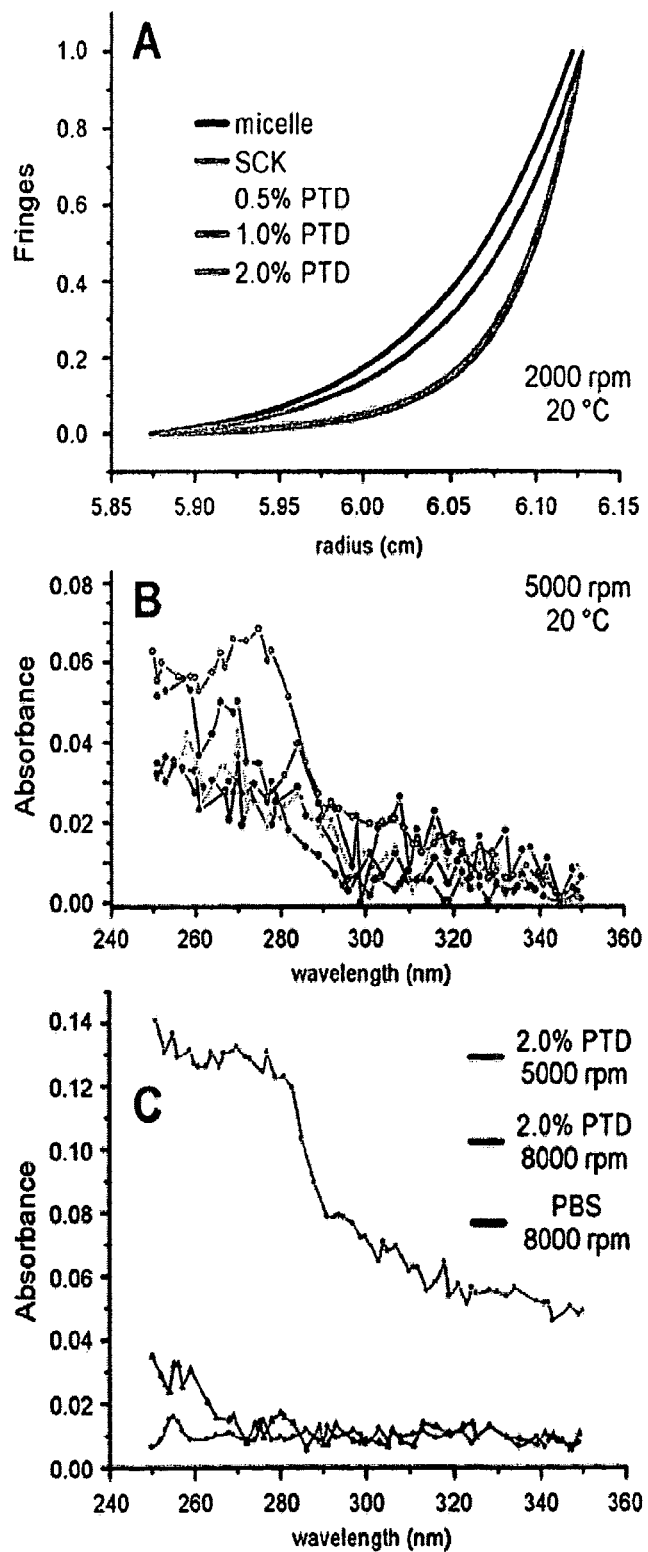
FIG. 13 shows the sedimentation equilibrium profiles the inventors collected using an interferometry detector for the micelles, SCKs and peptide-functionalized nanoparticles.

SE analysis of $M_w$ employed the nonlinear, least-squares fitting of sedimentation equilibrium profiles represented by the data in FIG. 13(A) to a single-component model with $\rho_H$ and v held constant as measured parameters. The initial concentration of the nanoparticle at the mensicus, $c_0$, of the sedimentation column, the baseline offset, $N_0$, and an apparent weight-average molecular weight, $M_{w,app}$, were calculated as adjustable parameters in the fitting procedure. The computed $M_{w,app}$ when expressed as $1/M_{w,app}$ and plotted against the initial loading concentration of SCK nanoparticle (FIG. 13(C)) showed a dependence on both c and the rotor speed. The observed trends are indicative of molecular weight heterogeneity and nonideal sedimentation due to interparticle interactions or cross-linking. Extrapolation of $1/M_{w,app}$ to zero concentration for the lowest rotor speed employed provided the evaluation of $M_w$. As summarized in Table 1, the 0% PTD-functionalized SCK nanoparticle produced a v of 0.556±0.007 mL/g, resulting in a $M_w$ of 4,000,000±151,000 g/mol. Dividing $M_w$ by the copolymer weight-average molecular weight, corrected for the molar mass increase due to 50% cross-linking of each copolymer chain (664 g/mol) resulted in a weight-average degree of aggregation, $N_{w,agg}$, of 185±7. The absolute weight-average molecular weights, $M_w$, of the PTD-functionalized SCK nanoparticles were also evaluated by SE analysis. Interestingly, $M_w$ for the 0.5%, 1%, and 2% PTD-functionalized SCKs were 31%, 37%, and 41% higher, respectively, than $M_w$ for 0% functionalized SCK. Functional-ization of the preformed SCK (0% PTD) with the peptide was expected to produce small $M_w$ increases through the incremental addition of molar mass from the PTD. The observed increases in $M_w$ exceed the expected increase by at least 10-fold, suggesting that functionalization with PTD was accompanied by a small percentage of internanoparticle cross-linking reactions or electrostatic aggregation events due to the zwitterionic character of the PTD-functionalized nanoparticles.

Collection of SE profiles using UV-visible detection optics allowed the analysis of the peptide content of the nanoparticles at centrifugation equilibrium. Free peptides were uniformly dispersed throughout the solution volume while the relatively massive particles were depleted from the meniscus along with the peptides bound to them. Therefore, the amount of free vs SCK-bound peptide in solution was determined by the ratio of absorbance at the meniscus to the absorbance of the unfunctionalized micelle and SCK. No absorbance for the tyrosine ($\lambda_{276}$) was detected near the meniscus in the 0.5% and 1.0% solutions relative to controls at 5,000 rpm, indicating that all of the absorbance from the tyrosine residue of the PTD sequence is associated with the SCK nanoparticle as shown in FIG. 13(B).

A slight amount of absorbance observed for the 2.0% functionalized SCK solution suggested free peptide in solution however, increasing the rotor speed to 8,000 rpm, which depleted the meniscus of nanoparticles, indicated that no free peptide was present in the solution (FIG. 4). This measurement is of particular importance for two reasons: (1) the presence of free peptide can compete with and inhibit the binding of the bioconjugate, and (2) the PTD sequence has measurable effects on in vitro cell viability and inflammatory response.

FIG. 13(A) shows sedimentation equilibrium profiles collected using an interferometry detector for the micelles, SCKs, and peptide-functionalized nanoparticles. The dramatic increase in weight average molecular weight ($M_w$) was due to a small percentage of interparticle crosslinking (covalent or electrostatic), which contributed significantly to the molecular weight calculations, FIG. 13(B) shows UV spectra, recorded near the meniscus of solutions at sedimentation equilibrium, showed negligible absorbance due to free tyrosine residues within the PTD, relative to controls. FIG. 13(C) shows repeating the test at 8,000 rpm indicated that the meniscus was fully depleted of SCK at 8,000 rpm, but not at 5,000 rpm, and also confirmed that all the PTD was attached to the SCK.

Particle Analysis. The SCK nanoparticles were characterized extensively to probe for the differences in size, surface charge, and morphology as a result of post-cross-linking functionalization with the arginine-rich PTD sequence. Dynamic light scattering (DLS) measurements were collected in PBS, pH 7.4. This precaution was used to minimize dilute solution aggregation of the nanoparticles. The polymeric micelle precursor to the SCK was shown to have a number-average diameter, $D_n$, of 38±3 nm. The corresponding SCK, prepared with 50% cross-linking of its shell, was found to have a $D_n$ of 37±2 nm. A comparison of $D_n$ values calculated using the nonnegatively constrained least squares (NNLS) model for the diameter distributions of the 0.5% (7), 1.0% (8), and 2.0% (9), PTD-functionalized nanoparticles resulted in values of 35±3, 36±3, and 32±4 nm, respectively. When the volume-average diameter, $D_v$, and the intensity-average diameter, $D_z$, distributions for the nanoparticles were calculated, the presence of small amounts of aggregated species, representing a maximum of 5 vol %, was apparent in the $D_v$ and $D_z$ diameter distributions. The likely source of these larger diameter fractions is interparticle crosslinking due to the presence of the PTD sequence; however, it is unknown whether the nature of the aggregation arises from covalent cross-linking or electrostatic attraction. These findings are consistent with the large increases noted in $M_w$ for the PTD-functionalized SCKs relative to $M_w$ obtained for preformed SCK, 6. Since these aggregated species were less than 100 nm in diameter, filtration and/or dialysis were not effective in their removal from the majority population of smaller nanoparticles. However, because these species represent less than 1% of the nanoparticle population by number, the contribution of these aggregates to data sets collected using imaging methods, such as atomic force microscopy (AFM), transmission electron microscopy (TEM) and confocal fluorescence microscopy, was negligible. Analysis of the SCKs by TEM depicted circular shapes that possessed narrow size distributions. The observed TEM nanoparticle diameters were smaller than those measured as $D_n$ in buffer solution, due to drying and the effects of the phosphotunstic acid staining process employed during the TEM sample preparation. Zeta potential measurements also showed a diminishment in the negative surface charge density with increasing functionalization. The zeta potential ($\zeta$) data for the functionalized SCKs are included in Table 1.

Figure 14:
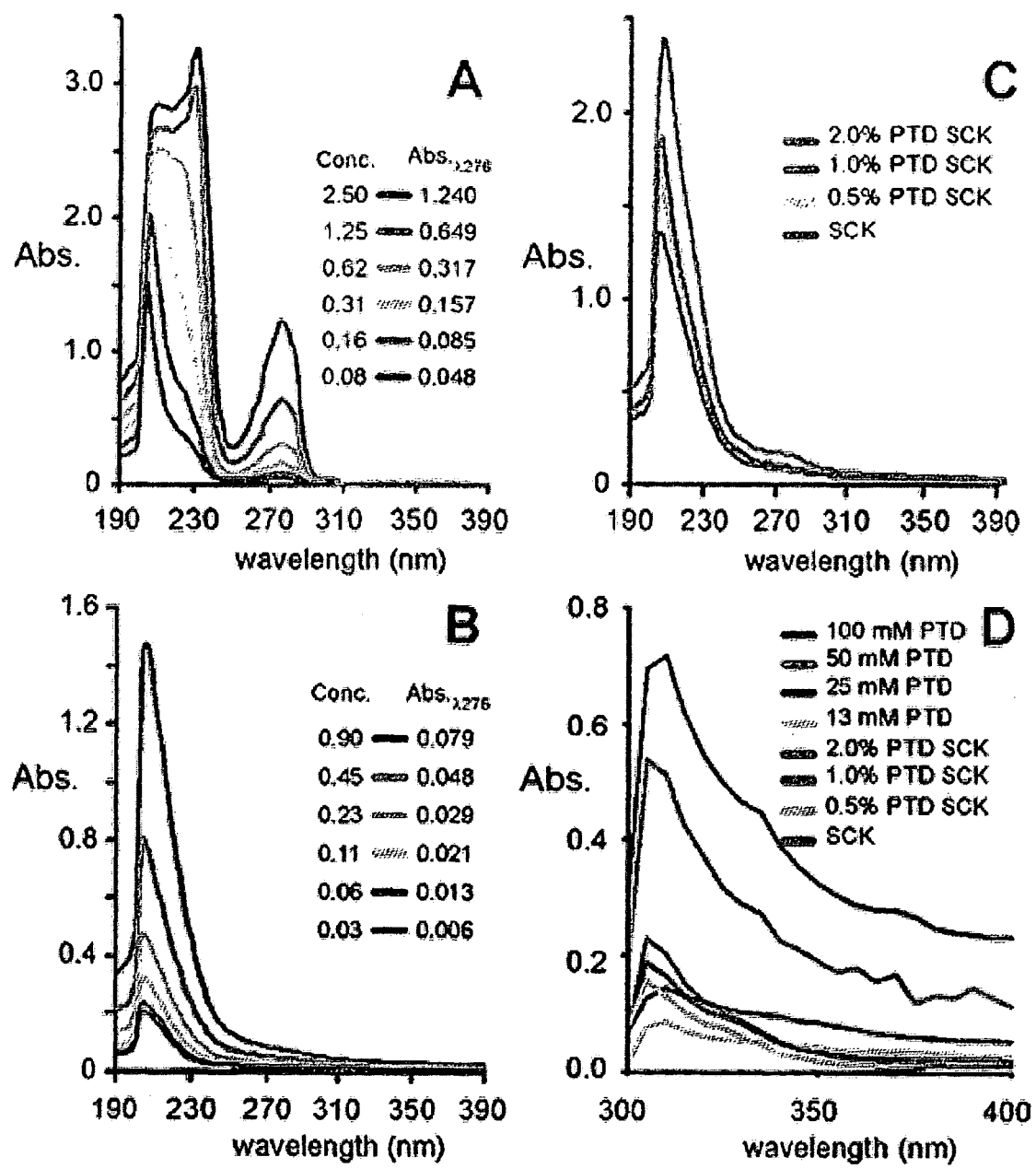
FIG. 14 shows UV visible spectroscopy which afforded the quantitative calculation of the number of peptides per particle by two different methods. The first method involved the simultaneous solving of two unknowns as determined from PTD (FIG. 14(A)) and SCK (FIG. 14(B)) concentration calibration plots at 230 nm and 276 nm. From the calibration curves generated from FIG. 14(A) and FIG. 14(B), the concentration of PTD in the respective SCK solutions shown in FIG. 14(C) were calculated. The large number of peptides calculated to be in the 2.0% sample is believed to be a result of the slight amount of turbidity present in that sample due to aggregation which is reflected in the absorbance measurement of that sample (orange). The second method involves the measurement of phenylglyoxal derivative formation FIG. 14(D). Phenylglyoxal reacts specifically with the guanidine groups on the side chains of arginine residues yielding a derivative with an absorbance red shifted (310 nm) from that of the parent compound. From a calibration curve generated from known amounts of PTD, the molar concentration of the peptide in unknown solutions was determined. Molar ratios were then applied to quantify the number of peptides per particle.

Quantification of PTD Functionalization. The number of peptides per particle in each sample was quantified using UV-visible spectroscopy and reaction of phenylglyoxal with the guanidine functionality of arginine as two independent methods of analysis. The number of peptides per particle was measured from UV spectroscopy (Equations 1-9) by solving simultaneously for the peptide and SCK concentration using absorbance measurements recorded at two different wavelengths, $\lambda_{230}$ and $\lambda_{276}$. Analysis of SCK samples 7, 8, and 9 resulted in values of 38, 86, and ~500 peptides per particle, respectively. The large number of peptides measured in sample 9 is a result of a slight amount of turbidity arising from aggregation, which dominates the absorbance measurement at 230 nm as shown in FIG. 14. The coupling efficiency was approximately 80% and correlated well with the expected peptide numbers.

FIG. 14 shows UV-visible spectroscopy afforded the quantitative calculation of the number of peptides per particle by two different methods. The first method involved the simultaneous solving of two unknowns as determined from PTD (A) and SCK (B) concentration calibration plots at $\lambda_{230}$ and $\lambda_{276}$. From the calibration curve generated from FIG. 14(A) and FIG. 14(B), the concentration of PTD in the respective SCK solutions (FIG. 14(C)) was calculated. The large number of peptides calculated to be in the 2.0% sample is a result of the slight amount of turbidity present in that sample due to aggregation, which is reflected in the absorbance measurement of that sample (orange). The second method involves the measurement of phenylglyoxal derivative formation (FIG. 14(D)). Phenylglyoxal reacts specifically with the guanidine groups on the side chains of arginine residues yielding a derivative with an absorbance red-shifted ($\lambda_{310}$) from that of the parent compound. From a calibration curve generated from known amounts of PTD the molar concentration of the peptide in unknown solutions was determined. Molar ratios were then applied to quantify the number of peptides per particle.

The second assay performed to quantify the number of peptides per particle employed absorbance measurements at 310 nm, which exhibited a negligible contribution from solution turbidity. Phenylglyoxal reacts specifically with the guanidine group of arginine residues under mild conditions. The PTD sequence contains six arginine residues which react with one phenylglyoxal moiety each in a mechanism outlined by Jairajpuri et al. (Biochem., 1998, 37, 10780-10791).

Measurements made using this method, again comparing molar ratios, resulted in degrees of functionalization of 41, 83, and 202 peptides for 7, 8, and 9, respectively. These values are in good agreement with the dual wavelength, simultaneous UV spectroscopic determinations for the degree of functionalization in 7 and 8. The value 202 determined by the phenylglyoxal method for 9 was in better agreement with expected values based on the measured $M_w$ for the SCK (Table 1). The validity of the phenylglyoxal method as a specific assay for the PTD moieties attached to a SCK was also confirmed by performing the same testal conditions for the nonfunctionalized SCK, as a negative control test, which showed no absorbance due to the phenylglyoxal derivatization and thus no reaction of phenylgloxal with the unfunctionalized SCK, (6).

Figure 15:
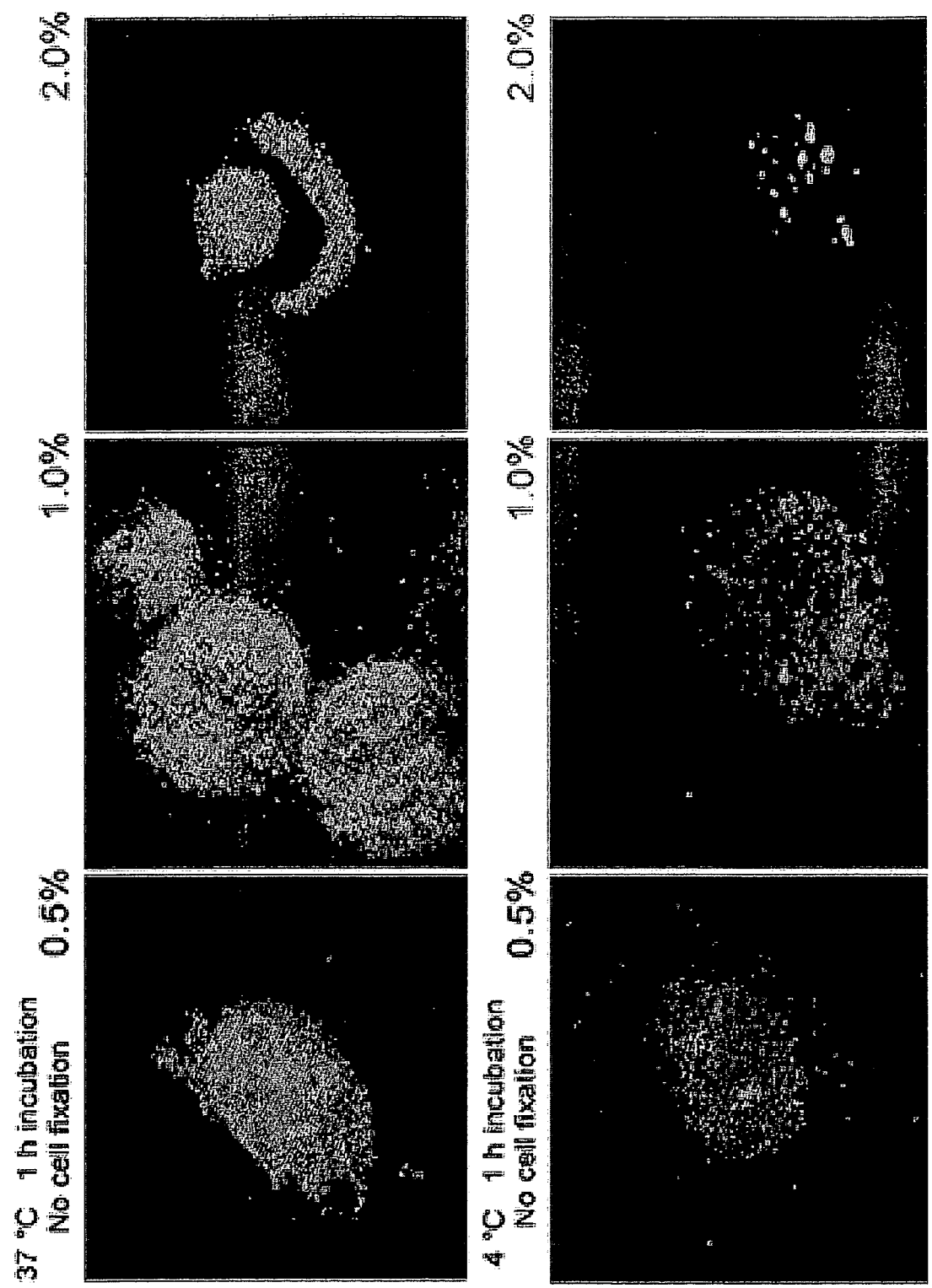
FIG. 15 depicts live cell confocal fluorescence microscopy showing internalization of the 0.5, 1.0 and 2.0% PTD-functionalized nanoparticles at both 37° C. and 4° C. in CHO cells. No uptake or internalization was seen for the unfunctionalized parent SCK under live cell conditions.

FIG. 15 shows live cell confocal fluorescence microscopy showing successful internalization of the 0.5, 1.0 and 2.0% PTD-functionalized nanoparticles at both 37° C. and 4° C. in CHO cells. No uptake or internalization was seen for the unfunctionalized parent SCK under live cell conditions.

Cell Transduction Tests. A mixture of 5 and (6)-carboxyfluorescein derivatized with a 2,2'-(ethylenedioxy)bis-(ethylamine) linker was conjugated to the PTD-functionalized nanoparticles to visually image binding interactions of the conjugates with mammalian cells using fluorescence microscopy. This type of fluorophore derivatization does not contribute to enhanced cellular uptake. The conjugation was performed on a molar equivalence basis and resulted in approximately 70 dye molecules per particle, assuming complete conversion. Free dye did not contribute to the analysis, as it was removed via dialysis against PBS. The cell uptake of PTD-functionalized SCKs was investigated by the in vitro transduction of CHO cells. Numerous examples exist describing the sequence specificity, mechanism, cofactor, and cell-type dependence on the efficiency of cellular uptake. The mechanism, efficiency, and energy dependence of the particle translocation was investigated in this instance by varying the metabolic conditions of the tests. Conditions included 1 h incubation times at 37° C. and 4° C. in serum free media, and in the presence of 0.1% sodium azide. Bright field, fluorescence, and confocal microscopies were performed on live cells as well as specimens that were fixed through 1 h incubations at ambient temperature in a 4% paraformaldehyde solution. Confocal microscopy of fixed cells clearly showed an accumulation of the fluorescent PTD functionalized nanoparticles inside the cells in all cases. Although the nonfunctionalized nanoparticles are also internalized, the apparent fluorescence intensities are qualitatively less than those of the PTD functionalized particles. Since fixation of cells involves the inherent perturbation of the cellular membrane, live cells were viewed without fixation to see whether rapid internalization occurred without the benefit of fixation.

Figure 16:
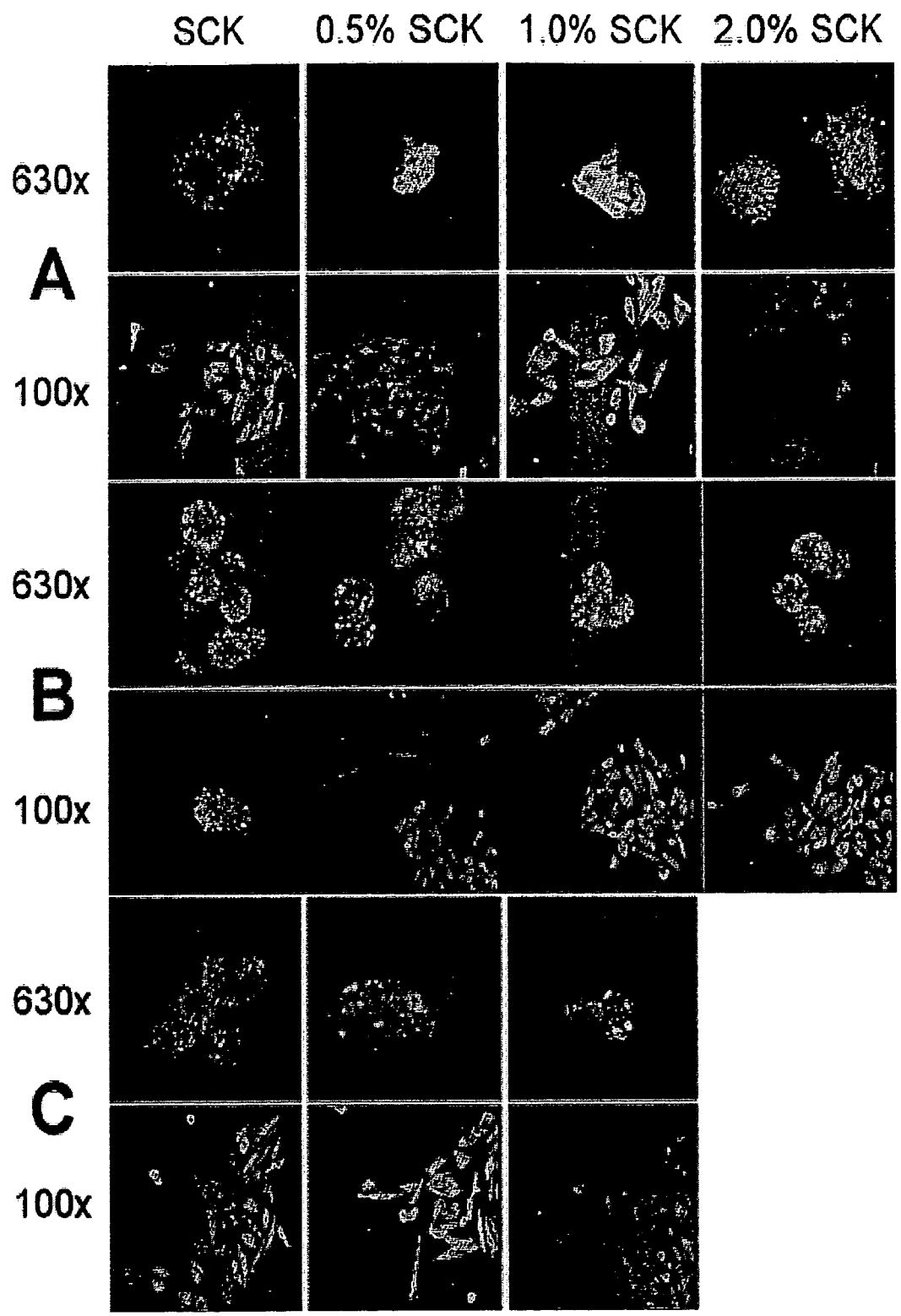
FIG. 16 shows confocal fluorescence microscopy of PTD-functionalized SCKs using CHO cells fixed with a 4% paraformaldehyde solution. It shows nonspecific uptake of the nonfunctionalized SCKs which was not observed in live cell tests, in addition to the qualitatively enhanced uptake in each of the PTD functionalized samples.
Figure 17:
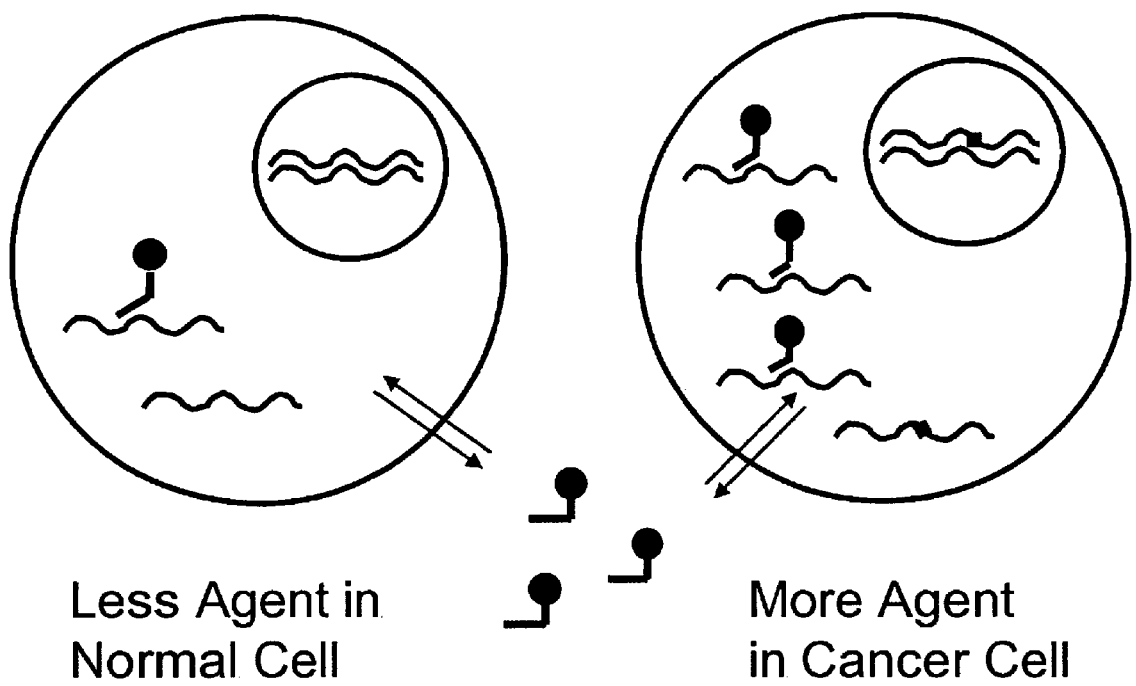
FIG. 17 is an inventors' schematic depicting antisense cellular targeting of prodrugs and probes.

FIG. 16 shows confocal fluorescence microscopy of PTD-functionalized SCKs using CHO cells fixed with a 4% paraformaldehyde solution commonly used in the literature, shows nonspecific uptake of the nonfunctionalized SCKs. which was not observed in the live cell tests, in addition to the qualitatively enhanced uptake in each of the PTD functionalized samples. FIG. 16(A) and FIG. 16(B) show the confocal reconstructions of the respective SCK samples at 37° C. and 4° C., respectively, following 1 h incubations and cell fixation. FIG. 16(C) shows CHO cells that were incubated for 1 h in 0.1% sodium azide with the SCK samples.

In the cases where the cells were not fixed with the 4% paraformaldehyde solution, the non-PTD-functionalized SCKs were not observed in the intracellular space under fluorescence conditions when incubated at 37° C. or 4° C., and therefore it was determined that they were either not internalized nonspecifically or not at a level that was readily measurable using optical or fluorescence microscopies. However, the 0.5%, 1.0%, and 2.0% PTD-functionalized SCK nano-particles were readily internalized at 37° C., 4° C., and in the presence of 0.1% sodium azide, regardless of disruptive fixative processes that may or may not contribute to an enhanced nonspecific effect.

Flow Cytometry Analysis. The efficiency of PTD-functionalized SCK cell transduction was quantified by fluorescence activated cell sorting (FACS). Data in Table 2 following, which indicate the percentage of cells that are fluorescent for the respective samples, depict a trend of increasing cell transduction efficiency with increasing PTD/SCK stoichiometry. The slight decrease in the efficiency of uptake at 4° C. and in the presence of sodium azide, which depletes cellular ATP, relative to measured values at physiological temperatures show that endocytotic processes are also contributing to the SCK internalization. However, it is evident that non-endocytotic pathways contribute significantly to cell entry. While FACS analysis of the PTD-functionalized SCKs suggests multiple mechanisms of uptake, the intracellular internalization as visualized by live cell confocal microscopy is evident FACS analysis does not discriminate between internalized and surface bound particles, and efforts to further quantify the efficiency of uptake and exchange of the respective samples by radiolabeling methods are ongoing. The involvement of a single cellular process governing the internalization process has been shown to be increasing unlikely. While the ionic interactions between the TAT-derivatized species and the cell membrane are generally thought to be the initial step in the internalization process, the overall negative surface charge density, as measured by zeta potential, of the PTD-functionalized SCK nanoparticles suggest that further evidence is required to bolster that assessment. Recently, Dowdy et al. (Nat. Med., 2004, 10, 310-315) have shown that TAT-fusion proteins were internalized in a multistep process starting with a receptor-independent association of the fusion protein with the cell surface followed by a lipid raft-dependent macropinocytosis, which was demonstrated to be independent of interleukin-2 receptor/raft-, caveolar- and clathrin-mediated endocytosis. While these findings shed critical new and thorough insights on the mechanism of internalization, additional research on the nature of the initial construct-cell surface association step is needed.

The assembly of well-defined polymeric nanoparticles has been described, and subsequent functionalization of the SCK nanoparticles with PTD has been shown to facilitate their transduction across cellular membranes. The numbers of peptides per SCK were controlled through stoichiometric balance and measured by two independent methods. The feasibility and efficiency of intracellular internalization were quantified and confirmed.

TABLE 1

Summary of Physical Characterization Data
Collected for the Parent SCK Nanoparticle and the PTD-Functionalized SCKs

| particle | v(L/g) | $M_w$ (×$10^6$ Da) | no. of peptides | $\zeta$(V) | DLS $D_n$ (nm) | TEM $D_{av}$ (nm) |
|---|---|---|---|---|---|---|
| micelle | n.d. | n.d. | 0 | −27 ± 0.7 | 38 ± 3 | 21.3 ± 3.8 |
| SCK | 0.556 ± 0.007 | 4.004 ± 0.151 | 0 | −20 ± 0.5 | 37 ± 2 | 18.3 ± 3.6 |
| 0.5% | 0.587 ± 0.009[a] | 5.900 ± 0.241 | 52 ± 2 | −28 ± 0.9 | 35 ± 3 | 20.2 ± 3.7 |
| 1.0% | 0.622 ± 0.009 | 7.017 ± 0.304 | 104 ± 4 | −23 ± 0.7 | 36 ± 3 | 21.4 ± 3.6 |
| 2.0% | 0.661 ± 0.007 | 7.818 ± 0.248 | 210 ± 10 | −22 ± 0.5 | 32 ± 4 | 21.6 ± 3.3 |

TABLE 2 the Quantification of PTD Functionalization in Each of the Respective SCK Samples Using Two Different Methods Afforded Similar Numbers of Peptides Per Particle

| particle | no. of peptides nominal | no. of peptides UV-vis | no. of peptides phenylglyoxal |
|---|---|---|---|
| SCK | 0 | 0 | 0 |
| 0.5% | 52 ± 2 | 38 | 41 |
| 1.0% | 104 ± 4 | 87 | 83 |
| 2.0% | 210 ± 10 | ~500 | 202 |

TABLE 3

Percentage of Fluorescent CHO Cells Following the Transduction of Fluorescein-Labeled SCKs and PTD-Functionalized SCKs Quantified by Fluorescence-Activated Cell Sorting

| particle | 37° C. | 4° C. | 37° C. w/NaN$_3$ | 4° C. w/NaN$_3$ |
|---|---|---|---|---|
| SCK | 5.6 | 7.3 | 5.2 | 7.1 |
| 0.5% | 33.9 | 10.3 | 16.3 | 8.5 |
| 1.0% | 42.9 | 32.6 | 25.7 | 12.3 |
| 2.0% | 47.0 | 36.4 | 51.8 | 13.8 |

EXAMPLE SET C

Peptide-Derivatized Shell-Cross-Linked Nanoparticles and Associated Biocompatibility Evaluation The inventors used conjugation of the protein transduction domain (PTD) from the HIV-1 Tat protein to shell cross-linked (SCK) nanoparticles as a method to successfully facilitate cell surface binding and cell transduction.

Following assembly, the constructs (SCKs) were evaluated in vitro and in vivo to obtain a preliminary biocompatibility assessment. The effects of SCK exposure on cell viability were evaluated using a metabolic 3-(4,5-dimethylthiazol-2-yl)-2,5-diphenyl-2H-tetrazolium bromide (MTT) and a fluorescent apoptosis assay. Furthermore, stages of apoptosis were quantified by flow cytometry. Although higher levels of peptide functionalization resulted in decreased metabolic function as measured by MTT assay, advantageously significant apoptosis was not observed below 500 mg/L for our samples.

To evaluate the potential immunogenic response of the peptide-derivatized constructs, a real-time polymerase chain reaction (RT-PCR) system that allows for the in vitro analysis and quantification of the cellular inflammatory responses tumor necrosis factor alpha (TNF-α) and interleukin-1 beta (IL1-β) was utilized. The inflammatory response to the peptide-functionalized SCK nanoparticles as measured by RT-PCR show statistically significant increases in the levels of both TNF-α and IL1-β relative to tissue culture polystyrene (TCPS). Fortunately, the measured cytokine levels did not preclude the further testing of SCKs in an in vivo mouse immunization protocol. In this limited assay living mice, measured increases in immunoglobulin G (IgG) concentration in the sera were minimal with no specific interactions being isolated, and more importantly, none of the mice (>50) subjected to the three 100 μg immunization protocol have died. Additionally, advantageously no gross morphological changes were observed in postmortem organ histology examinations.

Test Procedures

Materials. Fmoc-protected amino acids and preloaded solid-phase Wang resins were purchased from NovaBiochem-CalBiochem Corp (San Diego, Calif.). Sodium dodecyl sulfate (SDS), 3-(4,5-dimethylthiazol-2-yl)-2,5-diphenyl-2H-tetrazolium bromide (98%) (MTT), Tween20, mouse IgG (Fc, Sigma I-8765), and goat anti-mouse IgG alkaline phosphatase conjugate (Fc specific, Sigma A-1418) were purchased from Sigma Aldrick (St. Louis, Mo.). Alkaline phosphate substrate solution was purchased from BioRad (Hercules, Calif.). Spectra/Por dialysis membranes (Spectrum Laboratories, Inc., Rancho Dominguez, Calif.), 96-well polystyrene plates (Falcon), and ELISA plates (Nunc-Immuno, Maxisorp) were purchased from Fisher Scientific Company (Pittsburgh, Pa.). QuantiTect SYBR Green RT-PCR Kit and Rneasy Kit were obtained from Qiagen (Valencia, Calif.). Primer identification, isolation, and probe development were nearly identical to methods described in Bailey et al. (J. Biomed. Mater. Res., 2004, 69, 305-313 and J. Dental. Res., 2004).

Certain commercial materials and equipment are identified in this specification in order to specify adequately the test procedure. In no instance does such identification imply recommendation by the National Institute of Standards and Technology nor does it imply that the material or equipment identified is necessarily the best available for this purpose.

The Animal Facility at the Washington University Department of Biology in St. Louis, St. Louis, Mo. performed immunizations, sera collections, and organ histology. Animal studies were conducted under Protocol 20010343 approved by the Animal Studies Committee of Washington University in St. Louis, St. Louis, Mo.

Cell Lines. Mouse myeloma B cells (ATCC, Manassas, Va.), CRL-1581.1, and CHO cells (ATCC) were obtained as gifts from Washington University in St. Louis, St. Louis, Mo. Mouse myeloma B cells were cultured in RPMI (Life Technologies, Rockville, Md., USA) 1640 medium using TCM serum replacement (10%, volume fraction) obtained from Celox Laboratories (St. Paul, Minn.). RAW 264.7 cells were purchased from ATCC. RAW 264.7 and CHO cells were maintained in RPMI supplemented with 10% (volume fraction) heat-inactivated fetal bovine serum (FBS, Life Technologies, Rockville, Md., USA), in 5% $CO_2$:95% air (volume fractions) at 37° C. To harvest, RAW 264.7 cells were washed with calcium- and magnesium-free phosphate-buffered saline and subsequently incubated with Hank balanced salt solution (HBSS) to promote release from the flask.

Determining Cell Viability via MTT Assay. Mouse myeloma B cells were counted and diluted into fresh media at concentrations of 50,000 cells/mL and an aliquot (100 μL) was seeded to each well in a 96-well plate. After deposition of the cell suspension, the plates were placed in an incubator (37° C., 5% $CO_2$, volume fraction) and allowed to grow for 24 h. Fresh 96-well plates were loaded with sterile buffer (40 μL), and the first column of each row was loaded with polymer or SCK stock solutions of known concentration. The first columns in each plate were then diluted serially from columns 2 to 11. The last columns were held as controls with no polymer or SCK added. Fresh medium (50 μL) was then added to every well in the plates. The original plates were removed from the incubator, and the premixed sample solutions were added to the corresponding wells in each plate. After 24 h incubation, the inoculated plates were removed from the incubator, and an aliquot of MTT (Sigma) (20 μL, 5.00 mg/mL) in PBS (0.05 mol/L phosphate, 0.05 mol/L sodium chloride, pH 7.4) was added to each well. The plates were returned to the incubator and allowed to equilibrate for 2 h. After 2 h, extraction buffer (80 mL, 20% (mass fraction) SDS (Sigma) in 50:50 DMF:$H_2O$, volume fraction, pH 4.7) was added to each well to extract the aqueous insoluble formazan product. The plates were then returned to the incubator for 18 h to allow for the extraction after which the absorbance of each solution was measured at 560 nm. Concentrations were determined by the weight of lyophilized polymer sample dissolved in PBS and then adjusted for the dilution of the medium. Results are an average of four values, and the standard deviation is reported for each concentration.

Apoptosis Assay. Apoptotic analysis of RAW 264.7 cells was assessed using the Guava Nexin Kit (Guava Technologies, Hayward, Calif.). RAW 264.7 cells were plated in 12-well plates at 50,000 to 100,000 cells per well and allowed to adhere for 24 h, after which the cells were inoculated with 100 μL aliquots of the respective samples. The initial quantity of SCK was suspended in 0.500 mL of PBS. The respective samples were subsequently added to RAW 264.7 cultures (100 μL). After 24 h, the media was removed from the cells, and the cultures were washed with PBS. To promote release from the plate, the cells were incubated with 1 mL of HBSS for 30 min. The cells were then gently removed from the plate, and the volume was adjusted to 300 μL. The cell suspension was incubated with 5 μL of Nexin 7-AAD and 5 μL of Annexin V-PE for 5 min in a light-protected environment and subsequently analyzed.

Flow Cytometry. Apoptotic analysis of RAW 264.7 cells incubated on the thin films or in the presence of the nanoparticles was assessed using the Guava Nexin Kit (Guava Technologies, Hayward, Calif.). RAW 264.7 cells were plated in 24-well plates (50,000 to 100,000) cells per well and allowed to adhere on tyrosine-derived polycarbonate thin films or tissue culture polystyrene for 24 h prior to analysis by flow cytometry. Full testal details were described previously.

mRNA Extraction. Cells were plated in sterile 150 mm×25 mm nonpyrogenic polystyrene dishes (Daigger, Vernon Hills, Ill.). SCK nanoparticles were added to plated cells 24 h following seeding. The mRNA extraction was carried out using the materials and protocol provided in the Rneasy Kit from Qiagen (Valencia, Calif.). The mRNA extraction protocol was followed according to the manufacturer's specification, except a 21-gauge needle was used to homogenize the sample. The RNA was treated with RNA Secure immediately following elution and stored at −20° C. Standard spectrophotometric measurements were taken, and a 2% (mass fraction) agarose gel stained with 10 μg/mL ethidium bromide (Sigma, St. Louis, Mo.) was used to image the RNA. Densitometry was performed using the Versa Doc imaging system (Bio-Rad, Hercules, Calif.).

Standards. The plasmids containing the cDNA inserts for TNF-α, IL-1β, and the 18 S ribosomal subunit were purchased from ATCC. The plasmids were grown in luria-bertani (LB) medium (ATCC, medium 1065) with 100 μg/mL of ampicillin for selection purposes. Plasmid DNA was isolated using the Plasmid Giga Kit (Qiagen, Valencia, Calif.) following the Qiagen's protocol. Spectrophotometric measurements were made at 260 nm, and a 1% (mass fraction) agarose gel stained with 10 μg/mL ethidium bromide (Sigma, St. Louis, Mo.) was used to image the DNA. Densitometry was performed using the Versa Doc imaging system (Bio-Rad, Hercules, Calif.).

Primer Design. Primers were designed using Primerfinder (Whitehead Institute for Biomedical Research) for the RT-PCR tests. The primers generated were used in both PCR and RT-PCR tests. They are as follows: 18S: 5' AGCGAC-CAAAGGAACCATAA 3' and 3' CTCCTCCTCCTC-CTCTCTCG 5'; TNF-α: 5' TTTCCTCCCAATACCCCTTC 3' and 3' AGTGCAAAGGCTCCAAAGAA 5'; IL-1β: 5' TGTGAAATGCCACCTTTTGA 3' and 3' GTAGCTGCCA-CAGCTTCTCC 5'.

The amplicons generated from these primers are 204 base pairs, 202 base pairs, and 205 base pairs, respectively. DNA sequencing was performed using the Big Dye Terminator Kit (ABI, Foster City, Calif.) on a 310 DNA Genetic Analyzer (ABI, Foster City, Calif.).

RT-PCR. RT-PCR was carried out using the QuantiTect SYBR Green RT-PCR Kit and protocol (Qiagen, Valencia, Calif.). All RT-PCR tests were performed using the iCycler (Bio-Rad, Hercules, Calif.). The protocol utilizes the following thermal parameters: Reverse Transcription: 30 min at 50° C. Activation step: 15 min at 95° C. Three-step cycling: denaturation for 30 seconds at 95° C., annealing for 2 min at 57° C., extension for 2 min at 72° C. for 45 cycles. A melt curve was subsequently performed to analyze the products generated, which began at 50° C. and increased to 95° C. in 1° C. increments.

Immunization of Mice. For each sample, five live mice (female, balb c, 7 weeks old) were inoculated with 100 μL of polymer or SCK solution (1 mg/mL in PBS) at 0, 4, and 8 weeks. The mice were bled for preimmunoserum screening prior to the primary injection. Blood samples were then collected 14 d after 4 and 8-week booster immunizations, respectively. Serum was obtained after clotting at 4° C., for 24 h, and centrifugation. Serum samples were stored at −20° C. in small aliquots for later use.

Determining Antibody Titer by ELISA Assay. Samples for ELISA for the five mice were first prepared by dilution in five 96-well plates. PBS buffer (100 μL) was added to each well in the plates. The serum vials were thawed, and each serum sample (5 μL) was diluted 1:100 in PBS and was transferred, in quadruplicate, in aliquots (100 μL) to the first four wells in the top row of each corresponding plate. The serum obtained following the first booster immunization was added to the next four wells, and the serum obtained following the second booster immunization was added to the final four wells, columns 9 to 12. The serum was then serially diluted 2-fold in rows 2-7 in each plate. Following dilution, 100 μL from each well was transferred to a corresponding ELISA (Nunc-Immuno, Maxisorp) plate and incubated overnight at 4° C. The wells were washed three times with PBS (300 μL) containing 0.05% (mass fraction) Tween 20 (Sigma), and the remaining binding sites on the plates were blocked with sodium caseinate (100 μL, 2.5%, mass fraction, in PBS) followed by overnight incubation at 4° C. The wells were again washed three times, and a 1:40,000 dilution of goat anti-mouse IgG alkaline phosphatase conjugate (100 μL, Sigma) was added to each well and allowed to incubate for 1 h at room temperature before being washed five times. Alkaline phosphatase substrate solution (100 μL, Bio-Rad) was added to each well. Color development was allowed to take place for 30 min and then was quenched with 4 mol/L $H_2SO_4$ (50 μL per well). Absorption measurements were made at 405 nm. To determine the absolute antibody concentrations, mouse IgG standards were run in parallel with each ELISA plate. Serial dilutions of mouse IgG (from 5.00 to 0.08 μg/mL) were used to generate the linear calibration plot of absorbance vs concentration. The value corresponding to 0 g/mL was the background reading and was subtracted from all samples.

Results and Discussion

The assessment of material biocompatibility is a complicated process, which includes both in vitro and in vivo measurement methods, each of which depend on the physical and chemical nature of the material and the nature of the biological interaction. Surface characteristics such as hydrophobicity, morphology, surface charge, and chemical functionality are all known to play key roles in governing cell adhesion and proliferation. Several physicochemical parameters for the PTD-derivatized SCK nanoparticles whose syntheses and characterization are described in the previous example (B) are outlined in Table 1. However, a clear framework outlining the critical physiochemical and surface-mediated interactions within which to facilitate the development of materials minimally detrimental to cells does not exist. For applications concerning the delivery of macromolecules into cells, the enhanced efficiency of conjugate transduction must be weighed against any detrimental biological interactions including effects on both cell viability and immune response. The cell viabilities in the presence of the peptide-derivatized polymeric constructs were evaluated by MTT assay, which monitors enzymatic activity of a cell organelle (in this case mitochondria), and flow cytometry. Previously, the protein transduction sequence has been used at concentrations of up to 100 µmol/L without affecting the viability of certain cell lines (Suzuki et al., J. Biol. Chem., 2002, 277, 2437-2443).

Figure 7:
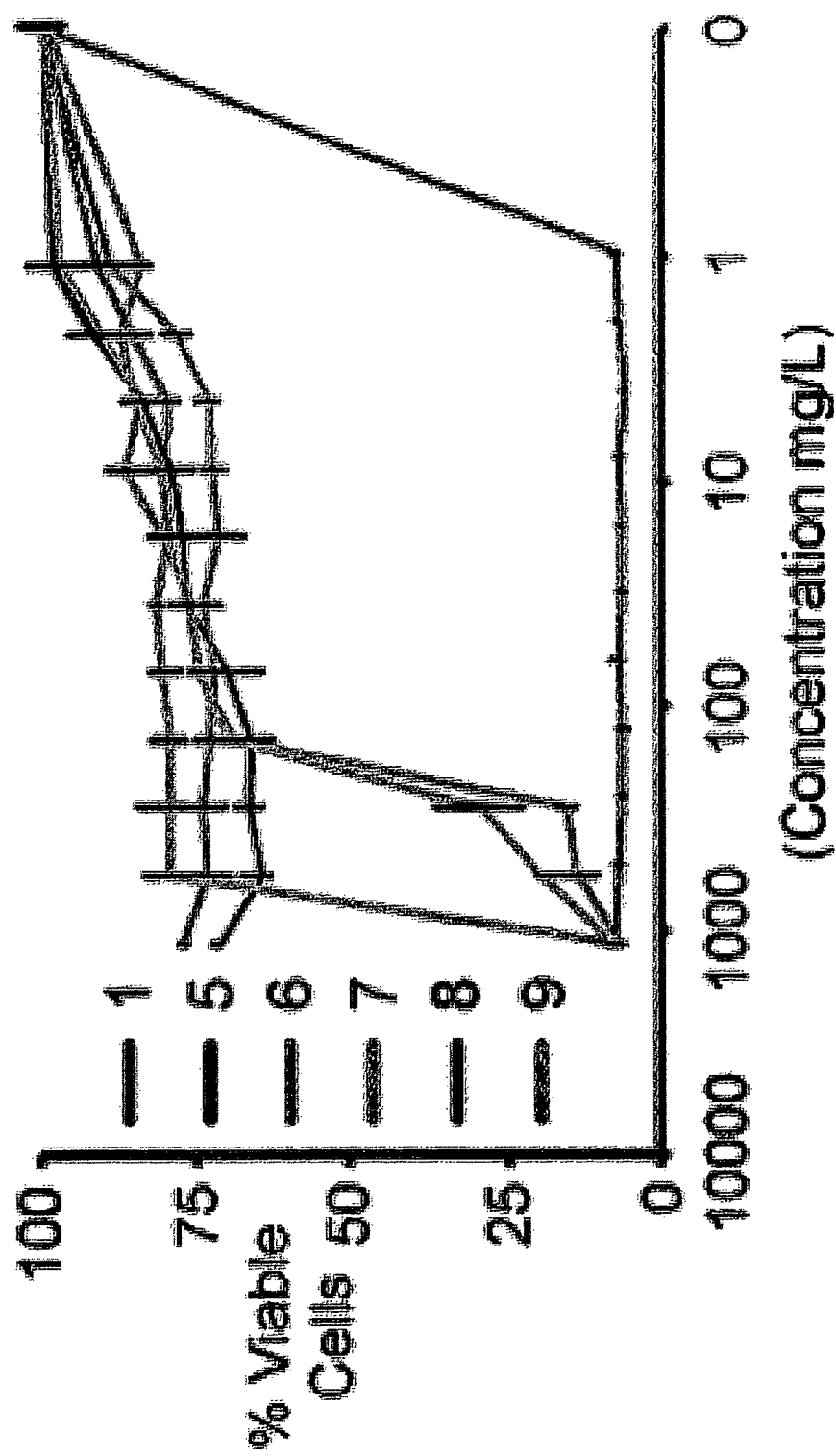
FIG. 7 shows that the inventors' conjugation of a PTD sequence to SCK has desired positive dramatic effects on resulting cell viability. The 2.0% PTD-functionalized SCK 9 is toxic to the cells between 7 mol/L to 13 mol/L in PTD. The 0.5% and 1.0% PTD-functionalized SCKs (7 and 8) are toxic between 14 mol/L to 28 and 7 mol/L to 15 mol/L in PTD, respectively. The parent micelles and SCKs (5 and 6) did not affect the viability of the cells at any measured concentration. Error bars are representative of one standard deviation from the mean of quadruplicate samples harvested form four separate wells of mouse myeloma B cells and are estimates of the standard uncertainties.

As illustrated by the data shown in FIG. 7, the PTD sequence, with four additional glycine residues, was found to decrease the enzymatic reduction of MTT in the mitochondria of mouse myeloma B cells at approximately 110 µmol/L concentrations. In contrast, the viabilities of the cells upon exposure to buffered solutions of micelles or SCKs remain 70 to 90% at concentrations above 100 mg/L. The small drop in viability is due primarily to the dilution of the media as shown by control tests in which buffer and no buffer were added to different cell populations. Exposure of the cells to the parent $PAA_{56}$-b-$PMA_{185}$ micelles, 5, and the corresponding unfunctionalized SCK, 6, did not affect cell viability up to 1125 mg/L concentrations. However, the derivatization of the nanoparticle with increasing numbers of the PTD sequence has a significant effect on the viability of the cell populations as measured by the enzymatic function. The 2.0% PTD-functionalized SCK 9 is toxic to the cells between (140 and 280) mg/L (7 µmol/L to 13 µmol/L in PTD). The 0.5% and 1.0% PTD-functionalized SCKs (7 and 8) are toxic between (560 and 1125) mg/L (14 µmol/L to 28 mmol/L and 7 µmol/L to 15 µmol/L in PTD, respectively).

In addition to the MTT enzymatic assay, the peptide-derivatized nanoparticles have been evaluated by a fluorescent flow cytometry test to determine the effects of incubation with SCKs upon the induction of apoptosis. Apoptosis is characterized by numerous morphological changes, the first of which involves the translocation of phosphatidylserine (PS) from the inner to the outer surface of the cellular plasma membrane. Once exposed to the extracellular environment, PS sites are accessible to Annexin V, a phospholipid binding protein with a high affinity for PS. For measurement purposes, Annexin V is conjugated to FITC and used for the identification of cells in the early stages of apoptosis via flow cytometry. Because PS binding sites are also accessible when the cells are in a necrotic state, Annexin V is not an absolute marker of apoptosis. Therefore, it is often used in conjunction with 7-aminoactinomysin, (7-AAD) which binds to exposed nucleic acids, when the cell membrane integrity is compromised. Cells that are negative (unstained) for both Annexin V and 7-AAD have no indications of apoptosis: PS translocation has not occurred, and the plasma membrane remains intact. Cells that are Annexin V (+) and 7-AAD (−), however, are in early apoptosis, as PS binding sites are exposed, but the plasma membrane is still intact. Cells that are (+) for both Annexin V and 7-AAD are either in the late apoptosis (irreversible) stage or are not viable.

Figure 8:
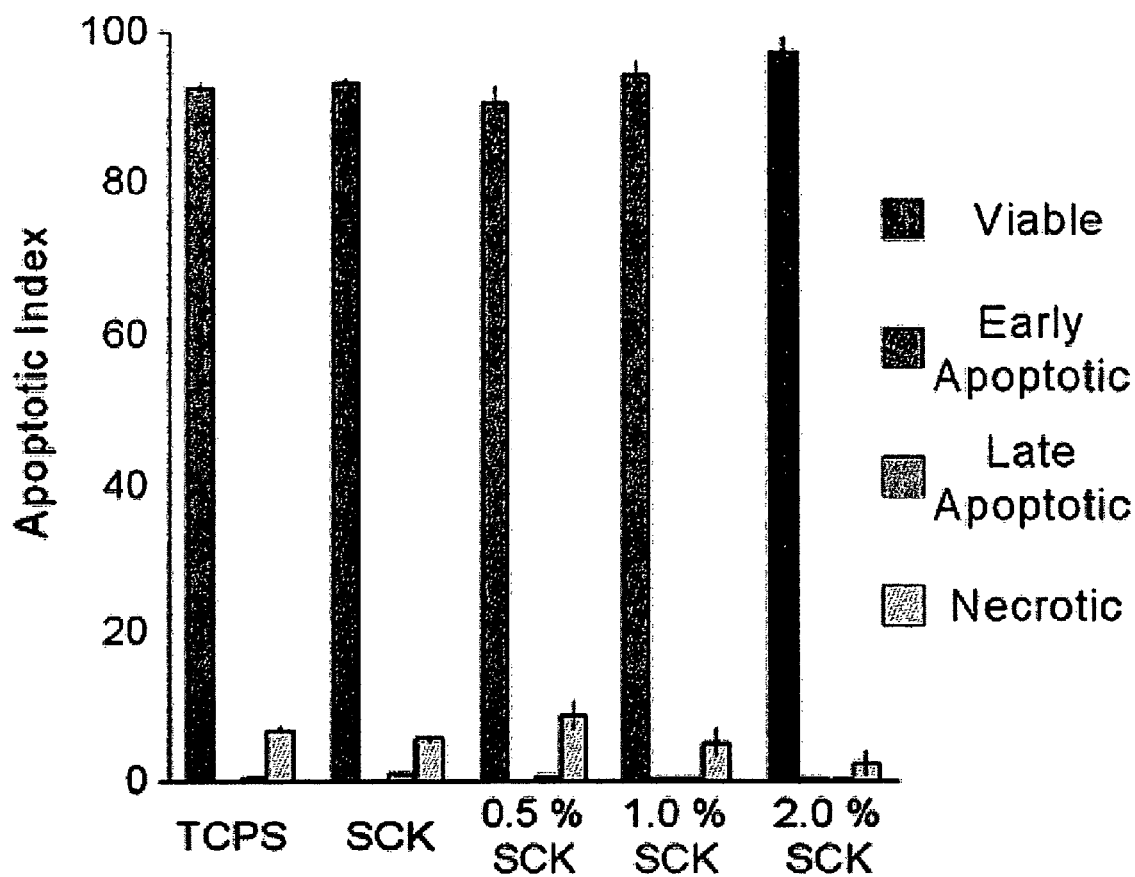
FIG. 8 shows four distinct populations of cells identified with flow cytometry (viable, early apoptotic, late apoptotic and necrotic) more in detail. Viable cells: Annexis V(−) and 7-AAD(−); early apoptotic; Annexin V (+) and 7-AAD(−); late state apoptotic: Annexin V (+) and 7-ADD (+) necrotic; Annexin V (−) and 7-ADD (+). Error bars are representative of one standard deviation from the mean of triplicate samples, each harvested from three separate populations of RAW 264.7 cells and the estimates are of the standard uncertainties.

The flow cytometry data shown in FIG. 8 indicate that the SCKs do not induce apoptosis at the concentrations tested. The total inoculated concentration was 0.5 mg/mL (500 mg/L) for each SCK sample. In addition, a visual assessment of the effects of exposure to PTD-derivatized SCKs at the 5 day time point indicated that the nanoparticles did not affect the continued growth of the cells nor did they induce significant morphological changes (data not shown). These results are comparable to the MTT assay results. Although the MTT assay depicts a shutdown in mitochondrial function at certain concentrations, exposure of each of the samples to the cells at concentrations of 500 mg/L did not lead to cellular apoptosis.

Figure 9:
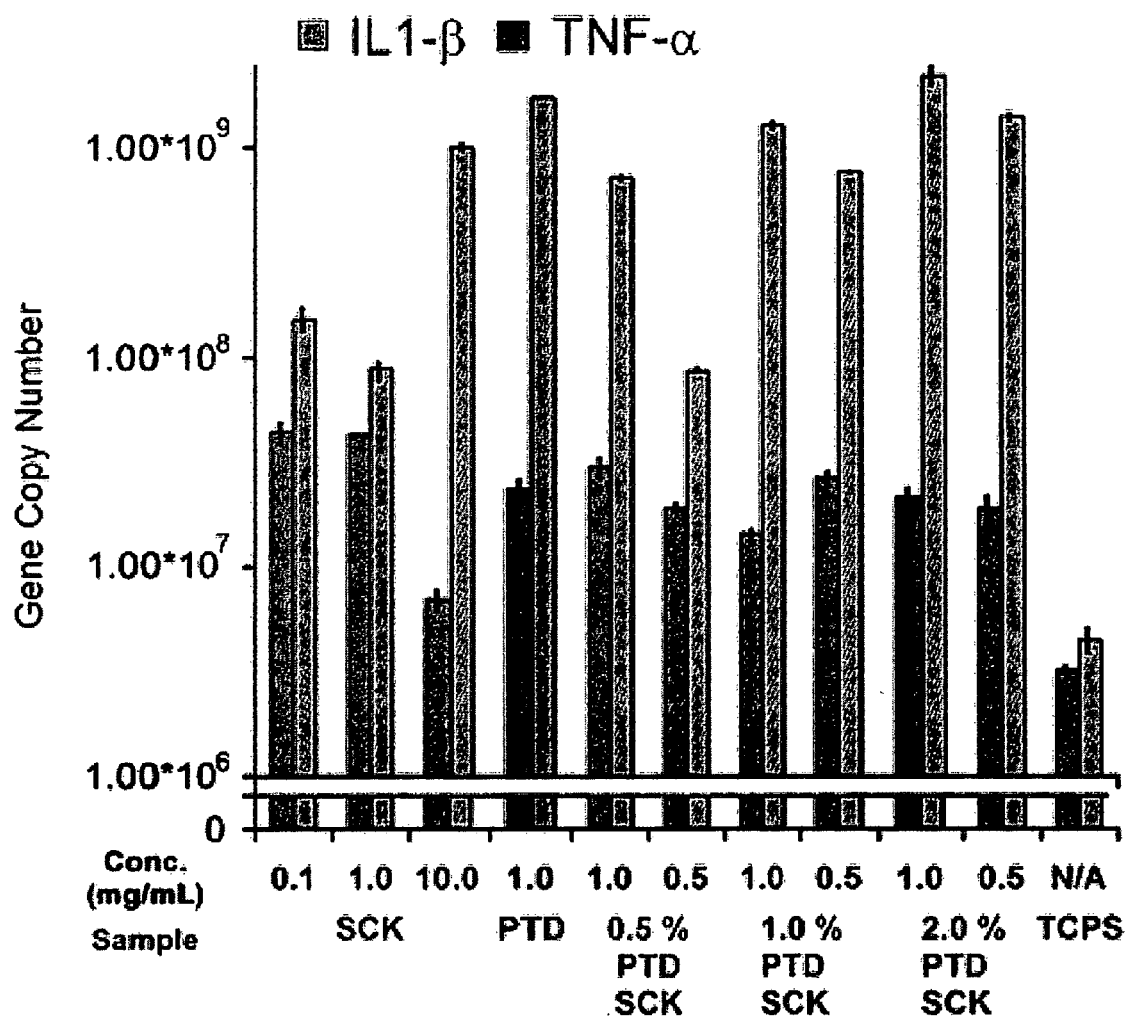
FIG. 9 shows a plot of inventors' data from genetic cellular inflammatory responses exhibited 24 hours after incubation with different concentrations of peptide functionalized SCK nanoparticles quantified by RT-PCR. These data depict minimal increases in the production of TNF-α and an elevation in the levels of IL-1 relative to tissue culture deviation from the mean of triplicate samples, each harvested from three separate populations of RAW 264.7 cells, and the estimates are of the standard uncertainties.

Immunogenicity Results. The extent of PTD functionality is of significant importance as it may affect the immune response. The nature of the response has significant clinical implications, as severe inflammatory responses may prevent in vivo applications. Recent literature has reported that the addition of HIV-1 TAT PTD enhances minigene epitope presentation in tissue culture, but the attachment of PTD to full-length proteins does not enhance the immune response of the construct (Liefert et al., Gene Ther., 2002, 9, 1422-1428). The reported data were for a 1:1 stoichiometry of PTD:protein, and it is unclear whether the presentation of multiple copies of the sequence on the surface of an SCK would have a synergistic or negligible effect on the cellular immune response. The initiation and propagation of an immune response is ultimately regulated by cytokines. Cytokines are the primary mediators of a host immune response and are able to both induce apoptosis and modulate survival through the activation of genes in response to bacterial toxins, inflammatory products, and other invasive stimuli. Two of the most important cytokines in the acute inflammatory response are tumor necrosis factor alpha (TNF-α) and interleukin-1 beta (IL1-β). TNF-α is synthesized and secreted by macrophages. TNF-α is part of a complex network of cytokines and is capable of initiating cascades, which control the synthesis and expression of signaling molecules, hormones, and their receptors. Knowledge of the cellular cytokine profile is key to identifying the processes involved in the immune response and crucial to the further elucidation on the physicochemical properties of the bioconjugate that are inducing the response. Another prominent cytokine involved in the inflammatory responses is interleukin-1 (IL-1). Although IL-1 protects the organism by enhancing the response to pathogens and initiating healing process, its overproduction can induce numerous pathological consequences including septic shock and leukemia. The measurement of mRNA levels has been used widely to measure cytokine proliferation, which is responsible for the initiation, mediation, and propagation of cellular inflammatory responses. The genetic expression profiles of IL-1β and TNF-α have been measured by real-time polymerase chain reaction (RT-PCR). In this study, the mRNA profiles of TNF-α and IL-1β in response to PTD, SCKs, and SCKs derivatized with increasing amounts of PTD sequences were investigated using RT-PCR. In the previous example, PTD was conjugated in (0.005, 0.01, and 0.02) molar ratios, relative to the acrylic acid residues in the shell, to the SCK nanoparticles resulting in SCK populations nominally possessing 52, 104, and 210 (41, 83, and 202 as measured by phenylglyoxal) PTD peptides per particle, respectively. RAW 264.7 cells were used because they retain the characteristics of primary cultured macrophages in vitro, including the ability to release cytokines. Cells were exposed to the respective SCK nanoparticle samples by adding the conjugates to the murine macrophages 24 h following seeding. After a 24 h incubation period, the mRNA was extracted from the cell populations. Using a reverse transcriptase enzyme, mRNA is converted to the cDNA template necessary for amplification. Once cDNA is generated, gene specific primers, a DNA polymerase, and a fluorescent moiety are utilized to amplify and label the amplicon generated. The gene product accumulation was then measured during the exponential phase of the amplification reaction. The copy number from each of the samples was obtained by extrapolating to a standard gene curve of known concentration and copy number to yield quantitative data. The assay also includes the analysis of mRNA that does not change in relative abundance (18S) during the course of treatment to serve as an internal control. The genetic profiles of the inflammatory response to SCKs (1-3), PTD (4), PTD-functionalized SCK nanoparticles (5-10), and tissue culture polystyrene (TCPS, 11) are shown in FIG. 9.

TNF-α mRNA synthesis was up-regulated 2-fold to 14-fold (depending on concentration) in response to exposure of the parent SCK nanoparticle, 6, over TCPS. It is interesting to note that the highest concentration, 10.0 mg/L, of the parent SCK 6 actually caused less of an increase, 2.2-fold, than lower concentrations, 0.1 and 1.0 mg/L, of SCK 6, 13.5-fold and 13.2-fold, respectively. When looking at the effects of parent SCK concentration on TNF-α production, the difference between 0.1 and 1.0 mg/mL is statistically insignificant, while the 10.0 mg/mL sample measures 6.1-fold less than at the 1.0 mg/mL level. Interestingly, the down-regulation of TNF-α has been demonstrated previously in liposome vectors formulated with cationic lipids. The measured TNF-α levels for the PTD-functionalized SCKs are less than the levels of the parent SCK in all cases (1.5-fold to 3.0-fold) and show no concentration or functionality dependence. The levels of TNF-measured in response to the peptide-functionalized nanoparticles, regardless of the extent of derivatization and concentration tested, are statistically insignificant when compared to the levels induced by the PTD domain itself. The copy numbers, fold increases, and the p values ($p<0.05$ significant at 95% confidence, derived from the students t-test) indicating statistical significance are listed in Table 2 following.

The measured increases of IL1-β production in response to PTD-, SCK-, and PTD-functionalized SCKs are much more pronounced than the copy number levels of TNF-α as compared to TCPS. The measured levels range from 18.8-fold to 483.5-fold increases over TCPS and 1-fold to 25.4-fold increase over SCKs of similar concentration and show statistical dependence with regard to both concentration and PTD functionalization. The differences in TNF-α and IL1-β expression measured in this series reflect different pathways of signal transduction with regard to both the time frame and the severity of the response to the respective inflammatory stimuli.

Following the in vitro measurements on cell viability and inflammatory response, the SCKs and PTD-derivatized SCKs were then tested in vivo to gauge their immunogenic response in balb/c mice. Enzyme-linked immunosorbent assays (ELISA) were used to quantify the increases in IgG production in response to immunization with the test compounds. Efforts to isolate specific responses by plating the SCKs on the ELISA plate prior to serum incubation were not successful due to an insignificant specific antibody response. This result can be attributed to two possible factors: (1) the nanoparticles could induce a nonspecific immune response, and (2) the sera used for the ELISA measurements were collected 14 days following the respective immunization, a sufficiently long time that any acute inflammatory response may have passed. We therefore decided to look at the increases in IgG concentration on an individual mouse basis to look for relatively large increases. FIG. 9 shows the three antibody titers determined for each mouse in the study. The PTD peptide by itself is not immunogenic after two booster immunizations, and the parent SCKs possessing poly(acrylic acid-co-acrylamide) shells display negligible values of titer increases over the control PBS injections. Those SCKs possessing various amounts of PTD functionality, 0.5%, 1.0%, and 2.0% (7, 8, and 9), qualitatively showed a general trend of increasing antibody titer in the serum with increasing degrees of nanoparticle functionalization. The relative increases in antibody titer relative to the initial value are listed in Table 2. Qualitatively, the only significant immunogenic response depicted arose from the 2.0% functionalized SCK, 9. The 0.5%, 1.0%, and 2.0% SCKs (7, 8, and 9) exhibited increases of 100% or more in 20% (1 of 5), 60% (3 of 5), and 100% (5 of 5) of the mice, respectively, following two booster injections.

While limited in scope, the immunogenicity results for the SCKs functionalized to a lesser degree are consistent with the literature, but when large numbers of PTD are presented, the particles do elicit an increase in IgG concentration within the serum. While no specific responses could be detected for the any of the SCK nanoparticles, it is perhaps more important that no deaths resulted from the mice (>50) being subjected to the immunization protocol (3×100 µg) and no gross morphological changes were observed in postmortem organ histology examinations.

SUMMARY

SCK nanoparticles were derivatized with various stoichiometric derivatizations with PTD and were evaluated in vitro and in vivo for biocompatibility. The initial evaluation and early identification of detrimental interactions between biological species and SCK nanoparticles are crucial to further efforts to develop in vivo applications. Apoptosis assays measured by flow cytometry have complemented enzymatic (MTT) toxicity results demonstrating a lack of detrimental effects on cell viability below 500 mg/L for all the samples. Although higher levels of peptide functionalization resulted in decreased metabolic function, loss of cell viability was observed at a sufficiently high concentration, suggesting the use of even 2% PTD-functionalized SCKs would not be prohibited in vivo. In addition, RT-PCR data provided quantitative information regarding the lack of immunogenicity elicited by SCKs and peptide-derivatized SCK nanoparticles. The inflammatory response to the peptide-functionalized SCK nanoparticles as measured by RT-PCR show increases in the levels of both TNF-α and IL1-β relative to TCPS. Although these levels are statistically significant and show large increases of IL1-β with increasing peptide functionalization, the levels did not preclude the preliminary testing of SCKs in vivo. An in vivo mouse immunization model found measured increases in IgG concentration were minimal with no specific interactions being identified, and more importantly, none of the mice (>50) subjected to the three 100 µg immunization protocol died. Additionally, no gross morphological changes were observed in postmortem organ histology examinations. While these in vitro assessments and preliminary in vivo tests show promising results, additional in vivo animal studies, which are currently in progress including biodistribution and nanoparticle clearance, are needed to compliment these initial findings and to extend the potential therapeutic applications of functionalized SCKs. However, up-regulation of IL1-β and larger than expected IgG increases for the 2.0% PTD-functionalized SCKs suggest that nanoparticles functionalized in polyvalent strategies may be interesting scaffolds for the attachment of known antigens for use in vaccination applications.

TABLE 1

Summary of Physical Characterization Data
Collected for the Parent SCK Nanoparticle and the PTD-Functionalized SCKs

| particle | v(L/g) | $M_w$ (×10$^6$ Da) | no. of peptides | ζ(V) | DLS $D_n$ (nm) | TEM $D_{av}$ (nm) |
|---|---|---|---|---|---|---|
| micelle | n.d. | n.d. | 0 | −27 ± 0.7 | 38 ± 3 | 21.3 ± 3.8 |
| SCK | 0.556 ± 0.007 | 4.004 ± 0.151 | 0 | −20 ± 0.5 | 37 ± 2 | 18.3 ± 3.6 |
| 0.5% | 0.587 ± 0.009$^a$ | 5.900 ± 0.241 | 52 ± 2 | −28 ± 0.9 | 35 ± 3 | 20.2 ± 3.7 |
| 1.0% | 0.622 ± 0.009 | 7.017 ± 0.304 | 104 ± 4 | −23 ± 0.7 | 36 ± 3 | 21.4 ± 3.6 |
| 2.0% | 0.661 ± 0.007 | 7.818 ± 0.248 | 210 ± 10 | −22 ± 0.5 | 32 ± 4 | 21.6 ± 3.3 |

TABLE 2 the Quantification of PTD Functionalization in
Each of the Respective SCK Samples Using Two Different
Methods Afforded Similar Numbers of Peptides Per Particle

| particle | no. of peptides nominal | no. of peptides UV-vis | no. of peptides phenylglyoxal |
|---|---|---|---|
| SCK | 0 | 0 | 0 |
| 0.5% | 52 ± 2 | 38 | 41 |
| 1.0% | 104 ± 4 | 87 | 83 |
| 2.0% | 210 ± 10 | ~500 | 202 |

TABLE 3

Relative Percent Increase in Antibody Titers
Quantified by ELISA Following Two Booster Injections
over Preimmunization Baseline Levels.

| Particle | 37° C. | 4° C. | 37° C. w/NaN$_3$ | 4° C. w/NaN$_3$ |
|---|---|---|---|---|
| SCK | 5.6 | 7.3 | 5.2 | 7.1 |
| 0.5% | 33.9 | 10.3 | 16.3 | 8.5 |
| 1.0% | 42.9 | 32.6 | 25.7 | 12.3 |
| 2.0% | 47.0 | 36.4 | 51.8 | 13.8 |

The present discovery provides novel systems and compositions for the treatment and monitoring of diseases (e.g., cancer). For example, the present discovery provides systems and compositions that target, and sense pathophysiological defects, allow for imaging of the defects, provide the appropriate therapeutic based on the diseased state, monitor the response to the delivered therapeutic, and identify residual disease. In preferred embodiments of the present discovery, the compositions are small enough to readily enter a patient's or subjects cells.

EXAMPLE—SET D

Micropet Imaging of MCF-7 Tumors in Mice Via unr mRNA-Targeted PNAs

In this example the inventors designed and synthesized three antisense and one sense hybrid PNAs (peptide nucleic acids) with a four-lysine tail at the carboxy terminus to the unr mRNA that is highly and abundantly overexpressed in a breast cancer cell line (MCF-7). A DOTA (1,4,7,10-tetraaza-cyclododecane-N,N',N'',N'''-tetraacetic acid) chelating moiety was added to the amino terminal end of the PNAs so that they could be radiolabeled with $^{64}$Cu for biodistribution and microPET imaging studies in normal and MCF-7 tumor bearing mice. All four PNA conjugates were successfully labeled with $^{64}$Cu under mild conditions with a specific activity of ca. 200 mCi/μmol (or 7,400 MBq/μmol) at time of injection. Biodistribution of two $^{64}$Cu-labeled conjugates with antisense and sense sequences of unr mRNA (PNA50 and PNA50S) were performed in normal balb/c mice via two injection modes (intravenous and intraperitoneal). Both conjugates exhibited a rather similar in vivo behavior featuring high uptake and long retention in kidney, and low uptake and efficient clearance in blood and muscle. The administration forms did not change the pattern of tissue distribution, while the intraperitoneal mode gave a much slower release rate of the conjugates. The MCF-7 tumor (100-320 mg) in CB-17 severe combined immunodeficiency (SCID) mice was imaged with all four $^{64}$Cu-labeled PNA conjugates by microPET probably because of the high specific activity, but the image contrast varies with different time points and different compounds. The quantification of microPET images was carried out to evaluate the concentration of the radiolabeled PNA conjugates in the regions of interest (ROIs), and the results are in agreement with the data of post imaging biodistribution study (24 h post injection). Of the PNA conjugates studied in this work, $^{64}$Cu-DOTA-Y-PNA50-K4 showed the best image quality of the tumor at all time points. As determined by the post imaging biodistribution, the tumor/muscle ratio (6.6±1.1) of $^{64}$Cu-DOTA-Y-PNA50-K4 is among the highest reported for radiolabeled oligonucleotides. Our work further strengthens the potential of antigene and antisense PNAs to be utilized as specific molecular probes for early detection of cancer and ultimately for patient-specific radiotherapy.

Test Procedures

Materials. DOTA-tris(t-Butyl ester) was purchased from Macrocyclics Inc. (Dallas, Tex.), diisopropylethylamine (DIEA), TFA, m-cresol and diethyl ether (anhydride) were purchased from Aldrich (St. Louis, Mo.). Fmoc-protected amino acids (D-Lys(Boc)-OH and Tyr(tBu)-OH) were purchased from NovaBiochem (La Jolla, Calif.). O-(7-Aza-benzo-triazol-1-yl)-1,1,3,3-tetramethyluronium hexafluorophosphate (HATU), Fmoc-XAL PEG-PS resin, PNA building blocks (Fmoc-A-(Bhoc)-OH, Fmoc-C-(Bhoc)-OH, Fmoc-G-(Bhoc)-OH and Fmoc-T-OH) and other reagents and solvents for PNA and peptide synthesis were purchased from Applied Biosystems (Foster City, Calif.). UV spectral data were acquired on a Bausch and Lomb Spectronic 1001 spectrophotometer or Varian Cary 100 Bio UV-Visible Spectrophotometer. Matrix-assisted laser desorption ionization (MALDI) mass spectra of PNA-peptide conjugates were measured on PerSeptive Voyager RP MALDI-time of flight (TOF) mass spectrometer using sinapinic acid as a matrix and calibrated versus insulin (average [M+H$^+$]=5734.5) that was present as an internal standard. High-pressure liquid chromatography was carried out on Beckman Coulter System Gold 126 with an array detector. Copper-64 was prepared on the Washington University Medical School in St. Louis, Mo. Cyclotron CS-15 cyclotron by the $^{64}$Ni(p,n)$^{64}$Cu nuclear reaction at a specific activity of 50-200 mCi/μg at the end of bombardment (EOB) as previously described. Water was distilled and then deionized (18 MΩ/cm$^2$) by passing through a Milli-Q water filtration system (Millipore Corp., Bedford, Mass.). Diethylenetriaminepentaacetic acid (DTPA), ammonium acetate, and sodium chloride were purchased from Fluka Chemie AG (Buchs, Switzerland). Dry powder in foil pouches for the preparation of 10 mM phosphate buffered saline (PBS), pH 7.4, and 4-(2-hydroxyethyl)piperazine-1-ethanesulfonic acid (HEPES) were purchased from Sigma-Aldrich (St. Louis, Mo.). Solvents (e.g., acetone, methanol, etc.) were purchased from Fisher Scientific (Pittsburgh, Pa.) and used as received. Saline (0.9% NaCl solution) was purchased from American Pharmaceutical Partners, Inc. (Schaumburg, Ill.). Centricons (YM-3: MWCO 3,000 Da) were purchased from Millipore Corporation (Bedford, Mass.). Fast protein liquid chromatography (FPLC) and radio-FPLC were performed using an Amersham Pharmacia Biotech ÄKTA FPLC (Amersham Biosciences Corp. Piscataway, N.J.) equipped with a Beckman 170 Radioisotope Detector (Beckman Instruments, Inc. Fullerton, Calif.). The Superdex™ 75 was bought from Amersham Biosciences Corp. (Piscataway, N.J.). PBS, Trypsin/EDTA, and cell culture media and additives were purchased from the tissue culture support center of Washington University School of Medicine (St. Louis, Mo.). Fetal bovine serum (FBS), Earle's balanced salt solution (BSS), and insulin were bought from Sigma (St. Louis, Mo.). CB-17 SCID mice were purchased from the Charles River Laboratories (Wilmington, Mass.).

Tissue culture and animal model. The MCF-7 cell line was obtained from American Type Culture Collection (ATCC, Manassas, Va.). MCF-7 cells were grown in Eagle's minimum essential medium (MEM) with Earle's BSS and 2 mM L-glutamine modified to contain 1 mM sodium pyruvate, 0.1 mM non-essential amino acids, 1.5 mg/mL sodium bicarbonate supplemented with 10% FBS and 0.01 mg/mL bovine insulin. To establish MCF-7 human breast xanografts, each CB-17 SCID mice was implanted with a 60-day subcutaneous (s.c.) slow release estrogen pellets (1.7 mg 17β-estradiol/pellet; Innovative Research of America, Sarasota, Fla.) 48 h prior to the s.c. injection of MCF-7 cells into the nape of neck. Cultured MCF-7 cells were harvested from monolayer using PBS and trypsin/EDTA, and suspended in media with FBS. The cell suspension was centrifuged and resuspended in PBS at the concentration of $1 \times 10^8$ cells per milliliter. It was then mixed 1:1 with Matrigel and injected s.c. ($1 \times 10^7$ cells per mouse, injection volume 200 μL) into the nape of the neck of CB-17 SCID mice (5-6 weeks of age). After the cell injection, the animals were monitored twice a week by general observations. The tumor was noticed to grow in the first week and allowed to grow five weeks to reach a palpable size for microPET imaging studies. The tumor weight was 100-320 mg as determined by post imaging biodistribution.

Synthesis of the DOTA-(D)-Y-PNA-K4 conjugates. $NH_2$-Y-PNA-K4 conjugates were synthesized continuously on universal support XAL-PEG-PS resin on a 2 μmol scale with standard solid phase Fmoc off chemistry in Expedite 8909 Synthesizer (Applied Biosystems) by loading the fifth and sixth building block channel with Fmoc-D-Lys and Fmoc Tyr(tBu) respectively and programming the sequence accordingly under standard automated PNA synthesis protocol. DOTA-tris(t-Butyl ester) (11.5 mg, 20 μmol) was dissolved in 100 μl NMP, then 100 μl HATU DMF solution (0.2 M) and 100 μl base solution (0.2 M DIEA, 0.3 M 2,6-lutidine in DMF) were added, the mixture was introduced into the cartridge containing PNA-K4-resin manually with a syringe and pushed back and forth with a second syringe to agitate the resin suspension every 10 min for 1 hour. Then the resin was washed with DMF and dichloromethane (DCM) and dried by passing nitrogen. Treatment of the resin with TFA/m-cresol (4:1) for 12 h at room temperature (r.t.) was used to cleave the conjugates and remove the side chain protective groups. Ethyl ether (8-10 volumes) was added to the TFA solution to precipitate the product as yellow solid. The crude product was purified by reversed phase HPLC on a Microsorb C18 column (300 Å pore, 5 μm particle size, 4.6×250 mm) using a 5% to 70% linear gradient of solvent B (0.1% TFA in acetonitrile) in A (0.1% TFA in water) over 65 min at the flow rate of 1 ml/min. The effluent was monitored by absorbance at 260 nm and the major peaks were collected, concentrated to dryness in vacuum, and characterized by MALDI-TOF mass spectrometry.

Radiolabeling of DOTA-Y-PNA-K4 conjugates with $^{64}Cu$. Copper-64 chloride (typically in 0.1 M HCl) was converted to Cu-citrate by adding an appropriate volume of 0.1M ammonium citrate buffer (pH 7.0) to the $^{64}CuCl_2$ solution. Prior to labeling, the stock solutions of DOTA-Y-PNA-K4 conjugates were heated at 80° C. for 10 min to minimize the self-pairing and plastic wall sticky property of the PNA conjugates. To 200 μL of a DOTA-Y-PNA-K4 conjugate solution (40 μM), 20 μL of $^{64}Cu$-citrate was added (2-4 mCi). The resulting solution was incubated at 60° C. for 1-2 h in a thermomixer (1,000 rpm). After incubation, 5 μL of 10 mM DTPA solution was added to the $^{64}Cu$-DOTA-Y-PNA-K4 solution. The solution was vortexed for a few seconds and left at r.t. for 10 min. It was then centrifuged at least two times through a Centricon-YM3 (MWCO 3,000 Da) with 10 mM PBS buffer (pH 7.4) to remove the $^{64}Cu$-DTPA complex and/or free $^{64}Cu$-activity. The radiochemical purity (RCP) of the $^{64}Cu$-labeled DOTA-Y-PNA-K4 conjugate was monitored by FPLC. The product was then diluted with 10 mM PBS buffer (pH 7.4) to prepare appropriate doses for biodistribution and microPET imaging studies.

FPLC analysis. A 100 μL of analyte was injected into a Superdex™ 75 gel filtration column, which was then eluted with 20 mM HEPES and 150 mM NaCl (pH 7.3) buffer at an isocratic flow rate of 0.5 mL/min. The UV wavelength was preset to 280 nm, the radioactivity was monitored by an online Beckman radio-detector. Under these conditions, the retention times of the $^{64}Cu$-DOTA-Y-PNA-K4 and DOTA-Y-PNA-K4 were ca. 31-35 min.

Biodistribution studies. All animal studies were performed in compliance with guidelines set by the Washington University in St. Louis, Mo. Animal Studies Committee. Copper-64 labeled DOTA-Y-PNA-K4 solutions were diluted with saline. Normal balb/c mice weighing 20-30 g (n=4 per time point) were anesthetized with isoflurane and injected with 10-12 μCi of activity via the tail vein (i.v.) or ca. 55 μCi of radioactivity via intraperitoneal (i.p.) injection. The injected volume of activity per mouse was 100 μL. The mice were anesthetized prior to sacrifice (by decapitation) at each time point. Organs of interest were removed, weighed, and counted. Standards were prepared and counted along with the samples to calculate the percent injected dose per gram (% ID/g) and percent injected dose per organ (% ID/organ).

MicroPET imaging studies. The microPET imaging studies were carried out using the microPET® R4 (rodent) scanner (Concorde Microsystems Inc., Knoxville, Tenn.). MCF-7 tumor-bearing CB-17 SCID mice were anesthetized with 1-2% vaporized isoflurane and injected with ca. 200-400 μCi of activity in 120 μL saline via the tail vein ($^{64}Cu$-DOTA-Y-PNA50: 210 μCi; $^{64}Cu$-DOTA-Y-PNA50S: 347 μCi; $^{64}Cu$-DOTA-Y-PNA5: 253 μCi; $^{64}Cu$-DOTA-Y-PNA7: 361 μCi). At specific time points (1 h, 4 h, and 24 h) post injection, the mice were re-anesthetized and then immobilized in a supine position on custom-built support beds with attached anesthetic gas nose cones for data collection. Within 4 h p.i., the imaging collection time was 10 min; at 24 h p.i., the imaging collection time was 20 min.

Radioactive tracer accumulation ($^{64}$Cu-labed PNAs) in a targeted organ was measured using the standardized uptake value (SUV). The SUVs were obtained by the quantification of the regions of interest (ROIs) by viewing these areas in the selected tissues and averaging the activity concentration corrected for decay over the contained voxels (multiple image slices) at the time points p.i.

$$SUV = \frac{\text{Radioactivity Concentration in } ROI[\mu Ci/cc]}{\text{Injection Dose}[\mu Ci] / \text{Animal Weight}[g]}$$

After the microPET imaging at 24 h p.i., the animals were sacrificed and biodistribution studies were performed. The ratios of tumor to blood (T/B) and tumor to muscle (T/M) were calculated. The unpaired t-test on the biodistribution and microPET quantitation data was performed using Prism, v. 4.00 (Graphpad, San Diego, Calif.).

Results

Selection of the antisense PNAs. The sequences of the antisense PNAs were selected by a procedure that will be described in greater detail in Example set E. Three of these antisense PNAs and one sense PNA were selected for imaging studies: PNA50 with a $K_d$ of 21 pM, PNA5, with a $K_d$ of 22 pM, PNA7 with a $K_d$ of 15 pM, and PNA50S (sense form of PNA50) with a $K_d$ of >10 nM in 0.1 M NaCl, 50 mM EDTA, 2 mM cacodylic acid.

Synthesis of DOTA-Y-PNA-K4 conjugates (Table 1). The PNAs were synthesized using standard automated solid phase Fmoc synthesis on an ABI 8909 DNA synthesizer with a PNA option (this synthesizer is no longer commercially available from the original manufacturer). The unnatural D-isomer of lysine was used to inhibit enzymatic degradation of the K4 permeation peptide unit. The DOTA group was added manually in the last step of the synthesis to the amino terminal ("5'-end") of the PNA via the commercially available tri-t-butylester, and the HPLC purified products characterized by MALDI-TOF.

Radiolabeling of DOTA-Y-PNA-K4 conjugates. Four DOTA-Y-PNA-K4 conjugates were all successfully radiolabeled with $^{64}$Cu in 0.1 M ammonium citrate buffer (pH 7.0) under mild conditions (at 60° C. for 1-2 h) in yields of 32-61% (decay corrected). After DTPA challenge of non-specifically bound $^{64}$Cu-activity and Centricon-YM3 (MWCO: 3,000 Da) separation, the radiochemical purity of the $^{64}$Cu-labeled PNA conjugates was nearly 100% as determined by radio-FPLC: both the radioactivity and UV (280 nm) curves only showed a single strong peak with the same retention time in the range of 30-35 min. The $^{64}$Cu-labeled PNA conjugates remained 100% intact after being kept in saline overnight.

Biodistribution of $^{64}$Cu-DOTA-Y-PNA-K4 conjugates in normal balb/c mice. In order to better evaluate the in vivo kinetics of the $^{64}$Cu-labeled PNA conjugates, the biodistribution studies were carried out with two different injection modes in normal balb/c mice: intravenous (tail vein) injection (i.v.) and intraperitoneal injection (i.p.).

Tail vein injection. The biodistribution data of $^{64}$Cu-DOTA-Y-PNA50-K4 and $^{64}$Cu-DOTA-Y-PNA50S-K4 in blood, liver, kidneys, and muscle are presented as percent of injected dose per organ (% ID/organ) at 20 min, 1 h, and 4 h post injection (p.i.) in FIG. 32. Both conjugates exhibited high kidney uptake and long retention. Within 1 h p.i., $^{64}$Cu-DOTA-Y-PNA50-K4 showed slightly higher kidney accumulation (37.4±1.8% ID/kidney at 20 min p.i. and 45.8±0.7% ID/kidney at 1 h p.i.) than $^{64}$Cu-DOTA-Y-PNA50S-K4 (35.6±0.6% ID/kidney at 20 min p.i. and 42.3±0.2% ID/kidney at 1 h p.i.). Out to 4 h p.i., $^{64}$Cu-DOTA-Y-PNA50-K4 exhibited significant kidney clearance (36.1±3.6% ID/kidney at 4 h p.i. P <0.02 as compared to the value at 1 h p.i.), while a drastic accumulation was observed for $^{64}$Cu-DOTA-Y-PNA50S-K4 (60.5±3.6% ID/kidney at 4 h p.i. P<0.005 as compared to the value at 1 h p.i.). In blood, liver, and muscle, the uptake of $^{64}$Cu-DOTA-Y-PNA50-K4 was slightly lower than that of $^{64}$Cu-DOTA-Y-PNA50S-K4 out to 4 h p.i. Both conjugates showed around 4% ID/organ of uptake in bone at 20 min p.i., but they were cleared to <1% ID/organ at 4 h p.i. Negligible uptake was observed in lung, spleen, heart, and brain for both compounds (<1% ID/organ).

Figure 33:
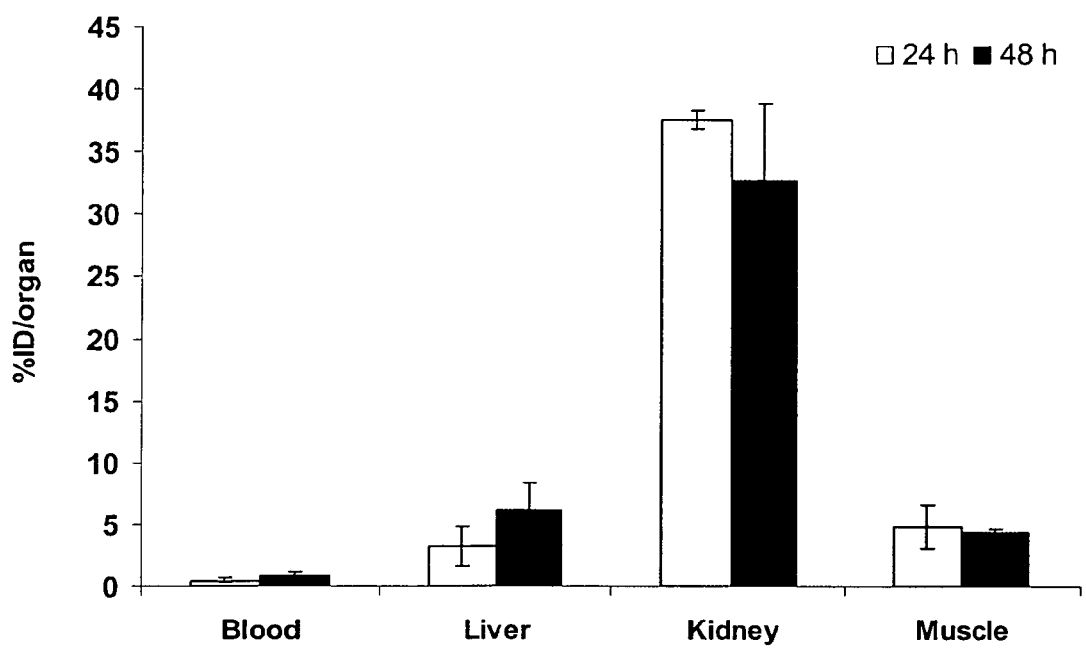
FIG. 33 shows biodistribution data of $^{64}$Cu-DOTA-PNA-K4 conjugates in selected organs of normal balb/c mice via intraperitoneal injection. Injection dose: 55 µCi/100 µL.
Figure 33:
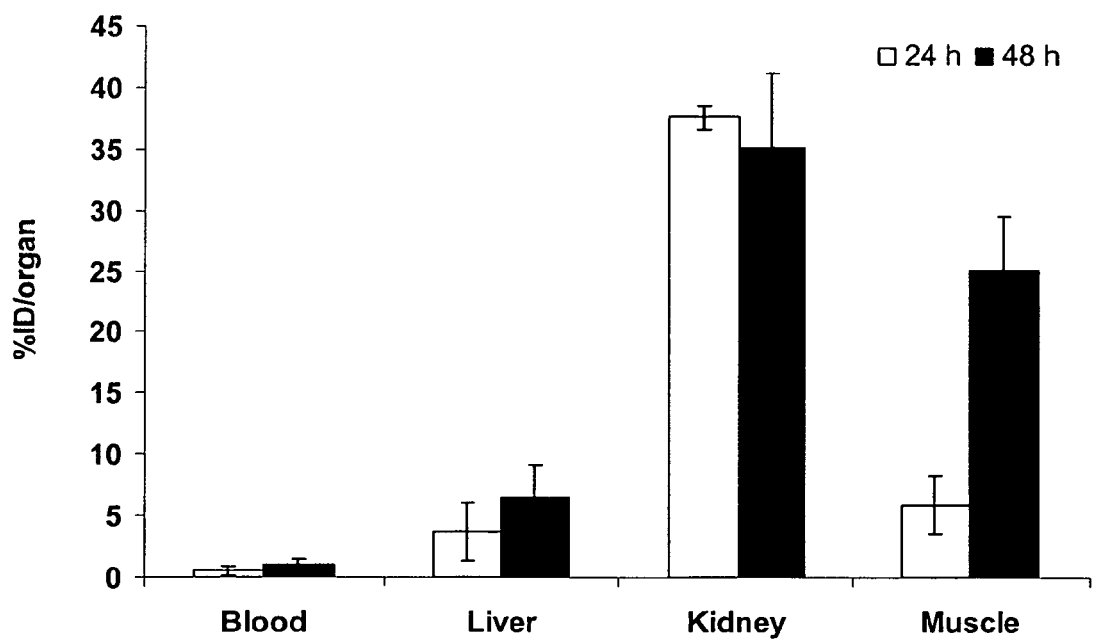

Intraperitoneal injection. The biodistribution of $^{64}$Cu-DOTA-Y-PNA50-K4 and $^{64}$Cu-DOTA-Y-PNA50S-K4 via the intraperitoneal injection mode was performed in normal balb/c mice (n=3) at 24 h and 48 h p.i. The biodistribution data in selected organs are shown in FIG. 33. Both compounds exhibited similar uptake in kidney and liver at 24 h p.i. ($^{64}$Cu-DOTA-Y-PNA50-K4: 37.5±0.7% ID/kidney and 3.2±1.6% ID/liver; $^{64}$Cu-DOTA-Y-PNA50S-K4: 37.6±1.0% ID/kidney and 3.7±2.4% ID/liver), which is comparable to the data of the i.v. mode at 20 min p.i. While no significant clearance was observed from kidney at 48 h p.i. for either compound ($^{64}$Cu-DOTA-Y-PNA50-K4: 33±6% ID/kidney; $^{64}$Cu-DOTA-Y-PNA50S-K4: 35±6% ID/kidney), it is apparent that both conjugates were accumulating in liver out to 48 p.i. ($^{64}$Cu-DOTA-Y-PNA50-K4: 6.1±2.1% ID/liver; $^{64}$Cu-DOTA-Y-PNA50S-K4: 6.5±2.6% ID/liver). Surprisingly, the muscle uptake of $^{64}$Cu-DOTA-Y-PNA50S-K4 drastically increased from 5.9±2.4% ID/muscle at 24 h p.i. to 25.0±4.4% ID/muscle at 48 h p.i., while $^{64}$Cu-DOTA-Y-PNA50-K4 maintained the same uptake level from 24 h (4.9±1.8% ID/muscle) to 48 h p.i. (4.5±0.2% ID/muscle). Both compounds exhibited low accumulation in other tissues (<1% ID/organ in lung, spleen, heart, and brain; <2% ID/organ in blood and bone; and <3% ID/organ in fat at 48 h p.i.).

MicroPET imaging of $^{64}$Cu-DOTA-Y-PNA-K4 conjugates. The microPET imaging was performed in MCF-7 tumor-bearing CB-17 SCID mice with $^{64}$Cu-DOTA-Y-PNA-K4 conjugates at 1 h, 4 h, and 24 h p.i. Of the four compounds, $^{64}$Cu-DOTA-Y-PNA50-K4 exhibited visually the highest image contrast of tumor, which was implanted in the nape of the neck, out to 24 h p.i. (FIG. 34(a)). Consistent with the biodistribution results, the microPET images (FIG. 35) showed that the kidneys were the primary organ of accumulation of the four PNA conjugates. As shown in FIG. 34(b), the solid tumor was also discernible from the surrounding tissues with $^{64}$Cu-DOTA-Y-PNA50S-K4. The tumor was clearly imaged with $^{64}$Cu-DOTA-Y-PNA5-K4 at 1 h p.i. (FIG. 34(c)), but not visible at either 4 h or 24 h p.i. Contrarily, $^{64}$Cu-DOTA-Y-PNA7-K4 was able to give a fairly good image of tumor at 24 h p.i. (FIG. 34(d)), but not at the earlier time points.

Figure 34:
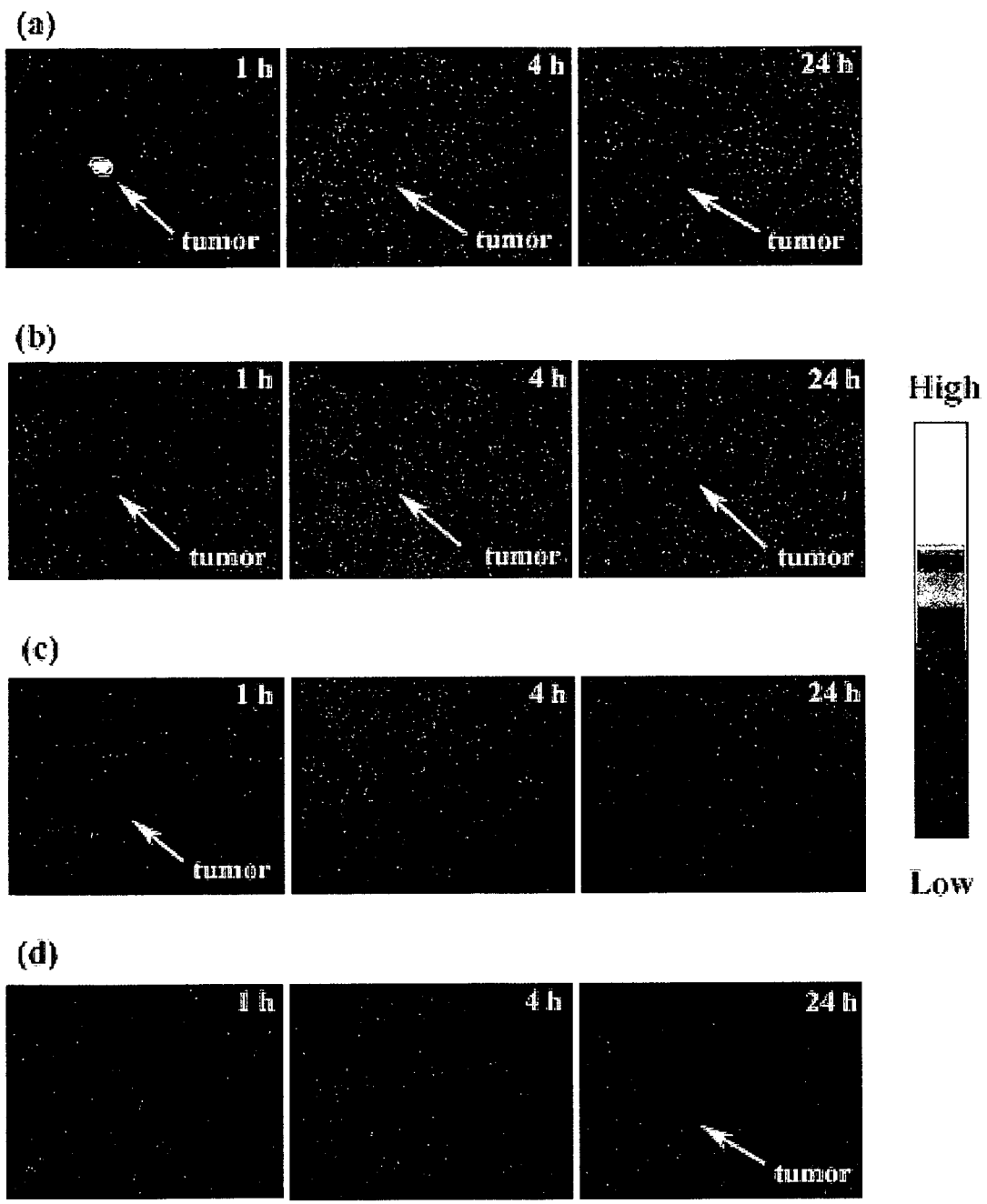
FIG. 34 shows MicroPET transaxial images of $^{64}$Cu-labeled PNA conjugates in MCF-7 tumor bearing CF-17 SCID mice.
Figure 35:
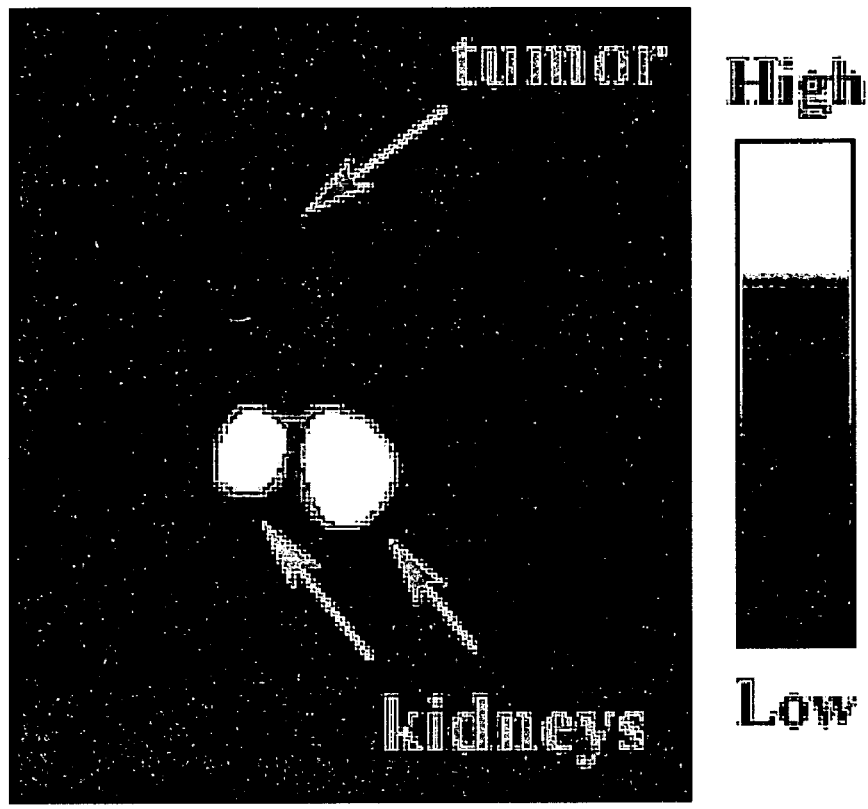
FIG. 35 shows MicroPET coronal image of $^{64}$Cu-DOTA-PNA50-K4 in a MCF-7 tumor bearing CF-17 SCID mouse at 1 h p.i. The intensity of the images was scaled by max/min of frame.

The microPET images were analyzed by the quantification of radiotracer accumulation in the regions of interest (ROIs). The time-activity curves of the four PNA conjugates in kidneys (represented by the left kidney), liver, and tumor were shown in FIG. 36. It is apparent that the quantitative data are in agreement with the microPET images (FIGS. 34 and 35). Kidneys had the highest concentrations of all four compounds as shown by the standard uptake values (SUVs). The $^{64}$Cu-labeled conjugates of PNA50, PNA50S and PNA5 showed slow clearance from kidneys and significant accumulation in liver from 1 h to 24 h p.i. While these three compounds exhibited similar uptake and retention in kidneys and liver, $^{64}$Cu-DOTA-Y-PNA7-K4 demonstrated significant different behavior. In kidneys, it showed the lowest uptake and the most efficient clearance out to 24 h p.i., whereas its liver concentration was the highest, which was around five times those of other compounds at 1 h p.i., and maintained about the same level out to 24 h p.i. Copper-64-DOTA-Y-PNA50-K4 showed the highest SUV (0.076±0.009) in tumor, followed by $^{64}$Cu-DOTA-Y-PNA5-K4 (SUV: 0.034±0.003) and $^{64}$Cu-DOTA-Y-PNA50S-K4 (SUV: 0.018±0.004) at 1 h p.i. While $^{64}$Cu-DOTA-Y-PNA50-K4 exhibited rapid washout from tumor out to 4 h p.i., the accumulation level of $^{64}$Cu-DOTA-Y-PNA50S-K4 remained steady within 24 h p.i. Consistent with the microPET images (FIG. 34d), an appreciable amount of $^{64}$Cu-DOTA-Y-PNA7-K4 was accumulated in tumor at 24 h p.i (SUV: 0.031±0.003).

Figure 37:
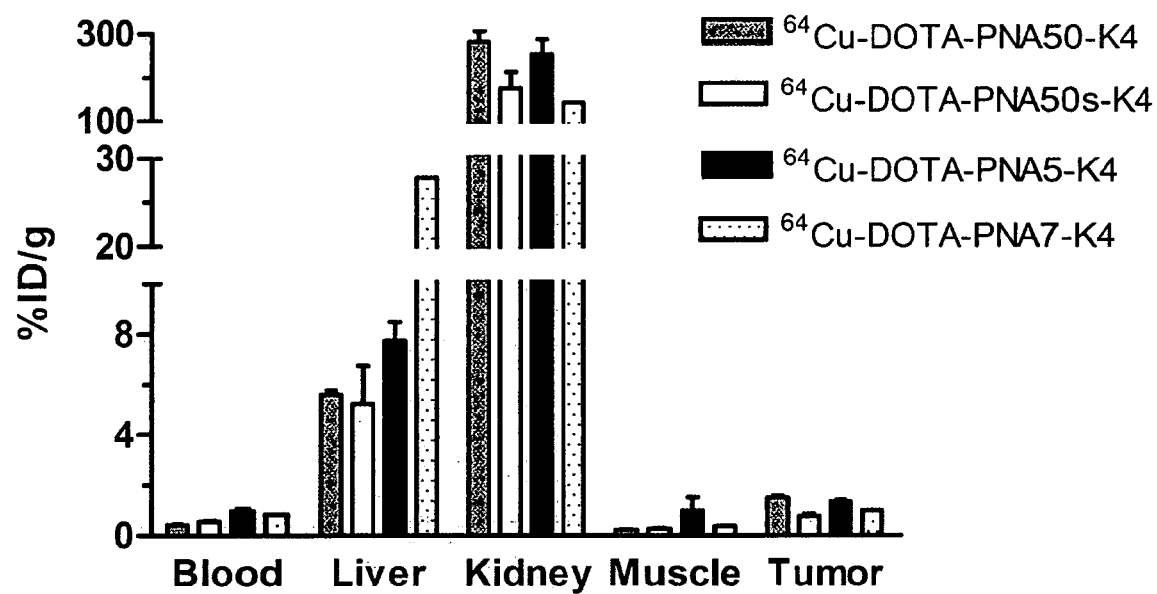
FIG. 37 shows biodistribution data of $^{64}$Cu-DOTA-PNA-K4 conjugates in MCF-7 tumor bearing CF-17 SCID mice post microPET imaging at 24 h p.i. Data are presented as percent injected dose per gram tissue (% ID/g) with error bars representing one standard deviation from the mean of of two living animals.
Figure 38:
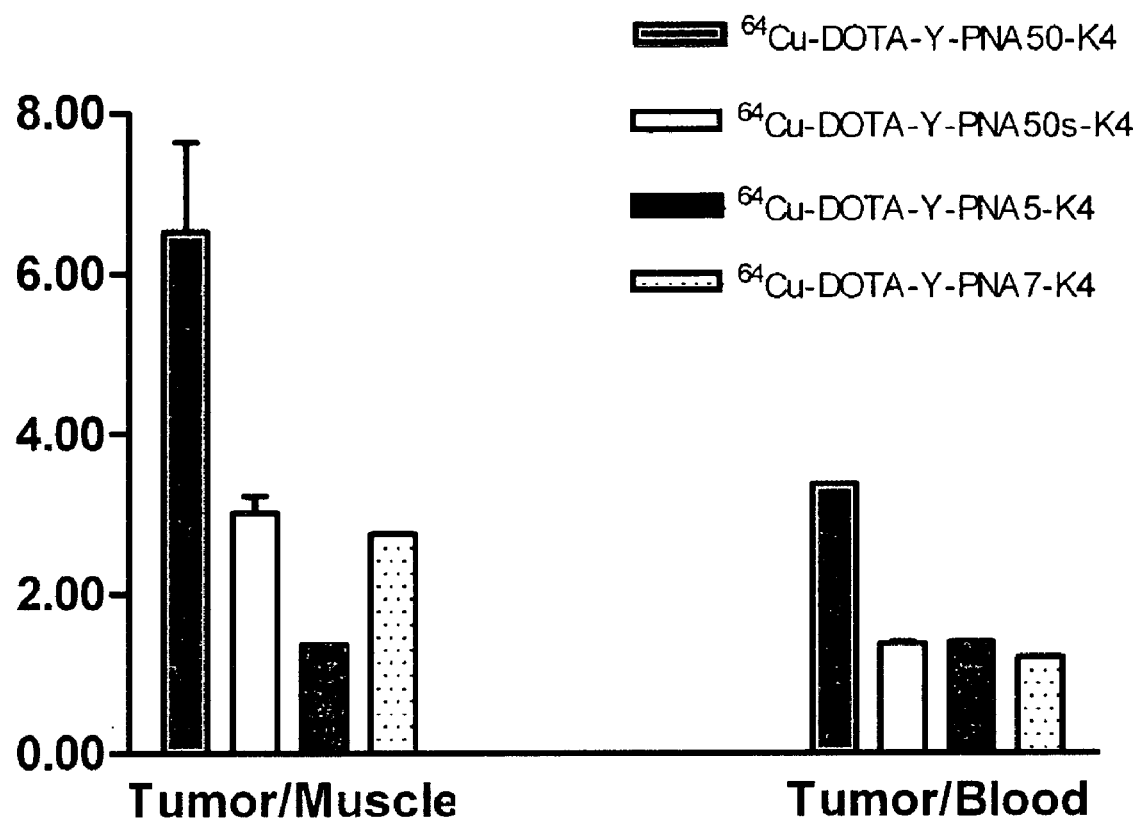
FIG. 38 shows tumor-to-muscle and tumor-to-blood ratios of $^{64}$Cu-DOTA-PNA-K4 conjugates in MCF-7 tumor bearing CF-17 SCID mice at 24 h p.i. Data were calculated from biodistribution results post-microPET imaging. Error bars representing one standard deviation from the mean of two living animals.

Biodistribution data of post imaging. The post imaging biodistribution experiments were carried out right after the microPET imaging at 24 p.i. The concentrations of the four PNA conjugates in blood, liver, kidneys, muscle, and tumor were represented by percent of injected dose per gram of tissue (% ID/g) as shown in FIG. 37. Copper-64-DOTA-Y-PNA50-K4 exhibited the highest concentration in kidneys (280±35% ID/g), followed by $^{64}$Cu-DOTA-Y-PNA5-K4 (251±50% ID/g), $^{64}$Cu-DOTA-Y-PNA50S-K4 (174±54% ID/g), and $^{64}$Cu-DOTA-Y-PNA7-K4 (143% ID/g). In liver, while $^{64}$Cu-DOTA-Y-PNA50-K4, $^{64}$Cu-DOTA-Y-PNA50S-K4 and $^{64}$Cu-DOTA-Y-PNA5-K4 showed similar low concentrations (5.6±0.3% ID/g, 5.2±2.2% ID/g, and 7.7±1.1% ID/g, respectively), the accumulation of $^{64}$Cu-DOTA-Y-PNA7-K4 was much higher (28% ID/g). This observation is consistent with the quantification results of the microPET images. Although $^{64}$Cu-DOTA-Y-PNA50-K4 and $^{64}$Cu-DOTA-Y-PNA5-K4 showed similar tumor uptake (1.50±0.11% ID/g and 1.35±0.11% ID/g, respectively), the tumor/muscle (T/M) ratio of the former (T/M: 6.6±1.1; n=2) is about five times that of the latter due to the high concentration of $^{64}$Cu-DOTA-Y-PNA5-K4 in muscle as shown in FIG. 38. The T/M ratios of $^{64}$Cu-DOTA-Y-PNA50S-K4 (3.0±0.2; n=2) and $^{64}$Cu-DOTA-Y-PNA7-K4 (2.75; n=1) are in between. Copper-64-DOTA-Y-PNA50-K4 also demonstrated the highest tumor/blood ratio (T/B: 3.4±0.0; n=2) among the $^{64}$Cu-labeled PNA conjugates.

Discussion

Our approach to the design of cell-specific imaging agents is based on (1) the identification of an abundant unique or uniquely overexpressed mRNA in the target cell (2) the selection of a high affinity antisense PNA for the target mRNA, (3) covalent attachment of a permeation peptide that allows for reversible cell entry, and (4) covalent or high affinity attachment of positron-emitting radionuclide with high specific activity. In our approach, the biological function of the mRNA is irrelevant, all that matters is that it is uniquely overexpressed and abundant in the target cell. As such this approach differs from other antisense approaches that often target oncogenes, which are only present in low copy number (<100). For this initial study we used SAGE analysis to identify the uniquely overexpressed (approximately 10-fold) and abundant unr mRNA in the MCF-7 cancer cell line (approximately 5000 copies/cell), and an RT-ROL assay to identify high affinity antisense binding sites on the mRNA. PNAs complementary to these sites were conjoined to the recently described permeation peptide Lys$_4$ and the highest affinity PNAs were conjoined to the $^{64}$Cu binding ligand DOTA to create the MCF-7 cell-specific PET imaging agent.

Antisense oligonucleotides have been reported as nuclear imaging probes (PET and SPECT) in forms of unmodified oligomers or viral/non-viral carrier-oligomer conjugates. While the carrier systems could significantly enhance the tumor accumulation of oligonucleotides due to the increased payload of the carriers, a major concern is how to address whether the biodistribution is determined by the carrier or the oligomer. This method may also encounter the common difficulties of drug delivery systems, such as sequestration by reticulo-endothelial system (RES) and immunogenicity of the carriers. It is self-evident that unmodified or minimally modified oligonucleotides should be studied in-depth before they could be applied to the gene transfection or drug delivery systems for various proposes.

As a special class of oligonucleotide analogs, the biological behavior of peptide nucleic acids has been extensively studied in vitro and in vivo since they were first proposed. In contrast, the utilization of PNAs as imaging probes of cancer for PET and SPECT is very limited, probably because the accumulation of the PNA imaging probes in the tumors could barely reach a detectable level. Recently, Sazani et al. (Nat. Biotechnol., 2002, 20, 1228-1233) reported that a PNA with four lysine at its N terminus exhibited superior in vivo properties and sequence-specific activity compared to its analog with one lysine. Therefore, we introduced the four-lysine tail to our unr mRNA targeting PNAs and further incorporated a DOTA chelating moiety for $^{64}$Cu microPET imaging and tissue distribution studies.

The labeling of DOTA-Y-PNA-K4 conjugates with $^{64}$Cu was straightforward. The radiochemical yields were reasonably high, and nearly perfect radiochemical purity was achieved after DTPA challenge of non-specifically bound $^{64}$Cu and centricon separation. The specific activity of the $^{64}$Cu-labeled PNA conjugates was ca. 200 mCi/µmol (7,400 MBq/µmol) at the injection time, which is the highest specific activity ever achieved for radiolabeled oligonucleotides to the best of knowledge. The radiolabeling conditions were optimized from the trials varying reaction temperature, time, pH, and media (data not shown).

Figure 32:
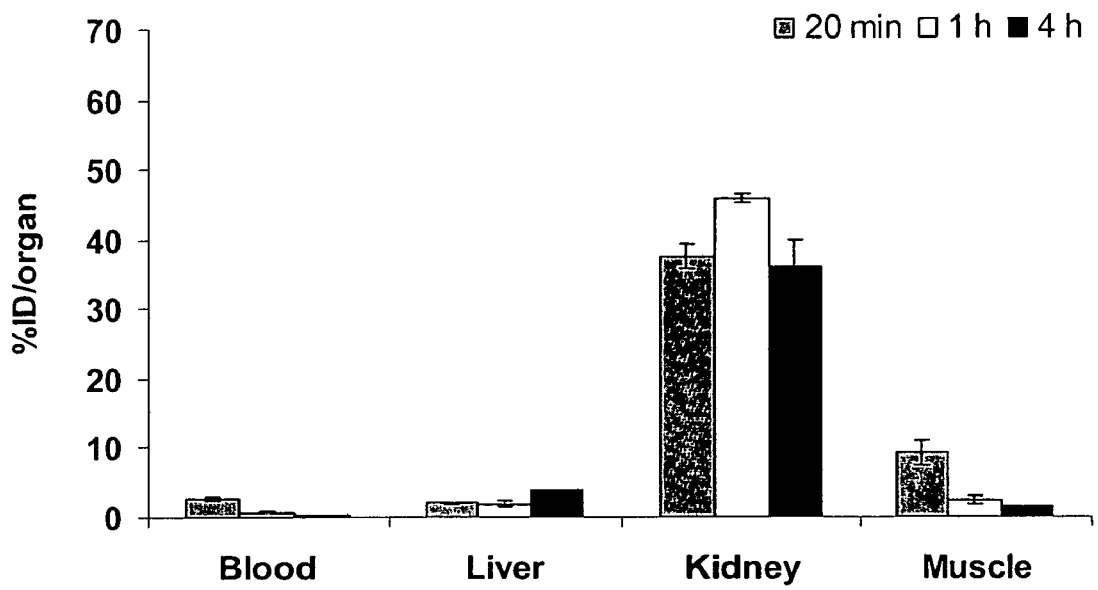
FIG. 32 shows biodistribution data of $^{64}$Cu-DOTA-PNA-K4 conjugates in selected organs of normal balb/c mice via the tail vein injection. Injection dose: 10-12 µCi/100 µL.
Figure 32:
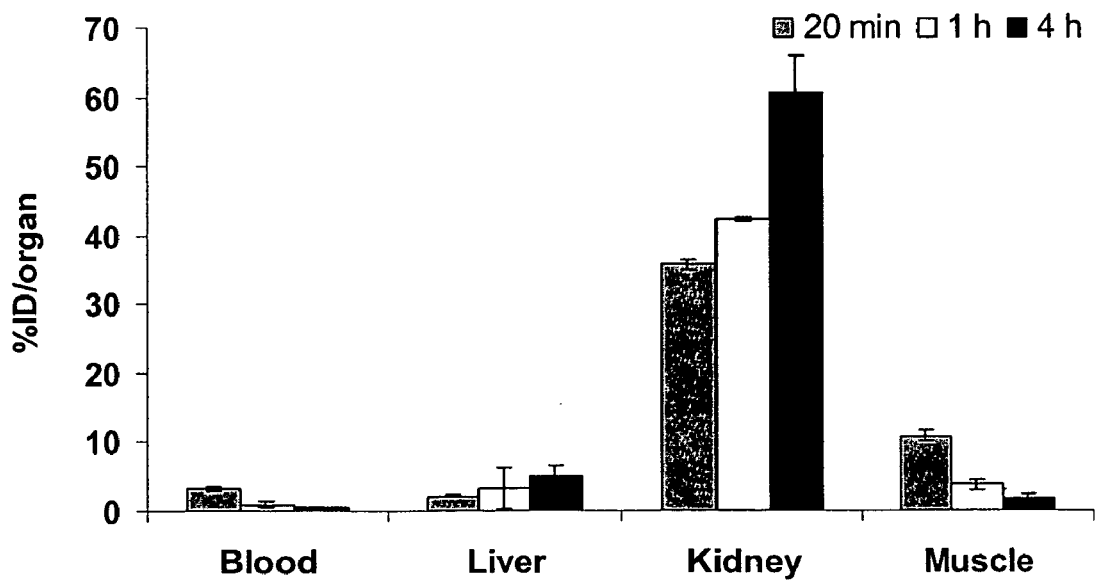

Concerned that our PNA conjugates might have rapid in vivo kinetics, we carried out biodistribution experiments in normal mice via i.v. and i.p. modes. The biodistribution via i.v. was performed within a short time period (4 h) post injection, while the i.p. experiment was conducted at 24 h and 48 h p.i. All the four PNA compounds showed high kidney uptake and long retention throughout time (FIGS. 32 and 33), no matter the injection mode. This observation is in agreement with McMahon's report on the in vivo behavior of PNAs (McMahon et al., Antisense Nucleic Acid Drug Dev, 2002, 12, 65-70). While both PNA conjugates with unr mRNA antisense (PNA50) and sense (PNA50S) sequences exhibited a very similar pattern of tissue distribution within 1 h p.i., the conjugate with sense sequence showed a remarkably higher accumulation in kidney than its antisense counterpart (P<0.005) at 4 h p.i. (FIG. 32) which must be related to the differences in their base composition or sequence. As a result of the rapid pharmacokinetics of PNAs, our PNA conjugates showed a very low level of uptake in blood (<4% ID/blood) at the first time point of the i.v. biodistribution (20 min p.i.), and efficient clearance after then (FIG. 32). The liver uptake was only around 5% ID/organ, which is at the similar level of the reported PNAs. The i.p. biodistribution showed the same profile as the i.v. experiment (FIGS. 32 and 33), which indicates that the tissue distribution of the PNA conjugates cannot be significantly altered by the administration modes. Interestingly, the PNA conjugates with sense sequence exhibited a significantly higher muscle accumulation at 48 h p.i. as compared to its antisense analog (P<0.002). It is possible that the sense PNA is complementary to the same or similar sequence found in mouse muscle, or that it shows some preferential affinity to some other biomolecule in muscle.

Figure 36:
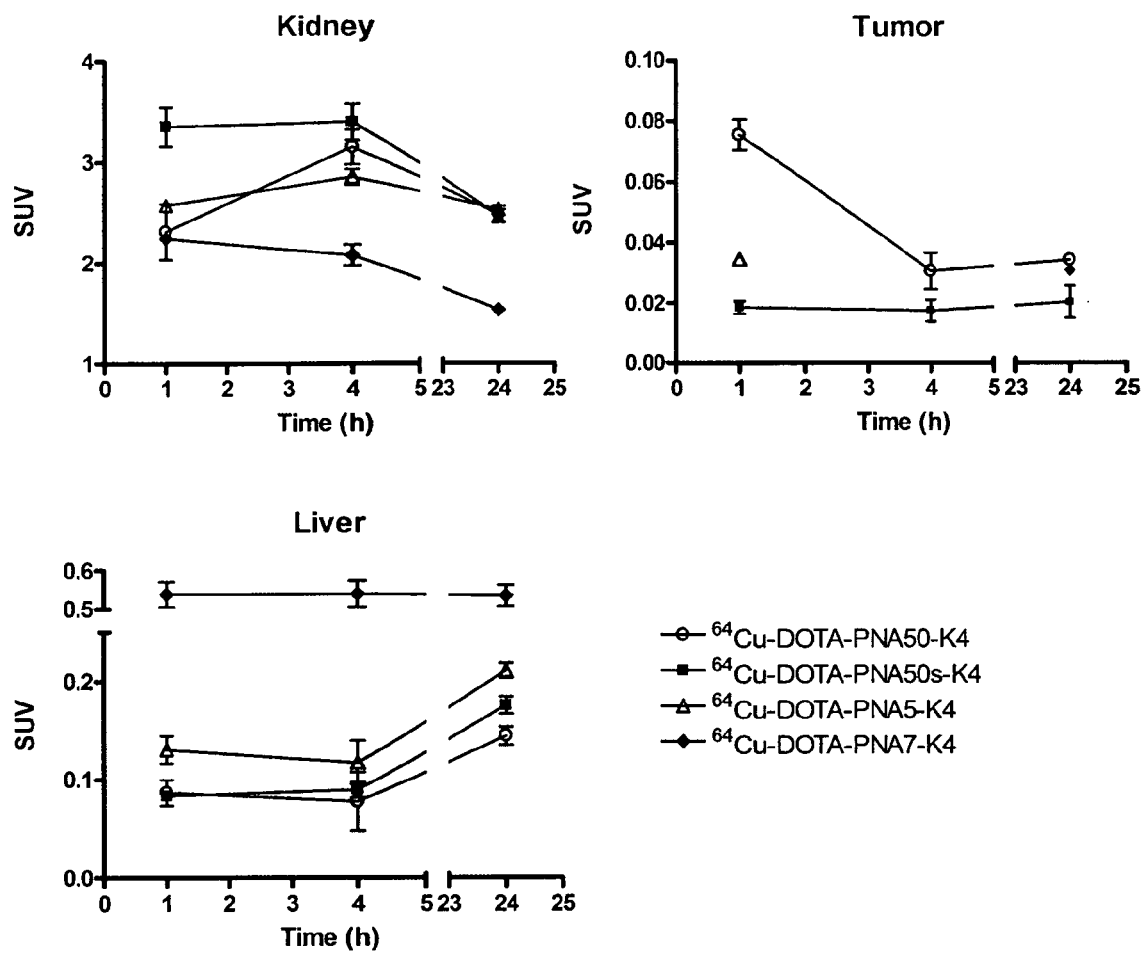
FIG. 36 shows time-activity curves of $^{64}$Cu-DOTA-PNA-K4 conjugates in MCF-7 tumor bearing CF-17 SCID mice. Data are obtained from averaging multiple microPET image slices in the selected organs and tumor, and presented as mean standard uptake values (SUV) with error bars representing one standard deviation from the mean of of three different slices.

As shown in the microPET images (FIG. 34), the tumor with the size of 100-320 mg in CB-17 SCID mice can be imaged with the four $^{64}$Cu-labeled PNA conjugates. This is probably because of their high specific activity, which is about 5 times higher than that of the most recently reported $^{68}$Ga-labeled oligonucleotide (Roivainen et al., J. Nucl. Med., 2004, 45, 347-355). However, the image contrast of tumor at different time points varies greatly with different compounds. At 1 h and 4 h p.i., the tumor was not detectable with $^{64}$Cu-DOTA-Y-PNA7-K4, whereas it gave a good tumor contrast at 24 h p.i. (FIG. 34(d)). Interestingly, $^{64}$Cu-DOTA-Y-PNA5-K4 behaved in the opposite way: it can only image the tumor at 1 h p.i., not at either 4 h or 24 h p.i. (FIG. 33(c)). Both $^{64}$Cu-DOTA-Y-PNA50-K4 and $^{64}$Cu-DOTA-Y-PNA50S-K4 showed the tumor image at all the three time points, but the former conjugate exhibited a much higher tumor to background contrast (FIGS. 34(a) and 34(b)). The quantitative analysis was performed on the microPET images, and the results are in good agreement with the post imaging biodistribution data (FIGS. 36 and 37). This further confirmed the quantitation capability of microPET techniques in the field of molecular imaging. Copper-64-DOTA-Y-PNA5-K4 exhibited a similar tumor uptake to $^{64}$Cu-DOTA-Y-PNA50-K4, however, the tumor was not discernible from the surrounding tissue at 24 h p.i. due to its relatively high accumulation in muscle and blood (FIG. 34). This observation clearly demonstrates that the rapid and efficient clearance from blood and muscle is one of the essential criteria for a good imaging agent besides the high uptake in target organs. To the best of our knowledge, $^{64}$Cu-DOTA-Y-PNA50-K4 has shown the highest and reproducible tumor/muscle ratio both at 4 h (7.9±3.3, data not presented) and at 24 h p.i. (6.6±1.1) among the reported non-carrier bound oligonucleotides in the detection of cancer in vivo via nuclear imaging modalities. Further modification of the conjugate of DOTA-PNA50 is under investigation to minimize the kidney accumulation while maintaining the tumor-targeting property.

In summary, we have designed and synthesized four PNA with a four-lysine tail at the C terminus, one with a sense sequence and three with antisense sequences for the unr mRNA, which is overexpressed in MCF-7 cell line. In order to evaluate their in vivo behavior and tumor-targeting property, we incorporated a DOTA-moiety into the PNAs so that the conjugates can be radiolabeled with $^{64}$Cu for biodistribution and microPET imaging studies in normal and MCF-7 tumor bearing mice. Of the PNA conjugated studied, $^{64}$Cu-DOTA-Y—PNA50-K4 showed the best image contrast of MCF-7 tumor in CB-17 SCID mice, and its tumor/muscle ratio is reproducible and the highest among the radiolabeled oligonucleotides that have been reported for in vivo detection of tumor. Our studies further indicate that antigene and antisense PNAs have great potential to be developed as oncogene- or mRNA-specific probes for early diagnosis of specific cancers. In addition, such antisense $^{64}$Cu-PNA constructs may also be able to function as patient specific therapeutics because of the decay characteristics of $^{64}$Cu when delivered in higher amounts.

EXAMPLE—SET E

Targeting MCF-7 Cells With Antisense PNA'S to Uniquely Overexpressed UNR mRNA

We discovered a uniquely overexpressed and highly abundant mRNA specific to a cell and successfully used that mRNA as an internal receptor for an antisense PNA molecule that showed it was capable of reversibly entering cells.

We discovered that our method is advantageous for targeting MCF-7 breast cancer cells which uniquely overexpress a very abundant unr mRNA (upstream of N-ras or N-ras related gene). Antisense binding sites on the unr mRNA were mapped by application of an improved RT-ROL assay, and a newly developed SAABS (serial analysis antisense binding sites) assay. The relative affinity of ODNs complementary to the antisense binding sites was obtained by a newly developed dot-blot assay. Dissociation constants for tight binding ODNs identified through the dot blot assay were obtained by a newly developed Dynabead assay. Hybrid PNAs corresponding to the ODNs with the highest affinities were synthesized with an N-terminal CysTyr and C-terminal Lys$_4$ sequence and their binding quantified by the Dynabead assay. Hybrid PNAs with $K_d$'s of approx. 10 pM for unr mRNA were identified in this manner and shown to bind to unr mRNA extracted from MCF-7 cells by a PCR assay. Two fluorescently labeled PNAs with the NLS (nuclear localization sequence) permeation peptide were shown to selectively bind to MCF-7 cells in vitro by both fluorescence microscopy and a bulk fluorescence assay, thereby validating this antisense approach for cancer cell targeting.

Identification and Selection of a cancer-specific overexpressed MRNA.

To validate the antisense cell targeting approach, we searched the NCBI SAGE database (http://www.ncbi.nlm.nih.gov/SAGE/) for abundant mRNAs that are >10-fold overexpressed in standard cancer cell lines compared to any normal cell lines. In doing so we discovered that the well studied MCF-7 breast cancer cell line contains an almost 10-fold higher amount of the unr mRNA (GI: 20070240), or upstream of N-RAS otherwise known as the NRAS-related gene, than normal cell lines, and is present at a level of about 5,000 tags/million, or roughly 5,000 copies per cell. We found a full length cDNA clone from the I.M.A.G.E. consortium (5285557 from the NIH_MGC_96 library, UniGene Libary 6001), and obtained the pBluescriptR vector containing the cDNA through the ATCC (American Tissue Culture Collection, #7020864). We were able to successfully produce the unr mRNA in high yield and homogeneity by in vitro transcription with T7 RNA polymerase. The unr mRNA was recovered for use as reported herein.

Figure 18:
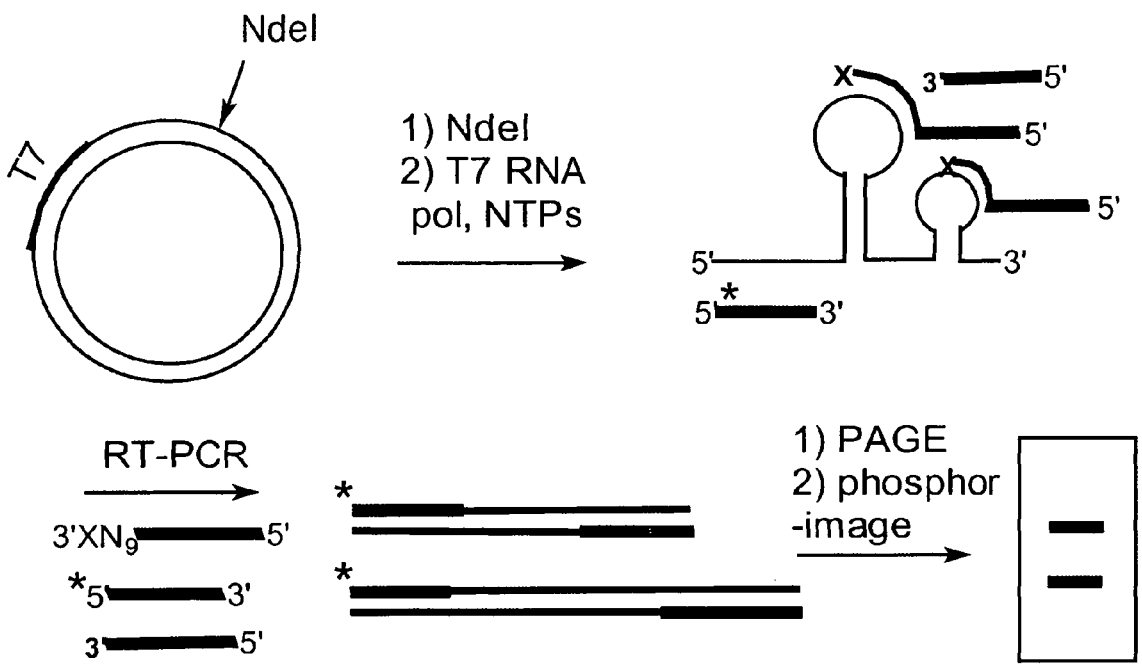
FIG. 18 depicts a modified RT-ROL assay. In this assay antisense binding sites are identified by the ability of a random 9-mer oligonucleotide library (ROL) terminating a specific base and a PCR tag to prime complementary DNA (cDNA) synthesis by reverse transcriptase (RT). The cDNA is then amplified by PCR with a radiolabeled primer having the same sense as the RNA, and an unlabelled primer having the same sequence as the PCR tag.
Figure 19:
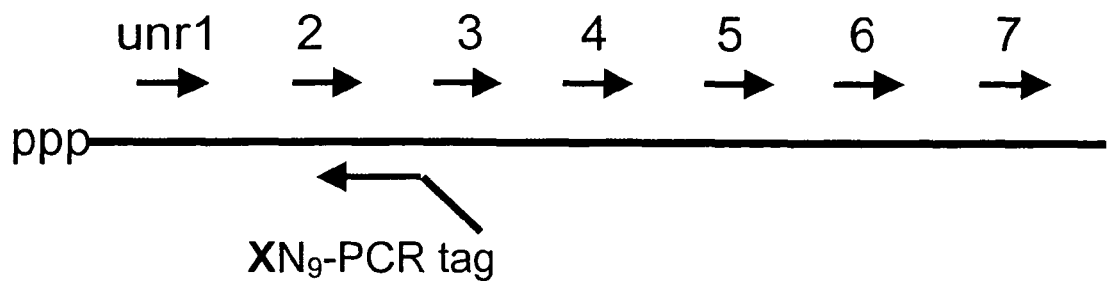
FIG. 19 shows in 19(A) primers used to map ODN accessible sites on unr transcript.
Figure 19:
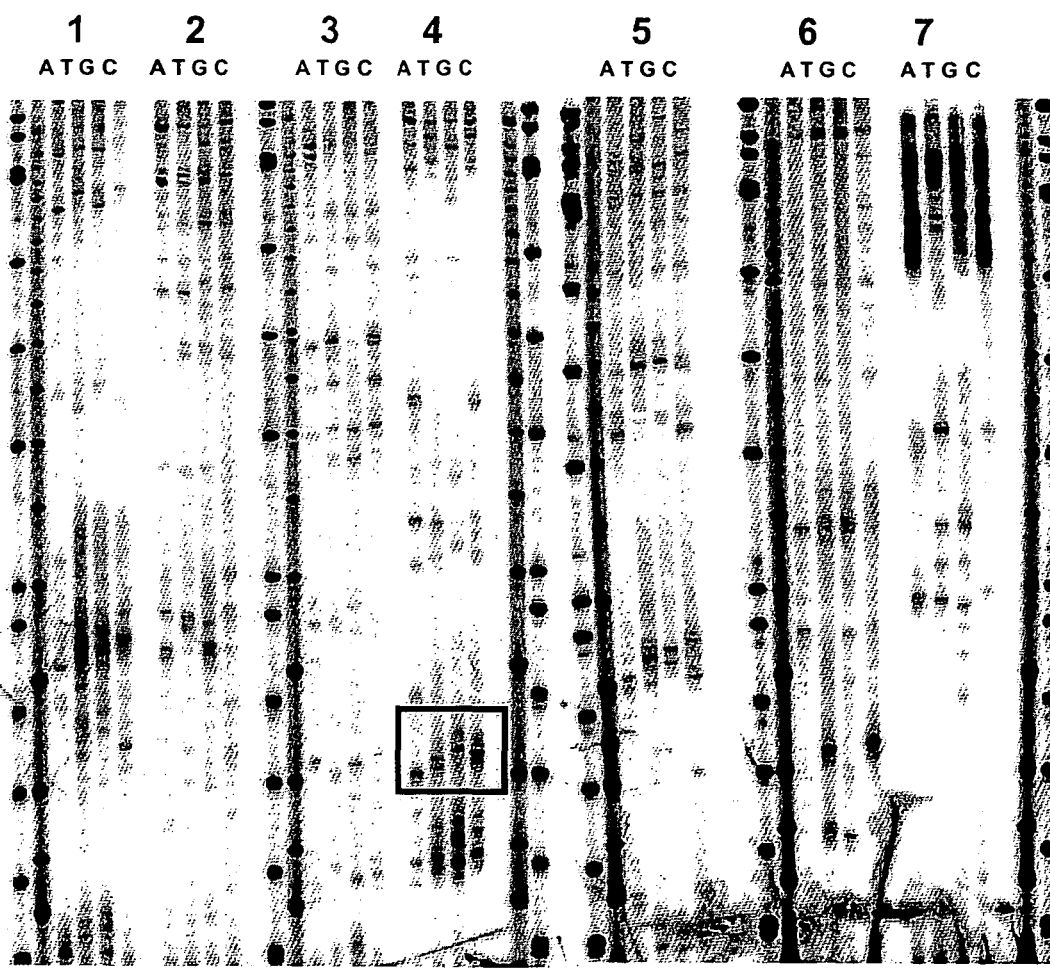
Figure 20:
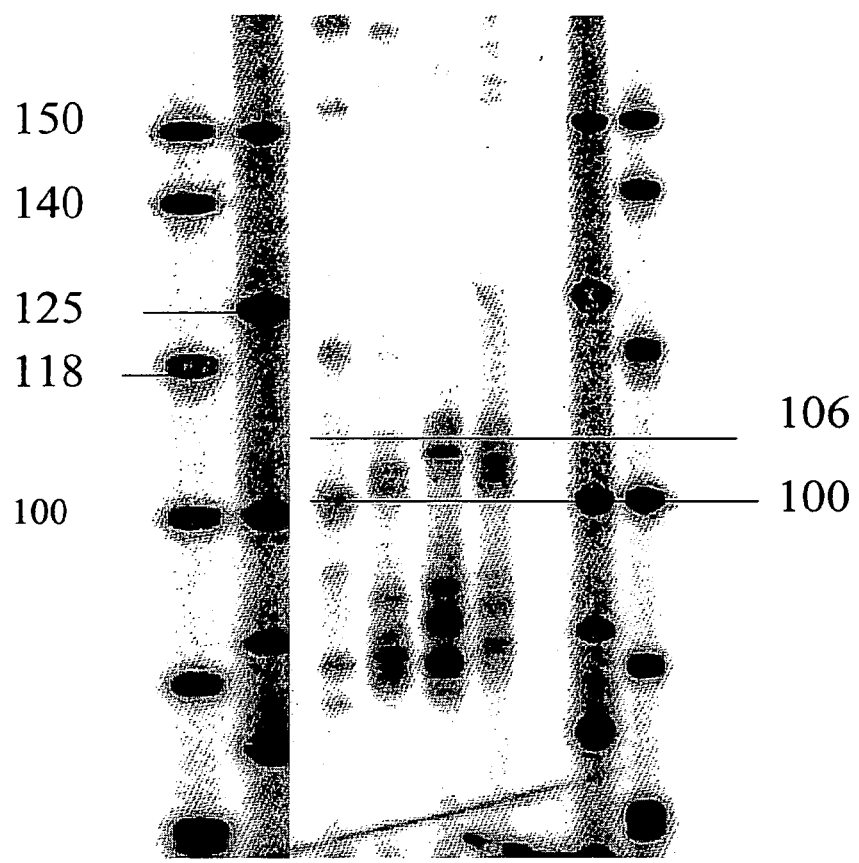
FIG. 20 shows interpretation of the RT-ROL gel.
Figure 20:
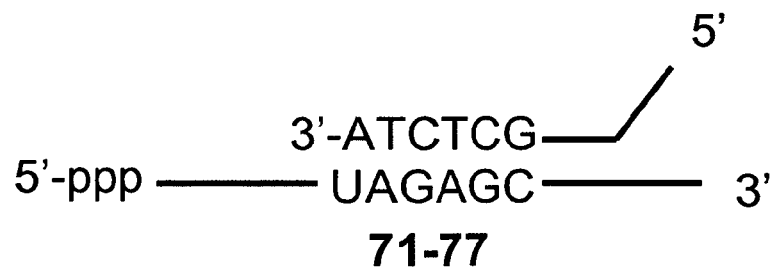

RT-ROL Assay. To identify the sites on the unr mRNA that could bind PNAs, we adopted and improved a mapping method based on using random oligonucleotides attached to a PCR tag to prime reverse transcription followed by PCR amplification. In the original method priming end was a completely random sequence, making it difficult to precisely assign the PCR products to a specific sequence. To get around this problem we synthesized a set of four separate primers each containing a PCR tag and a random 9-mer terminating in unique nucleotide (FIG. 18) thereby making it much easier to assign the PCR product bands to specific sequences. The entire unr mRNA was mapped in this way using 7 forward primers (unrX) for each section of the transcript and the PCR tag on the random oligodeoxynucleotide library (FIG. 19(A)). A number of discrete PCR bands were observed (FIG. 19) which were then analyzed to reveal the ODN binding sites (FIG. 20). Approximately 50 antisense sites on the unr mRNA were identified by this RT-ROL assay.

Serial Analysis of Antisense Binding Sites—SAABS. A potential problem with the RT-ROL assay is that that priming of reverse transcription might be sensitive to secondary structure, and as a result, the intensity of the PCR bands produced in the RT-ROL assay might not correspond to the actual binding affinity. To eliminate this problem we developed an enzyme independent method for mapping antisense binding sites that adapts methodology used in SAGE (Serial Analysis of Gene Expression) to determine the sequence and relative frequency of members of a random library of ODNs that bind to an mRNA molecule.

Figure 21:
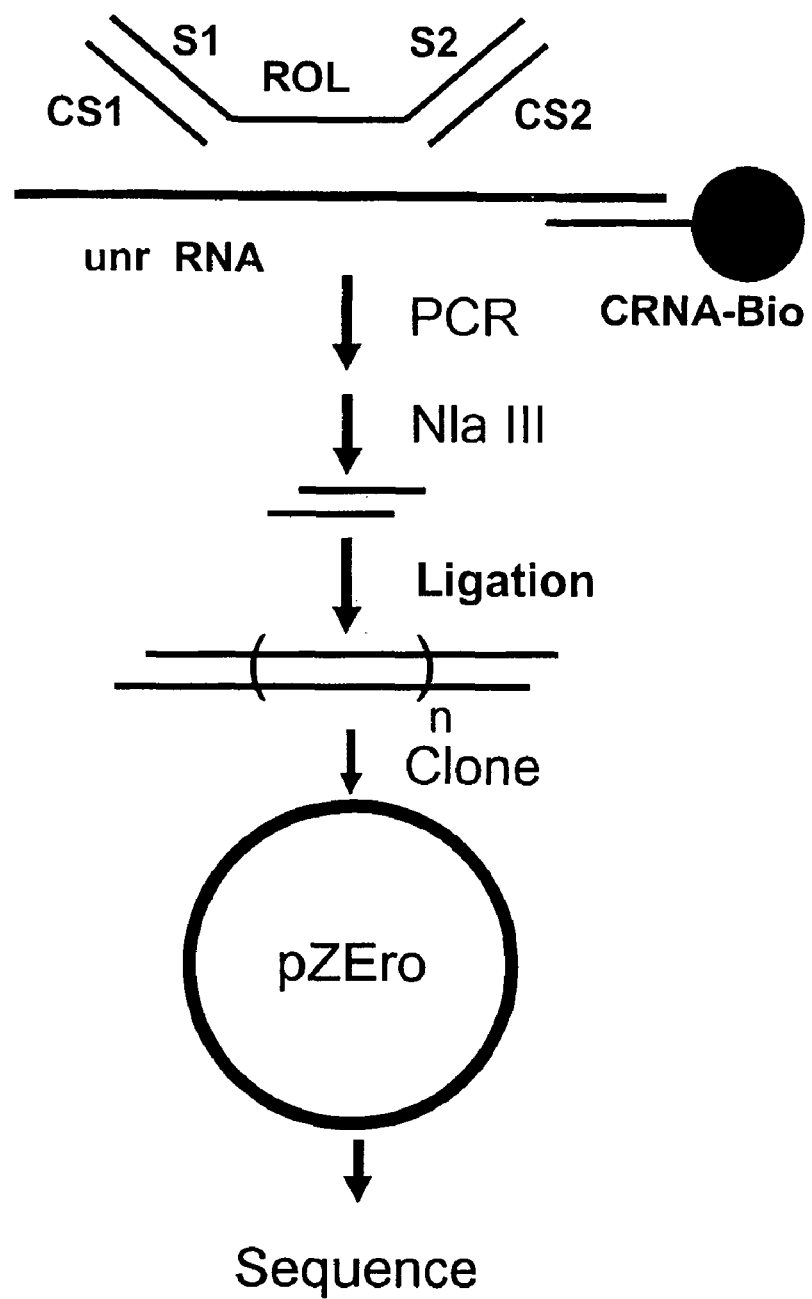
FIG. 21 depicts the results of an SAABS assay. A random 8-mer oligodeoxynucleotide library (ROL) flanked by two PCR tags is incubated with mRNA bound to a Dynabead through hybridization of the attached cRNA-Bio, and then separated from the unbound sequence by a magnetic field. The bound sequence is then PCR amplified, restricted with NlaIII concatenated by ligation, cloned in pZEro and sequenced as shown in FIG. 21. Further, the sequences of the ODNs are as follows: S1-ROL-S2: GGATTTGCTGGTGCAACATGN$_8$CATGAAGCTTGA AATTCGAGG; S1: GGATTTGCTGGTGCAACATG; CS1: CATGTTGCACCAGCAAATCC; CS2: CCTCGAAT-TCAAGCTTCATG; CRNA-Bio:Biotin-TGGTCCTCA-GAATTAAAGCATAATG.
Figure 22:
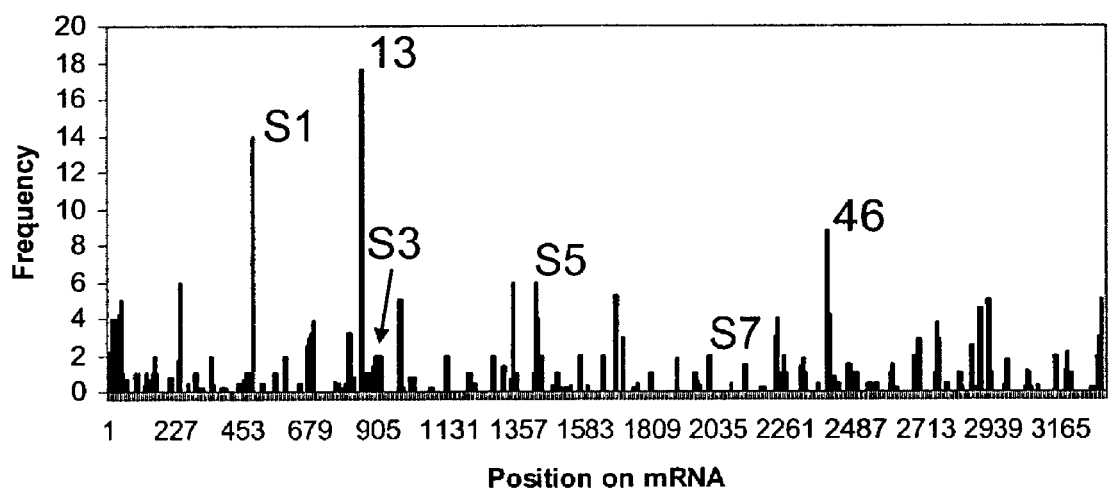
FIG. 22 shows frequency distribution of the antisense binding sequences obtained from the SAABS assay. The 8-mer sequences were retrieved from the sequenced clones and aligned with the mRNA sequence. Some of the sites identified correspond to sites found by the RT-ROL assay (13 and 46), whereas others were uniquely detected by the SAABS assay and denoted with an S prefix (S1, S3, S5 and S7).

The overall procedure is shown in FIG. 21, and consists of incubating a random ODN library linked to two PCR tags with a RNA molecule that is bound to a Dynabead. The PCR tags are prevented from hybridizing to the mRNA by binding to the complementary ODNs CS I and CS2. Following incubation with the mRNA, the Dynabeads are spun down and washed to remove unbound ODNs. The bound ODNs are then PCR amplified with biotinylated primers Bio-S1 and Bio-S2, restricted to give 12-mers, separated from the cleaved PCR tags by strepavidin, concatenated by ligation, cloned into the pZero plasmid, and transfected into E. coli. Plasmids containing inserts are then sequenced, and the sequence of the antisense ODNs are extracted from between the restriction sites and matched to their complementary site on the RNA sequence by a computer algorithm. The relative frequency of the antisense sequences found bound to the unr mRNA is plotted against mRNA position in FIG. 22. Some of these sites had already been detected by the RT-ROL assay. Fifteen of the highest frequency sites were chosen for further analysis.

Dynabead Dot Blot Assay. To determine the relative affinity of ODNs for the antisense binding sites determined by the RT-ROL and SAABS assays, we developed a sensitive and semi quantitative dot blot assay. In our first attempts we used a standard protocol that involves photocrosslinking of antisense ODNs to a nylon membrane and then quantifying the amount of radiolabeled mRNA that becomes bound. Unfortunately, this technique did not appear to be very reproducible, probably because of the non-uniformity of UV crosslinking of ODNs of varying sequence to the nylon membrane.

In developing a better dot blotting method for screening ODN binding sites, we investigated the use of Dynabeads to anchor the RNA to the blot. We found that the binding capacity of the streptavidin coated beads for biotinylated unr mRNA produced by transcription in the presence of Bio-dUTP, to be about 1 pmol of RNA/20 µL of Dynabeads (FIG. 23A) and that the Dynabead bound mRNA could bind about one half an equivalent of a radiolabeled ODN under saturating conditions (FIG. 23(B)).

Figure 23:
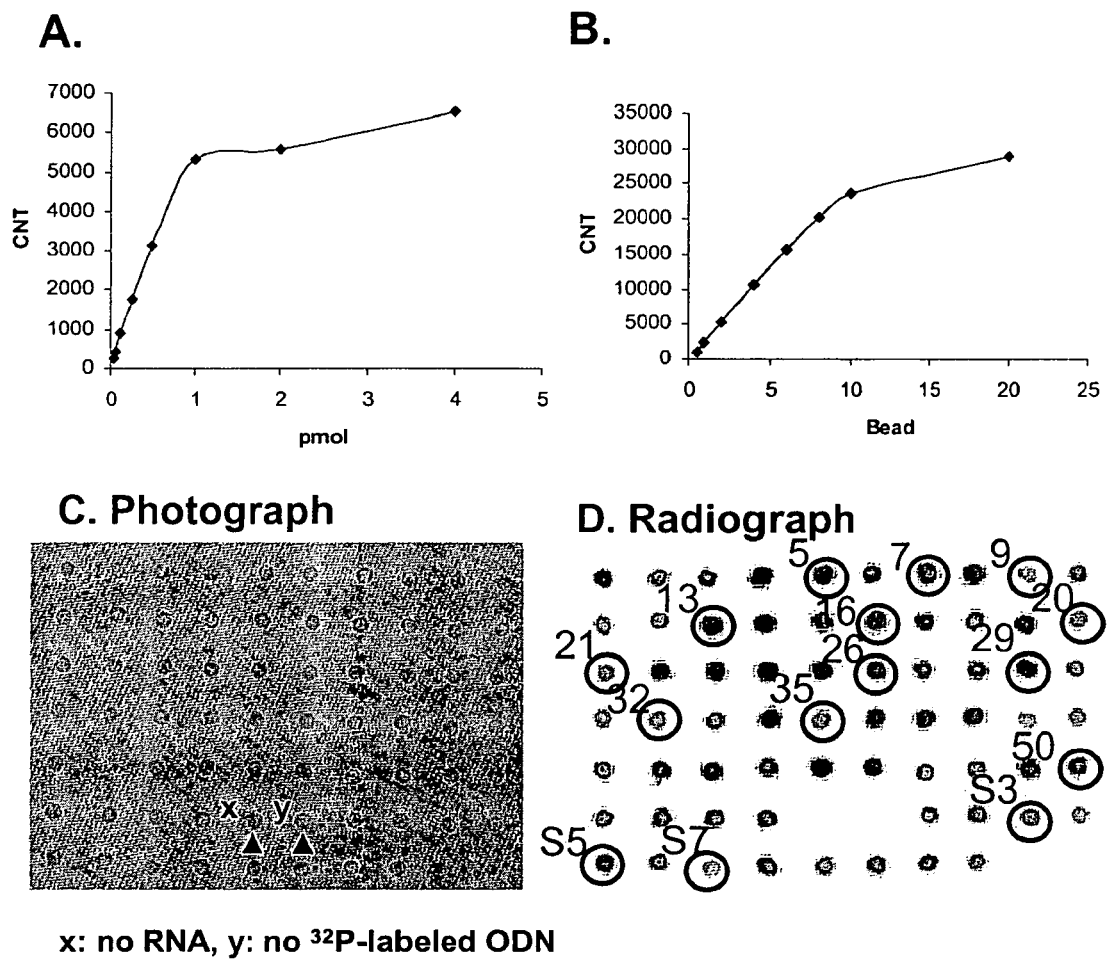
FIG. 23 shows the results of a Dynabead-based dot blot assay to determine relative binding affinity of ODNs.

The Dynabeads were then used to bind the mRNA to the nylon membrane in the dot blot assay (FIG. 23(C) and FIG. 23(D)) to assess the relative binding affinities of 20-mer ODNs for binding sites identified by the RT-ROL and SAABS methods that we had previously reported. ODNs for the quantitative assays were chosen from both high affinity binding sites and low affinity binding sites and the sequence optimized by shifting to the 5'- or 3'-end to minimize self-complementarity and shortened to 15-mers to minimize unfavorable electrostatic interactions (indicated by x-2 in the code for the ODN, where x=the parental ODN). On the basis of this assay, about 15 ODNs were selected for more quantitative asssays.

Figure 24:
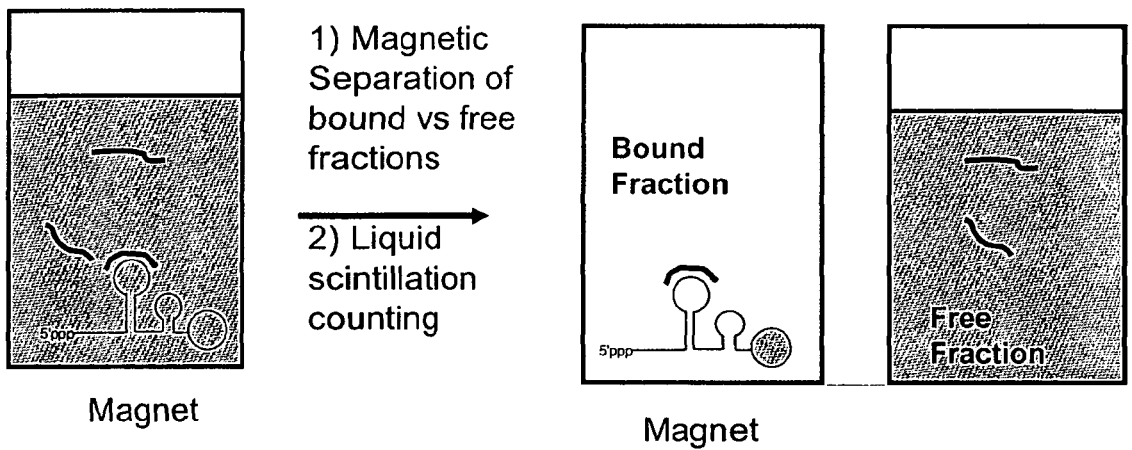
FIG. 24 is an inventors' schematic depicting the results of a Dynabead-based quantitative binding assay. The solution containing free ODN is physically separated from the ODN bound to the RNA by a magnetic field and is quantified by liquid scintillation counting.
Figure 25:
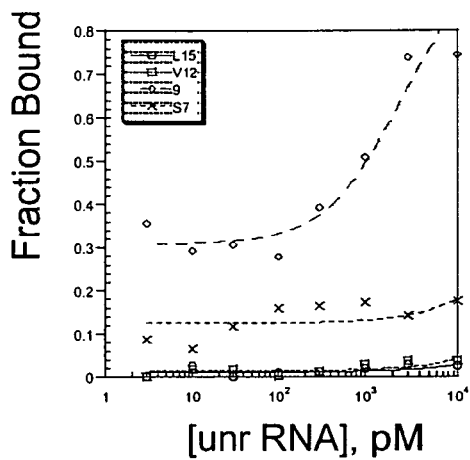
FIG. 25 provides inventors' data curve fits of the data from the Dynabead ODN binding assay depicted in FIG. 24.
Figure 25:
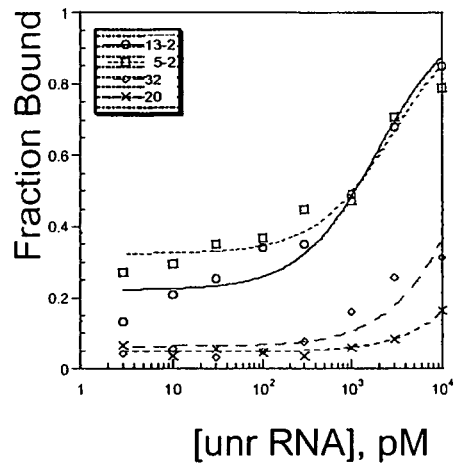
Figure 25:
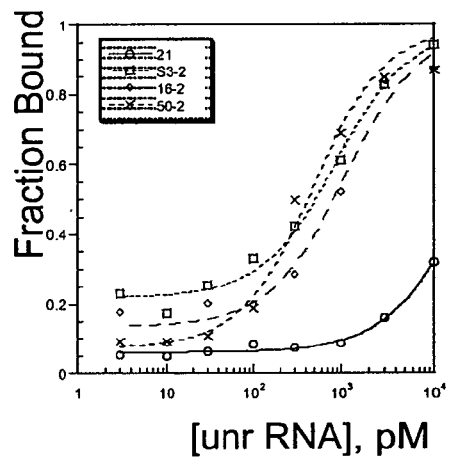
Figure 25:
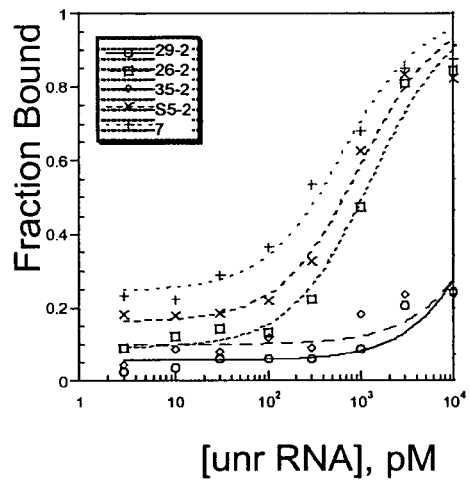

Dynabead ODN Binding Assay. Initially we attempted to obtain ODN binding constants to the unr mRNA by a Centricon centrifugal filtration assay. In this assay 5'-$^{32}$P-radiolabeled ODN incubated with increasing concentrations of mRNA, and bound ODN is separated from free ODN by centrifugation through a filter that does not allow the mRNA, and any ODN-bound mRNA to pass through the filter. Unfortunately, this method did not work very well due due to problems with non-specific binding the filter. To get around this problem, we developed a new Dynabead-based assay method which makes use of a magnetic field to separate molecules bound to a Dynabead from free molecules in solution without the use of a filter (FIG. 24). The unr mRNA was attached by using streptavidin coated Dynabeads and biotinylated RNA produced by transcription in the presence of Bio-dUTP. The Dynabead method gave much better results than the Centricon-based method, though it appeared that there was a variable amount of non-specific binding which resulted in measurable radioactivity in the bound fraction at low concentrations of mRNA no ODN should be bound (FIG. 25). This non-specific binding could be easily subtracted during the non-linear least squares fitting used to determine the dissociation constants (see testal section). As can be seen in Table 1, 5 ODNs show $K_d$s of 1 nM or less, and 9 have $K_d$s of less than 3 nM.

Figure 10:
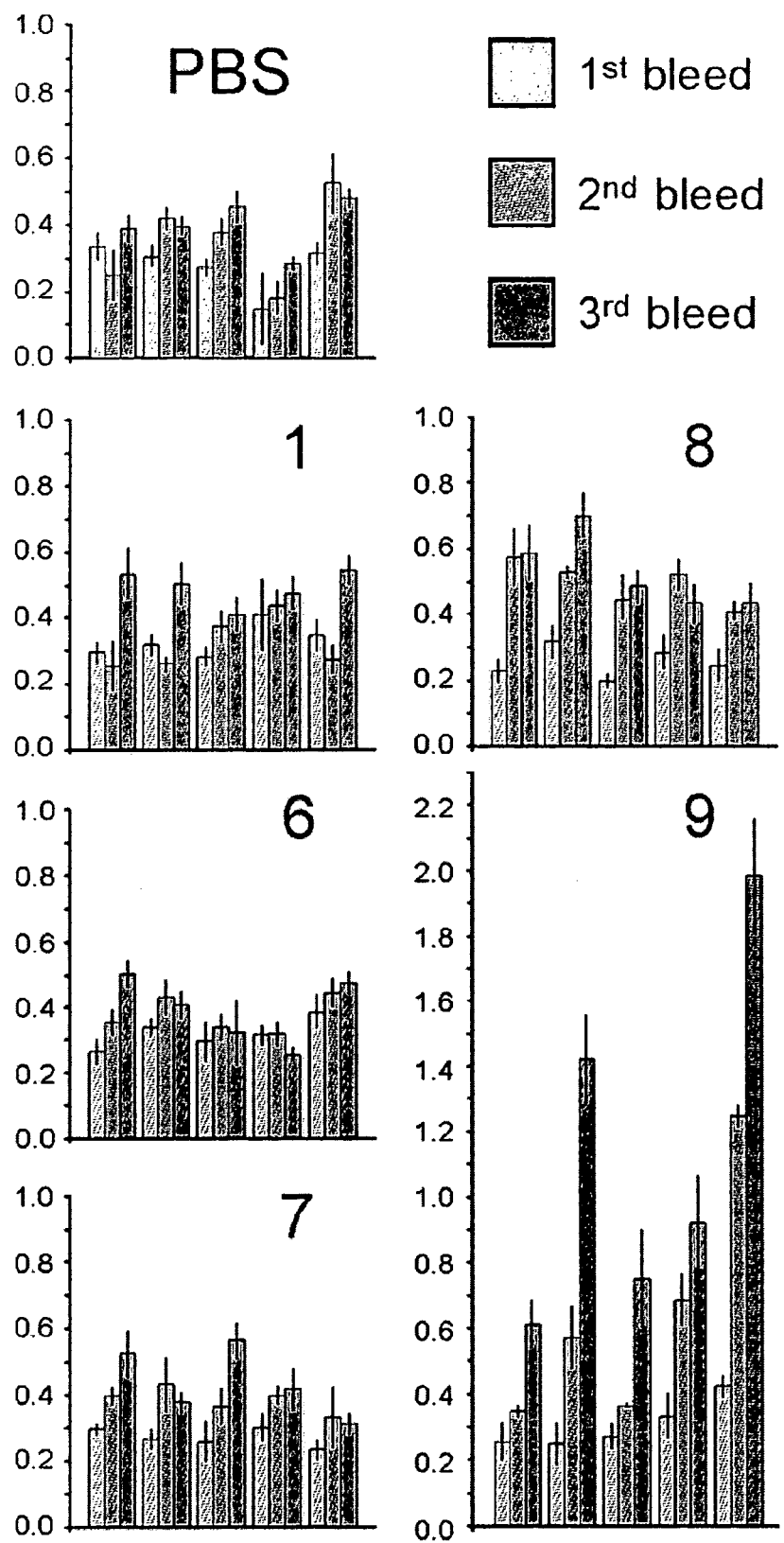
FIG. 10 shows each group of three bars within a data set corresponding to a titer measurement from an individual living mouse. The red bars correspond to the prebled, the orange bars represent the bleed two weeks after the first booster immunization, and the yellow bars represent the bleed two weeks following the end booster immunization. Detrimental immunogenic effects, relative to controls, are negligible in all samples except for the 2.0% (9) sample which suggests that the quantity of PTD and the manner in which it is presented on the surface have a synergistic effect that is able to produce an immune response significantly greater than the response elicited by the peptide itself. Error bars are representative of one standard deviation from the mean of triplicate samples harvested from two separate serum vials and the estimates are of the standard uncertainties.

Design and Synthesis of the antisense PNAs. Because ODNs are readily degraded in vivo and additionally cause cleavage of the mRNA transcript to which they are bound via RNase H enzyme activity, they are not suitable for in vivo targeting. Peptide nucleic acid (PNA) is ideally suited for this purpose because it is a nucleic acid analog with a peptide backbone in place of a sugar phosphate backbone that is highly resistant to degradation, does not activate RNase H activity and also has high affinity for complementary mRNA. We therefore designed hybrid PNAs corresponding to the 4 tightest binding ODNs, and ODN 5-2 which is less tightly bound. A sense sequence corresponding to PNA50-2S was also made as a control. The PNAs were synthesized with 4 lysines at the carboxy terminus (FIG. 10), as a permeation peptide for in vitro and in vivo studes in mice, and to aid in water solubilization and in mRNA binding. A cysteine—tyrosine sequence was added to the amino terminal end to enable attachment of reporter groups to the cysteine, and radioiodination of the tyrosine. The PNAs were synthesized by standard solid phase Fmoc chemistry on an ABI Expedite 8909 automated synthesizer, purified by reverse phase HPLC, and characterized by molecular weight determination by MALD-TOF (Table 2).

Figure 26:
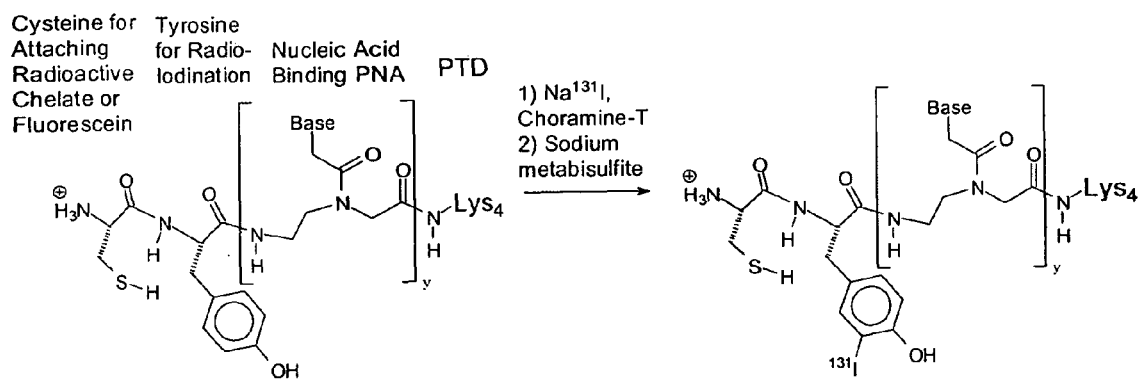
FIG. 26 shows design and radioiodination of PNAs with $^{131}$I. PNAs contained a tyrosine which can be readily iodinated by $I_2$ under neutral conditions. The $^{131}I_2$ was successfully produced in situ by oxidation with chloramine-T.
Figure 27:
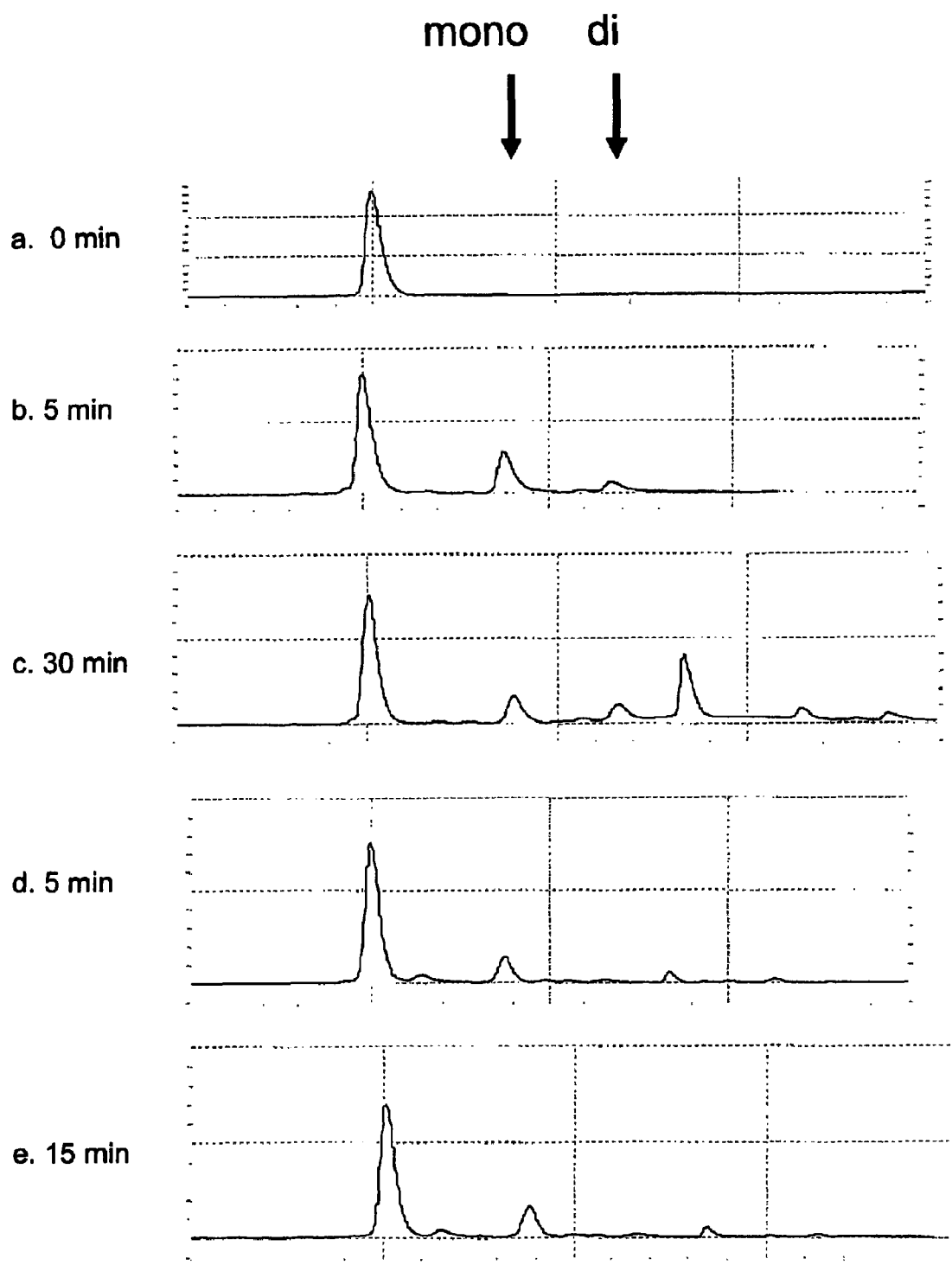
FIG. 27 shows successful iodination reactions including HPLC analysis of iodination reaction with chloramine-T (b & c) and IODO-beads (d & e) for the times shown. Products were identified by MALDI-TOF.

PNA binding affinity. The binding affinity of the PNAs for the unr mRNA were determined by monitoring bound and free $^{131}$I-labeled PNA as a function of mRNA concentration using the Dynabead method that we developed for the ODNs (FIG. 24). We chose $^{131}$I to label the PNAs because of the high specific activity in which it can be obtained and its short half-life of 8 days. The PNAs were radiolabeled by a published procedure previously used to label PNAs with $^{124}$I utilizing chloramine-T as an oxidant (FIG. 26). We also checked the integrity of the PNA produced under theses conditions by repeating the labeling test with a short PNA test sequence, DOTA-Tyr-ATGC-Lys with non-radioactive iodine by the chloramine-T method and also by IODO-beads and analyzed the products by MALDI. We found that at 5 min reaction time, both methods lead primarily to the mono-iodinated compound and some of the diiodinated compound (tyrosine can react twice), but that at longer times, other products are produced (FIG. 27). Thus the 5 min time period appears to be optimal for radiolabeling by I-131.

Figure 28:
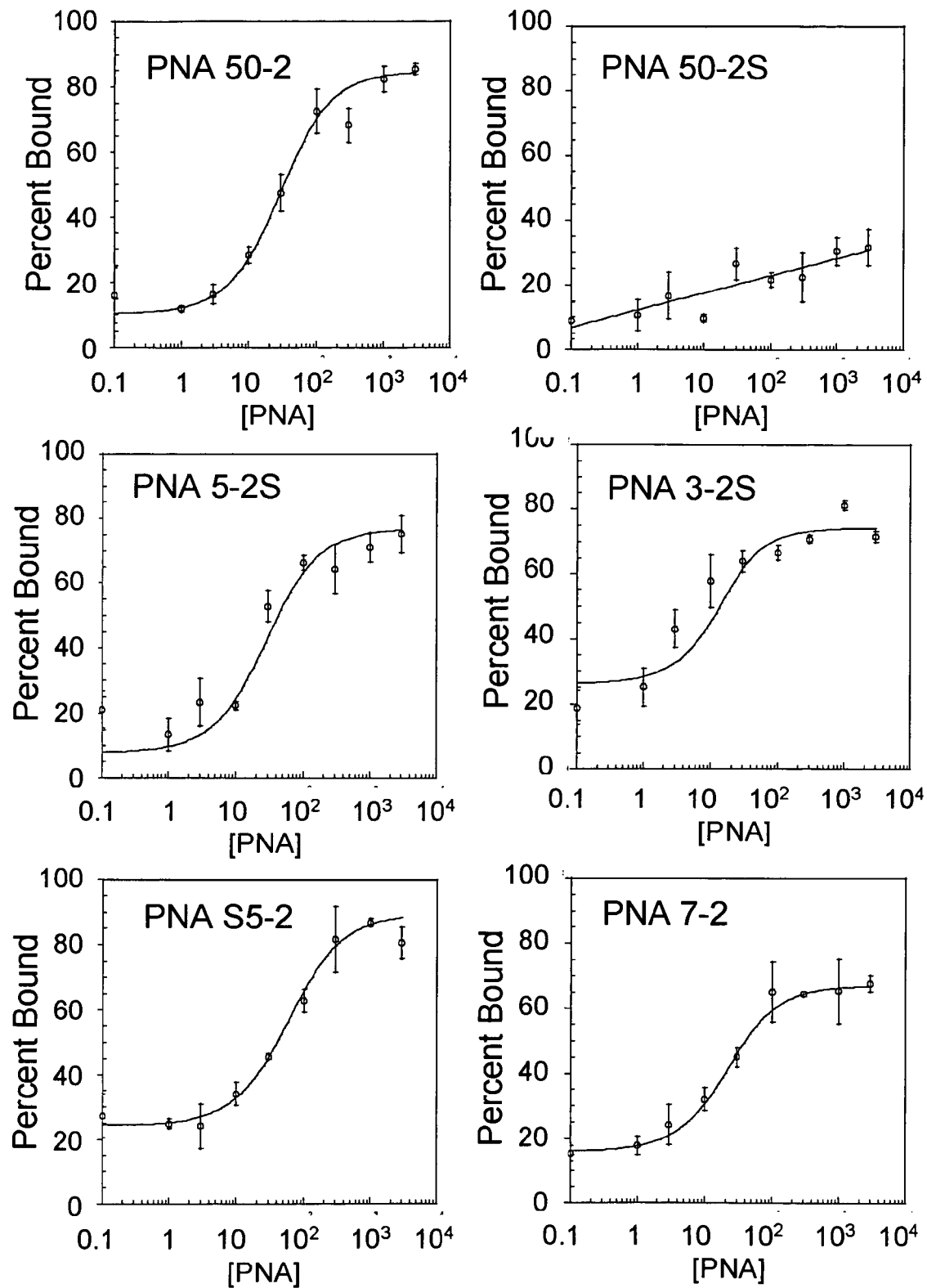
FIG. 28 shows inventors' data curve fits to the PNA binding data from the Dynabead assay. The error bars represent the standard deviation of the average of three tests.

In the first set of PNA binding tests we discovered that we were not recovering the entire radioactivity. We were able to trace this to non-specific binding of the PNA to the standard polyethylene microfuge tubes. After ordering and testing a number of tubes and microtiter plates advertised as minimizing binding of peptides and nucleic acids, we found that the Corning NBS microtiter plates had the lowest binding affinity. Individual tubes were obtained by sawing the plates into pieces. Triplicate sets of data were obtained and a plot of % bound as a function of RNA concentration was fit to a simple two state binding equilibrium as we had done for the ODNs (FIG. 28). The $K_d$s for the PNAs and the corresponding ODNs are tabulated in Table 3. As expected, the PNAs show very high binding affinity (low $K_d$s) for the tested sites on the unr mRNA with $K_d$s that range from 7 to 50 pM at 0.1 M salt.

The binding affinities of the PNAs for the sites are much greater (lower $K_d$s) than that of the corresponding ODNs. The difference is binding affinity under physiological conditions is likely to be much greater than it would appear from the tabulated data since the PNA dissociation constants were obtained at the physiological concentration of 0.1 M NaCl, whereas the ODN dissociation constants were acquired at 1 M salt. At 0.1 M salt the $K_d$s for the ODNs are expected to be greater due to electrostatic repulsions, whereas the PNAs are expected to have lower $K_d$s due to favorable electrostatic attraction with the $Lys_4$ tail. The control PNA, PNA 50-2S which is identical in sequence to the mRNA target showed no significant binding in the range of RNA concentrations that bound tightly to the antisense sequences.

Binding of PNA50-2 to unr mRNA isolated from MCF-7 cells.

Figure 29:
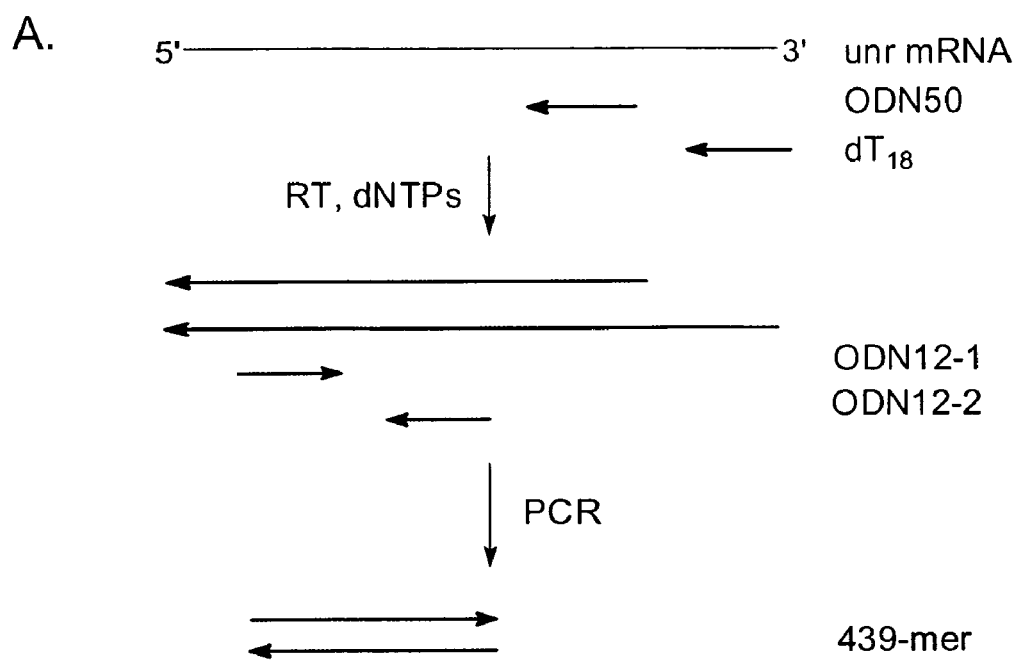
FIG. 29 shows RT-PCR assay for demonstrated successful binding of PNA50 to unr mRNA isolated from MCF-7 cells. A) dT18, B) ODN50, C) PNA50, D) PNA50+ODN50, E) PNA50+ODN50+dT18, F) PNA50S+ODN50, G) PNA50S+ODN50+dT18H) no PNA or ODN. (RT is reverse transcriptase, PCR was carried out with Taq polymerase.)
Figure 29:
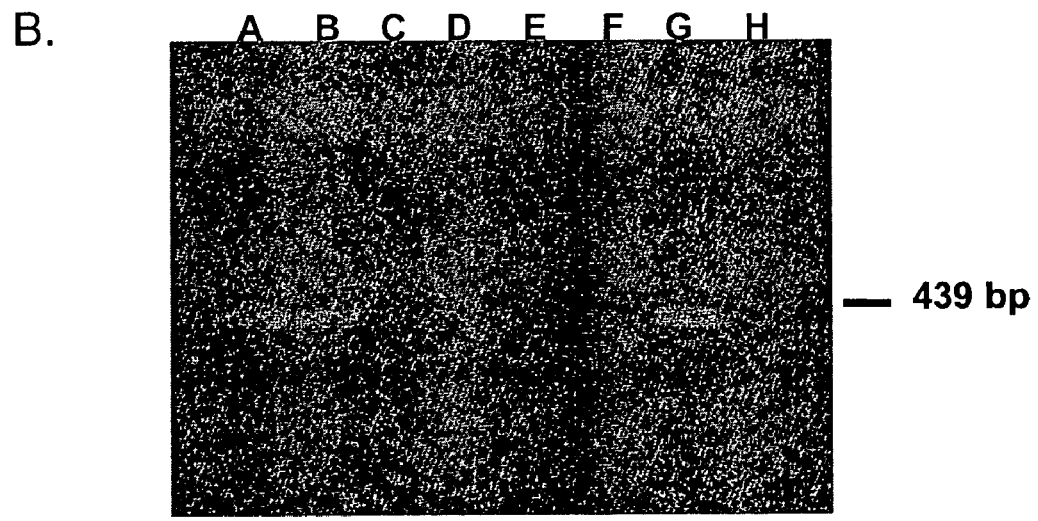

To determine whether or not the 50-2 antisense binding site identified by the RT-ROL and SAABS assays on unr mRNA produced by T7 RNA polymerase in vitro exists on unr mRNA produced by MCF-7 cells in vivo we devised a simple RT-PCR assay. For this assay, total RNA from MCF-7 is subjected to RT-PCR with various combinations of primers as illustrated in FIG. 29. If reverse transcription takes place from either the 50-2 site with ODN50-2 or the polyA tail with a $dT_{18}$ primer, and extends to the end of the mRNA, one should get a 439-mer PCR product when one uses the two PCR primers UNR12-1 and UNR12-2. Indeed, if $dT_{18}$ is used as a primer, (Lane A of FIG. 29) a PCR product is indeed observed, as it is when ODN50-2 alone is used as a primer (lane B), demonstrating that this site is accessible in unr mRNA produced by MCF-7 cells. When PNA50-2 alone is used no product is visible as PNAs cannot serve as primers for reverse transcriptase (Lane C). When ODN50 is used in the presence of PNA50, no PCR product is again observed, which is consistent with the much tighter binding affinity of PNA than DNA for the same site on the mRNA (Lane D). When PNA50 is present during extension by $dT_{18}$ no PCR product is seen suggesting that PNA50 binds so tightly that it can block reverse transcription past this site (Lane E). When the sense PNA, PNA50S is incubated with ODN50 no PCR product is observed which is consistent with duplex formation between PNA50S and ODN50 (Lane F). When the same reaction is carried out in the presence of $dT_{18}$, a PCR product is observed (Lane G) as expected since there is nothing to block reverse transcriptase from elongating $dT_{18}$. Together, the results of these tests confirm that both ODN50 and PNA50 bind to the unr mRNA produced by MCF-7 cells, and furthermore that PNA50 binds much more tightly than ODN50, as bourne out by results of the binding assays.

Figure 30:
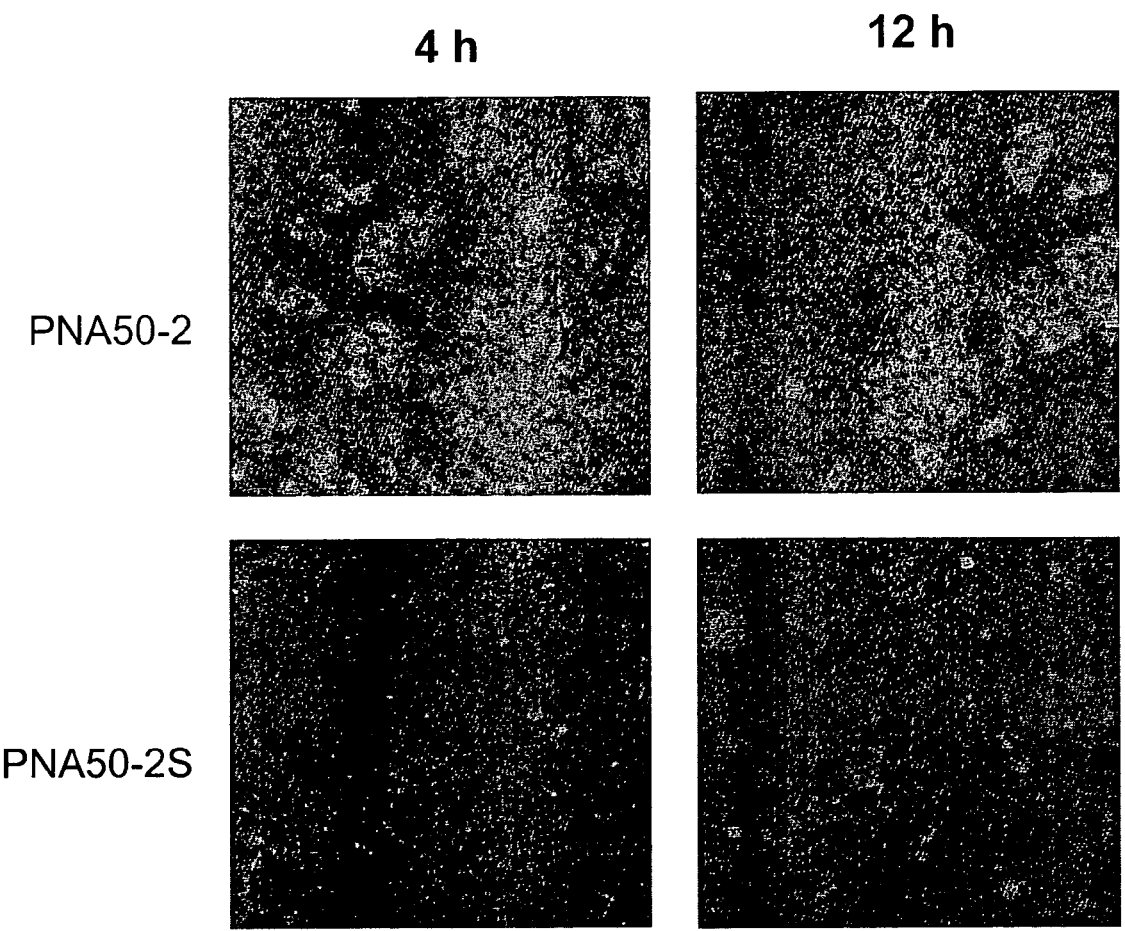
FIG. 30 shows fluorescence microscopy of MCF-7 cells following incubation with the PNAs shown for the times shown.
Figure 31:
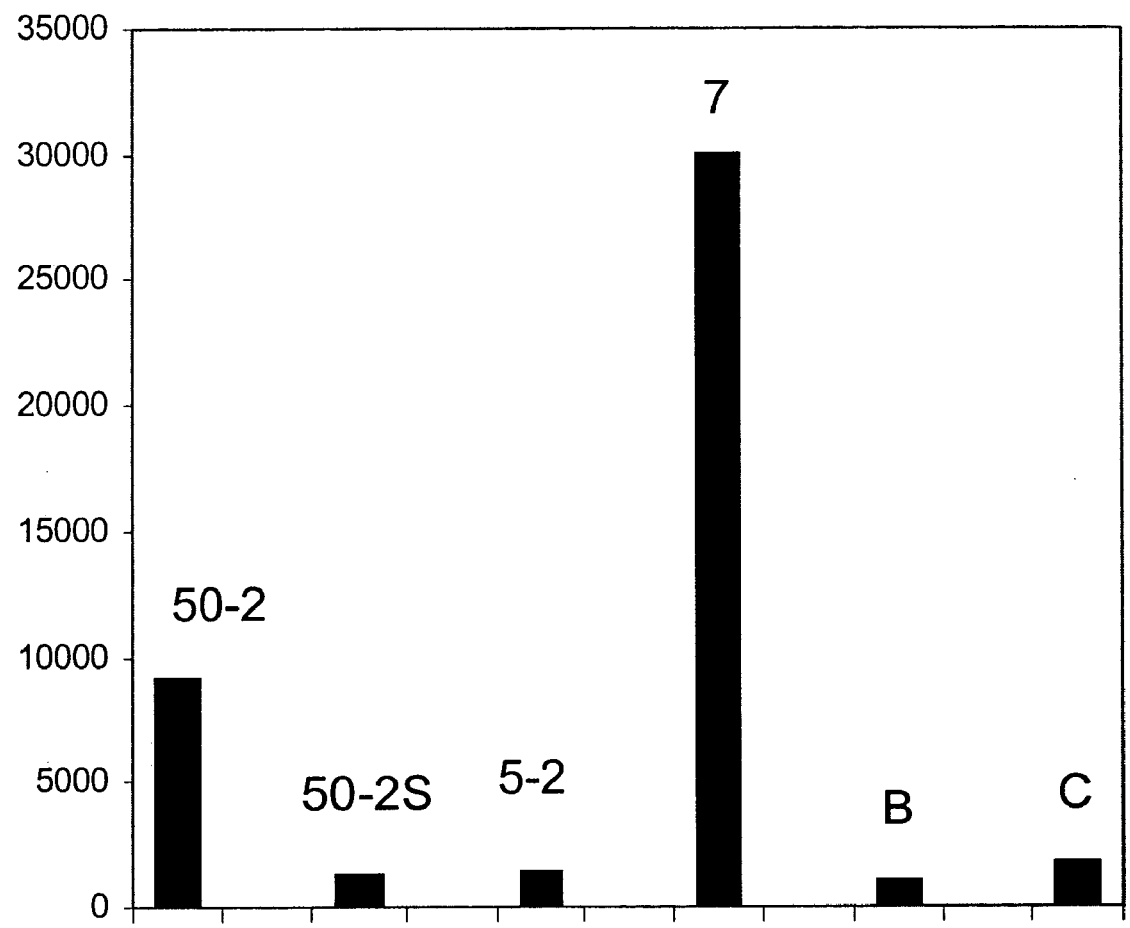
FIG. 31 shows fluorescence of MCF-7 cell lysates following 24 hour incubation with fluorescein labeled PNAs. Bars 1-4 show the PNAs fluorescein coupled to their amino terminus and the NLS peptide sequence to their carboxyterminus. B shows a blank control with no fluorescently labeled PNA added. C shows fluorescein labeled NLS sequence without a PNA attached.

Binding of Fluorescently labeled PNAs to MCF-7 cells. Initially we expected that Cys-Tyr-PNA-$Lys_4$ hybrid PNAs would be able to enter cells in vitro because of the prescence of the $Lys_4$ permeation peptide and that we could study this process by labeling the cysteine with a fluorescent reporter group. Unfortunately, we found that the fluorescein labeled PNAs formed aggregates and did not enter the cells, whereas a fluorescein labeled $CysArg_9$ peptide did. To see if changing the permeation peptide would help with the cell culture targeting tests we synthesized a series of fluorescently PNAs with the nuclear localization sequence (NLS), KPKKKRKV (Table 2) following, which contains an additional lysine and arginine, along with a proline and valine. When MCF-7 cells were incubated with 1.0 µM Flu-PNA-NLS for 4 h, 24 h and 48 h, and then washed 5 times with PBS prior to fixation with paraformaldehyde, PNA50-2 and PNA7 showed that highest fluorescence staining of the cells, whereas PNA5-2 and PNA50-2S showed comparitively little (FIG. 30). To get a more quantitative assessment of the targeting capabilities of the PNAs, the MCF-7 cells were treated as above with the fluorescein labeled PNAs for 24 h. Following this the cells were lysed and the fluorescence of the mixture was measured at 520 nm with excitation at 488 nm on a SPEX fluorimeter. In this assay, PNA7 showed the highest binding with about 12-fold higher fluorescence that the controls (FIG. 31). PNA50-2 was next best with 4-fold higher fluorescence. PNA5-2 did not show any significant binding, despite having show a high affinity for unr mRNA in vitro.

Overall

We have developed and successfully used a modified RT-ROL and a new SAABS methodology for identifying antisense binding sites on mRNA produced in vitro, and Dynabead-based assays for determining the binding affinity of antisense ODNs and PNAs for these sites. Furthermore, we showed that antisense PNAs against the unr mRNA which is abundantly overexpressed in the MCF-7 breast cancer cell line concentrates within these cells when attached to the NLS permeation peptide, whereas a non-complementary sequence did not.

Materials and Methods

Image clone 5285557 containing the unr (upstream of N-ras) mRNA sequence (D1S155E, NM_007158.2, GI: 20070240, ATTC clone #7020864). pZero plasmid for SAGE analysis is from Invitrogen. The MCF-7 cell line was obtained the Washington University Medical School in St. Louis. 5(6)-carboxyfluorescein succinimidyl ester (5(6)-FAM SE) was purchased from Molecular Probes, diisopropylethylamine (DEA), trifluoroacetic acid (TFA), m-cresol and diethyl ether (anhydride) were purchased from Aldrich. α-N-9-Fluorenyl-methoxycarbonyl (Fmoc) protected amino acids (Val-OH, Pro-OH, Lys(Boc)-OH and Arg(Pbf)-OH) were purchased from NovaBiochem.O-(7-Azabenzo-triazol-1-yl)-1,1,3,3-tetramethyluronium hexafluorophosphate (HATU), Fmoc-XAL PEG-PS resin, PNA building blocks (Fmoc-A-(Bhoc)-OH, Fmoc-C-(Bhoc)-OH, Fmoc-G-(Bhoc)-OH and Fmoc-T-OH) and other reagents and solvents for PNA and peptide synthesis were purchased from PerSeptive Biosystems. Fluorescence spectra were recorded on SPEX Fluoromax instrument. UV spectral data were acquired on a Bausch and Lomb Spectronic 1001 spectrophotometer or Varian Cary 100 Bio UV-Visible Spectrophotometer. Matrix-assisted laser desorption ionization (MALDI) mass spectra of PNA-peptide conjugates were measured on PerSeptive Voyager RP MALDI-time of flight (TOF) mass spectrometer using sinapinic acid as a matrix and calibrated versus insulin (average $[M+H^+]=5734.5$) that was present as an internal standard. High-pressure liquid chromatography was carried out on Beckman Coulter System Gold 126 with Microsorb RP C18 column (300 Å pore, 5 µm particle size, 4.6×250 mm) using 1 mL/min linear gradients of solvent B (0.1% TFA in acetonitrile) in A (0.1% TFA in water). Peptide-PNA conjugates were quantified by spectrophotometric A260 values.

Successful production of unr RNA. Transcription reactions were carried out using the Promega RiboMAX Large Scale RNA production system utilizing the T7 promoter at the 5'-end of the unr gene in the IMAGE clone and cleaving the clone at the unique NdeI site at the 3'-end of the gene prior to transcription. Transcription was allowed to proceed with T7 RNA polymerase and NTPs for 3 h at 37° C., and was followed by DNase treatment, LiCl precipitation, phenol extraction, and ethanol precipitation. NTPs were then removed with a NucAway spin column. Radiolabeled RNA was produced with [α-$^{32}$P]-UTP. The final purified unr RNA is quite homogeneous and corresponds in size to the expected 3.4 Kb transcript. For the Dynabead assay, the unr mRNA was transcribed in the presence of Bio-dUTP.

RT-ROL mapping of antisense sites on unr RNA. The ODNs for mapping the antisense binding sites on the unr RNA by the modified RT-ROL assay are shown in FIG. 35. The mapping was carried out by mixing the RNA and random oligo library at 65° C. for 5 min with dNTPs followed by a quickly chilling in ice and then adding ribonuclease inhibitor, heating to 24° C. for 10 min, then 42° C. for 2 min and then adding SuperScript, and then incubating at 42° C. for 50 min, then inactivating by heating at 70° C. for 15 min. Then 5'-end-labeled PCR primer, dNTPs, and Taq polymerase was added and subjected to 30 cycles of PCR (94° C.-1 min, 55° C. 1 min, 72° C. 1 min, 72° C. 10 min, 4° C.). The products were then run on 6% denaturing polyacrylamide gels.

SAABS Method for Mapping Antisense Sites on unr mRNA. Dynabeads (Dynabead®M-280streptavidin, Dynal-Biotech) were first washed with solution A (DEPC-treated 0.1 M NaOH, DEPC-treated 0.05 M NaCl), followed by three times with solution B (DEPC-treated 0.1 M NaCl), and then washed two times with 100 µL of hybridization solution (1M NaCl, Tris-HCl pH 7.4). The beads were then resuspended in 50 µl of hybridization solution. The RNA (3 µL of 3 µg/µl) was incubated with 2 µl of CRNA-Bio (4.7 µg/µl) and of 45 µl of hybridization buffer at 65° C. for 5 min, and then cooled at room temperature for 10 min. The RNA solution was then added to a suspension of the beads at 25° C. for 20 min. The beads were then washed three times using hybridization buffer, and then resuspended in 50 µl of hybridization solution. The ROL ODN (5 µl) were then annealed with the complementary ODNs CS1 (12 µl), and CS2 (8.6 µl) in hybridization buffer (23 µl) by heating at 65° C. for 5 min, and then cooled to room temperature for 10 min. The RNA solution was then mixed with S1-ROL-S2 together with 2 µl RNasein inhibitor, and incubated at 27° C. for 1 h. During the incubation, the beads were resuspended every 15 min by pipetting. Following the incubation, the beads were washed 6 times with the hybridization solution and then resuspended in 100 µl of H$_2$O. Thirty cycles of PCR were carried out with Taq DNA polymerase, and 5'-biotinylated S1 and CS2 primers. After amplification, the reaction mix was directly loaded onto a 12% denaturing PAGE gel and electrophoresis was carried out at 10 V/cm for 4 hours. The 50 bp band was excised and purified by use of Strepavidin beads. The 50 bp PCR product was directly digested with Nla III at 37° C. overnight to release the tags. The digested product was loaded onto 4% agarose gel and run at 10 V/cm. After staining the gel with 0.25 µg/ml ethidium bromide, the 12 bp band was excised. Ligation of the 12-mers was carried out at 16° C. for overnight. Concatemers were isolated using the Qiaquick Gel Extraction Kit (Qiagen), following the manufacturer's manual. The pellet was dissolved in ligation buffer and ligation was carried out with T4 DNA Ligase and ATP at 16° C. for 2 h. The mixture was then electrophoresed on a 1% agarose gel (TAE) and fractions with 300-500 bp length were excised. Concatemers were ligated into the SphI site of pZero-1 (Invitrogen) with T4 DNA ligase and ATP for 4 h at 16° C. and then transfected into *E. coli*, following the manufacturer's manual (Oneshot®Top10, invitrogen). The transfectants were plated on low salt LB plates containing 50 µg/ml Zeocin™ and incubate for about 18 h at 37° C. Zeocin™ resistant transformants were picked using pipette tips, incubated in 5 ml SOB containing 50 µl/ml Zeocin™ and grown overnight at 37° C. Plasmid DNA was prepared by the Rapid method (Molecular Clone) and Plasmid min prep kit (Qiageon). Digest DNA using XbaI and HindIII, analyze digestion in 1% agarose gel. Plasmids containing sizable inserts were then forwarded for sequence analysis using the Sp6 primer.

ODN Dynabead Binding Assay. The radiolabeled ODN (100 pM) was incubated with the 0.003 nM-10 nM of biotinylated mRNA and 1 µL of Rnase inhibitor for 4 h at 37° C. in a total volume of 100 µL. Then Dynabeads M-280 Steptaviden (Dynal Biotech) were added, 25 µL for 10 nM RNA, 12.5 µL for 3 nM RNA and 5 µL for all other concentrations of RNA, and mixed for 30 min. The beads were separated by a magnet and the solution removed. The beads were resuspended in 100 µL of water and both solutions counted by liquid scintillation to give free and bound fractions directly.

ODN Binding Data Analysis. A plot of fraction bound vs. mRNA concentration was fitted by non-linear least squares fitting with the Kalaidagraph program to the following analytical curve:

$$F_B = C + \frac{(1-C)*(([ODN]+K_d+[RNA]) - \sqrt{([ODN]+K_d+[RNA])^2 - 4\cdot[ODN]\cdot[RNA]}}{2\cdot[ODN]} w$$

here:
C=fraction of ODN non-specifically bound
[ODN]=total ODN concentration
[RNA]=total RNA concentration
$K_d$=dissociation constant PNA-Lys$_4$ peptide synthesis and purification. The hybrid PNA-peptides were synthesized in 2 µmol scale on an ABI 8909 automated DNA/PNA synthesizer using Fmoc chemistry and the manufacturer's protocols, reagents and PNA monomers. After completion of automated synthesis, PNAs were cleaved from the solid support and the bases were deprotected using trifluoroacetic acid:m-cresol (4:1) for 2 h and then precipitated with diethyl ether. The hybrid PNA-peptides were purified by reverse phase chromatography on a Microsorb-MV 300-5 column, (250×4.6 mm column, 300 A pore sizes, Varian Inc.) C-18 column with a 0-5% B/5 min, 5-60% B/30 min, 60-95% B/5 min, 95% B for 5 min, 95%-0%/10 min where A=0.1% TFA in water, B=0.08% TFA in CH$_3$CN. The fractions containing the products were evaporated to dryness in a Savant Speedvac, and redissolved in pure water.

Radioiodination of the PNA-peptides with $^{131}$I. The PNA-peptides were radioiodinated by a procedure described for iodination of PNAs with $^{125}$I. Thus Na$^{131}$I (12 µL, 5 mCi/120 µL solution from Amersham) was added to 2 µL of water and 2 µL of 1 M sodium phosphate, pH 7, then 2 µL of 100 µM NaI was added, followed by 4 µL of 1 mM chloramine-T and 4 µL of 100 µM PNA. The reaction was mixed by micropipetting, and allowed to stand for 5 min at room temperature and quenched with 4 µL of 10 mM sodium metabisulfite. The reaction mixture was then diluted with 80 µL of water and placed onto a Waters Sep-Pak cartridge (Vac C18, 6 cc, Part # WAT036905) that had been prewashed with 5 mL of 0.1% TFA in water. The unreacted Na$^{131}$I (average of 27% of the total radioactivity) was washed out with 10 mL of 0.1% TFA in water. This was followed by 5-10 mL of 5% acetonitrile in 0.1% TFA/water, which contained little radioactivity. The radiolabeled PNA-peptide (average of 42% of the radioactivity) was eluted with 5 mL of 40% CH$_3$CN in 0.1% TFA/water, leaving an average of 31% of the total radioactivity on the column. The average recovery of the labeled PNA-peptide was 57%. An aliquot of the fraction containing the labeled PNA-peptide was then diluted down to make a 100 µM stock solution. The actual concentration was then determined base on the activity of the solution in comparison to the 5 mL stock solution.

PNA Dynabead Binding Assay. The Dynabead assay was carried out as described above for the ODNs except that Corning non-binding assay tubes were used that were cut out of Corning® 96 Well White Flat Bottom Polystyrene NBS™ Microplates (Corning #3600) which have a polyethylene oxide-like surface. The binding tests were carried out in triplicate. Specifically, the radiolabeled PNA (13-26 pM) was incubated with the 0.1-1000 pM of biotinylated mRNA and 1 µL of RNAse inhibitor for 4 h at 37° C. in a total volume of 100 µL of 0.1 M NaCl, 50 mM EDTA, 2 mM cacodylic acid. Then 5 µL Dynabeads M-280 Steptaviden (Dynal Biotech) were added and mixed for 2 h. The beads were separated by a magnet and the supernatant transferred to a liquid scintillation vial. The beads were washed with 100 µL buffer three times and the washes transferred to the first scintillation vial. The beads were then transferred to a liquid scintillation vial by suspending in 100 µL of buffer three times. Liquid scintillation fluid (5 mL of CytoScint plus) was then added and both scintillation vials counted by liquid scintillation to give free and bound fractions directly.

PNA Binding Data Analysis. The binding data for three tests was averaged and analyzed by fitting the % bound (% B) vs RNA concentration data to the analytical expression shown below for a two state binding equilibrium using a non-linear least squares fitting algorithm in Kalaidagraph in which the data was weighted according to their standard deviations. NSB is the % non-specifically bound (to be fit), SB is the % specifically bound (to be fit), [PNA] is the concentration of PNA used (a constant), [RNA] equals the concentration of RNA, a variable, and $K_d$ is the dissociation constant for the PNA (to be fit).

$$\%_B = NSB + \frac{(SB) * (([PNA] + K_d + [RNA]) - \sqrt{([PNA] + K_d + [RNA])^2 - 4 \cdot [PNA] \cdot [RNA]})}{2 \cdot [PNA]}$$

Synthesis of the Flu-PNAs-NLS conjugates. A solid supported NLS peptide (NH$_2$-KPKKKRKV-) was synthesized on a 2 µmol scale by manual benchtop Fmoc off synthesis on the universal support XAL-PEG-PS resin. Deprotection was carried out with 20% piperidine in DMF (v/v) and the coupling step was conducted in presence of N-Fmoc amino acid, HATU (4.0 eq) and DIEA (8 eq) in DMF. Capping was conducted with 5% acetic anhydride and 6% lutidine in DMF, alternate washing was applied between each procedure with methanol and DMF, after sequential amino acid coupling cycles finished, the resulted peptide-resin was washed with DMF and DCM and loaded in Expedite 8909 Synthesizer (Applied Biosystems) without deprotection. The PNAs-peptide conjugates were synthesized continuously by coupling PNA building blocks on N-terminus of NLS peptide which is attached on resin under standard automated PNA synthesis protocol. The cartridge containing NH$_2$-PNA-peptide-resin was taken out of the synthesizer after PNA synthesis was complete. 5(6)-Carboxyfluorescein succinimidyl ester (10.7 mg, 20 µmol) was dissolved in 300 µl DMF, after DIEA (11 ul, 60 µmol) was added, the mixture was introduced into the cartridge with syringe and push the solution back and forth to agitate the resin suspension once 10 min during 1 hour. Then the resin was washed with DMF and DCM and dried by passing nitrogen. TFA/m-cresol (4:1) was used to cleave the conjugates and remove the side chain protective groups by treating Flu-PNA-peptide-resin for 2 h at RT 8-10 fold of ethyl ether was added into isolated TFA mixture to precipitate the expected product as yellow solid. The resulted crude products were purified by reversed phase HPLC on a Microsorb C18 column (300 Å pore, 5 µm particle size, 4.6×250 mm) using 5% to 70% linear gradient of solvent B (0.1% TFA in acetonitrile) in A (0.1% TFA in water) over 65 min at the flow rate of 1 ml/min. The effluent was monitored by absorbance at both 260 nm and 440 nm and the major peaks were collected, concentrated to dryness in vacuo, and characterized by MALDI-TOF mass spectrometry.

Assessment of MCF-7 targeting ability of Flu-PNA-NLS conjugates by fluorescent microscopy and a bulk fluorescent assay. The MCF-7 cell line was obtained from American Type Culture Collection (ATCC), and was grown in Eagle's Minimal Essential medium with Earle's balanced salt solution and 2 mM L-glutamine (EMEM) (ATCC), supplemented with 0.01 mg/ml bovine insulin, 10% fetal bovine serum (Gibco), penicillin (20 units/ml) and streptomycin (20 µg/ml) (Gibco), at 37° C. in a humid atmosphere containing 5% CO$_2$. MCF-7 were seeded onto eight-well glass chamber slides (Nunc; Naperville, Ill.), and grown to ~60% confluence. The culture medium removed and the cells were washed with PBS and 300 µl of fresh culture medium with 1.0 µM Flu-PNAs was added. The cells were incubated at 37° C. in a humid atmosphere containing 5% CO$_2$ for 4 h, 24 h and 48 h, and then washed five times with PBS. The cells were fixed at room temperature by addition of 4% (v/v) paraformaldehyde in PBS for 20 min, followed by three rinses with PBS. The cells were mounted with fluorescence antifading mounting medium following the recommended procedures of the manufacturer (Vector Laboratories, Burlingame, Calif.). Preparations were analyzed by fluorescence microscopy. The MCF-7 cells were treated as above with fluorescein labeled PNA NLS conjugates for 24 h. Following this the cells were lysed and the fluorescence of the mixture was measured at 520 nm with excitation at 488 nm on a SPEX fluorimeter.

Table 1. Binding affinity of the antisense ODNs by the Dynabead assay. The site number "x-y" is given as the nucleotide "x" in the mRNA (start codon at 448) followed by the length, "y". The code number "x-y" refers to sequence "x" used for the dot blot tests, and if followed by a 2 refers to a modified second generation sequence that overlaps the original sequence).

| Site | ODN sequence | Code | $K_d$ (nM) | SD |
| --- | --- | --- | --- | --- |
| 2851-15 | TGGTGTGCTTTGTGG | 50-2 | 0.43 | 0.08 |
| 676-15 | TTTCCCAGTCCGTCG | 7-2 | 0.6 | 0.12 |
| 901-15 | ATCTCCAGTTTCCAG | S3-2 | 0.8 | 0.1 |
| 1414-15 | TTTGTCACGTCGGTC | S5-2 | 0.9 | 0.2 |
| 1145-15 | CATTTCTGTCCTTGA | 16-2 | 1.1 | 0.2 |
| 1802-15 | CATCCTCAGCCTCCT | 26-2 | 1.2 | 0.2 |
| 839-15 | CACTTCCCCATTACG | 13-2 | 1.9 | 0.4 |
| 727-20 | ATTCGTTCTTCAGGGAGGAT | 9 | 2.6 | 0.7 |

-continued

| Site | ODN sequence | Code | $K_d$ (nM) | SD |
|---|---|---|---|---|
| 476-15 | TATGTCCATTGTTGT | 5-2 | 2.8 | 0.6 |
| 2020-20 | CCAAAATTATCCTTCAGAGT | 32 | 21 | 5 |
| 1396-20 | TCTGTTGAAATATTAAACCT | 21 | 26 | 1.5 |
| 1927-15 | CCTCTGTTTGTCACT | 29-2 | 33 | 8 |
| 2114-15 | TGTCCCCCAGTTCCA | 35-2 | 40 | 14 |
| 1389-20 | AATATTAAACCTAACATGGT | 20 | 73 | 9.4 |
| 2115-15 | ATGTCCCCCAGTTCC | S7 | 147 | 120 |
| na | CGATTGGAGCGC | V-12 | 344 | 148 |
| na | AGATCGCAACTCATA | L-15 | 588 | 406 |

TABLE 2

Structure and characterization of PNA conjugates.

| PNA | Conjugate | Calc'd | MW from MALDI-TOF Found |
|---|---|---|---|
| 5-2 | Cys-Tyr-CATTATGTCCATTGTTGT-Lys$_4$ | 5641 | 5648, 5643.4 |
| 7-2 | Cys-Tyr-TTTCCCAGTCCGTCGGTC-Lys$_4$ | 5588 | 5595.4, 5592.4 |
| 50-2 | Cys-Tyr-TGGTGTGCTTTGTGGATG-Lys$_4$ | 5778.5 | 5786, 5785, 5781.9 |
| S5-2 | Cys-Tyr-TAATTTGTCACGTCGGTC-Lys$_4$ | 5651 | 5657.2, 5650.8, 5667, 5661 |
| S3-2 | Cys-Tyr-TATCTCCAGTTTCCAGCT-Lys$_4$ | 5571 | 5580.4, 5571.8 |
| 50-2S | Cys-Tyr-CATCCACAAAGCACACCA-Lys$_4$ | 5561.5 | 5569.4, 5566.8, 5569.1 |
| 5-2 | Flu-CATTATGTCCATTGTTGT-KPKKKRKV | 6353.58 | 6361.14 |
| 7-2 | Flu-TTTCCCAGTCCGTGGGTC-KPKKKRKV | 6136.62 | 6144.22 |
| 50-2 | Flu-TGGTGTGCTTTGTGGATG-KPKKKRKV | 6216.57 | 6222.19 |
| 50-2S | Flu-CATCCACAAAGCACACCA-KPKKKRKV | 6163.55 | 6168.93 |

TABLE 3

Binding affinity of Cys-Tyr-PNA-Lys$_4$ by the Dynabead binding assay.

| Site | PNA Sequence | Code | $K_d$ (pM) | SD |
|---|---|---|---|---|
| 2828-18 | TGGTGTGCTTTGTGGATG | 50-2 | 21 | 5 |
| 653-18 | TTTCCCAGTCCGTCGGTC | 7-2 | 15 | 4 |
| 879-18 | TATCTCCAGTTTCCAGCT | S3-2 | 7 | 3 |
| 1394-18 | TAATTTGTCACGTCGGTC | S5-2 | 50 | 6 |
| 456-18 | CATTATGTCCATTGTTGT | 5-2 | 22 | 6 |
| na | CATCCACAAAGCACACCA | 50-2S | >10,000 | nd | na—not applicable, nd—not determined

EXAMPLE—SET F

Micropet Imaging of MCF-7 Tumors in Mice Via unr mRNA-Targeted PNAs Conjugated to Shell Cross-Linked Nanoparticles (SCKs)

In this example the inventors synthesized one targeting and one control nanoparticle bearing the antisense PNA50 and the sense PNAS sequences, respectively, to image the unr mRNA that is highly and abundantly overexpressed in a breast cancer cell line (MCF-7). A DOTA (1,4,7,10-tetraazacyclododecane-N,N',N'',N'''-tetraacetic acid) chelating moiety was conjugated to the surface of the nanoparticles so that they could be radiolabeled with $^{64}$Cu for biodistribution and microPET imaging studies in MCF-7 tumor bearing mice. Furthermore, the protein transduction domain (PTD) of the HIV-1 TAT protein (see SEQ ID 1) was conjugated for cell membrane crossing. The two nanoparticle were successfully labeled with $^{64}$Cu under mild conditions and were injected in CB-17 severe combined immunodeficiency (SCID) mice bearing MCF-7 xenografts (ca. 100 mg). MicroPET imaging revealed uptake of both targeting and control PNA-conjugated nanoparticles in MCF-7 tumors. However, the uptake of the SCK-PNA50 conjugate was higher compared to the SCK-PNA50S. Post-imaging biodistribution data comparison (24 h post injection) revealed a similar tumor specificity for SCK-conjugated and free PNA50 over PNA50S, suggesting the potential of PNA-conjugated SCKs as tumor specific molecular probes for early detection of cancer and ultimately for patient specific radiotherapy.

Test Procedures

SCKs and PNAs were synthesized and purified as reported in Examples set A and E, respectively. PNA50, PNA50S, PTD and DOTA were conjugated on the surface of the SCKs as reported in Example set B. Radiolabeling with $^{64}$Cu and purification of DOTA-SCK(PTD)-PNA50 and DOTA-SCK(PTD)-PNA50S were carried out as reported in Example set D. MCF-7 xenografted CB-17 SCID mice were obtained as described in Example set D.

MicroPET imaging studies. The microPET imaging studies were carried out using the microPET® R4 (rodent) scanner (Concorde Microsystems Inc., Knoxville, Tenn.). MCF-7 tumor-bearing CB-17 SCID mice were anesthetized with 1-2% vaporized isoflurane and injected with ca. 100-150 µCi of activity in 100 µL saline via the tail vein. At specific time points (1 h, 4 h, and 24 h) post injection, the mice were re-anesthetized and then immobilized in a supine position on custom-built support beds with attached anesthetic gas nose cones for data collection. After the microPET imaging at 24 h p.i., the animals were sacrificed and biodistribution studies were performed. The ratios of tumor to blood (T/B) and tumor to muscle (T/M) were calculated.

Results

The sequences of the antisense and sense PNAs were selected by a procedure that was described in Example set E. PNA50 with a $K_d$ of 21 pM for the 2828-18 binding site of the unr mRNA and PNA50S with a $K_d$ of >10 nM were selected to be conjugated on the SCK surface to obtain a targeting construct and a control one, respectively. Together with the PNAs, the nanoparticles were conjugated to PTD for cell membrane cressing and to DOTA for $^{64}$Cu-labeling. The two nanoconjugates were successfully radiolabeled with $^{64}$Cu in 0.1 M ammonium citrate buffer (pH 6.5) under mild conditions (3 h at 60° C.).

After DTPA challenge of non-specifically bound $^{64}$Cu-activity and Centricon-YM100 (MWCO: 100,000 Da) separation, the radiochemical purity of the $^{64}$Cu-labeled PNA conjugates was nearly 100% as determined by radio-FPLC.

CB-17 SCID mice bearing MCF-7 xenografts were administered of $^{64}$Cu-DOTA-SCK(PTD)-PNA50 and $^{64}$Cu-DOTA-SCK(PTD)-PNAS via tail vein injection. The mice were imaged at 1 h, 4 h and 24 h post injection, then they were euthanized, the main organs were explanted, weighed and counted in a gamma counter together with standards to obtain the percent injected dose per gram tissue (% ID/g) and the percent injected dose per organ (% ID/organ).

Figure 39:
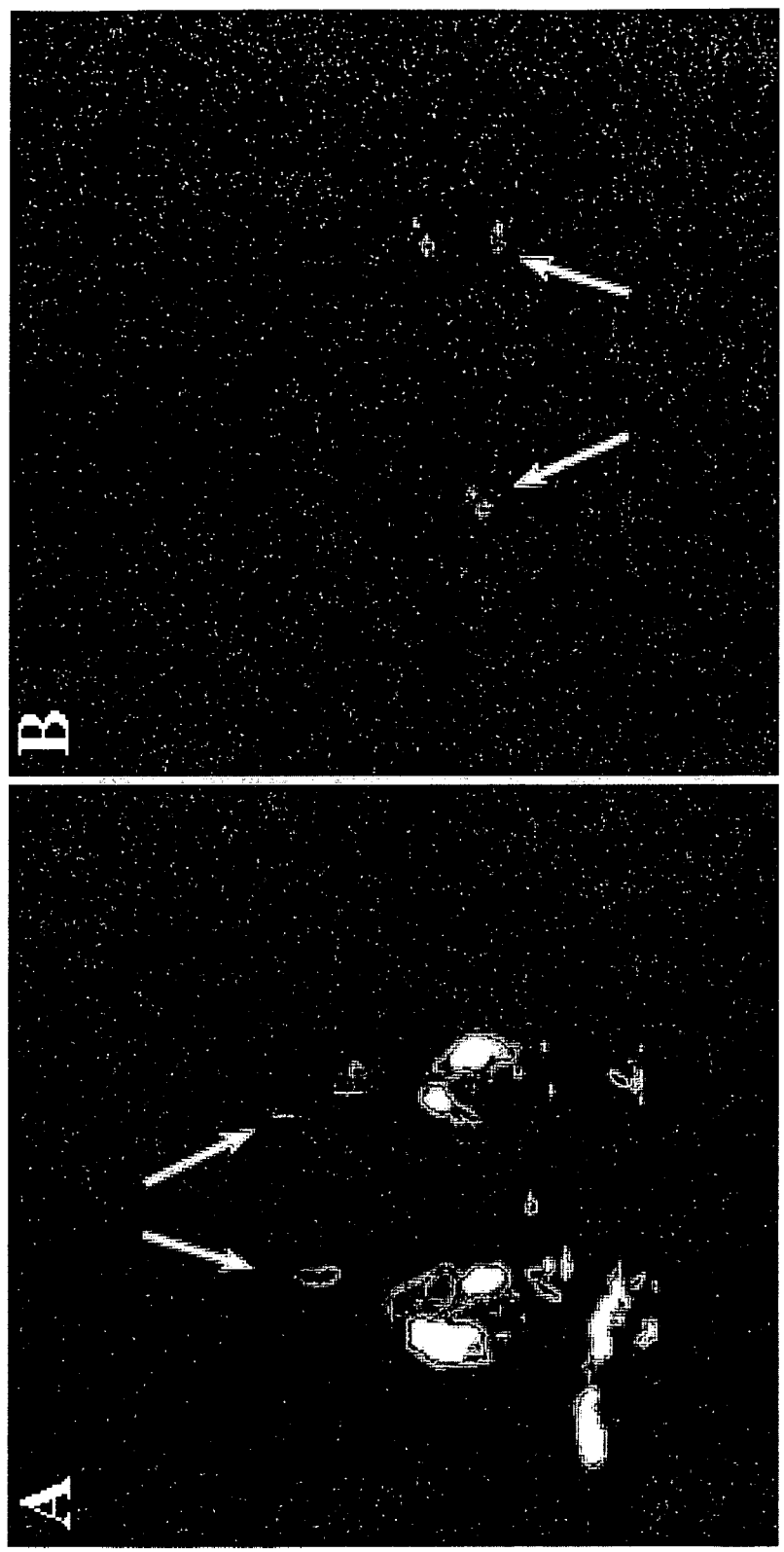
FIG. 39 shows MicroPET coronal (FIG. 39(A)) and transaxial (FIG. 39(B)) images of two mice administered with $^{64}$Cu-DOTA-SCK(PTD)-PNA50 and $^{64}$Cu-DOTA-SCK(PTD)-PNA50S (left and right mouse, respectively. Ca. 150 μCi/100 μl injected per mouse) at 1 h p.i. The intensity of the images was scaled by max/min of frame. Tumors are indicated by solid white arrows.

The microPET images in FIG. 39 show the two mice administered with $^{64}$Cu-DOTA-SCK(PTD)-PNA50 (left) and $^{64}$Cu-DOTA-SCK(PTD)-PNA50S (right) side by side 1 h post injection (Panel A: coronal slice; Panel B: transaxial slice; tumors are indicated by a white solid arrow). Visually, $^{64}$Cu-DOTA-SCK(PTD)-PNA50 exhibits the highest image contrast of tumor, which is implanted in the nape of the neck.

The post-imaging biodistribution results are consistent with this finding and the tumor/muscle and tumor/blood ratios (FIG. 40) confirm that the antisense PNA (PNA50) maintains a higher target specificity compared to the control (PNA50S) upon conjugation to the surface of the nano-scale polymeric scaffold (SCK).

TABLE 1

Post imaging biodistribution data in MCF-7 xenograft bearing SCID mice administered with $^{64}$Cu-DOTA-SCK(PTD)-PNA50 and $^{64}$Cu-DOTA-SCK(PTD)-PNAS (ca. 150 µCi/100 µl). The data are presented as percent injected dose per gram tissue (% ID/g) and percent injected dose per organ (% ID/organ)

| | % ID/gram | | % ID/organ | |
| --- | --- | --- | --- | --- |
| | $^{64}$Cu-DOTA-SCK(PTD)-PNA50 | $^{64}$Cu-DOTA-SCK(PTD)-PNA50S | $^{64}$Cu-DOTA-SCK(PTD)-PNA50 | $^{64}$Cu-DOTA-SCK(PTD)-PNA50S |
| blood | 0.4631 | 0.4969 | 0.5382 | 0.6226 |
| lung | 4.2941 | 2.1310 | 0.4792 | 0.2272 |
| liver | 4.9879 | 3.5876 | 3.7090 | 2.9515 |
| spleen | 1.6291 | 1.9820 | 0.0738 | 0.0920 |
| kidney | 3.2609 | 2.3850 | 0.3858 | 0.2726 |
| muscle | 0.2502 | 0.2754 | 1.7028 | 2.0214 |
| fat | 0.4821 | 0.2491 | 1.1044 | 0.6154 |
| heart | 0.8383 | 0.9867 | 0.0573 | 0.0759 |
| brain | 0.1361 | 0.1291 | 0.0496 | 0.0455 |
| bone | 1.4135 | 0.1372 | 2.5576 | 0.2677 |
| tumor | 1.2979 | 0.7534 | 0.1887 | 0.1002 |

Figure 41:
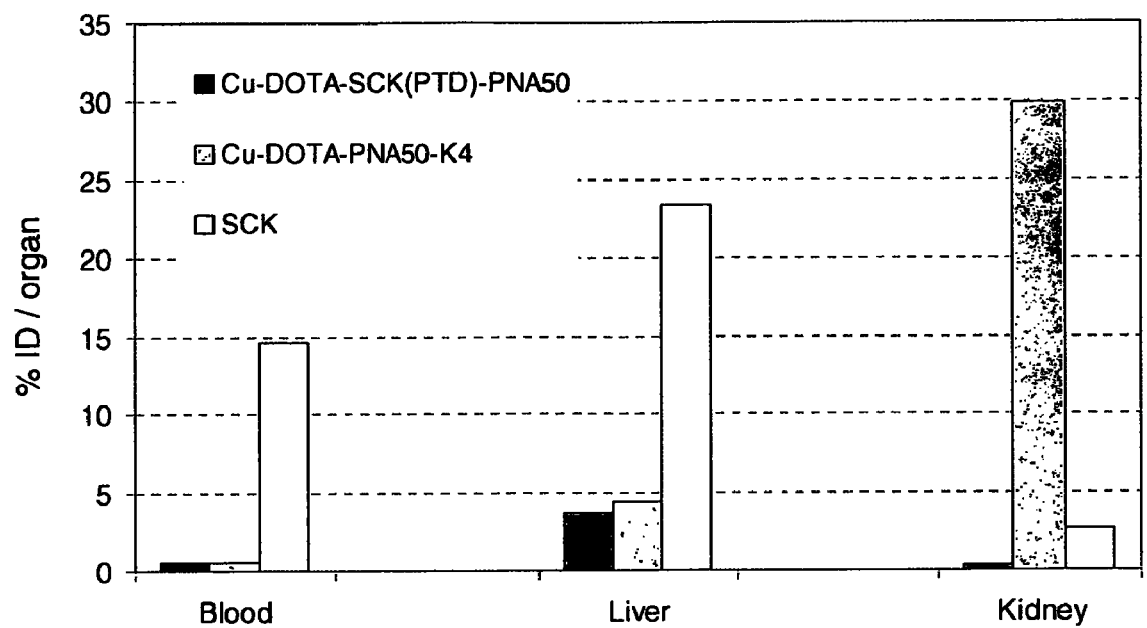
FIG. 41 shows post microPET imaging biodistribution data obtained from mice administered with $^{64}$Cu-DOTA-SCK(PTD)-PNA50, $^{64}$Cu-DOTA-PNA50, and $^{64}$Cu-TETA-SCK. Data are presented as percent injected dose per organ (% ID/organ).

Compared to the native SCK, the PNA- and PTD-conjugated nanoparticles have a lower accumulation in blood ($^{64}$Cu-TETA-SCK: 1.05±0.33% ID/g; $^{64}$Cu-DOTA-SCK(PTD)-PNA50: 0.4631% ID/g; $^{64}$Cu-DOTA-SCK(PTD)-PNA50S: 0.4969% ID/g) and liver ($^{64}$Cu-TETA-SCK: 23.34±3.76% ID/organ; $^{64}$Cu-DOTA-SCK(PTD)-PNA50: 3.7090% ID/organ; $^{64}$CU-DOTA-SCK(PTD)-PNA50S: 2.9515% ID/organ). At the same time, the derivatized SCKs have a lower uptake in kidney at 24 h post injection, as compared to the non-conjugated PNAs ($^{64}$Cu-DOTA-SCK(PTD)-PNA50: 0.3858% ID/organ; $^{64}$Cu-DOTA-SCK(PTD)-PNA50S: 0.2726% ID/organ; $^{64}$Cu-DOTA-PNA50-K4: 29.95±3.28% ID/organ; $^{64}$Cu-DOTA-PNA50S-K4: 22.72±8.45% ID/organ). The comparison of the biodistribution data in blood, kidney and liver is depicted in FIG. 41.

Figure 40:
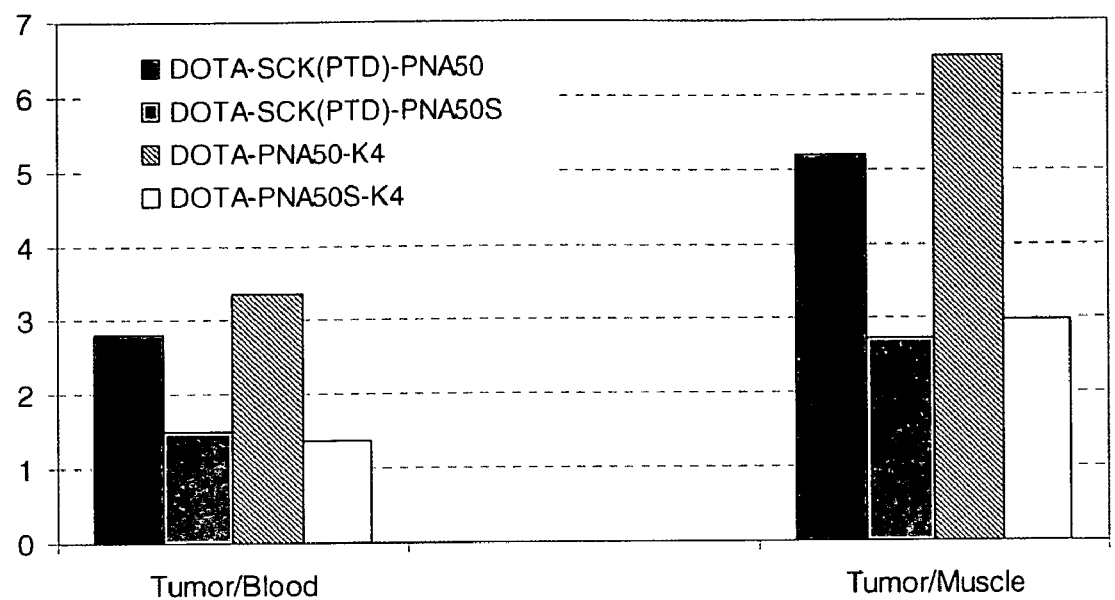
FIG. 40 shows tumor-to-muscle and tumor-to-blood ratios of PNA-conjugated SCKs in comparison with the free PNAs. Data were calculated from post microPET imaging biodistribution results from two living animals.

In summary, we have designed and synthesized two shell cross-linked nanoparticle bearing PNAs with different affinity for a mRNA overexpressed in MCF-7 tumor cells (ca. 5000 copies per cell): a targeting SCK conjugated with the antisense sequence PNA50 and a control SCK conjugated with the sense sequence PNA50s. Upon conjugation to the nanoparticle, the antisense sequence maintained a highest affinity for the target mRNA compared to the sense sequence, as confirmed by both microPET imaging (FIG. 39) and post-imaging biodistribution (FIG. 40). The MCF-7 tumors accumulated the radiotracers and were clearly visible despite the decreased bioavailability of the PNA-conjugated nanoparticle, as confirmed by the low blood uptake of $^{64}$Cu-DOTA-SCK(PTD)-PNA50 as compared to the free $^{64}$Cu-DOTA-PNA50-K4 (FIG. 41). At the same time, the PNA-SCK construct exhibited a more favorable clearance profile from the main excretory organs compared to both the native nanoparticles and oligonucleotide analogs, as confirmed by the uptake values in kidney and liver (FIG. 41). These findings suggest PNA-conjugates SCKs are promising tools for imaging of mRNA overexpressing or uniquely expressing tumors in vivo and ultimately may allow for the development of effective agents for patient specific radiotherapy.

What is claimed is:

1. A diagnostic target-specific imaging probe comprising an intracellular targeting ligand comprising a peptide nucleic acid, wherein the peptide nucleic acid is SEQ ID NO: 3, or a nuclease resistant oligonucleotide analog, wherein the nuclease resistant oligonucleotide analog is a MOE-mRNA of SEQ ID NO: 3 or a LNA of SEQ ID NO: 3, wherein the SEQ ID NO: 3 binds selectively to an uniquely expressed or overexpressed mRNA, wherein the uniquely expressed or overexpressed mRNA is an unr mRNA, a permeation peptide, and at least one detectably labeled compound.

2. A pharmaceutical kit comprising the diagnostic target-specific imaging probe of claim 1 and a pharmaceutically acceptable carrier, excipient, diluent, or saline composition.

3. The diagnostic target-specific imaging probe of claim 1, wherein the permeation peptide is selected from the group consisting of a HIV-1 TAT protein transduction domain, KPKKKRKV, GRKKRR, and four lysine residues.

4. The diagnostic target-specific imaging probe of claim 1, wherein the at least one detectably labeled compound is selected from the group consisting of a fluorophore, a radionucleotide, and combinations thereof.

5. A diagnostic target-specific imaging probe comprising an intracellular targeting ligand comprising a permeation peptide, a peptide nucleic acid, wherein the peptide nucleic acid is SEQ ID NO: 3, and at least one detectably labeled compound.

6. The diagnostic target-specific imaging probe of claim 5, wherein the permeation peptide is selected from the group consisting of a HIV-1 TAT protein transduction domain, KPKKKRKV, GRKKRR, and four lysine residues.

7. The diagnostic target-specific imaging probe in accordance with claim 5, further comprising a shell crosslinked knedel shell crosslinked nanoparticle.

8. The diagnostic target-specific imaging probe in accordance with claim 1, further comprising a shell crosslinked knedel shell crosslinked nanoparticle.

* * * * *